US008664363B2

(12) United States Patent
Jones et al.

(10) Patent No.: US 8,664,363 B2
(45) Date of Patent: Mar. 4, 2014

(54) HUMANIZED ANTI-CD22 ANTIBODIES AND THEIR USE IN TREATMENT OF ONCOLOGY, TRANSPLANTATION AND AUTOIMMUNE DISEASE

(71) Applicant: MedImmune, LLC, Gaithersburg, MD (US)

(72) Inventors: Tarran Jones, Radlett (GB); David G. Williams, Epsom (GB)

(73) Assignee: MedImmune, LLC, Gaitherburg, MD (US)

( * ) Notice: Subject to any disclaimer, the term of this patent is extended or adjusted under 35 U.S.C. 154(b) by 0 days.

(21) Appl. No.: 13/781,009

(22) Filed: Feb. 28, 2013

(65) Prior Publication Data

US 2013/0266558 A1 Oct. 10, 2013

Related U.S. Application Data

(62) Division of application No. 11/715,307, filed on Mar. 6, 2007, now Pat. No. 8,389,688.

(60) Provisional application No. 60/779,804, filed on Mar. 6, 2006.

(51) Int. Cl.
*C07K 16/00* (2006.01)
*C07K 16/28* (2006.01)
*C07K 16/46* (2006.01)
*A61K 39/395* (2006.01)
*A61K 39/00* (2006.01)

(52) U.S. Cl.
USPC .......... 530/387.1; 530/387.3; 530/387.9; 530/388.2; 424/130.1; 424/133.3; 424/134.1

(58) Field of Classification Search
None
See application file for complete search history.

(56) References Cited

U.S. PATENT DOCUMENTS

| | | | |
|---|---|---|---|
| 4,816,567 A | 3/1989 | Cabilly et al. |
| 5,484,892 A | 1/1996 | Tedder et al. |
| 5,530,101 A | 6/1996 | Queen et al. |
| 5,595,721 A | 1/1997 | Kaminski et al. |
| 5,686,072 A | 11/1997 | Uhr et al. |
| 5,789,554 A | 8/1998 | Leung et al. |
| 5,831,142 A | 11/1998 | Tedder |
| 5,843,398 A | 12/1998 | Kaminski et al. |
| 5,859,205 A | 1/1999 | Adair et al. |
| 6,015,542 A | 1/2000 | Kaminski et al. |
| 6,022,521 A | 2/2000 | Wahl et al. |
| 6,090,365 A | 7/2000 | Kaminski et al. |
| 6,183,744 B1 | 2/2001 | Goldenberg |
| 6,187,287 B1 | 2/2001 | Leung et al. |
| 6,251,362 B1 | 6/2001 | Wahl et al. |
| 6,254,868 B1 | 7/2001 | Leung et al. |
| 6,287,537 B1 | 9/2001 | Kaminski et al. |
| 6,306,393 B1 | 10/2001 | Goldenberg |
| 6,331,415 B1 | 12/2001 | Cabilly et al. |
| 6,399,061 B1 | 6/2002 | Anderson et al. |
| 6,455,043 B1 | 9/2002 | Grillo-Lopez |
| 6,921,846 B1 | 7/2005 | Tedder |
| 7,534,427 B2 | 5/2009 | Goldenberg et al. |
| 7,829,086 B2 | 11/2010 | Hilbert et al. |
| 7,837,995 B2 | 11/2010 | Goldenberg |
| 7,910,103 B2 | 3/2011 | Goldenberg |
| 2002/0071807 A1 | 6/2002 | Goldenberg |
| 2003/0124058 A1 | 7/2003 | Goldenberg |
| 2003/0133930 A1 | 7/2003 | Goldenberg |
| 2003/0202975 A1 | 10/2003 | Tedder |
| 2004/0001828 A1 | 1/2004 | Tuscano et al. |
| 2004/0202658 A1 | 10/2004 | Benyunes |
| 2005/0118182 A1 | 6/2005 | Pastan et al. |
| 2007/0258981 A1 | 11/2007 | Hilbert et al. |
| 2007/0264260 A1 | 11/2007 | Tuscano et al. |
| 2008/0118505 A1 | 5/2008 | Tedder |
| 2011/0182887 A1 | 7/2011 | Hilbert et al. |

FOREIGN PATENT DOCUMENTS

| | | |
|---|---|---|
| EP | 0669836 B1 | 9/1995 |
| EP | 0866131 A2 | 9/1998 |
| EP | 0 660 721 B1 | 10/2008 |
| JP | 2006/506955 A | 3/2006 |
| WO | WO 91/13974 | 9/1991 |

(Continued)

OTHER PUBLICATIONS

Carvello et al. "Inotuzumab Ozogamicin Murin Analog-Mediated B-cell depletion reduces anti-islet allo- and autoimmune responses", Diabetes, 61, 2012, pp. 155-165.*

(Continued)

*Primary Examiner* — Daniel E Kolker
*Assistant Examiner* — James Rogers
(74) *Attorney, Agent, or Firm* — Mueting, Raasch & Gebhardt, P.A.

(57) ABSTRACT

Provided herein are chimeric and humanized versions of anti-CD22 mouse monoclonal antibody, HB22.7, which comprise human or humanized framework regions of the immunoglobulin heavy chain variable region ("VH") and light chain variable region ("VK"). The FW regions may contain one or more backmutations in which a human FW residue is exchanged for the corresponding residue present in the parental mouse heavy or light chain. The human or humanized VH framework regions may comprise one or more of the following residues: a valine at position 24 of FW1, a glycine at position 49 of FW2, and an asparagine at position 73 of FW3, numbered according to Kabat. Further provided are pharmaceutical and immunotherapeutic compositions, and methods using anti-CD22 antibodies that preferably mediate human ADCC, CDC, and/or apoptosis for: the treatment of B cell diseases in humans, including B cell malignancies, autoimmune disease, GVHD, humoral rejection, and post-transplantation lymphoproliferative disorder.

9 Claims, 53 Drawing Sheets

(56) References Cited

FOREIGN PATENT DOCUMENTS

Figure 1A:
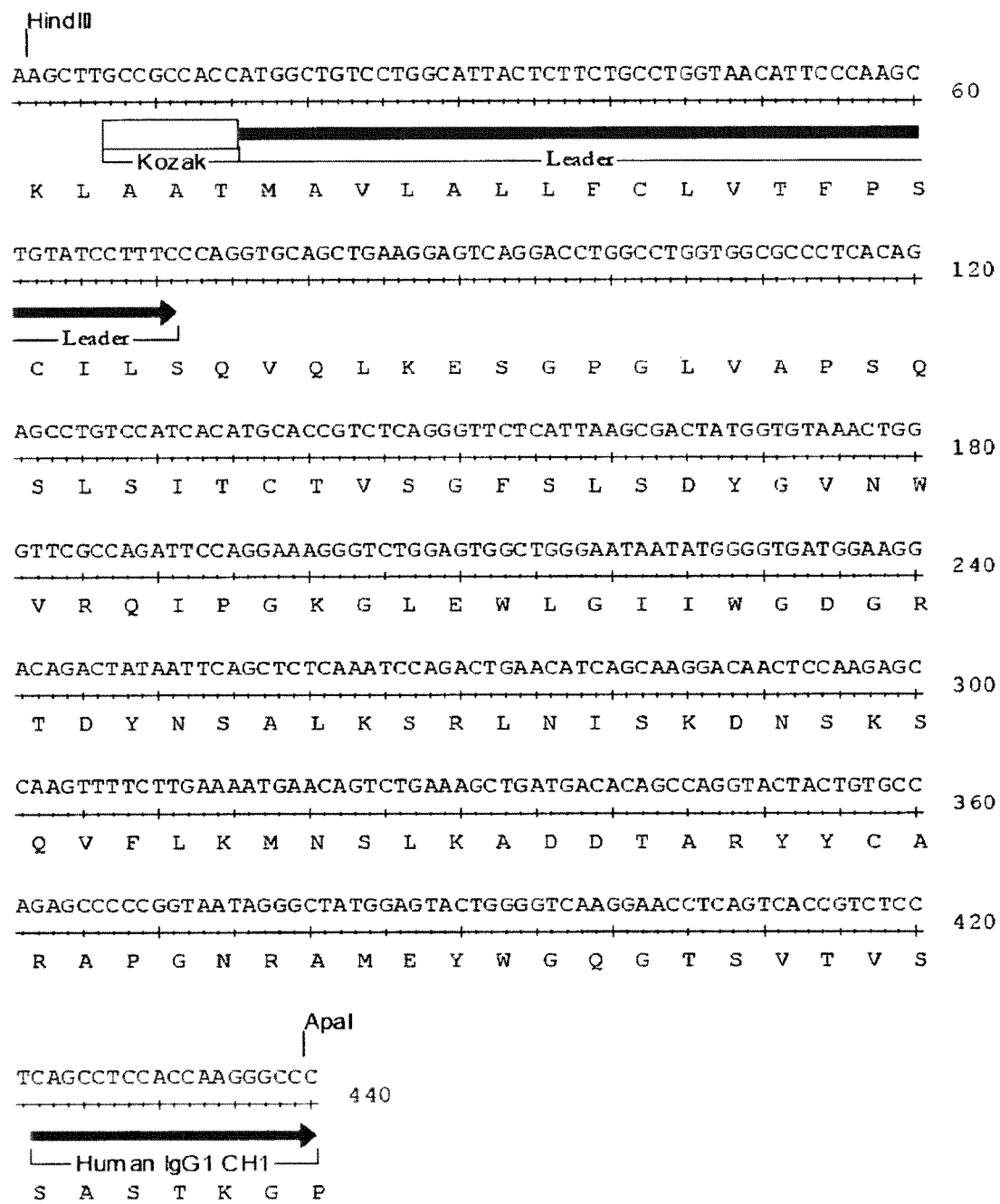

| WO | WO 94/27638 | 12/1994 |
|----|----|----|
| WO | WO 00/67796 | 11/2000 |
| WO | WO 00/74718 A1 | 12/2000 |
| WO | WO 01/97858 A2 | 12/2001 |
| WO | WO 03/072036 A2 | 9/2003 |
| WO | WO 03/072736 A2 | 9/2003 |
| WO | WO 03/093320 A2 | 11/2003 |
| WO | WO 2007/103469 A2 | 9/2007 |
| WO | WO 2007/103469 A3 | 9/2007 |
| WO | WO 2007/103470 A2 | 9/2007 |

OTHER PUBLICATIONS

Dorner et al. "Targeting CD22 as a strategy for treating systemic autoimmune diseases" Therapeutics and Clinical Risk Management, 2007, 3(5), pp. 953-959.*
Shirota et al. "Biologic treatments for systemic rheumatic diseases" Oral Dis. 2008, 14(3) 206-216.*
"Anti-human Fas monoclonal antibody CH11 light chain cDNA," Database Geneseq [Online] (Jan. 18, 1999) retrieved from EBI accession No. GSN:AAV66736.
"Anti-human Fas monoclonal antibody CH11 light chain," Database Geneseq [Online] (Jan. 18, 1999) retrieved from EBI accession No. GSN:AAW71889.
Abaza et al., 1992, "Effects of amino acid substitutions outside an antigenic site on protein binding to monoclonal antibodies of predetermined specificity obtained by peptide immunization: demonstration with region 94-100 (antigenic site 3) of myoglobin," J. Protein Chem. 11(5):433-444.
Abbas et al., 2003, Cellular and Molecular Immunology, 5th Ed., Saunders Publishing, pp. 506-512.
American Cancer Society and National Comprehensive Cancer Network, Oct. 2003, "Non-Hodgkin's Lymphoma—Treatment Guidelines for Patients," Version 1, pp. 1-76.
American Heritage Dictionary of the English Language, "Cure," 4th Ed., Houghton Mifflin Company, Publishers (2000).
Anderson et al., 1997, "Targeted anti-cancer therapy using rituximab, a chimaeric anti-CD20 antibody (IDEC-C2B8) in the treatment of non-Hodgkin's B-cell lymphoma," Biochem. Soc. Transac. 25:705-708.
Araoz et al., 1999, "CT and MR imaging of primary cardiac malignancies," Radiographics 19(6):1421-1434.
Benjamini et al., 2000, Immunology, 4th Ed., Wiley-Liss Publishers, p. 60.
Bergmann et al., 1998, "Abnormal surface expression of sialoglycans on B lymphocyte cell lines from patients with carbohydrate deficient glycoprotein syndrome I A (CDGS I A)," Glycobiology 8(10): 963-972.
Brorson et al., 1999, "Mutational analysis of avidity and fine specificity of anti-levan antibodies," J. Immunol. 163:6694-6701.
Brummell et al., 1993, "Probing the combining site of an anti-carbohydrate antibody by saturation-mutagenesis: role of the heavy-chain CDR3 residues," Biochem. 32:1180-1187 (Abstract).
Buchsbaum et al., 1992, "Therapy with unlabeled and 131I-labeled pan-B-cell monoclonal antibodies in nude mice bearing Raji Burkitt's lymphoma xenografts," Cancer Res. 52(23):6476-6481.
Burks et al., 1997, "In vitro scanning saturation mutagenesis of an antibody binding pocket," Proc. Natl. Acad. Sci. USA 94:412-417.
Carnahan et al., 2003, "Epratuzumab, a humanized monoclonal antibody targeting CD22: Characterization of in vivo properties," Clin. Cancer Res. 9:3982s-3990s.
Casset et al., 2003, "A peptide mimetic of an anti-CD4 monoclonal antibody by rational design," Biochem. Biophys. Res. Comm 307:198-205.
Chaouchi et al., 1995, "B cell antigen receptor-mediated apoptosis. Importance of accessory molecules CD19 and CD22, and of surface IgM cross-linking," J. Immunol. 154(7):3096-3104.

Chen et al., 1999, "Selection and analysis of an optimized anti-VEGF antibody: crystal structure of an affinity-matured Fab in complex with antigen," J. Mol. Biol. 293:865-881.
Coleman et al.., 2003, "Epratuzumab: Targeting B-Cell Malignancies through CD22," Clin. Cancer Res. 9:3991S-4S.
Colman et al., 1994, "Effects of amino acid sequence changes on antibody-antigen interactions," Res. Immunol. 145(1):33-36.
De Pascalis et al., 2002, "Grafting of 'abbreviated' complementarity-determining regions containing specificity-determining residues essential for ligand contact to engineer a less immunogenic humanized monoclonal antibody," J. Immunol. 169:3076-3084.
De Vita et al., 2002, "Efficacy of selective B cell blockade in the treatment of rheumatoid arthritis: evidence for a pathogenetic role of B cells," Arthritis Rheumatism 46:2029-2033.
Declaration of Thomas F. Tedder, Ph.D. dated Nov. 14, 2003, pp. 1-2.
Declaration of Thomas F. Tedder, Ph.D. Under 37 C.F.R. § 1.132 dated May 27, 1995, pp. 1-7.
Dufner et al., 2006, "Harnessing phage and ribosome display for antibody optimization," Trends Biotechnol. 24:523-529.
Edwards et al., 2001, "Sustained improvement in rheumatoid arthritis following a protocol designed to deplete B lymphocytes," Rheumatology 40:205-211.
Engel et al., 1993, "The same epitope on CD22 of B lymphocytes mediates the adhesion of erythrocytes, T and B lymphocytes, neutrophils, and monocytes," J. Immunol., 150(11):4719-4732.
Engel et al., 1995, "Identification of the ligand-binding domains of CD22, a member of the immunoglobulin superfamily that uniquely binds a sialic acid-dependent ligand," J. Exp. Med. 181:1581-1586.
Flavell et al., 1997, "Systemic therapy with 3BIT, a triple combination cocktail of anti-CD19, -CD22, and - CD38-saporin immunotoxins, is curative of human B-cell lymphoma in severe combined immunodeficient mice," Cancer Res. 57:4824-4829.
Friedberg, 2004, "Developing new monoclonal antibodies for aggressive lymphoma: a challenging road in the rituximab era," Clin Cancer Res. 10(16):5297-5298.
Ghetie et al., 1991, "Antitumor activity of Fab' and IgG-anti-CD22 immunotoxins in disseminated human B lymphoma grown in mice with severe combined immunodeficiency disease: effect on tumor cells in extranodal sites," Cancer Res. 51(21):5876-5880.
Ghetie et al., 1992, "The antitumor activity of an anti-CD22 immunotoxin in SCID mice with disseminated Daudi lymphoma is enhanced by either an anti-CD19 antibody or an anti-CD19 immunotoxin" Blood 80(9):2315-2320.
Ghetie et al., 1996, "Combination immunotoxin treatment and chemotherapy in SCID mice with advanced, disseminated Daudi lymphoma," Int. J. Cancer 68(1):93-96.
Goldenberg et al., 1990, "Monoclonal antibody therapy of cancer," N. J. Med. 87(11 Spec No):913-918.
Goldenberg, 1994, "New developments in monoclonal antibodies for cancer detection and therapy," CA Cancer J. Clin. 44(1):43-64.
Haas et al., 2006, "CD22 regulates normal and malignant B survival in vivo," J. Immunol. 177:3063-3073.
Harris et al., 1994, "A revised European-American classification of lymphoid neoplasms: a proposal from the International Lymphoma Study Group," Blood 84(5):1361-1392.
Hekman et al., 1991, "Initial experience with treatment of human B cell lymphoma with anti-CD19 monoclonal antibody," Cancer Immunol. Immunother. 32(6):364-372.
Holm et al., 2007, "Functional mapping and single chain construction of the anti-cytokeratin 8 monoclonal antibody TS1," Mol. Immunol. 44:1075-1084.
Jacobsen et al., 1997, "Epidemiology and Estimated Population Burden of Selected Autoimmune Diseases in the United States," Clin Immunol. Immunopathol. 84:223-243.
Janeway et al., 1997, Immunobiology, 3rd Ed., Garland Publishing, Inc. New York, pp. 3:1-3:2.
Jang et al., 1998, "The structural basis for DNA binding by an anti-DNA autoantibody," Mol. Immunol. 35:1207-1217.
Juweid et al., 1995, "Treatment of non-Hodgkin's lymphoma with radiolabeled murine, chimeric, or humanized LL2, an anti-CD22 monoclonal antibody," Cancer Res. 55(23 Suppl):5899s-5907s.

(56) References Cited

OTHER PUBLICATIONS

Kabat et al., 1991, "Sequences of Proteins of Immunological Interest," (U.S. Department of Health and Human Services, Washington, D.C.) 5th ed., pp. xv-xvi.
Kaminski et al., 1993, "Radioimmunotherapy of B-Cell Lymphoma with [131I]Anti-B1 (Anti-CD20) Antibody," N. Eng. J. Med. 329:459-465.
Kantor et al., 1997, "An unbiased analysis of V(H)-D-J(H) sequences from B-la, B-lb, and conventional B cells[1,2]," J. Immunol. 158(3):1175-1186.
Keppler et al., 1999, "Differential sialylation of cell surface glycoconjugates in a human B lymphoma cell line regulates susceptibility for CD95 (APO-1/Fas)-mediated apoptosis and for infection by a lymphotropic virus" Glycobiology 9(6): 557-569.
Khazaeli et al., 1994, "Low V-region immunogenicity of therapeutic doses of 131I-LL2 mouse monoclonal antibody in lymphoma patients," J. Immunother. 16(2):170 (abstract No. 89).
Kobayashi et al., 1999, "Tryptophan H33 plays an important role in pyrimidine (6-4) pyrimidone photoproduct binding by a high-affinity antibody," Protein Engineering 12:879-884.
Kreitman et al., 1993, "Pseudomonas exotoxin-based immunotoxins containing the antibody LL2 or LL2-Fab' induce regression of subcutaneous human B-cell lymphoma in mice," Cancer Res. 53(4):819-825.
Kreitman et al., 1999, "Complete regression of human B-cell lymphoma xenografts in mice treated with recombinant anti-CD22 immunotoxin RFB4(dsFv)-PE38 at doses tolerated by cynomolgus monkeys," Int. J. Cancer, 81:148-155.
Law et al., 1994, "Regulation of lymphocyte activation by the cell-surface molecule CD22," Immunol. Today, 15:442-449.
Law. et al, 1995, "Ig domains 1 and 2 of murine CD22 constitute the ligand-binding domain and bind multiple sialylated ligands expressed on B and T cells," J. Immunol., 155:3368-3376.
Leandro et al., 2002, "Clinical outcome in 22 patients with rheumatoid arthritis treated with B lymphocyte depletion," Ann. Rheum. Dis. 61:883-888.
Leblond et al., 1995, "Lymphoproliferative disorders after organ transplantation: a report of 24 cases observed in a single center," J. Clin. Oncol. 13(4):961-968.
Lederman et al., 1991, "A single amino acid substitution in a common African allele of the CD4 molecule ablates binding of the monoclonal antibody, OKT4," Mol. Immunol. 28(11):1171-1181.
Leonard et al., 1999, "Epratuzumab, a new anti-CD22, humanized, monoclonal antibody, for the therapy of non-Hodgkin's lymphoma (NHL): phase I/II trial results," Blood 94(suppl. 1, part 1): 92a-93a, Abstract No. 404.
Leonard et al., 2003, "Phase I/II trial of epratuzumab (humanized anti-CD22 antibody) in indolent non-Hodgkin's lymphoma," J. Clin. Oncol. 21(16):3051-3059.
Leonard et al., 2004, "Epratuzumab, a humanized anti-CD22 antibody, in aggressive non-Hodgkin's lymphoma: phase I/II clinical trial results," Clin. Cancer Res. 10(16):5327-5334.
Leonard et al., 2005, "Combination antibody therapy with epratuzumab and rituximab in relapsed or refractory non-Hodgkin's lymphoma," J. Clin. Oncol. 23(22):5044-5051.
Leung et al., 1994, "Chimerization of LL2, a rapidly internalizing antibody specific for B cell lymphoma," Hybridoma 13(6):469-476.
Leung et al., 1995, "Construction and characterization of a humanized, internalizing, B-cell (CD22)-specific, leukemia/lymphoma antibody, LL2," Mol. Immunol. 32(17-18):1413-1427.
Li et al., 1980, "beta-Endorphin omission analogs: dissociation of immunoreactivity from other biological activities," Proc. Natl. Acad. Sci. U.S.A. 77(6):3211-3214.
Li et al., 2000, "Three-dimensional structures of the free and antigen-bound Fab from monoclonal antilysozyme antibody HyHEL-63," Biochemistry, . 39:6296-6309.
Lindén et al., 2005, "Dose-fractionated radioimmunotherapy in non-Hodgkin's lymphoma using DOTA-conjugated, 90Y-radiolabeled, humanized anti-CD22 monoclonal antibody, epratuzumab," Clin. Cancer Res. 11(14):5215-5222.
Losman et al., 1997, "Generation of a high-producing clone of a humanized anti-B-cell lymphoma monoclonal antibody (hLL2)," Cancer, 80(12 Suppl):2660-2666.
Maas et al., 1991, "Mechanisms of tumor regression induced by low doses of interleukin-2," In Vivo, 5:637-641.
MacCallum et al., 1996, "Antibody-antigen interactions: contact analysis and binding site topography," J. Mol. Biol. 262:732-745.
Maloney et al., 1994, "Phase I clinical trial using escalating single-dose infusion of chimeric anti-CD20 monoclonal antibody (IDEC-C2B8) in patients with recurrent B-cell lymphoma," Blood 84(8):2457-2466.
Maloney et al., 1997, "IDEC-C2B8 (Rituximab) anti-CD20 monoclonal antibody therapy in patients with relapsed low-grade non-Hodgkin's lymphoma," Blood 90:2188-2195.
Maloney et al., 1997, "IDEC-C2B8: results of a phase I multiple-dose trial in patients with relapsed non-Hodgkin's lymphoma," J. Clin. Oncol. 15:3266-3274.
Martin et al., 2009, "Imaging and Pharmacokinetics of 64Cu-DOTA-HB22.7 Administered by Intravenous, Intraperitoneal, or Subcutaneous Injection to Mice Bearing Non-Hodgkin's Lymphoma Xenografts," Mol. Imaging Biol., 11: 79-87.
May et al., 1986, "Selective killing of normal and neoplastic human B cells with anti-CD19- and anti-CD22-ricin A chain immunotoxins," Cancer Drug Delivery 3(4):261-272.
McLaughlin et al., 1998, "Clinical status and optimal use of rituximab for B-cell lymphomas," Oncology 12:1763-1769.
"Metastasis," Definition on Wikipedia [on-line], Dec. 13, 2010, retrieved from the Internet<http://en.wikipedia.org/wiki/Metastasis>, pp. 1-8.
Morrison et al., "Genetically engineered antibody molecules," Advances in Immunology, vol. 44: 65-92.
Newton et al., 2001, "Potent and Specific Antitumor Effects of an Anti-CD22-targeted Cytotoxic Ribonuclease: Potential for the Treatment of Non-Hodgkin Lymphoma," Blood 97:528-535.
"Non-Hodgkin Lymphoma" Definition on National Cancer Institute at the National Institutes of Health [on-line], Sep. 22, 2011, retrieved from the Internet: <http://.cancer.gov/cancertopics/types/non-hodgkin>, p. 1.
Notice of Opposition to European Patent EP 0 660 721, filed on Jul. 29, 2009 in the European Patent Office.
O'Donnell et al., 2009, "Dose, timing, schedule, and the choice of targeted epitope alter the efficacy of anti-CD22 immunotherapy in mice bearing human lymphoma xenografts," Cancer Immunol. Immunother., 58:2051-2058.
O'Donnell et al., 2009, "Treatment of non-Hodgkin's lymphoma xenografts with the HB22.7 anti-CD22 monoclonal antibody and phosphatase inhibitors improves efficacy," Cancer Immunol. Immunother., 58:1715-1722.
O'Donnell et al., 2009, "Phosphatase inhibition augments anti-CD22-mediated signaling and cytotoxicity in non-hodgkin's lymphoma cells," Leukemia Res., 33:964-969.
Office Action; U.S. Appl. No. 11/715,308, date mailed: Jun. 16, 2008, pp. 1-6.
Office Action; U.S. Appl. No. 11/715,308, date mailed: Nov. 4, 2008, pp. 1-13.
Office Action; U.S. Appl. No. 11/715,308, date mailed: Jun. 24, 2009, pp. 1-8.
Office Action; U.S. Appl. No. 11/715,308, date mailed: Jan. 7, 2010, pp. 1-6.
Notice of Allowability; U.S. Appl. No. 11/715,308, date mailed: Jun. 24, 2010, pp. 1-10.
Office Action, U.S. Appl. No. 10/371,797, date mailed May 3, 2006, pp. 1-9.
Office Action, U.S. Appl. No. 10/371,797, date mailed Oct. 17, 2005, pp. 1-19.
Office Action, U.S. Appl. No. 11/592,750, date mailed Jul. 8, 2009, pp. 1-11.
Office Action, U.S. Appl. No. 11/592,750, date mailed Jan. 14, 2010, pp. 1-15.
Office Action, U.S. Appl. No. 11/592,750, date mailed Sep. 29, 2011, 1-15.
Office Action, U.S. Appl. No. 11/890,743, date mailed Jan. 6, 2010, pp. 1-10.

(56) References Cited

OTHER PUBLICATIONS

Office Action, U.S. Appl. No. 11/890,743, date mailed Aug. 18, 2010, pp. 1-11.
Onrust et al., 1999, "Rituximab," Drugs 58:79-88.
Pezzutto et al., 1987, "Amplification of Human B Cell Activation by a Monoclonal Antibody to the B Cell-Specific Antigen CD22, Bp 130/140," J. Immunol., 138:98-103.
Pezzutto et al., 1988, "Role of the CD22 Human B Cell Antigen in B Cell Triggering by Anti-Immunoglobulin," J. Immunol., 140:1791-1795.
Poe et al., 2004, "CD22 Regulates B lymphocyte function in vivo through both ligand-dependent and ligand-independent mechanisms," Nat. Immunol. 5(10):1078-1087.
Powell et al., 1993, "Natural Ligands of the B Cell Adhesion Molecule CD22β Carry N-Linked Oligosaccharides with α-2, 6-Linked Sialic Acids That Are Required for Recognition," J. Bio. Chem., 268:7019-7027.
Press et al., 2001, "Immunotherapy of Non-Hodgkin's lymphomas," Hematology 221-240.
Qu et al., 2005, "Development of humanized antibodies as cancer therapeutics," Methods 36(1):84-95.
Reff et al., 1994, "Depletion of B cells in vivo by a chimeric mouse human monoclonal antibody to CD20," Blood 83:435-455.
Renner et al., 1997, "Monoclonal antibodies in the treatment of non-Hodgkin's lymphoma: Recent results and future prospects," Leukemia 11(Suppl): S55-S59.
Reply of the Patent Proprietor to the Notice of Opposition of EP 0 600 721 B1, May 11, 2010, pp. 1-25.
Rudikoff et al., 1982, "Single amino acid substitution altering antigen-binding specificity," Proc. Natl. Acad. Sci. U.S.A. 79(6):1979-1983.
Sato et al., 1998, "CD22 negatively and positively regulates signal transduction through the B lymphocyte antigen receptor," Semin Immunol. 10:287-297.
Schriever et al, 1989, "Isolated Human Follicular Dendritic Cells Display a Unique Antigenic Phenotype." J. Exp. Med, 169: 2043-2048.
Score Search Results Details for U.S. Appl. No. 11/592,750, Alignment of MAb 4197X light chain variable region (Accession No. AAR70828) with Seq ID No: 23 of U.S. Appl. No. 11/592,750, Jul. 6, 2009, pp. 1-2.
Sharkey et al., 1994, "Treatment of non-Hodgkin's lymphoma (NHL) with LL2, an anti-CD22 monoclonal antibody," J. Immunother. 16(2):160 (abstract 48).
Silverman et al., 2003, "Rituximab therapy and autoimmune disorders: prospects for anti-B cell therapy," Arthritis & Rheum. 48:1484-1492.
Smith et al., 2003, "Rituximab (monoclonal anti-CD20 antibody): mechanisms of action and resistance," Oncogene 22:7359-7368.
St.Clair & Tedder, 2006, "New prospects for autoimmune disease therapy: B cells on deathwatch." Arthritis and Rheumatism 54(1):1-9.
Stamenkovic et al., 1990, "The B-cell antigen CD22 mediates monocyte and erythrocyte adhesion," Nature, 345:74-79.
Stein et al., 1993, "Epitope Specificity of the anti-(B cell lymphoma) monoclonal antibody LL2," Cancer Immunology and Immunotherapy, 37(5):293-298.
Submission of Opponent in Response to Summons to Oral Proceedings, in Opposition Proceedings Against European Patent No. EP 0660721, Jan. 7, 2011, pp. 1-24.
Submission of Patent Proprietor in Response to Summons to Oral Proceedings, in Opposition Proceedings Against European Patent No. EP 0660721, Jan. 5, 2011, pp. 1-5.
Summons to Attend Oral Proceedings in Opposition Proceedings Against European Patent No. EP 0660721, Sep. 29, 2010, pp. 1-7.
Tedder et al., 1994, "CD20: a regulator of cell-cycle progression of B lymphocytes," Immunol. Today 15:450-454.

Tedder et al., 1997, "CD22, a B lymphocyte-specific adhesion molecule that regulates antigen receptor signaling," Annu. Rev. Immunol. 15:481-504.
Tedder et al., 1997, "The CD19-CD21 Complex Regulates Signal Transduction Thresholds Governing Humoral Immunity and Autoimmunity," Immunity, 6:107-118.
Tedder et al., 2005, "CD22: A multifunctional receptor that regulates B lymphocyte survival and Signal transduction," Adv. Immunol. 88:1-50.
Tedder et al., 2005, "The CD19-CD21 Signal Transduction Complex of B Lymphocytes Regulates the Balance between Health and Autoimmune Disease: Systemic Sclerosis as a Model System," Curr. Dir. Autoimmun., 8:55-90.
Torres et al., 1992, "Identification and characterization of the murine homologue of CD22, a B lymphocyte-restricted adhesion molecule," J. Immunol. 149:2641-2649.
Tumor, Definition on Wikipedia[on-line], Dec. 22, 2010, retrieved from the Internet<http://en.wikipedia.org/wiki/Tumor##>, pages 1-2.
Tuscano et al., 1996, "Engagement of the adhesion receptor CD22 triggers a potent stimulatory signal for B cells and blocking CD22/CD22L interactions impairs T-cell proliferation," Blood, 87(11):4723-4730.
Tuscano et al., 1996, "Involvement of p72syk kinase, p53/561yn kinase and phosphatidyl inositol-3 kinase in signal transduction via the human B lymphocyte antigen CD22," Eur. J. Immunol. 26(6):1246-1252.
Tuscano et al., 1999, "CD22 cross-linking generates B-cell antigen receptor-independent signals that activate the JNK/SAPK signaling cascade," Blood 94(4):1382-1392.
Tuscano et al. 2003, "B lymphocytes contribute to autoimmune disease pathogenesis: current trends and clinical implications," Autoimmunity Rev., 2:101-108.
Tuscano et al., 2003, "Anti-CD22 ligand-blocking antibody HB22.7 has independent lymphomacidal properties and augments the efficacy of $^{90}$Y-DOTA-peptide-Lym-1 in lymphoma xenografts," Blood, 101(9): 3641-3647.
Vajdos et al., 2002, "Comprehensive functional maps of the antigen-binding site of an anti-ErbB2 antibody obtained with shotgun scanning mutagenesis," J. Mol. Biol. 320:415-428.
Van Horssen et al., 1996, "Highly potent CD22-recombinant ricin a results in complete cure of disseminated malignant B-cell xenografts in SCID mice but fails to cure solid xenografts in nude mice," Int. J. Cancer, 68:378-383.
Van Regenmortel, 1996, "Mapping epitope structure and activity: from one-dimensional prediction to four-dimensional description of antigenic specificity," Methods: A Companion to Methods in Enzymology 9(3):465-472.
Vose et al., 1996, "Therapy of refractory non-Hodgkin's lymphoma (NHL) with 1311-LL2 (anti-CD22) radioimmunotherapy (RIT): Results of a repetitive dosing trial," Blood 88(10 suppl. 1, part 1-2): 567A (abstract 2258; 38$^{th}$ Annual Meeting of the American Society of Hematology, Orlando, FL.
Weiner et al., 1999, "Monoclonal antibody therapy of cancer," Semin Oncol. 26:43-51.
Wilson et al., 1991, "cDNA cloning of the B cell membrane protein CD22: a mediator of B-B cell interactions," J. Exp Med., 173:137-146.
Wu et al., 1999, "Humanization of a murine monoclonal antibody by simultaneous optimization of framework and CDR residues," J. Mol. Biol. 294:151-162.
International Search Report, dated Aug. 13, 2008 of International application No. PCT/US2007/05883.
Office Action, dated Jun. 1, 2012 of U.S. Appl. No. 11/592,750.
Roitt et al., 2000, Immunology Illustrated, (original Fifth Edition), Feb. 1, Nankodo Co., Ltd.; p. 71-82.
Written Opinion, dated Aug. 13, 2008 of International application No. PCT/US2007/05883.

(56) References Cited

OTHER PUBLICATIONS

Beiboer et al., 2000, "Guided selection of a pan carcinoma specific antibody reveals similar binding characteristics yet structural divergence between the original murine antibody and its human equivalent," J. Mol. Biol. 296:833-849.

Padlan, 1994, "Anatomy of the antibody molecule," Molecular Immun. 31(3):169-217.

Klimka et al., 2000, "Human anti-CD30 recombinant antibodies by duided phage antibody selection using cell panning," British Journal of Cancer 83:252-260.

Paul, 1993, "Fundamental Immunology," 3$^{rd}$ Edition, 292-295.

Rudikoff et al., 1982, "Single amino acid substitution altering antigen-binding specificity," Proc. Natl. Acad. Sci. USA 79:1979-1983.

* cited by examiner chHB227 VH [SEQ ID NO:1]
AAGCTTGCCGCCACCATGGCTGTCCTGGCATTACTCTTCTGCCTGGTAACATTCCCAAGCTGTATCCTTTCCAGTGCAGCTGGAGGAGTCAGGACCTGAAGGAGTCAGGACCTGGCCTGGTGGCGCCCTCACAGAGCCTGTCCATCACATGCACCGTCT
CAGGGTTCTCATTAAGCGACTATGGTGTAAACTGGGTTCGCCAGATTCCAGGAAAGGGTCTGGAGTGGCTGGGAATAATATGGGGTGATGGAAGGACAGACTATAATTCAGCTCTCAAATCCAGACTGAACATCAGCAAGGACAA
CTCCAAGAGCCAAGTTTTCTTGAAAATGAACAGTCTGCAAAGTCTGAAGACTGAAGTCTGAAGACTACTGTGCCAGAGCCCGTAATGGGGTTATGGAGTACTGGGGTCAAGGAACCTCAGTCACCGTCTCCTCAGCCTCCACCAAG
GGCCC chHB227 VH [SEQ ID NO:2]
1...5...10...15...20...25...30...35ab...40...45...50...abc.55...60...65...70...75...80..abc.
KLAATMAVLALLFCLVTFPSCILSQVQLKESGPGLVAPSQSLSITCTVSGFSLSDYGVN--WVRQIPGKGLEWLGIIW---GDGRTDYNSALKSRLNISKDNSKSQVFLKMNSLK
85...90...95..100abcdefghij..105..110...
ADDTARYYCARAPGNRA--------MEYWGQGTSVTVSSASTKGP...

HB227 VH [SEQ ID NO:5]
CAGGTGCAGCTGCAGGAGTCAGGACCTGGCCTGGTGGCGCCCTCACAGAGCCTGTCCATCACATGCACCGTCTCAGGGTTCTCATTAAGCGACTATGGTGTAAACTGGGTTCGCCAGATTCCAGGAAAGGGTCTGGAGTGGCTGG
GAATAATATGGGGTGATGGAAGGACAGACTATAATTCAGCTCTCAAATCCAGACTGAACATCAGCAAGGACAACTCCAAGAGCCAAGTTTTCTTGAAAATGAACAGTCTGCAAAGTCTGAAGACACAGCCAGTACTATTGTGCCAG
AGCCCCGGTAATGGGGTTATGGAGTACTGGGGTCAAGGAACCTCAGTCACCGTCTCC

HB227 VH [SEQ ID NO:7]
1...5...10...15...20...25...30...35ab...40...45...50...abc.55...60...65...70...75...80..abc.
QVQLKESGPGLVAPSQSLSITCTVSGFSLSDYGVN--WVRQIPGKGLEWLGIIW---GDGRTDYNSALKSRLNISKDNSKSQVFLKMNSLK
85...90...95..100abcdefghij..105..110...
ADDTARYYCARAPGNRA--------MEYWGQGTSVTVS Leader sequences are *italicized*.
CDR sequences are underlined.

FIG. 1B chHB227 VK [SEQ ID NO:3]

AAGCTTGCCGCCACCATGAAGTCACAGAGTCAGGTCTTCGTCTTCCTGTTACTGTGTGTCTCCGGTGCTCATGGGAGTATTGTGATGACCCAGACTCCCAAATTCCTGCTTGTATCAGCAGGAGACAGGATTACCTTAACCTGCA
AGGCCAGTCAGAGTGTGACTAATGATGTAGCTTGGTACCAACAGAAGCCAGGGCAGTCTCCTAAACTGCTGATATACTATGCATCCAATCGCTACACTGGAGTCCCTGATCGCTTCACTGGCAGTGGATATGGGACGGATTTCAC
TTTCACCATCAGCAGTGTGCAGGCTGAAGACCTGGCAGTTTATTTCTGTCAGCAGGATTATAGGTCTCCGGACCGTTCGGTGGAGGCACCAAGCTGGAAATCAAACGTGAGTGGATCC chHB227 VK [SEQ ID NO:4]

1...5...10...15...20...25..ABCDEF.30....5...40...45...50...55...60...65...70...75...80...85...
KLAATMKSQTQVFVFLLLCVSGAHGSIVMTQTPKFLLVSAGDRITLTCKASQ-----SVTNDVAWYQQKPGQSPKLLIYYASNRYTGVPDRFTGSGYGTDFTFTISTVQAEDLAVYFC

90...95ABCDEF..100..105.A.110
QQDYRSP------WTFGGGTKLEIKREWI

HB227 VK [SEQ ID NO:26]

AGTATTGTGATGACCCAGACTCCCAAATTCCTGCTTGTATCAGCAGGAGACAGGATTACCTTAACCTGCAAGGCCAGTCAGAGTGTGACTAATGATGTAGCTTGGTACCAACAGAAGCCAGGGCAGTCTCCTAAACTGCTGATAT
ACTATGCATCCAATCGCTACACTGGAGTCCCTGATCGCTTCACTGGCAGTGGATATGGGACGGATTTCACTTTCACCATCAGCACTGTGCAGGCTGAAGACCTGGCAGTTTATTTCTGTCAGCAGGATTATAGGTCTCCGTGGAC
GTTCGGTGGAGGCACCAAGCTGGAAATCAAA

HB227 VK [SEQ ID NO:27]

1...5...10...15...20...25..ABCDEF.30....5...40...45...50...55...60...65...70...75...80...85...90...95ABCDEF..100..105.A.110
SIVMTQTPKFLLVSAGDRITLTCKASQ-----SVTNDVAWYQQKPGQSPKLLIYYASNRYTGVPDRFTGSGYGTDFTFTISTVQAEDLAVYFCQQDYRSP------WTFGGGTKLEI

Leader sequences are *italicized*.
CDR sequences are underlined.

FIG. 2B

```
Kabat        1...5...10...15...20...25...30...35ab..40...45...50.abc.55...60...65
Canonical             c  cc c         c                                    c  cc
Vernier      v                        vvvv                      vvv
Interface                             *  *                      i ii       i ii
200%VdW      * *                                                * * *
HB227 VH     QVQLKESGPGLVAPSQSLSITCTVSGFSLSDYGVN--NVRQIPGKGLEWLGIIW---GDGRTDYNSALKS
VH46898      ---Q----A--K-T-T-TL----F-----TRQMSVN-I---P---A---D----N-DDTFYSAS--T
                                          CDR1                      CDR2

Kabat        66..70...75...80..abc.85...90...95.100abcdefghij..105..110...
Canonical         c                        c
Vernier      v v v v                       vv                     v
Interface    *    *                        i i i                  i
200%VdW      **** *                        * * *                  *
HB227 VH     RLNISKDNSKSQVFLKMNSLKADDTARYYCARAPGNRA-------NEYWGQGTSVTVSS
VH46898      --S-----T---N-V-R-TNVDPV---T--f----SLYDSDSFYLFY----HA-----V----
                                                  CDR3
```

FIG. 4

Vh46898 VH [SEQ ID NO: 6]
1...5...10...15...20...25...30...35ab...40...45...50..abc..55...60...65...70...75...80..abc..85...90...95..100abcdefghij..105..110...
QVQLQESGPALVKPTQTLILTCTFSGFSLSTRGMSVNWIRQPPGKALEWLARID---WDDDTFYSASLKTRLSISKDTSKNQVVLRMTNVDPVDTATYFCARASLYDSDSFYLFY---HAYWGQGTVTVSS

V2-70 germline VH [SEQ ID NO:8]
CAGGTCACCTTGAAGGAGTCTGGTCCTGCGCTGGTGAAACCCACAGACCCTCACACTGACCTGCACCTTCTCTGGGTTCTCACTCAGCACTAGTGGAATGCGTGTGAGCTGGATCCGTCAGCCCCCAGGAAGGCCCTGG
AGTGGCTTGCACGCATTGATTGGGATGATGATAAATTCTACAGCACATCTCTGAAGACCAGGCTCACCATCTCCAAGGACACCTCCAAAAACCAGGTGGTCCTTACAATGACCAACATGGACCCTGTGGACACAGCCACGTATTA
C
QVTLKESGPALVKPTQTLTLTCTFSGFSLSTSGMRVSWIRQPPGKALEWLARID---WDDDKFYSTSLKTRLISKDTSKNQVVLTMTNVDPMDTATYY

V2-70 VH [SEQ ID NO:9]
1...5...10...15...20...25...30...35ab...40...45...50..abc..55...60...65...70...75...80..abc..85...90.
QVTLKESGPALVKPTQTLTLTCTFSGFSLSTSGMRVSWIRQPPGKALEWLARID---WDDDKFYSTSLKTRLISKDTSKNQVVLTMTNVDPMDTATYY

IC4 VH Genbank X65736 [SEQ ID NO:10]
GGTGCAGCTGCAGGAGTCGGGCCCAGGACTGGTGAAGCCTTCGGAGACCCTGTCCCTCACCTGCACTGTCTCTGGTGGCTCCATCAGTAGTTTCTACTGGAGCTGGATCCGGCAGTCCCCAGGGAAGGGACTGGAGTGGATTG
GGTATATCTATTATACTGGGAGCACCAATTATAACCCCTCCCTCAAGAGTCGAGTCACCATATCAGTAGACACGTCCAAGAACCAGTTCTCCCTGAAGCTGATCTCTGTGACTGCTGCGGACACGGCCGTGTATTACTGTGCGAG
AGATTCTGGAGCGCCCTGGCCCCGAAACTTTGACTACTGGGGCCAGGGAACCCTGGTCACCGTCTCCTCA
QVQLQESGPGLVKPSETLSLTCTVSGGSISSFYWS--WIRQSPGKGLEWIGYIYY--TGSTNYNPSLKSRVTISVDMSKNQFSLKLISLTAADTAVYYCARDSGSAWPR-----NFDYWGQGTLVTVSS

IC4 VH Genbank X65736 [SEQ ID NO:11]
1...5...10...15...20...25...30...35ab...40...45...50..abc..55...60...65...70...75...80..abc..85...90...95..100abcdefghi..105..110...
QVQLQESGPGLVKPSETLSLTCTVSGGSISSFYWS--WIRQSPGKGLEWIGYIYY--TGSTNYNPSLKSRVTISVDMSKNQFSLKLISLTAADTAVYYCARDSGSAWPR-----NFDYWGQGTLVTVSS

HB227-(V2-70+ IC4) [SEQ ID NO:12]
CAGGTCACCTTGAAGGAGTCTGGTCCTGCGCTGGTGAAACCCACAGACCCTCACCTGCACCTTCTCTGGTTCCTCACTCAGCGACTATGGTGTAAACTGGATCCGTCAGCCTCCAGGGAAGGCCCTGAGTGGCTTG
CAATATATGGGGTGATGGAGGACAGACTATAATTCAGTCTCAAATCAGTCTCCAAGGCTCCACCATCTCCAAAAACCAGGTGGTCCTTAGAATGACCAACGTGGACCCTGTGGACACAGCCACGTATTCTCTGCAAG
AGCCCCCGGTATAATAGGCCTATGGGCCAGGGAACCCTGGTCACCGTCTCCTCA
QVTLKESGPALVKPTQTLTLTCTFSGSSLSDYGVN--WIRQPPGKALEWLAIIW---GDGRTDYNSALKSRLTISKDTSKNQVVLTMNVDPMDTATYYCARAPGNRA------MEYWGQGTLVTVSS

HB227-(V2-70 + IC4) [SEQ ID NO:13]
1...5...10...15...20...25...30...35ab...40...45...50..abc..55...60...65...70...75...80..abc..85...90...95..100abcdefghi..105..110...
QVTLKESGPALVKPTQTLTLTCTFSGSSLSDYGVN--WIRQPPGKALEWLAIIW---GDGRTDYNSALKSRLTISKDTSKNQVVLTMNVDPMDTATYYCARAPGNRA------MEYWGQGTLVTVSS CDR sequences are underlined.

FIG. 5B

HB227-VH46898 [SEQ ID NO:14]
CAGGTCCAGTTGCAGGAGTCTGGTCCTGCGCTGGTGAAACCCACAGACCCTCACACTGACCTGCACCTTCTCTGGGTTCTCACTCAGCGACTATGGTGTAAACTGGATCCGTCAGCCCCCAGGAAGGGCCTGAGTGGCTTG
CAATATATGGGGTGATGGACAGACAGATATAATTCAGCTCTCAAATCCAGGCTCAGCATCTCAAGGACACACCTCCAAGAACCTCCAAAAACCAGGTGTCCTTAGAATGACCAACGTGGACCCTGTGGACACAGCCACGTATTTCTGTGCAAG
AGCCCCCGGTAATAGGGCTACTGAGTACTGGGGCCAGGGAACCCTGGTCACCGTCCTCA

HB227-VH46898 [SEQ ID NO:15]
1...5...10...15...20...25...30...35ab...40...45...50.abc.55...60...65...70...75...80.abc.85...90...95.100abcdefghi..105..110...
QVQLQESGPALVKPTQTLTLTCTFSGFSLSDYGVN--WIRQPPGKALEWLAIIW---GDGRTDYNSALKSRLSISKDTSKNQVVLRMTNVDPVDTATYFCARAPGNRAM------EYWGQGTVVTVSS

HB227RHB [SEQ ID NO:16]
ATGGACACACTTTGCTCCACACTGCTCCTGCTCATCCCTTCAGGTCTTGTCCAGGTCCAGTTGCAGGAGTCTGGTCCTGCGCTGGTGAAACCACAGACCCTCACACTGACCTGCACCTTCTCTGGGTTCTCACTCA
GCGACTATGGTGTAAACTGGATCCGTCAGCCGCCAGGGAAGGCCCTGAGCTGCTTGCAATATATGGGTGATGGAAGGACAGACTATAATTCAGCTCTCAAATCCAGGCTCTCAAATCCAGGCTCTCAAATCCAGGACACCTCCAAGGAACCTCCAAAAACCAGGT
GTCCTTAGAATGACCAACGTGGACCCTGTGGACACAGCCACGTATTTCTGTGCAAGAGAGCCCCCGGTAATAGGGCTATGGAGTACTGGGGCCAGGGAACCTGGTCACCGTCACCGTCTCCTCA

HB227RHB [SEQ ID NO:17]
1...5...10...15...20...25...30...35ab...40...45...50.abc.55...60...65...70...75...80.abc.85...90...95.100abc
MDTLCSTLLLLTIPSWVLSQVQLQESGPALVKPTQTLTLTCTFSGFSLSDYGVN--WIRQPPGKALEWLAIIW---GDGRTDYNSALKSRLSISKDTSKNQVLRMTNVDPVDTATYFCARAPGNRAM-- defghi..105..110...
------EYWGQGTVVTVSS

Leader sequences are *italicized*.
CDR sequences are underlined.

FIG. 5D

HB227RHC [SEQ ID NO:18]
ATGGACACACTTTGCTCCTGCTGCTGACCATCCCTTCTGCTGACCTGTCCAGTCCAGTGCAGCTGCAGGAGTCCGGCCTGAGCCAGTCCTGGTGAAACCACAGACCCTCACTCA
GCGACTATGGTGTAAACTGGATCCGTCAGCCCCAGGAAGGCCTGGAGTGGCTTGGAATATATGGGGATGGAAGGACAGACATAATTCAGTCTCAAATCAGGCTCAGACATTCCAAGGACAACTCCAAAAACCAGGT
GGTCCTTAGAATGACCAACGTGGACCCTGTGGACACACTGGAGTACTGGGGCCAGGGAACCGTGGTCACCGTCTCCTCA

1...5...10...15...20...25...30...35ab..40...45...50..abc.55...60...65...70...75...80..abc.85...90...95..100abc
*MDTLCSLLLLTIPSWVLSQVQLQESGPALVKPTQTLTLTCTFSGFSLSDYGVN--WIRQPPGKALEWLG*IIW---GDGRTDYNSALKSRLSISKDNSKNQVVLRMTNVDPVDTATYFCARAPGNRAM--
defghi..105..110...
-----*EYWGQGTVVTVSS*

HB227RHD [SEQ ID NO:19]
ATGGACACACTTTGCTCCACGCTCCTGCTGCTGACAATCCCCTCTGCTGACCTGTCCAGTGCAGCTGCAGGAGTCCGGCCTGAGCCAGTCCTGGTGAAACCACAGACCCTCACTCTGACCTGCACCTTCTCTGGTTCTCACTCA
GCGACTATGGTGAAACTGGATCCGTCAGCCCCCAGGGAAGGCCTGGAGTGGCTTGGAATATATGGGGATGGAAGGACAGACATAATTCAGTCTCAAATCAGGCTCAGACATTCCAAGGACAACTCCAAAAACCAGGT
GGTCCTTAGAATGACCAACGTGGACCCTGTGGACACACTGGAGTACTGGGGCCAGGGAACCGTGGTCACCGTCTCCTCA

1...5...10...15...20...25...30...35ab..40...45...50..abc.55...60...65...70...75...80..abc.85...90...95..100abc
*MDTLCSTLLLLTIPSWVLSQVQLQESGPALVKPTQTLTLTCTFSGFSLSDYGVN--WIRQPPGKALEWLG*IIW---GDGRTDYNSALKSRLSISKDNSKNQVVLRMTNVDPVDTATYFCARAPGNRAM--
defghi..105..110...
-----*EYWGQGTVVTVSS*

HB227RHE [SEQ ID NO:20]
ATGGACACACTTTGCTCCACGCTCCTGCTGCTGACAATCCCCTCTGCTGACCTGTCCAGTGCAGCTGCAGGAGTCCGGCCTGAGCCAGTCCTGGTGAAACCACAGACCCTCACTCTGACCTGCACCTTCTCTGGTTCTCACTCA
GCGACTATGGTGAAACTGGATCCGTCAGCCCCCAGGGAAGGCCTGGAGTGGCTTGGAATATATGGGGATGGAAGGACAGACTATAATTCAGCTCCAAATCAGGCTCAGACATTCCAAGGACACCTCCAAAACCAGGT
GGTCCTTAGAATGACCAACGTGGACCCTGTGGACACACTGGAGTACTGGGGCCAGGGAACCGTGGTCACCGTCTCCTCA

1...5...10...15...20...25...30...35ab..40...45...50..abc.55...60...65...70...75...80..abc.85...90...95..100abc
*MDTLCSTLLLLTIPSWVLSQVQLQESGPALVKPTQTLTLTCTFSGFSLSDYGVN--WIRQPPGKALEWLG*LIW---GDGRTDYNSALKSRLSISKDFSKNQVVLRMTNVDPVDTATYFCARAPGNRAM--
defghi..105..110...
-----*EYWGQGTVVTVSS*

HB227RHE [SEQ ID NO:21]
ATGGACACACTTTGCTCCACGCTCCTGCTGCTGACAATCCCCTCTGCTGACCTGTCCAGTGCAGCTGCAGGAGTCCGGCCTGAGCCAGTCCTGGTGAAACCACAGACCCTCACTCTGACCTGCACCTTCTCTGGTTCTCACTCA
GCGACTATGGTGAAACTGGATCCGTCAGCCCCCAGGGAAGGCCTGGAGTGGCTTGGAATATATGGGGATGGAAGGACAGACTATAATTCAGCTCCAAATCAGGCTCAGACATTCCAAGGACACCTCCAAAACCAGGT
GGTCCTTAGAATGACCAACGTGGACCCTGTGGACACACTGGAGTACTGGGGCCAGGGAACCGTGGTCACCGTCTCCTCA

1...5...10...15...20...25...30...35ab..40...45...50..abc.55...60...65...70...75...80..abc.85...90...95..100abc
*MDTLCSTLLLLTIPSWVLSQVQLQESGPALVKPTQTLTLTCTFSGFSLSDYGVN--WIRQPPGKALEWLA*IIW---GDGRTDYNSALKSRLSISKDFSKNQVVLRMTNVDPVDTATYFCARAPGNRAM--
defghi..105..110...
-----*EYWGQGTVVTVSS*

Leader sequences are *italicized*.
CDR sequences are underlined.

FIG. 5F

HB227RHF [SEQ ID NO:24]

ATGGACACACTTTGCTCCACGCTCCTGCTGCTGACCATCCCTTCATGGGTCTCTGTCCAGGTCCAGTTGCAGGAGTCTGGCCTGGTGAACCACACAGACCCTCACACTGACCTGCACCGTCTCTGGGTTCTCACTCA
GCGACTATGGTGTAAACTGGATCCGTCAGCCTCCAGGGAAGGCCCTGGAGTGGCTTGGAGTGATGGGTGATATGGGTGTCTCAAGAGACAGACTATAATTCAGCTCTCAAATCAGGCTCTCAAATCAGCTCTCAAAACCAGGT
GGTCCTTAGAATGACCAACGTGACCCTGTGACACAGCCACGTATTTCTGTGCAAGAGACCCCCGGTAATAGGGCTATGGAGTATTGGGGCCAGGGAACCGTGGTCACCGTCTCCTCA

HB227RHF [SEQ ID NO:25]

```
       1...5...10...15...20...25...30...35ab...40...45...50..abc.55...60...65...70...75...80..abc.85...90...95..100abc
MDTLCSTLLLLTIPSWVLSQVQLQESGPALVKPTQTLTLTCTVSGFSLSDYGVN--WIRQPPGKALEWLGIIW----GDGRTDYNSALKSRLSISKDNSKNQVLRMTNVDPVDTATYFCARAPGNRAM--
defghi..105..110...
-----EYWGQGTVTVSS
```

Leader sequences are *italicized*.
CDR sequences are underlined.

FIG. 5G

```
                                                                                        c
                          1...5...10...15...20...25..abcdef.30...35...40...45...50...55...60...65
Kabat                                                                                            c
Canonical                 c                        c   c              c        c  cc             v
Vernier                   v v                               vv           vvvv
Interface                                                   i i i        i i
HB227 VK                  SIVMTQTPKFLLVSAGDRITLTCKASQ------SVTNDVAWYQQKPGQSPKLLIYYASNRYTGVPDRFTGS
AJ388641+Clone 47 FW      D------S-SS-SA-V---V-I--Q---     DIS-YLN------KA------D---LE----S---S--
AJ388641                  --Q----SPSS-SA-V---V-I--Q---     DIS-YLN------KA------D---LE----S---S--
                                          CDR1                           CDR2

66..70...75...80...85...90...95abcdef..100..105.a.110
Kabat                                      c              c  cc
Canonical                 c                                           v
Vernier                   v vv v                          i i
Interface
HB227 VK                  GYGTDFTFTISTVQAEDLAVYFCQQDYRSP-----WTFGGGTKLEI
AJ388641+Clone 47 FW      -S------L---SL-P--F-T-Y---YDNL-PWAS  Y------V--  KRT
AJ388641                  -S------------SL-P--I-T-Y---YDNL-PWAS  Y---Q------  KRT
                                              CDR3
```

FIG. 6

AJ388641 VK [SEQ ID NO:28]
GACATCCAGATGACCCAGTCCATCCTGTCTGCATCTGTAGGAGACAGAGTCACCATCACTTGCCAGGCGAGTCAGGACATTAGCAACTATTTAAATTGGTATCAGCAGAAACCAGGGAAAGCCCCTAAGCTCCTGATCT
ACGATGCATCCAATTTGGAAACAGGGGTCCCATCAAGGTTCAGTGGAAGTGGATCTGGGACAGATTTTACTTTCACCATCAGCAGCCTGCAGCCTGAAGATATTGCAACATATTACTGTCAACAGTATGATAATCTCCCTCCGTG
GGCTTCGTACACTTTTGGCCAGGGGACCAAGCTGGAGATCAAACGAACT

AJ388641 VK [SEQ ID NO:29]
1...5...10...15...20...25..ABCDEF.30....5...40....45...50...55...60...65...70...75...80...85...90...95ABCDEF..100..105.A.110
DIQMTQSPSSLSASVGDRVTITCQASQ     DISNYLNWYQQKPGKAPKLLIYDASNLETGVPSRFSGSGSGTDFTFTISSLQPEDIATYYCQQYDNLPPWAS  YTFGQGTKLEI KRT

AJ388641 CDRs with predicted VL Clone 47 framework regions [SEQ ID NO:30]
GACATCGTGATGACCCAGTCTCCATCCTCCCTGTCTGCATCTGTAGGAGACAGAGTCACCATCACTTGCCAGGCGAGTCAGGACATTAGCAACTATTTAAATTGGTATCAGCAGAAACCAGGGAAAGCCCCTAAGCTCCTGATCT
ACGATGCATCCAATTTGGAAACAGGGGTCCCATCAAGGTTCAGTGGAAGTGGATCTGGGACAGATTTGACCATCAGCAGCCTGCAGCCTGAAGATTTTGCAACATATTACTGTCAACAGTATGATAATCTCCCTCCGTG
GGCTTCGTACACTTTTGGCCAGGGGACCAAGGTGGAGATCAAACGAACT

AJ388641 CDRs with predicted VL CLONE 47 framework regions [SEQ ID NO:31]
1...5...10...15...20...25..ABCDEF.30....5...40....45...50...55...60...65...70...75...80...85...90...95ABCDEF..100..105.A.110
DIVMTQSPSSLSASVGDRVTITCQASQ     DISNYLNWYQQKPGKAPKLLIYDASNLETGVPSRFSGSGSGTDFTLTISSLQPEDFATYYCQQYDNLPPWAS  YTFGQGTKVEI KRT

HB227-Clone 47 [SEQ ID NO:32]
GACATCGTGATGACCCAGTCTCCATCCTCCCTGTCTGCATCTGTAGGAGACAGAGTCACCATCACTTGCAAGGCCAGTCAGTGTGACTGTAGCTGGTATCAGCAGAAACCAGGGAAAGCCCCTAAGCTCCTGATCT
ACTATGCATCCAATCGCTACACTGGGGTCCCATCAAGGTTCAGTGGAAGTGGATCTGGGACAGATTTTACTTTGACCATCAGCAGCCTGCAGCCTGAAGATTTTGCAACATATTACTGTCAGCAGGATTATAGGTCTCCGTGGAC
GTTTGGCGGCGGGACCAAGGTGGAGATGAAACGAACT

HB227-Clone 47 [SEQ ID NO:33]
1...5...10...15...20...25..ABCDEF.30....5...40....45...50...55...60...65...70...75...80...85...90...95ABCDEF..100..105.A.110
DIVMTQSPSSLSASVGDRVTITCKASQ-----SVTNDVAWYQQKPGKAPKLLIYYASNRYTGVPSRFSGSGSGTDFTLTISSLQPEDFATYYCQQDYRSP------WTFGGGTKVEI KRT CDR sequences are underlined.

FIG. 7B

HB227 RKA [SEQ ID NO:34]
ATGGACATGAGGGTCCCTGCTCAGCTCCTGGGGCTCCTGCAGCTCTGGCTCTCAGGTGCCAGATGTGACTGTGATGACCCAGTCTCCAGCTTCCCTCTCTGCATCTCCTGTCTGATGACCCAGTCTCCAGCAGCCAGTC
AGAGTGTGACTAATGATGTAGCTTGGTATCAGCAGAAACCAGGGAAAGCCCCTAAGCTCCTGATCTATTACGCATCCAATCGCTACACTGGGGTCCCATCGCGGTTCAGTGGCAGTGGATCTGGGACAGATTTACTTTGACCAT
CAGCAGCCTGAAGATTTTGCAACATATTACTGTCAGCAGGATTATAGGTCTCCGTGGACGTTCGGCCAAGGGACCAAGGTGGAGATCAAACGAACT

1...5...10...15...20...25..ABCDEF.30...5...40...45...50...55...60...65...70...75...80...85...
MDMRVPAQLLGLLLQLWLSGARCDIVMTQSPSSLSASVGDRVTITCKASQ------SVTNDVAWYQQKPGKAPKLLIYYASNRYTGVPSRFSGSGSGTDFTLTISSLQPEDFATYYC

90...95ABCDEF..100...105.A.110
QQDYRSP-----WTFGGGTKVEI KRT

HB227 RKB [SEQ ID NO:35]
ATGGACATGAGGGTCCCTGCTCAGCTCCTGGGGCTCCTGCAGCTCTGGCTCTCAGGTGCCAGATGTGACATCGTGATGACCCAGTCTCCAGCATCCCTGTCTGCATCTGTAGGAGACAGAGTCACCATCACTTGCAAGGCCAGTC
AGAGTGTGACTAATGATGTAGCTTGGTATCAGCAGAAACCAGGGAAAGCCCCTAAGCTCCTGATCTATTATGCATCCAATCGCTACACTGGGGTCCCATCCAATCGGGTCAGTGGTCCATCGGGTGAAGTTCAGTGGCAGTGGATCTGGGACAGATTTCACTTTCACCAT
CAGCAGCCTGCAGCCTGAAGATTTTGCAACATATTTCTGTCAGCAGGATTATAGGTCTCCGTGGACGTTTGGCCAAGGGACCAAGGTGGAGATCAAACGAACT

1...5...10...15...20...25..ABCDEF.30...5...40...45...50...55...60...65...70...75...80...85...
MDMRVPAQLLGLLLQLWLSGARCDIVMTQSPSSLSASVGDRVTITCKASQ------SVTNDVAWYQQKPGKAPKLLIYYASNRYTGVPSRFSGSGSGTDFTLTISSLQPEDFATYFC

90...95ABCDEF..100...105.A.110
QQDYRSP-----WTFGGGTKVEI KRT

HB227 RKC [SEQ ID NO:36]
ATGGACATGAGGGTCCCTGCTCAGCTCCTGGGGCTCCTGCAGCTCTGGCTCTCAGGTGCCAGATGTGACATCGTGATGACCCAGTCTCCATCCTCCCTGTCTGCATCTGTAGGAGACAGAGTCACCATCACTTGCAAGGCCAGTC
AGAGTGTGACTAATGATGTAGCTTGGTATCAGCAGAAACCAGGGAAAGCCCCTAAGCTCCTGATCTATTATGCATCCAATCGCTACACTGGGGTCCCATCAATCGGGTCCATCACTGGGTGATGTCAGTGGCAGTGGATCTGGGACAGATTTCACTCTCACCAT
CAGCAGCCTGCAGCCTGAAGATTTTGCAACATATTACTGTCAGCAGGATTATAGGTCTCCGTGGACGTTCGGCCAAGGGACCAAACGAACT

1...5...10...15...20...25..ABCDEF.30...5...40...45...50...55...60...65...70...75...80...85...
MDMRVPAQLLGLLLQLWLSGARCDIVMTQSPSSLSASVGDRVTITCKASQ------SVTNDVAWYQQKPGKAPKLLIYYASNRYTGVPSRFSGSGSGTDFTLTISSLQPEDFATYFC

90...95ABCDEF..100...105.A.110
QQDYRSP-----WTFGGGTKVEI KRT

HB227 RKC [SEQ ID NO:37]
[similar sequence]

HB227 RKC [SEQ ID NO:38]
[similar sequence]

HB227 RKC [SEQ ID NO:39]
[similar sequence]

Leader sequences are *italicized*.
CDR sequences are underlined.

FIG. 7D

```
              1...5...10...15...20...25...30...35ab..40...45...50..abc.55...60...65
Kabat                               c cc  c                          c  cc
Canonical                         vvvv                             vvv
Vernier                                            i  ii            ii
Interface              v                         *                 ***
200%VdW                **                      ***
HB227 VH        QVQLKESGPGLVAPSQSLSITCTVSGFSLSDYGVN---WVRQIPGKGLEWLGIIW---GDGRTDYNSALKS
AJ556657 VH     ---E---G-V-R-GR--RLS-AA---TFDQ-AIH---I--A------VTV-SP--VGNEQH-AASV-G
                                              CDR1                       CDR2

66..70...75...80..abc.85...90...95..100abcdefghij..105..110...
Kabat                  c                        c                         v
Canonical       v v v v v                      vv                         i
Vernier         *                              iii i                  
Interface       **** *                         ***
200%VdW
HB227 VH        RLNISKDNSKSQVFLKMNSLKADDTARYYCARAPGNRA--------MEYWGQGTSVTVSS
AJ556657 VH     -FTV-RN--NNTLS-Q----TTE--V---GDVTTVTTGY----FD-----VL----
                                                   CDR3
```

FIG. 12

AJ556657 [SEQ ID NO: 40]
CAGGTCAGTTGGAAGAATCTGGGGGAGGCGTGGTCCGCCTGGAGTTCCCTGAGGCTCTCCTGTGCAGCCCTGGATTCACCTTCGATCAGTATGCGATTCACTGGATCCGCCAGGCTCCAGGCAAGGGGCTAGAGTGGGTGA
CAGTTATTCACCTGTCGGCAACGAGCAACATTACGCAGCGTCCGTGAAGGGCCGATTCACCGTCTCCAGAAACAACACTCTCCAAATGAACAGCCTGAGTCTCCAAATGAACAGCCTGAGACTGAGGACACGGCTGTCTATTATTGTGT
GAGGGGGGATGTCGTGACTACGGTTACTTTGATTACTGGGGCCAGGGAGTCCTGGTCACCGTCTCCTCT

AJ556657 [SEQ ID NO: 41]
1...5...10...15...20...25...30...35ab..40...45...50..abc.55...60...65...70...75...80..abc.
QVQLEESGGGVVRPGRSLRLSCAASGFTFDQYAIH--WIRQAPGKGLEWTVISP-VGNEQHYAASVKGRFTVSRNNSNNTLSLQMNSLT 85...90...95..100abcdefghij..105..110...
TEDTAVYYCVRGDVVTVTTGY----FDYWGQGVLVTVS

HB227-AJ556657 [SEQ ID NO: 42]
CAGGTGCAGTTGGAAGAATCTGGGGGAGGCGTGTCCGCGCTGGAGGTCCCTGAGGCTCTCCTGTGCAGCCTGGATTCACCTTCGATGACTATGGTGTAAACTGGATCCGCCAGGCTCCAGGCAAGGGCTAGAGTGGGTGA
CAATAATATGGTGATGAAGGACAGAGACTATATTCAGTCGACTCCAAATCCCGATTCAGTCTCCAAATCCCGAGAAACAACTCCCAACAACAACTGAGTCTCCAAATGAACAGCCTGAGTCTCCTATTATTGTGTGAG
GGCCCCCGGTAATAGGGCTATGGAGTACTGGGGCCAGGGAGTCCTGGTCACCGTCTCCTCT

HB227-AJ556657 [SEQ ID NO: 43]
1...5...10...15...20...25...30...35ab..40...45...50..abc.55...60...65...70...75...80..abc.
QVQLEESGGGVVRPGRSLRLSCAASGFTFDDYGVN--WIRQAPGKGLEWVTIIW---GDGRTDYNSALKSRFTVSRNNSNNTLSLQMNSLT 85...90...95..100abcdefghij..105..110...
TEDTAVYYCVRAPGNRA-------MEYWGQGVLVTVS CDR sequences are underlined.

FIG. 13B

HB227-AJ556657 WITH VH3-30 LEADER [SEQ ID NO:44]
ATGGAGTTTGGGCTGAGCTGGGTTTTCCTCGTGCTGCTTTTAAGAGGTGCCAGTGTGACAGTGTCAGTTGGAAGAATCTGGGGAGGCGTTGGTCCTGGAGCCTCTGAGCCTCTCGAGGCCCTCCGGCTCCAGGCAAGGGCTCCAGGGAAGGGACTGGAAGGACAGACTATTAATTCCCGATTCAGCTCTCAAATCCCAGATTCACCGTCTCCAGAGAAACAACTCCAACACACACT
ATGACTATGGTGTAAACTGACAGCCCTGACAATGGAGCCTGTCTATTATTGTGTGAGGGCTATGGGGGCTAATAGGGCCCCCGGTATACTGGAGTATCGGGGCCAGGAGTCCTGGTCACCGTCTCCTCT
GAGTCTCCAAATGACAGCCTGACAACTGAACAGCCCTGACAACAGCCTGTCTATTATTGTGTGAGGGCTATG

85...90...95..100abcdefghij..105..110...
*MEFGLSWVFLVALLRGVQCQVQLEESGGGVVRPGRSLRLSCAASGFTFDDYGVN--WIRQAPGKGLEWVTIIW---GDGRTDYNSALKSRFTVSRNNSNNTLSLQMNSLT*
TEDTAVYYCVRAPGNRA-------MEYWGQGVLVTVS

HB227-AJ556657 WITH VH3-30 LEADER [SEQ ID NO:45]
1...5...10...15...20...25...30...35ab...40...45...50..abc.55...60...65...70...75...80..abc.
*MEFGLSWVFLVALLRGVQCQVQLEESGGGVVRPGRSLRLSCAASGFTFDDYGVN--WIRQAPGKGLEWVTIIW---GDGRTDYNSALKSRFTVSRNNSNNTLSLQMNSLT*
85...90...95..100abcdefghij..105..110...
TEDTAVYYCVRAPGNRA-------MEYWGQGVLVTVS

HB227RHO - VH3-30 BACKMUTATED [SEQ ID NO:46]
ATGGAGTTTGGGCTGAGCTGGGTTTTCCTCGTTGCTCTTTTAAGAGGTGTCCAGTGTCAGGTGCAGCTGGTGGAGTCTGGGGGAGGCTGGTCCGGCCTGGGAGGTCCCTGAGACTCTCCTGTGCAGCCTCTGGATTCACCTTAA
GCGACTATGGTGAGCTGGGTTTGTCAGTGGGTGGGGAATAATGGGGTGATGGGGTAATAGGGCCCCCGGTAATACTGGAGTATGGAGCCTGCGCGTCGACTGACCGTCCCTGGTCACCGTCTCCTCT
GAGTCTCCAAATGACAGCCTGACAACTGAACAGCCCTGACAACAGCCTGTCTATTATTGTGTGAGGGCTATG

85...90...95..100abcdefghij..105..110...
*MEFGLSWVFLVALLRGVQCQVQLEESGGGVVRPGRSLRLSCAASGFTLSDYGVN--WIRQAPGKGLEWVGIIW---GDGRTDYNSALKSRLTVSRNNSNNTLSLQMNSLT*
TEDTAVYYCVRAPGNRA-------MEYWGQGVLVTVS

HB227RHO - VH3-30 BACKMUTATED [SEQ ID NO:47]
1...5...10...15...20...25...30...35ab...40...45...50..abc.55...60...65...70...75...80..abc.
*MEFGLSWVFLVALLRGVQCQVQLEESGGGVVRPGRSLRLSCAASGFTLSDYGVN--WIRQAPGKGLEWVGIIW---GDGRTDYNSALKSRLTVSRNNSNNTLSLQMNSLT*
85...90...95..100abcdefghij..105..110...
TEDTAVYYCVRAPGNRA-------MEYWGQGVLVTVS

HB227RHOv2 - VH2-50 [SEQ ID NO:48]
ATGGACACACTTTGCTCCACGCTCCTGCTGCTGACCATCCTCATGGCCTCTTGTCCAGGTGCAGCTTGGAAGAATCTGGGGCAGTCAGTGAAGGTCTCCTGCAAGGCTTCTGGATACACCTTTAA
GCGACTATGGTGTAAACTGGGTTCAGCAGCCCCGGCACAAGGCCCTGAGTGGATGGGATGGATTTCTAATTCAGCTGGTAATAATGGGGTGATGGGACAGACTATTATGGGCCCCGGATATCAGACCAGCGATGGAGTATGAGACTCTCCAACTCCAACACACACT
GAGTCTCCAAATGACAGCCTGACAACTGAACAGCCCTGACAAT

85...90...95..100abcdefghij..105..110...
*MDTLCSTLLLLTIPSWVLSQVQLEESGGGVVRPGRSLRLSCAASGFTLSDYGVN--WIRQAPGKGLEWVGIIW---GDGRTDYNSALKSRLTVSRNNSNNTLSLQMNSLT*
TEDTAVYYCVRAPGNRA-------MEYWGQGVLVTVS

HB227RHOv2 - VH2-50 [SEQ ID NO:49]
1...5...10...15...20...25...30...35ab...40...45...50..abc.55...60...65...70...75...80..abc.
*MDTLCSTLLLLTIPSWVLSQVQLEESGGGVVRPGRSLRLSCAASGFTLSDYGVN--WIRQAPGKGLEWVGIIW---GDGRTDYNSALKSRLTVSRNNSNNTLSLQMNSLT*
85...90...95..100abcdefghij..105..110...
TEDTAVYYCVRAPGNRA-------MEYWGQGVLVTVS Leader sequences are *italicized*.
CDR sequences are underlined.

FIG. 13D

HB227RHOv2A - VH2-50 [SEQ ID NO:50]
ATGGACACACTTTGCTCCACGCTCCTGCTCCTGACCATCCCTTCAGTTCTGTCCCAGGTCTTGTCCCAGGTGCAGCTCCTTCGTGAGGCTCTCCTGTGCAGCCTCTGATTCACCTTCA
GCGACTATGGTGTAAACTGGGTGATCCGCCAGCTCCCAGGCAAGGGCCTAGAGTGGGTCGGAATCATATATGGTGATGGAAGGACAGACTATAATTCAGCTCTCAAATCCCGACTCACCGTCTCCAGAAACGTCTCCAGAAACTCCAACAACACT
GAGTCTCCAAATGACAGCCTGACAACTGAGGACGCGGTCTGCTATTATTGTGTGAGACCCCCGTATGGGGCCAGGAGTCCTGGTCACCGTCTCCTCA

85...90...95...100abcdefghij..105..110...
MDTLCSTLLLLTIPSWVLSQVQLEESGGGVVRPGRSLRLSCAASGFTFSDYGVN--WIRQAPGKGLEWVGIIW---GDGRTDYNSALKSRLTVSRNNSNNTLSLQMNSLT
TEDTAVYYCVRAPGNRA-------MEYWGQGVLVTVS

HB227RHOv2B - VH2-50 [SEQ ID NO:51]
ATGGACACACTTTGCTCCACGCTCCTGCTCCTGACCATCCCTTCATGGGTCTTGTCCCAGGTCCAGGTGCAGTTGGAAGAATCTGGGGGAGGCGTGGTCCGGCCTGGAGGGTCCCTGAGACTCTCCTGTGCAGCCTCTGGATTCACCTTAG
ATGATTATGGTGTGAAACTGGGTCCGCCAGGCTCCAGGGAAGGGGTTGGAGTGGGTGGAGATCACAATAATTGGGTGATGGTGTGAGATCCCACAGGACTATAATCAGCTCTCAAATCCCGACTCTCCAAGACTGACCGTCTCCAGAAACAACTCCAACAACACT
GAGTCTCCAAATGACAGCCTGAAAACTGAAGATACTGGGGTCTGCTATTATTGTGTGAGACCCCCGTAATAGGGCTATGAGTACTGGGGCCAGGAGTCCTGGTCACCGTCTCCTCA

85...90...95...100abcdefghij..105..110...
MDTLCSTLLLLTIPSWVLSQVQLEESGGGVVRPGRSLRLSCAASGFTLDDYGVN--WIRQAPGKGLEWVGIIW---GDGRTDYNSALKSRLTVSRNNSNNTLSLQMNSLT
TEDTAVYYCVRAPGNRA-------MEYWGQGVLVTVS

HB227RHOv2B - VH2-50 [SEQ ID NO:52]
ATGGACACACTTTGCTCCACGCTCCTGCTCCTGACCATCCCTTCAGTTCTGTCCCAGGTCCAGGTGCAGTTGGAAGAATCTGGGGGAGGCGTGGTCCGGCCTGGAGGGTCCCTGAGACTCTCCTGTGCAGCCTCTGGATTCACCTTCA
ATGATTATGGTGTAAACTGGGTGATCCGCCAGCTCCCAGGGAAGGGCCTGGAGTGGGTCGGAATCACAATAATTGGGTGATGGTGTGAGATCCCACAGGACTATAATCAGCTCTCAAATCCCGACTCTCCAAGACTGACCGTCTCCAGAAACGTCTCCAACAACACT
GAGTCTCCAAATGACAGCCTGACAACTGAGGACGCGGTCTGCTATTATTGTGTGAGACCCCCGTATGGGGCCAGGAGTCCTGGTCACCGTCTCCTCA

85...90...95...100abcdefghij..105..110...
MDTLCSTLLLLTIPSWVLSQVQLEESGGGVVRPGRSLRLSCAASGFTLDDYGVN--WIRQAPGKGLEWVGIIW---GDGRTDYNSALKSRLTVSRNNSNNTLSLQMNSLT
TEDTAVYYCVRAPGNRA-------MEYWGQGVLVTVS

HB227RHOv2C - VH2-50 [SEQ ID NO:54]
ATGGACACACTTTGCTCCACGCTCCTGCTCCTGACCATCCCTTCAGTTCTGTCCCAGGTCCAGGTGCAGTTGGAAGAATCTGGGGGAGGCGTGGTCCGGCCTGGAGGGTCCCTGAGACTCTCCTGTGCAGCCTCTGGATTCACCTTAA
GCGACTATGGTAAATGGGTGACAATGGGTCCGCCAGGCTCCAGGGAAGGGGTTGGAGTGGGTGACAATAATTGGGTGATGGTGTGAGATACTGGGCCCCGGTAATAGGGCTATGAGTACTGGGGCCAGGAGTCCTGGTCACCGTCTCCAGAAACAACTCCAACAACACT
GAGTCTCCAAATGAACAGCCTGACAACTGAGGACGCGGTCTGCTATTATTGTGTGAGACCCCCGTAATAGGGCTATGAGTACTGGGGCCAGGAGTCCTGGTCACCGTCTCCTCA

85...90...95...100abcdefghij..105..110...
MDTLCSTLLLLTIPSWVLSQVQLEESGGGVVRPGRSLRLSCAASGFTLSDYGVN--WIRQAPGKGLEWVTIW---GDGRTDYNSALKSRLTVSRNNSNNTLSLQMNSLT
TEDTAVYYCVRAPGNRA-------MEYWGQGVLVTVS

HB227RHOv2C - VH2-50 [SEQ ID NO:55]
ATGGACACACTTTGCTCCACGCTCCTGCTCCTGACCATCCCTTCAGTTCTGTCCCAGGTCCAGGTGCAGTTGGAAGAATCTGGGGGAGGCGTGGTCCGGCCTGGAGGGTCCCTGAGACTCTCCTGTGCAGCCTCTGATTCACCTTAA
GCGACTATGGTAAATGGGTGACAATGGGTCCGCCAGGCTCCAGGGAAGGGGTTGGAGTGGGTGACAATAATTGGGTGATGGTGTGAGATACTGGGCCCCGGTAATAGGGCTATGAGTACTGGGGCCAGGAGTCCTGGTCACCGTCTCCAGAAACAACTCCAACAACACT
GAGTCTCCAAATGAACAGCCTGACAACTGAGGACGCGGTCTGCTATTATTGTGTGAGACCCCCGTAATAGGGCTATGAGTACTGGGGCCAGGAGTCCTGGTCACCGTCTCCTCA

85...90...95...100abcdefghij..105..110...
MDTLCSTLLLLTIPSWVLSQVQLEESGGGVVRPGRSLRLSCAASGFTLSDYGVN--WIRQAPGKGLEWVTIW---GDGRTDYNSALKSRLTVSRNNSNNTLSLQMNSLT
TEDTAVYYCVRAPGNRA-------MEYWGQGVLVTVS Leader sequences are *italicized*.
CDR sequences are underlined.

FIG. 13F

HB227RHOv2D - VH2-50 [SEQ ID NO:56]
*ATGGACACACTTTGCTGCTGCTGCTGCTGACCATCCCTTCATGGCTCTTTGTCCTGAGTCAGGTGCAGGTGCAGCTGGTGGAGTCTGGGGGAGGCTTGGTCCAGCCTGGGAGGTCCCTGAGACTCTCCTGTGCAGCCTCTGGATTCACCTTAA
GCGACTATGGTGTAAACTGGATCCGCCAGGCTCCAGGGAAGGGCTAGAGTGGGTGGCAATAATATGGGTAATGGGTAATGGAAGGACAGACTATAATTCAGTCTCAAATCCCAGTCTCACCGTCTCCAGAAACAACTCCAACACAACACT
GAGTCTCCAAATGAACAGCCTGACAACTGAGGACACGGCTGTCTATTATTGTGTGAGAGCCCCGGTAATAGGGCTACTGGAGTACTGGGGCCAAGGGAGTCTGGTCACCGTCTCCTCA*

HB227RHOv2D - VH2-50 [SEQ ID NO:57]
1...5...10...15...20...25...30...35ab...40...45...50..abc.55...60...65...70...75...80..abc.
*MDTLCSTLLLLTIPSWVLSQVQLEESGGGVVRPGRSLRLSCAASGFTLSDYGVN--WIRQAPGKGLEWVGIIW---GDGRTDYNSALKSRFTVSRNNSNNTLSLQMNSLT*
85...90...95..100abcdefghij..105..110...
*TEDTAVYYCVRAPGNRA------MEYWGQGVLVTVS*

HB227RHOv2ACD - VH2-50 [SEQ ID NO:58]
*ATGGACACACTTTGCTGCTGCTGCTGCTGACCATCCCTTCATGGCTCTTTGTCCTGAGTCAGGTGCAGCTGGTGGAGTCTGGGGGAGGCTTGGTCCAGCCTGGGAGGTCCCTGAGACTCTCTGTGCAGCCTCTGGATTCACCTTCA
GCGACTATGGTGTAAACTGGGTCCGCCAGGCTCCAGGGAAGGGGCTAGAGTGGGTGGCAGTCTACAATATATGGGTGATGGAAGGACAGACTATAATTCAGTCTCAAATCCCAGTCTCACCGTCTCCAGAAACAACTCCAACACAACACT
GAGTCTCCAAATGAACAGCCTGACAACTGAGGACACGGCTGTCTATTATTGTGTGAGAGCCCCGGTAATAGGGCTACTGGAGTACTGGGGCCAGGGAGTCTGGTCACCGTCTCCTCA*

HB227RHOv2ACD - VH2-50 [SEQ ID NO:59]
1...5...10...15...20...25...30...35ab...40...45...50..abc.55...60...65...70...75...80..abc.
*MDTLCSTLLLLTIPSWVLSQVQLEESGGGVVRPGRSLRLSCAASGFTFSDYGVN--WIRQAPGKGLEWVTIIW---GDGRTDYNSALKSRFTVSRNNSNNTLSLQMNSLT*
85...90...95..100abcdefghij..105..110...
*TEDTAVYYCVRAPGNRA------MEYWGQGVLVTVS*

HB227RHOv2ABCD - VH2-50 [SEQ ID NO:60]
*ATGGACACACTTTGCTGCTGCTGCTGCTGACCATCCCTTCATGGCTCTTTGTCCTGAGTCAGGTGCAGTTGCAGGTGCAGTTGGTGGAGTCTGGGGGAGGCGTTGGTCCGGCCTGGGAGGTCCCTGAGGCTCTCCTGTGCAGCCTCTGGATTCACCTTCG
ATGACTATGGTGTAAACTGGATCCGCCAGGCTCCAGGGAAGGGGCTAGAGTGGGTCGACAATATATGGGTCGATGGAAGGACAGACTATAATTCAGTCTCAAATCCCAGTCTCACCGTCTCCAGAAACAACTCCAACACAACACT
GAGTCTCCAAATGAACAGCCTGACAACTGAGGACACGGCTGTCTATTATTGTGTGAGAGCCCCGGTAATAGGGCTACTGGAGTACTGGGGCCAGGGAGTCCTGGTCACCGTCTCCTCA*

HB227RHOv2ABCD - VH2-50 [SEQ ID NO:61]
1...5...10...15...20...25...30...35ab...40...45...50..abc.55...60...65...70...75...80..abc.
*MDTLCSTLLLLTIPSWVLSQVQLEESGGGVVRPGRSLRLSCAASGFTFDDYGVN--WIRQAPGKGLEWVTIIW---GDGRTDYNSALKSRFTVSRNNSNNTLSLQMNSLT*
85...90...95..100abcdefghij..105..110...
*TEDTAVYYCVRAPGNRA------MEYWGQGVLVTVS*

Leader sequences are *italicized*.
CDR sequences are underlined.

FIG. 13G

Human VH with lowest FW identity to HB22.7 VH but high
identity at residues 24, 26, 39, 45 and 73

| Human VH clone name | FW Score | VCI Score | VCI residues |
|---|---|---|---|
| Residue Kabat number | | | 02222223334444667779990<br>24678907957897791381345 |
| V/C/I Identity | | | VCCVVVVIIIVVVVCVVIVCV |
| Alternative Canonicals For HB22.7VH | | | -TG------------R----R- |
| | | | A ------------K----K |
| | | | V ------------V----G |
| | | | G ------------I----S |
| | | | S ------------ ----H |
| | | | ------------ ----N |
| | | | ------------ ----T |
| | | | ------------ ----A |
| HB22.7 VH | 86 | 22 | VVGFSLSVQLWLGLIKNVYARW |
| 673 | 51 | 14 | VAGFTFSVQLWVAFIRNLYARW |
| AJ556657 | 50 | 13 | VAGFTFDIQLWVTFVRNLYVRW |
| AJ556703 | 52 | 15 | VGGFTFSVQLWLALIRNLYAKW |
| AJ556712 | 52 | 15 | VGGFTFSVQLWLALIRNLYAKW |
| AJ556713 | 52 | 15 | VGGFTFSVQLWLALIRNLYAKW |
| 25354 | 50 | 13 | VSGFTFNVQLWVSFIRNLYARW |
| AF376954 | 51 | 14 | LAGFPFRVQLWVSVIRNVYH W |
| AF376955 | 51 | 14 | VAGFRFGVQLWVSFIRNLYATW |
| AY052532 | 50 | 13 | GAGFTFSVQLWVSFIRNLYARW |
| M23691 | 50 | 13 | VAGFTFSIQLWVAFIRNLYARW |
| 44977 | 51 | 14 | VAGIPFSVQLWVAFIRNVYARW |
| AB067248 | 53 | 17 | VAGFTFSVQLWISFIRNMFVKW |
| AJ556642 | 51 | 15 | VAGFTFDIQLWVTFIRNLYVRW |
| AJ556644 | 50 | 15 | VAGFTFDIQLWVTFVRNLYVRW |
| 40394 | 50 | 13 | VVGGSFRIQLWIGVIVTFYARW |

FIG. 16A

| Human VH clone name | FW Score | VCI Score | VCI residues |
|---|---|---|---|
| Residue Kabat number | | | 02222223334444667779990<br>24678907957897913813 45 |
| 40570 | 51 | 14 | IVGGPLSIQLWIGVIIMFFARW |
| 40903 | 50 | 13 | VVGGSFNIQLWIGVIVKFYARW |
| AX167737 | 50 | 13 | VVGASLDIQLWIAVIMTLYARW |
| U68224 | 51 | 14 | IVGGPLSIQLWIGVIIMFFARW |
| 117 | 50 | 13 | VGGYSFTVQLWMGVIAKAYARW |
| 165 | 51 | 14 | VGGYTFNVQLWMGVIAKAYARW |
| 602 | 50 | 13 | MAGFNFSVQLWVGFIRDAYTPW |
| 667 | 50 | 13 | VAGFTVSVQLWVSFIRDVYARF |
| 723 | 51 | 14 | VGGFSFTVQLWVGVIAKAYARW |
| 747 | 51 | 14 | VGGFSFTVQLWVGVIAKAYARW |
| 25893 | 50 | 13 | VGGYTFSVQLWMGVIVKAYARW |
| 29976 | 51 | 14 | VGGYSISVQLWLGVIAKAYATW |
| 29979 | 50 | 13 | VGGYSFSVQLWMGVIAKAYAKW |
| 30001 | 50 | 13 | VGGYSFTVQLWMGVIAKAYARW |
| AB063882 | 50 | 13 | VAGYTFTVQLWMGFFLTAYARW |
| AB066958 | 51 | 14 | VAGYSFTVQLWVGFFLTAYARW |
| AB066964 | 51 | 14 | VAGYSFTVQLWVGFFLTAYARW |
| AB067138 | 50 | 13 | VAGGHFTVQLWIGVLITFYARW |
| 38277 | 51 | 14 | VAGFTFKVQLWVSFIRNLYVKW |
| S65761 | 51 | 14 | VAGFTFSVQLWVAFVRDVYTTW |
| 748 | 50 | 14 | EGGYRFTVQLWMGVIVKAYARW |
| 878 | 50 | 14 | IFGFSLSIQLWLALGKTVFAHW |
| 29973 | 50 | 14 | VDGNSFTVQLWMGVIARAFASW |
| 46911 | 51 | 15 | SLGFSLTFQLWLALIRTVYARW |
| AB004303 | 56 | 21 | VAGFTVSVQLWVSFIRILYATW |
| 40569 | 51 | 14 | VVGGSVSSIKLEWVIVTFYARW |
| 32035 | 52 | 15 | LVGGSISGIKLLEVIVTFYASW |
| 44473 | 51 | 14 | LVGGSISGIKLEWVIVTFYARW |
| 329 | 50 | 13 | LVGGSISGIKLEWVIVTIYARW |
| 23961 | 51 | 14 | LVGGSISGIKLEWVIVTFYASW |

FIG. 16B

| Human VH clone name | FW Score | VCI Score | VCI residues |
|---|---|---|---|
| Residue Kabat number | | | 0222223334444667779990<br>2467890795789791381345 |
| AJ555264 | 50 | 13 | LVGGSISGIKLEWVIVTFYARW |
| 25069 | 50 | 13 | VVGGSISSIKLEYVIVTFYARW |
| AJ519242 | 51 | 14 | IAGFTFSVQPWVSFIRDLYVKW |
| AJ556676 | 50 | 13 | LVGGSISGIKLEWVIVTFYARW |
| AJ556683 | 50 | 13 | VVGGSVSTVKLEWVIVTFFASW |
| AJ556687 | 51 | 14 | VVGGSISSVKLEWAIVKFYARW |
| AJ556750 | 50 | 13 | VVGASITSIKLEWVILPFFARW |
| AJ556763 | 50 | 13 | VVGDSVTSIQLEWLIETFYASW |
| AJ556770 | 50 | 13 | VVGDSVTSIQLEWLIETFYASW |
| U80123 | 51 | 14 | VVGGSISSIKLEWVIVTFYARW |
| U80175 | 51 | 14 | VVGGSISSIKLEWVIVTFYARW |
| AJ556768 | 50 | 14 | VVGDSVTSVQLEWLIETFYASW |
| AJ556769 | 50 | 14 | VVGDSVTSIQLEWLIETFYASW |
| U84183 | 50 | 14 | VVGGSISSIKLEWVIVTFYARW |
| X95746 | 50 | 14 | VVGGSISSIKLEWVIVTFYARW |
| Y12437 | 50 | 14 | VVGGSISSIKLEWVIVTFYARW |
| AF376955 | 51 | 14 | VAGFRFGVQLWVSFIRNLYATW |
| 44497 | 50 | 13 | VAGFTFSVQLYISVIRNLYARW |
| AJ555272 | 53 | 16 | IFGFSLSIQLWLALIKTVYAHW |
| 29989 | 51 | 14 | VDGNSFSVQLWMGVIVKAYARW |
| D11016 | 55 | 22 | EAGFTFSVQLWVGFIRDLYTTW |
| 40088 | 52 | 19 | AARFTFRIQLWVSFIRNLYARW |
| 25351 | 50 | 13 | LVVGSISGIKLEWVIVTFFARW |

FIG. 16C

| Acceptor Sequence Name | Humanized Version Name | ACCEPTOR SEQUENCE: |
|---|---|---|
| HB22.7 VH | | QVQLKESGPGLVAPSQSLSITCTVSGFSLSDYGVN--WVRQIPGKGLEWLGIIW---GDGRTDYNSALKSRLNISKDNSKSQVFLKMNSLKADDTARYYCARAPGNRA------MEYWGQGTSVTVS |
| AJ556657 | HB227RHO | QVQLEESGGGVVRPGRSLRLSCAASGFTFDQYAIH--WIRQAPGKGLEWTVISP--VGNEQHYAASVKGRFTVSRNNSNNTLSLQMNSLTTEDTAVYYCVRGDVVTVTTGY-----FDYWGQGVLVTVS |
| AB067248 | HB227RHN | EVQLVESGGGLVQPGGSLRLSCAASGFTFSSHAMG--WVRQAPGKGLEWISGVSR--SGEYTFYEGSVRGRFIISRDNYKNTMSLQMYSLSAADTAIYFCVKYDTDPVM------GSDWGQGTMVTVS |
| AJ556642 | HB227RHM | QVQLEESGGGVVRPGRSLRLSCAASGFTFDQYAIH--WIRQAPGKGLEWTVISP--VGNEQHYAASVKGRFTISRNNSNNTLSLQMNSLTTEDTAVYYCVRGDVVTVTTGY-----FDYWGQGVLVTVS |
| AJ556644 | HB227RHL | QVQLEESGGGVVRPGRSLRLSCAASGFTFDQYAIH--WIRQAPGKGLEWTVISP--VGNEQHYAASVKGRFTVSRNNSNNTLSLQMNSLTTEDTAVYYCVRGDVVTVTTGY-----FDYWGQGVLVTVS |
| AF376954 | HB227RHK | ELQLVESGGGFVQPGGSLRLSCAASGFPFRNYNMH--WVRQGPGKGLVWVSRIVS--DGSSANYADSVKGRVTISRDNAKMVYPQMNSLRAEDTAMYYCHCYGSTESSDYY------EDYWGQGTLVTVS |

FIG. 17

A.  B.

C.  D.

SEQUENCE LISTING

```
<160> NUMBER OF SEQ ID NOS: 202

<210> SEQ ID NO 1
<211> LENGTH: 440
<212> TYPE: DNA
<213> ORGANISM: Artificial Sequence
<220> FEATURE:
<223> OTHER INFORMATION: chHB227 VH

<400> SEQUENCE: 1
aagcttgccg ccaccatggc tgtcctggca ttactcttct gcctggtaac attcccaagc      60
```

```
tgtatccttt cccaggtgca gctgaaggag tcaggacctg gcctggtggc gccctcacag    120
agcctgtcca tcacatgcac cgtctcaggg ttctcattaa gcgactatgg tgtaaactgg    180
gttcgccaga ttccaggaaa gggtctggag tggctgggaa taatatgggg tgatggaagg    240
acagactata attcagctct caaatccaga ctgaacatca gcaaggacaa ctccaagagc    300
caagttttct tgaaaatgaa cagtctgaaa gctgatgaca cagccaggta ctactgtgcc    360
agagcccccg gtaatagggc tatggagtac tggggtcaag aacctcagt caccgtctcc     420 tcagcctcca ccaagggccc                                                 440

<210> SEQ ID NO 2
<211> LENGTH: 147
<212> TYPE: PRT
<213> ORGANISM: Artificial Sequence
<220> FEATURE:
<223> OTHER INFORMATION: chHB227 VH

<400> SEQUENCE: 2

Lys Leu Ala Ala Thr Met Ala Val Leu Ala Leu Leu Phe Cys Leu Val
 1               5                  10                  15

Thr Phe Pro Ser Cys Ile Leu Ser Gln Val Gln Leu Lys Glu Ser Gly
                20                  25                  30

Pro Gly Leu Val Ala Pro Ser Gln Ser Leu Ser Ile Thr Cys Thr Val
            35                  40                  45

Ser Gly Phe Ser Leu Ser Asp Tyr Gly Val Asn Trp Val Arg Gln Ile
        50                  55                  60

Pro Gly Lys Gly Leu Glu Trp Leu Gly Ile Ile Trp Gly Asp Gly Arg
65                  70                  75                  80

Thr Asp Tyr Asn Ser Ala Leu Lys Ser Arg Leu Asn Ile Ser Lys Asp
                85                  90                  95

Asn Ser Lys Ser Gln Val Phe Leu Lys Met Asn Ser Leu Lys Ala Asp
            100                 105                 110

Asp Thr Ala Arg Tyr Tyr Cys Ala Arg Ala Pro Gly Asn Arg Ala Met
        115                 120                 125

Glu Tyr Trp Gly Gln Gly Thr Ser Val Thr Val Ser Ser Ala Ser Thr
    130                 135                 140

Lys Gly Pro
145

<210> SEQ ID NO 3
<211> LENGTH: 409
<212> TYPE: DNA
<213> ORGANISM: Artificial Sequence
<220> FEATURE:
<223> OTHER INFORMATION: chHB227 VK

<400> SEQUENCE: 3
aagcttgccg ccaccatgaa gtcacagacc caggtcttcg tatttctact gctctgtgtg     60
tctggtgctc atgggagtat tgtgatgacc cagactccca aattcctgct tgtatcagca    120
ggagacagga ttaccttaac ctgcaaggcc agtcagagtg tgactaatga tgtagcttgg    180
taccaacaga agccagggca gtctcctaaa ctgctgatat actatgcatc caatcgctac    240
actggagtcc ctgatcgctt cactggcagt ggatatggga cggatttcac tttcaccatc    300
agcactgtgc aggctgaaga cctggcagtt tatttctgtc agcaggatta taggtctccg    360
tggacgttcg gtggaggcac caagctggaa atcaaacgtg agtggatcc                409
```

```
<210> SEQ ID NO 4
<211> LENGTH: 136
<212> TYPE: PRT
<213> ORGANISM: Artificial Sequence
<220> FEATURE:
<223> OTHER INFORMATION: chHB227 VK

<400> SEQUENCE: 4

Lys Leu Ala Ala Thr Met Lys Ser Gln Thr Gln Val Phe Val Phe Leu
 1               5                  10                  15

Leu Leu Cys Val Ser Gly Ala His Gly Ser Ile Val Met Thr Gln Thr
            20                  25                  30

Pro Lys Phe Leu Leu Val Ser Ala Gly Asp Arg Ile Thr Leu Thr Cys
        35                  40                  45

Lys Ala Ser Gln Ser Val Thr Asn Asp Val Ala Trp Tyr Gln Gln Lys
     50                  55                  60

Pro Gly Gln Ser Pro Lys Leu Leu Ile Tyr Tyr Ala Ser Asn Arg Tyr
 65                  70                  75                  80

Thr Gly Val Pro Asp Arg Phe Thr Gly Ser Gly Tyr Gly Thr Asp Phe
                 85                  90                  95

Thr Phe Thr Ile Ser Thr Val Gln Ala Glu Asp Leu Ala Val Tyr Phe
            100                 105                 110

Cys Gln Gln Asp Tyr Arg Ser Pro Trp Thr Phe Gly Gly Gly Thr Lys
        115                 120                 125

Leu Glu Ile Lys Arg Glu Trp Ile
    130                 135

<210> SEQ ID NO 5
<211> LENGTH: 348
<212> TYPE: DNA
<213> ORGANISM: Murine
<220> FEATURE:
<223> OTHER INFORMATION: Mouse HB22.7 VH

<400> SEQUENCE: 5
caggtgcagc tgaaggagtc aggacctggc ctggtggcgc cctcacagag cctgtccatc     60
acatgcaccg tctcagggtt ctcattaagc gactatggtg taaactgggt tcgccagatt    120
ccaggaaagg gtctggagtg gctgggaata atatggggtg atggaaggac agactataat    180
tcagctctca atccagact gaacatcagc aaggacaact ccaagagcca agttttcttg    240
aaaatgaaca gtctgaaagc tgatgacaca gccaggtact actgtgccag agccccggt    300 aatagggcta tggagtactg gggtcaagga acctcagtca ccgtctcc               348

<210> SEQ ID NO 6
<211> LENGTH: 126
<212> TYPE: PRT
<213> ORGANISM: Artificial Sequence
<220> FEATURE:
<223> OTHER INFORMATION: Vh46898 VH

<400> SEQUENCE: 6

Gln Val Gln Leu Gln Glu Ser Gly Pro Ala Leu Val Lys Pro Thr Gln
 1               5                  10                  15

Thr Leu Ile Leu Thr Cys Thr Phe Ser Gly Phe Ser Leu Ser Thr Arg
            20                  25                  30

Gly Met Ser Val Asn Trp Ile Arg Gln Pro Pro Gly Lys Ala Leu Glu
        35                  40                  45

Trp Leu Ala Arg Ile Asp Trp Asp Asp Asp Thr Phe Tyr Ser Ala Ser
     50                  55                  60
```

```
Leu Lys Thr Arg Leu Ser Ile Ser Lys Asp Thr Ser Lys Asn Gln Val
 65                  70                  75                  80

Val Leu Arg Met Thr Asn Val Asp Pro Val Asp Thr Ala Thr Tyr Phe
                 85                  90                  95

Cys Ala Arg Ala Ser Leu Tyr Asp Ser Asp Ser Phe Tyr Leu Phe Tyr
            100                 105                 110

His Ala Tyr Trp Gly Gln Gly Thr Val Val Thr Val Ser Ser
        115                 120                 125

<210> SEQ ID NO 7
<211> LENGTH: 116
<212> TYPE: PRT
<213> ORGANISM: Murine
<220> FEATURE:
<223> OTHER INFORMATION: Mouse HB22.7 VH

<400> SEQUENCE: 7

Gln Val Gln Leu Lys Glu Ser Gly Pro Gly Leu Val Ala Pro Ser Gln
 1               5                  10                  15

Ser Leu Ser Ile Thr Cys Thr Val Ser Gly Phe Ser Leu Ser Asp Tyr
                20                  25                  30

Gly Val Asn Trp Val Arg Gln Ile Pro Gly Lys Gly Leu Glu Trp Leu
            35                  40                  45

Gly Ile Ile Trp Gly Asp Gly Arg Thr Asp Tyr Asn Ser Ala Leu Lys
 50                  55                  60

Ser Arg Leu Asn Ile Ser Lys Asp Asn Ser Lys Ser Gln Val Phe Leu
 65                  70                  75                  80

Lys Met Asn Ser Leu Lys Ala Asp Asp Thr Ala Arg Tyr Tyr Cys Ala
                 85                  90                  95

Arg Ala Pro Gly Asn Arg Ala Met Glu Tyr Trp Gly Gln Gly Thr Ser
            100                 105                 110

Val Thr Val Ser
        115

<210> SEQ ID NO 8
<211> LENGTH: 288
<212> TYPE: DNA
<213> ORGANISM: Artificial Sequence
<220> FEATURE:
<223> OTHER INFORMATION: V2-70 germline VH

<400> SEQUENCE: 8
caggtcacct tgaaggagtc tggtcctgcg ctggtgaaac ccacacagac cctcacactg      60
acctgcacct tctctgggtt ctcactcagc actagtggaa tgcgtgtgag ctggatccgt     120
cagcccccag ggaaggccct ggagtggctt gcacgcattg attgggatga tgataaattc     180
tacagcacat ctctgaagac caggctcacc atctccaagg acacctccaa aaaccaggtg     240
gtccttacaa tgaccaacat ggaccctgtg acacagcca cgtattac                   288

<210> SEQ ID NO 9
<211> LENGTH: 96
<212> TYPE: PRT
<213> ORGANISM: Artificial Sequence
<220> FEATURE:
<223> OTHER INFORMATION: V2-70 VH

<400> SEQUENCE: 9

Gln Val Thr Leu Lys Glu Ser Gly Pro Ala Leu Val Lys Pro Thr Gln
 1               5                  10                  15

Thr Leu Thr Leu Thr Cys Thr Phe Ser Gly Phe Ser Leu Ser Thr Ser
```

-continued

```
                 20                  25                  30
Gly Met Arg Val Ser Trp Ile Arg Gln Pro Gly Lys Ala Leu Glu
             35                  40                  45

Trp Leu Ala Arg Ile Asp Trp Asp Asp Lys Phe Tyr Ser Thr Ser
 50                  55                  60

Leu Lys Thr Arg Leu Thr Ile Ser Lys Asp Thr Ser Lys Asn Gln Val
65                  70                  75                  80

Val Leu Thr Met Thr Asn Val Asp Pro Met Asp Thr Ala Thr Tyr Tyr
                 85                  90                  95
```

<210> SEQ ID NO 10
<211> LENGTH: 360
<212> TYPE: DNA
<213> ORGANISM: Artificial Sequence
<220> FEATURE:
<223> OTHER INFORMATION: IC4 VH Genbank X65736

<400> SEQUENCE: 10

```
caggtgcagc tgcaggagtc gggcccagga ctggtgaagc cttcggagac cctgtccctc      60
acctgcactg tctctggtgg ctccatcagt agtttctact ggagctggat ccggcagtcc     120
ccagggaagg gactggagtg gattgggtat atctattata ctgggagcac caattataac     180
ccctccctca gagtcgagt caccatatca gtagacatgt ccaagaacca gttctccctg      240
aagctgatct ctctgaccgc tgcggacacg gccgtgtatt actgtgcgag agattctggc     300
agcgcctggc ccgaaacttt tgactactgg ggccagggaa ccctggtcac cgtctcctca     360
```

<210> SEQ ID NO 11
<211> LENGTH: 120
<212> TYPE: PRT
<213> ORGANISM: Artificial Sequence
<220> FEATURE:
<223> OTHER INFORMATION: IC4 VH Genbank X65736

<400> SEQUENCE: 11

```
Gln Val Gln Leu Gln Glu Ser Gly Pro Gly Leu Val Lys Pro Ser Glu
 1               5                  10                  15

Thr Leu Ser Leu Thr Cys Thr Val Ser Gly Gly Ser Ile Ser Ser Phe
             20                  25                  30

Tyr Trp Ser Trp Ile Arg Gln Ser Pro Gly Lys Gly Leu Glu Trp Ile
             35                  40                  45

Gly Tyr Ile Tyr Tyr Thr Gly Ser Thr Asn Tyr Asn Pro Ser Leu Lys
 50                  55                  60

Ser Arg Val Thr Ile Ser Val Asp Met Ser Lys Asn Gln Phe Ser Leu
65                  70                  75                  80

Lys Leu Ile Ser Leu Thr Ala Ala Asp Thr Ala Val Tyr Tyr Cys Ala
                 85                  90                  95

Arg Asp Ser Gly Ser Ala Trp Pro Arg Asn Phe Asp Tyr Trp Gly Gln
                100                 105                 110

Gly Thr Leu Val Thr Val Ser Ser
            115                 120
```

<210> SEQ ID NO 12
<211> LENGTH: 351
<212> TYPE: DNA
<213> ORGANISM: Artificial Sequence
<220> FEATURE:
<223> OTHER INFORMATION: HB227-(V2-70+ IC4)

<400> SEQUENCE: 12

```
caggtcacct tgaaggagtc tggtcctgcg ctggtgaaac ccacacagac cctcacactg      60
acctgcacct tctctgggtt ctcactcagc gactatggtg taaactggat ccgtcagccc     120
ccagggaagg ccctggagtg gcttgcaata atatggggtg atggaaggac agactataat     180
tcagctctca atccaggct caccatctcc aaggacacct ccaaaaacca ggtggtcctt      240
agaatgacca acgtggaccc tgtggacaca gccacgtatt tctgtgcaag agcccccggt     300
aatagggcta tggagtactg gggccaggga accgtggtca ccgtctcctc a              351
```

<210> SEQ ID NO 13
<211> LENGTH: 117
<212> TYPE: PRT
<213> ORGANISM: Artificial Sequence
<220> FEATURE:
<223> OTHER INFORMATION: HB227-(V2-70+ IC4)

<400> SEQUENCE: 13

```
Gln Val Thr Leu Lys Glu Ser Gly Pro Ala Leu Val Lys Pro Thr Gln
  1               5                  10                  15

Thr Leu Thr Leu Thr Cys Thr Phe Ser Gly Phe Ser Leu Ser Asp Tyr
             20                  25                  30

Gly Val Asn Trp Ile Arg Gln Pro Pro Gly Lys Ala Leu Glu Trp Leu
         35                  40                  45

Ala Ile Ile Trp Gly Asp Gly Arg Thr Asp Tyr Asn Ser Ala Leu Lys
     50                  55                  60

Ser Arg Leu Thr Ile Ser Lys Asp Thr Ser Lys Asn Gln Val Val Leu
 65                  70                  75                  80

Thr Met Thr Asn Val Asp Pro Met Asp Thr Ala Thr Tyr Tyr Cys Ala
                 85                  90                  95

Arg Ala Pro Gly Asn Arg Ala Met Glu Tyr Trp Gly Gln Gly Thr Leu
            100                 105                 110

Val Thr Val Ser Ser
        115
```

<210> SEQ ID NO 14
<211> LENGTH: 351
<212> TYPE: DNA
<213> ORGANISM: Artificial Sequence
<220> FEATURE:
<223> OTHER INFORMATION: HB227-VH46898

<400> SEQUENCE: 14

```
caggtccagt tgcaggagtc tggtcctgcg ctggtgaaac ccacacagac cctcacactg      60
acctgcacct tctctgggtt ctcactcagc gactatggtg taaactggat ccgtcagccc     120
ccagggaagg ccctggagtg gcttgcaata atatggggtg atggaaggac agactataat     180
tcagctctca atccaggct cagcatctcc aaggacacct ccaaaaacca ggtggtcctt      240
agaatgacca acgtggaccc tgtggacaca gccacgtatt tctgtgcaag agcccccggt     300
aatagggcta tggagtactg gggccaggga accgtggtca ccgtctcctc a              351
```

<210> SEQ ID NO 15
<211> LENGTH: 117
<212> TYPE: PRT
<213> ORGANISM: Artificial Sequence
<220> FEATURE:
<223> OTHER INFORMATION: HB227-VH46898

<400> SEQUENCE: 15

```
Gln Val Gln Leu Gln Glu Ser Gly Pro Ala Leu Val Lys Pro Thr Gln
  1               5                  10                  15
```

```
Thr Leu Thr Leu Thr Cys Thr Phe Ser Gly Phe Ser Leu Ser Asp Tyr
        20                  25                  30

Gly Val Asn Trp Ile Arg Gln Pro Pro Gly Lys Ala Leu Glu Trp Leu
        35                  40                  45

Ala Ile Ile Trp Gly Asp Gly Arg Thr Asp Tyr Asn Ser Ala Leu Lys
50                  55                  60

Ser Arg Leu Ser Ile Ser Lys Asp Thr Ser Lys Asn Gln Val Val Leu
65                  70                  75                  80

Arg Met Thr Asn Val Asp Pro Val Asp Thr Ala Thr Tyr Phe Cys Ala
                85                  90                  95

Arg Ala Pro Gly Asn Arg Ala Met Glu Tyr Trp Gly Gln Gly Thr Val
            100                 105                 110

Val Thr Val Ser Ser
            115
```

<210> SEQ ID NO 16
<211> LENGTH: 408
<212> TYPE: DNA
<213> ORGANISM: Artificial Sequence
<220> FEATURE:
<223> OTHER INFORMATION: HB227RHB

<400> SEQUENCE: 16

```
atggacacac tttgctccac gctcctgctg ctgaccatcc cttcatgggt cttgtcccag      60
gtccagttgc aggagtctgg tcctgcgctg gtgaaaccca cacagaccct cacactgacc     120
tgcaccttct ctgggttctc actcagcgac tatggtgtaa actggatccg tcagcccccca    180 gggaaggccc tggagtggct tgcaataata tggggtgatg gaaggacaga ctataattca     240
gctctcaaat ccaggctcag catctccaag gacacctcca aaaaccaggt ggtccttaga     300
atgaccaacg tggaccctgt ggacacagcc acgtatttct gtgcaagagc ccccggtaat     360
agggctatgg agtactgggg ccagggaacc gtggtcaccg tctcctca                 408
```

<210> SEQ ID NO 17
<211> LENGTH: 136
<212> TYPE: PRT
<213> ORGANISM: Artificial Sequence
<220> FEATURE:
<223> OTHER INFORMATION: HB227RHB

<400> SEQUENCE: 17

```
Met Asp Thr Leu Cys Ser Thr Leu Leu Leu Thr Ile Pro Ser Trp
1               5                   10                  15

Val Leu Ser Gln Val Gln Leu Gln Glu Ser Gly Pro Ala Leu Val Lys
            20                  25                  30

Pro Thr Gln Thr Leu Thr Leu Thr Cys Thr Phe Ser Gly Phe Ser Leu
        35                  40                  45

Ser Asp Tyr Gly Val Asn Trp Ile Arg Gln Pro Pro Gly Lys Ala Leu
    50                  55                  60

Glu Trp Leu Ala Ile Ile Trp Gly Asp Gly Arg Thr Asp Tyr Asn Ser
65                  70                  75                  80

Ala Leu Lys Ser Arg Leu Ser Ile Ser Lys Asp Thr Ser Lys Asn Gln
                85                  90                  95

Val Val Leu Arg Met Thr Asn Val Asp Pro Val Asp Thr Ala Thr Tyr
            100                 105                 110

Phe Cys Ala Arg Ala Pro Gly Asn Arg Ala Met Glu Tyr Trp Gly Gln
        115                 120                 125
```

<210> SEQ ID NO 18
<211> LENGTH: 408
<212> TYPE: DNA
<213> ORGANISM: Artificial Sequence
<220> FEATURE:
<223> OTHER INFORMATION: HB227RHC

<400> SEQUENCE: 18

```
atggacacac tttgctccac gctcctgctg ctgaccatcc cttcatgggt cttgtcccag      60
gtccagttgc aggagtctgg tcctgcgctg gtgaaaccca cacagaccct cacactgacc     120
tgcaccttct ctgggttctc actcagcgac tatggtgtaa actggatccg tcagccccca     180
gggaaggccc tggagtggct tggaataata tgggtgatg aaggacaga ctataattca       240
gctctcaaat ccaggctcag catctccaag acaactcca aaaccaggt ggtccttaga       300
atgaccaacg tggaccctgt ggacacagcc acgtatttct gtgcaagagc ccccggtaat    360
agggctatgg agtactgggg ccagggaacc gtggtcaccg tctcctca                  408
```

<210> SEQ ID NO 19
<211> LENGTH: 136
<212> TYPE: PRT
<213> ORGANISM: Artificial Sequence
<220> FEATURE:
<223> OTHER INFORMATION: HB227RHC

<400> SEQUENCE: 19

```
Met Asp Thr Leu Cys Ser Thr Leu Leu Leu Thr Ile Pro Ser Trp
 1               5                  10                  15

Val Leu Ser Gln Val Gln Leu Gln Glu Ser Gly Pro Ala Leu Val Lys
            20                  25                  30

Pro Thr Gln Thr Leu Thr Leu Thr Cys Thr Phe Ser Gly Phe Ser Leu
        35                  40                  45

Ser Asp Tyr Gly Val Asn Trp Ile Arg Gln Pro Pro Gly Lys Ala Leu
    50                  55                  60

Glu Trp Leu Gly Ile Ile Trp Gly Asp Gly Arg Thr Asp Tyr Asn Ser
65                  70                  75                  80

Ala Leu Lys Ser Arg Leu Ser Ile Ser Lys Asn Ser Lys Asn Gln
                85                  90                  95

Val Val Leu Arg Met Thr Asn Val Asp Pro Val Asp Thr Ala Thr Tyr
            100                 105                 110

Phe Cys Ala Arg Ala Pro Gly Asn Arg Ala Met Glu Tyr Trp Gly Gln
        115                 120                 125

Gly Thr Val Val Thr Val Ser Ser
    130                 135
```

<210> SEQ ID NO 20
<211> LENGTH: 408
<212> TYPE: DNA
<213> ORGANISM: Artificial Sequence
<220> FEATURE:
<223> OTHER INFORMATION: HB227RHD

<400> SEQUENCE: 20

```
atggacacac tttgctccac gctcctgctg ctgaccatcc cttcatgggt cttgtcccag      60
gtccagttgc aggagtctgg tcctgcgctg gtgaaaccca cacagaccct cacactgacc     120
tgcaccttct ctgggttctc actcagcgac tatggtgtaa actggatccg tcagccccca     180
```

-continued

```
gggaaggccc tggagtggct tggaataata tggggtgatg gaaggacaga ctataattca      240
gctctcaaat ccaggctcag catctccaag gacacctcca aaaaccaggt ggtccttaga      300
atgaccaacg tggaccctgt ggacacagcc acgtatttct gtgcaagagc ccccggtaat      360
agggctatgg agtactgggg ccagggaacc gtggtcaccg tctcctca                  408
```

<210> SEQ ID NO 21
<211> LENGTH: 136
<212> TYPE: PRT
<213> ORGANISM: Artificial Sequence
<220> FEATURE:
<223> OTHER INFORMATION: HB227RHD

<400> SEQUENCE: 21

```
Met Asp Thr Leu Cys Ser Thr Leu Leu Leu Thr Ile Pro Ser Trp
 1               5                  10                  15

Val Leu Ser Gln Val Gln Leu Gln Glu Ser Gly Pro Ala Leu Val Lys
                20                  25                  30

Pro Thr Gln Thr Leu Thr Leu Thr Cys Thr Phe Ser Gly Phe Ser Leu
            35                  40                  45

Ser Asp Tyr Gly Val Asn Trp Ile Arg Gln Pro Pro Gly Lys Ala Leu
        50                  55                  60

Glu Trp Leu Gly Ile Ile Trp Gly Asp Gly Arg Thr Asp Tyr Asn Ser
65                  70                  75                  80

Ala Leu Lys Ser Arg Leu Ser Ile Ser Lys Asp Thr Ser Lys Asn Gln
                85                  90                  95

Val Val Leu Arg Met Thr Asn Val Asp Pro Val Asp Thr Ala Thr Tyr
            100                 105                 110

Phe Cys Ala Arg Ala Pro Gly Asn Arg Ala Met Glu Tyr Trp Gly Gln
        115                 120                 125

Gly Thr Val Val Thr Val Ser Ser
    130                 135
```

<210> SEQ ID NO 22
<211> LENGTH: 408
<212> TYPE: DNA
<213> ORGANISM: Artificial Sequence
<220> FEATURE:
<223> OTHER INFORMATION: HB227RHE

<400> SEQUENCE: 22

```
atggacacac tttgctccac gctcctgctg ctgaccatcc cttcatgggt cttgtcccag       60
gtccagttgc aggagtctgg tcctgcgctg gtgaaaccca cacagaccct cacactgacc      120
tgcaccttct ctgggttctc actcagcgac tatggtgtaa actggatccg tcagccccca      180
gggaaggccc tggagtggct tgcaataata tggggtgatg gaaggacaga ctataattca      240
gctctcaaat ccaggctcag catctccaag gacaactcca aaaaccaggt ggtccttaga      300
atgaccaacg tggaccctgt ggacacagcc acgtatttct gtgcaagagc ccccggtaat      360
agggctatgg agtactgggg ccagggaacc gtggtcaccg tctcctca                  408
```

<210> SEQ ID NO 23
<211> LENGTH: 136
<212> TYPE: PRT
<213> ORGANISM: Artificial Sequence
<220> FEATURE:
<223> OTHER INFORMATION: HB227RHE

<400> SEQUENCE: 23

Met Asp Thr Leu Cys Ser Thr Leu Leu Leu Thr Ile Pro Ser Trp

```
                1               5                  10                 15
        Val Leu Ser Gln Val Gln Leu Gln Glu Ser Gly Pro Ala Leu Val Lys
                       20                  25                  30

Pro Thr Gln Thr Leu Thr Leu Thr Cys Thr Phe Ser Gly Phe Ser Leu
                       35                  40                  45

Ser Asp Tyr Gly Val Asn Trp Ile Arg Gln Pro Pro Gly Lys Ala Leu
                       50                  55                  60

Glu Trp Leu Ala Ile Ile Trp Gly Asp Gly Arg Thr Asp Tyr Asn Ser
         65                 70                  75                  80

Ala Leu Lys Ser Arg Leu Ser Ile Ser Lys Asp Asn Ser Lys Asn Gln
                       85                  90                  95

Val Val Leu Arg Met Thr Asn Val Asp Pro Val Asp Thr Ala Thr Tyr
                       100                 105                 110

Phe Cys Ala Arg Ala Pro Gly Asn Arg Ala Met Glu Tyr Trp Gly Gln
                       115                 120                 125

Gly Thr Val Val Thr Val Ser Ser
                       130                 135

<210> SEQ ID NO 24
<211> LENGTH: 408
<212> TYPE: DNA
<213> ORGANISM: Artificial Sequence
<220> FEATURE:
<223> OTHER INFORMATION: HB227RHF

<400> SEQUENCE: 24
atggacacac tttgctccac gctcctgctg ctgaccatcc cttcatgggt cttgtcccag      60
gtccagttgc aggagtctgg tcctgcgctg gtgaaaccca cacagaccct cacactgacc     120
tgcaccgtct ctgggttctc actcagcgac tatggtgtaa actggatccg tcagccccca     180
gggaaggccc tggagtggct tgcaataata tggggtgatg gaaggacaga ctataattca     240
gctctcaaat ccaggctcag catctccaag acaactccaa aaaccaggt ggtccttaga      300 atgaccaacg tggaccctgt ggacacagcc acgtatttct gtgcaagagc ccccggtaat     360
agggctatgg agtactgggg ccagggaacc gtggtcaccg tctcctca                  408

<210> SEQ ID NO 25
<211> LENGTH: 136
<212> TYPE: PRT
<213> ORGANISM: Artificial Sequence
<220> FEATURE:
<223> OTHER INFORMATION: HB227RHF

<400> SEQUENCE: 25

Met Asp Thr Leu Cys Ser Thr Leu Leu Leu Leu Thr Ile Pro Ser Trp
          1               5                  10                 15

Val Leu Ser Gln Val Gln Leu Gln Glu Ser Gly Pro Ala Leu Val Lys
                       20                  25                  30

Pro Thr Gln Thr Leu Thr Leu Thr Cys Thr Val Ser Gly Phe Ser Leu
                       35                  40                  45

Ser Asp Tyr Gly Val Asn Trp Ile Arg Gln Pro Pro Gly Lys Ala Leu
                       50                  55                  60

Glu Trp Leu Gly Ile Ile Trp Gly Asp Gly Arg Thr Asp Tyr Asn Ser
         65                 70                  75                  80

Ala Leu Lys Ser Arg Leu Ser Ile Ser Lys Asp Asn Ser Lys Asn Gln
                       85                  90                  95

Val Val Leu Arg Met Thr Asn Val Asp Pro Val Asp Thr Ala Thr Tyr
                       100                 105                 110
```

```
Phe Cys Ala Arg Ala Pro Gly Asn Arg Ala Met Glu Tyr Trp Gly Gln
        115                 120                 125
Gly Thr Val Val Thr Val Ser Ser
    130                 135

<210> SEQ ID NO 26
<211> LENGTH: 321
<212> TYPE: DNA
<213> ORGANISM: Murine
<220> FEATURE:
<223> OTHER INFORMATION: Mouse HB22.7 VK

<400> SEQUENCE: 26
agtattgtga tgacccagac tcccaaattc ctgcttgtat cagcaggaga caggattacc      60
ttaacctgca aggccagtca gagtgtgact aatgatgtag cttggtacca acagaagcca     120
gggcagtctc ctaaactgct gatatactat gcatccaatc gctacactgg agtccctgat     180
cgcttcactg gcagtggata tgggacggat ttcactttca ccatcagcac tgtgcaggct     240
gaagacctgg cagtttattt ctgtcagcag gattataggt ctccgtggac gttcggtgga     300
ggcaccaagc tggaaatcaa a                                               321

<210> SEQ ID NO 27
<211> LENGTH: 106
<212> TYPE: PRT
<213> ORGANISM: Murine
<220> FEATURE:
<223> OTHER INFORMATION: Mouse HB22.7 VK

<400> SEQUENCE: 27

Ser Ile Val Met Thr Gln Thr Pro Lys Phe Leu Leu Val Ser Ala Gly
  1               5                  10                  15

Asp Arg Ile Thr Leu Thr Cys Lys Ala Ser Gln Ser Val Thr Asn Asp
             20                  25                  30

Val Ala Trp Tyr Gln Gln Lys Pro Gly Gln Ser Pro Lys Leu Leu Ile
         35                  40                  45

Tyr Tyr Ala Ser Asn Arg Tyr Thr Gly Val Pro Asp Arg Phe Thr Gly
     50                  55                  60

Ser Gly Tyr Gly Thr Asp Phe Thr Phe Thr Ile Ser Thr Val Gln Ala
 65                  70                  75                  80

Glu Asp Leu Ala Val Tyr Phe Cys Gln Gln Asp Tyr Arg Ser Pro Trp
                 85                  90                  95

Thr Phe Gly Gly Gly Thr Lys Leu Glu Ile
            100                 105

<210> SEQ ID NO 28
<211> LENGTH: 339
<212> TYPE: DNA
<213> ORGANISM: Artificial Sequence
<220> FEATURE:
<223> OTHER INFORMATION: AJ388641 VK (Human)

<400> SEQUENCE: 28
gacatccaga tgacccagtc tccatcctcc ctgtctgcat ctgtaggaga cagagtcacc      60
atcacttgcc aggcgagtca ggacattagc aactatttaa attggtatca gcagaaacca     120
gggaaagccc ctaagctcct gatctacgat gcatccaatt ggaaacaggg gtcccatca      180 aggttcagtg gaagtggatc tgggacagat tttactttca ccatcagcag cctgcagcct     240
gaagatattg caacatatta ctgtcaacag tatgataatc tccctccgtg gcttcgtac      300
```

```
actttttggcc aggggaccaa gctggagatc aaacgaact                        339
```

<210> SEQ ID NO 29
<211> LENGTH: 113
<212> TYPE: PRT
<213> ORGANISM: Artificial sequence
<220> FEATURE:
<223> OTHER INFORMATION: AJ388641 VK (Human)

<400> SEQUENCE: 29

```
Asp Ile Gln Met Thr Gln Ser Pro Ser Ser Leu Ser Ala Ser Val Gly
  1               5                  10                  15

Asp Arg Val Thr Ile Thr Cys Gln Ala Ser Gln Asp Ile Ser Asn Tyr
             20                  25                  30

Leu Asn Trp Tyr Gln Gln Lys Pro Gly Lys Ala Pro Lys Leu Leu Ile
         35                  40                  45

Tyr Asp Ala Ser Asn Leu Glu Thr Gly Val Pro Ser Arg Phe Ser Gly
     50                  55                  60

Ser Gly Ser Gly Thr Asp Phe Thr Phe Thr Ile Ser Ser Leu Gln Pro
 65                  70                  75                  80

Glu Asp Ile Ala Thr Tyr Tyr Cys Gln Gln Tyr Asp Asn Leu Pro Pro
                 85                  90                  95

Trp Ala Ser Tyr Thr Phe Gly Gln Gly Thr Lys Leu Glu Ile Lys Arg
            100                 105                 110

Thr
```

<210> SEQ ID NO 30
<211> LENGTH: 339
<212> TYPE: DNA
<213> ORGANISM: Artificial Sequence
<220> FEATURE:
<223> OTHER INFORMATION: AJ388641 CDRs with predicted VL Clone 47
      framework regions

<400> SEQUENCE: 30

```
gacatcgtga tgacccagtc tccatcctcc ctgtctgcat ctgtaggaga cagagtcacc      60
atcacttgcc aggcgagtca ggacattagc aactatttaa attggtatca gcagaaacca     120
gggaaagccc ctaagctcct gatctacgat gcatccaatt tggaaacagg ggtcccatca     180
aggttcagtg gaagtggatc tgggacagat tttactttga ccatcagcag cctgcagcct     240
gaagattttg caacatatta ctgtcaacag tatgataatc tccctccgtg ggcttcgtac     300
actttttggcg gcgggaccaa ggtggagatc aaacgaact                           339
```

<210> SEQ ID NO 31
<211> LENGTH: 113
<212> TYPE: PRT
<213> ORGANISM: Artificial Sequence
<220> FEATURE:
<223> OTHER INFORMATION: AJ388641 CDRs with predicted VL Clone 47
      framework regions

<400> SEQUENCE: 31

```
Asp Ile Val Met Thr Gln Ser Pro Ser Ser Leu Ser Ala Ser Val Gly
  1               5                  10                  15

Asp Arg Val Thr Ile Thr Cys Gln Ala Ser Gln Asp Ile Ser Asn Tyr
             20                  25                  30

Leu Asn Trp Tyr Gln Gln Lys Pro Gly Lys Ala Pro Lys Leu Leu Ile
         35                  40                  45

Tyr Asp Ala Ser Asn Leu Glu Thr Gly Val Pro Ser Arg Phe Ser Gly
     50                  55                  60
```

```
Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Asp Asn Leu Pro Pro
                 85                  90                  95

Trp Ala Ser Tyr Thr Phe Gly Gly Gly Thr Lys Val Glu Ile Lys Arg
            100                 105                 110

Thr

<210> SEQ ID NO 32
<211> LENGTH: 327
<212> TYPE: DNA
<213> ORGANISM: Artificial Sequence
<220> FEATURE:
<223> OTHER INFORMATION: HB227-Clone 47 (VK)

<400> SEQUENCE: 32
gacatcgtga tgacccagtc tccatcctcc ctgtctgcat ctgtaggaga cagagtcacc     60
atcacttgca aggccagtca gagtgtgact aatgatgtag cttggtatca gcagaaacca    120
gggaaagccc ctaagctcct gatctactat gcatccaatc gctacactgg ggtcccatca    180
aggttcagtg gaagtggatc tgggacagat tttactttga ccatcagcag cctgcagcct    240
gaagattttg caacatatta ctgtcagcag gattataggt ctccgtggac gtttggcggc    300
gggaccaagg tggagatcaa acgaact                                        327

<210> SEQ ID NO 33
<211> LENGTH: 109
<212> TYPE: PRT
<213> ORGANISM: Artificial Sequence
<220> FEATURE:
<223> OTHER INFORMATION: HB227-Clone 47 (VK)

<400> SEQUENCE: 33

Asp Ile Val Met Thr Gln Ser Pro Ser Ser Leu Ser Ala Ser Val Gly
  1               5                  10                  15

Asp Arg Val Thr Ile Thr Cys Lys Ala Ser Gln Ser Val Thr Asn Asp
                 20                  25                  30

Val Ala Trp Tyr Gln Gln Lys Pro Gly Lys Ala Pro Lys Leu Leu Ile
             35                  40                  45

Tyr Tyr Ala Ser Asn Arg Tyr Thr Gly Val Pro Ser Arg Phe Ser Gly
         50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Asp Tyr Arg Ser Pro Trp
                 85                  90                  95

Thr Phe Gly Gly Gly Thr Lys Val Glu Ile Lys Arg Thr
            100                 105

<210> SEQ ID NO 34
<211> LENGTH: 393
<212> TYPE: DNA
<213> ORGANISM: Artificial Sequence
<220> FEATURE:
<223> OTHER INFORMATION: HB227 RKA

<400> SEQUENCE: 34
atggacatga gggtccctgc tcagctcctg gggctcctgc agctctggct ctcaggtgcc     60
agatgtgaca tcgtgatgac ccagtctcca tcctccctgt ctgcatctgt aggagacaga    120
gtcaccatca cttgcaaggc cagtcagagt gtgactaatg atgtagcttg gtatcagcag    180
```

```
aaaccaggga agcccctaa gctcctgatc tactatgcat ccaatcgcta cactggggtc      240
ccatcaaggt tcagtggaag tggatctggg acagatttta ctttgaccat cagcagcctg      300
cagcctgaag attttgcaac atattactgt cagcaggatt ataggtctcc gtggacgttt      360
ggcggcggga ccaaggtgga gatcaaacga act                                   393
```

<210> SEQ ID NO 35
<211> LENGTH: 110
<212> TYPE: PRT
<213> ORGANISM: Artificial Sequence
<220> FEATURE:
<223> OTHER INFORMATION: HB227 RKA

<400> SEQUENCE: 35

```
Met Asp Met Arg Val Pro Ala Gln Leu Leu Gly Leu Leu Gln Leu Trp
  1               5                  10                  15

Leu Ser Gly Ala Arg Cys Asp Ile Val Met Thr Gln Ser Pro Ser Ser
             20                  25                  30

Leu Ser Ala Ser Val Gly Asp Arg Val Thr Ile Thr Cys Lys Ala Ser
         35                  40                  45

Gln Ser Val Thr Asn Asp Val Ala Trp Tyr Gln Gln Lys Pro Gly Lys
     50                  55                  60

Ala Pro Lys Leu Leu Ile Tyr Tyr Ala Ser Asn Arg Tyr Thr Gly Val
 65                  70                  75                  80

Pro Ser Arg Phe Ser Gly Ser Gly Ser Gly Thr Asp Phe Thr Leu Thr
                 85                  90                  95

Ile Ser Ser Leu Gln Pro Glu Asp Phe Ala Thr Tyr Tyr Cys
            100                 105                 110
```

<210> SEQ ID NO 36
<211> LENGTH: 393
<212> TYPE: DNA
<213> ORGANISM: Artificial Sequence
<220> FEATURE:
<223> OTHER INFORMATION: HB227 RKB

<400> SEQUENCE: 36

```
atggacatga gggtccctgc tcagctcctg gggctcctgc agctctggct ctcaggtgcc      60
agatgtgaca tcgtgatgac ccagtctcca tcctccctgt ctgcatctgt aggagacaga     120
gtcaccatca cttgcaaggc cagtcagagt gtgactaatg atgtagcttg gtatcagcag     180
aaaccaggga agcccctaa gctcctgatc tactatgcat ccaatcgcta cactggggtc     240
ccatcaaggt tcagtggaag tggatctggg acagatttta ctttgaccat cagcagcctg     300
cagcctgaag attttgcaac atatttctgt cagcaggatt ataggtctcc gtggacgttt     360
ggcggcggga ccaaggtgga gatcaaacga act                                   393
```

<210> SEQ ID NO 37
<211> LENGTH: 131
<212> TYPE: PRT
<213> ORGANISM: Artificial Sequence
<220> FEATURE:
<223> OTHER INFORMATION: HB227 RKB

<400> SEQUENCE: 37

```
Met Asp Met Arg Val Pro Ala Gln Leu Leu Gly Leu Leu Gln Leu Trp
  1               5                  10                  15

Leu Ser Gly Ala Arg Cys Asp Ile Val Met Thr Gln Ser Pro Ser Ser
             20                  25                  30
```

```
Leu Ser Ala Ser Val Gly Asp Arg Val Thr Ile Thr Cys Lys Ala Ser
        35                  40                  45

Gln Ser Val Thr Asn Asp Val Ala Trp Tyr Gln Gln Lys Pro Gly Lys
 50                  55                  60

Ala Pro Lys Leu Leu Ile Tyr Tyr Ala Ser Asn Arg Tyr Thr Gly Val
 65                  70                  75                  80

Pro Ser Arg Phe Ser Gly Ser Gly Ser Gly Thr Asp Phe Thr Leu Thr
                85                  90                  95

Ile Ser Ser Leu Gln Pro Glu Asp Phe Ala Thr Tyr Phe Cys Gln Gln
               100                 105                 110

Asp Tyr Arg Ser Pro Trp Thr Phe Gly Gly Gly Thr Lys Val Glu Ile
           115                  120                 125

Lys Arg Thr
   130
```

<210> SEQ ID NO 38
<211> LENGTH: 393
<212> TYPE: DNA
<213> ORGANISM: Artificial Sequence
<220> FEATURE:
<223> OTHER INFORMATION: HB227 RKC

<400> SEQUENCE: 38

```
atggacatga gggtcccctgc tcagctcctg gggctcctgc agctctggct ctcaggtgcc    60
agatgtgaca tcgtgatgac ccagtctcca tcctccctgt ctgcatctgt aggagacaga   120
gtcaccatca cttgcaaggc cagtcagagt gtgactaatg atgtagcttg gtatcagcag   180
aaaccaggga agcccctaa gctcctgatc tactatgcat ccaatcgcta cactggggtc    240
ccagaaaggt tcagtggaag tggatatggg acagatttta ctttgaccat cagcagcctg   300
cagcctgaag attttgcaac atatttctgt cagcaggatt ataggtctcc gtggacgttt   360
ggcggcggga ccaaggtgga gatcaaacga act                                393
```

<210> SEQ ID NO 39
<211> LENGTH: 131
<212> TYPE: PRT
<213> ORGANISM: Artificial Sequence
<220> FEATURE:
<223> OTHER INFORMATION: HB227 RKC

<400> SEQUENCE: 39

```
Met Asp Met Arg Val Pro Ala Gln Leu Leu Gly Leu Leu Gln Leu Trp
 1               5                  10                  15

Leu Ser Gly Ala Arg Cys Asp Ile Val Met Thr Gln Ser Pro Ser Ser
            20                  25                  30

Leu Ser Ala Ser Val Gly Asp Arg Val Thr Ile Thr Cys Lys Ala Ser
        35                  40                  45

Gln Ser Val Thr Asn Asp Val Ala Trp Tyr Gln Gln Lys Pro Gly Lys
 50                  55                  60

Ala Pro Lys Leu Leu Ile Tyr Tyr Ala Ser Asn Arg Tyr Thr Gly Val
 65                  70                  75                  80

Pro Asp Arg Phe Ser Gly Ser Gly Tyr Gly Thr Asp Phe Thr Leu Thr
                85                  90                  95

Ile Ser Ser Leu Gln Pro Glu Asp Phe Ala Thr Tyr Phe Cys Gln Gln
               100                 105                 110

Asp Tyr Arg Ser Pro Trp Thr Phe Gly Gly Gly Thr Lys Val Glu Ile
           115                  120                 125

Lys Arg Thr
```

-continued

<210> SEQ ID NO 40
<211> LENGTH: 369
<212> TYPE: DNA
<213> ORGANISM: Artificial Sequence
<220> FEATURE:
<223> OTHER INFORMATION: AJ556657

<400> SEQUENCE: 40

```
caggtgcagt tggaagaatc tgggggaggc gtggtccggc ctgggaggtc cctgaggctc    60
tcctgtgcag cctctggatt caccttcgat cagtatgcga ttcactggat ccgccaggct   120
ccaggcaagg ggctagagtg ggtgacagtt atttcacctg tcggcaacga gcaacattac   180
gcagcgtccg tgaaggggcg attcaccgtc tccagaaaca actccaacaa cacactgagt   240
ctccaaatga acagcctgac aactgaggac acggctgtct attattgtgt gagggggggat   300
gtcgtgacta cggtgactac gggttacttt gattactggg gccagggagt cctggtcacc   360
gtctcctct                                                           369
```

<210> SEQ ID NO 41
<211> LENGTH: 122
<212> TYPE: PRT
<213> ORGANISM: Artificial Sequence
<220> FEATURE:
<223> OTHER INFORMATION: AJ556657

<400> SEQUENCE: 41

```
Gln Val Gln Leu Glu Glu Ser Gly Gly Gly Val Val Arg Pro Gly Arg
  1               5                  10                  15

Ser Leu Arg Leu Ser Cys Ala Ala Ser Gly Phe Thr Phe Asp Gln Tyr
             20                  25                  30

Ala Ile His Trp Ile Arg Gln Ala Pro Gly Lys Gly Leu Glu Trp Val
         35                  40                  45

Thr Val Ile Ser Pro Val Gly Asn Glu Gln His Tyr Ala Ala Ser Val
     50                  55                  60

Lys Gly Arg Phe Thr Val Ser Arg Asn Asn Ser Asn Asn Thr Leu Ser
 65                  70                  75                  80

Leu Gln Met Asn Ser Leu Thr Thr Glu Asp Thr Ala Val Tyr Tyr Cys
                 85                  90                  95

Val Arg Gly Asp Val Val Thr Thr Val Thr Thr Gly Tyr Phe Asp Tyr
            100                 105                 110

Trp Gly Gln Gly Val Leu Val Thr Val Ser
        115                 120
```

<210> SEQ ID NO 42
<211> LENGTH: 351
<212> TYPE: DNA
<213> ORGANISM: Artificial Sequence
<220> FEATURE:
<223> OTHER INFORMATION: HB227-AJ556657

<400> SEQUENCE: 42

```
caggtgcagt tggaagaatc tgggggaggc gtggtccggc ctgggaggtc cctgaggctc    60
tcctgtgcag cctctggatt caccttcgat gactatggtg taaactggat ccgccaggct   120
ccaggcaagg ggctagagtg ggtgacaata tatgggggtg atggaaggac agactataat   180
tcagctctca atcccgatt caccgtctcc agaaacaact ccaacaacac actgagtctc   240
caaatgaaca gcctgacaac tgaggacacg gctgtctatt attgtgtgag ggccccggt   300
```

```
aatagggcta tggagtactg gggccaggga gtcctggtca ccgtctcctc t            351
```

<210> SEQ ID NO 43
<211> LENGTH: 116
<212> TYPE: PRT
<213> ORGANISM: Artificial Sequence
<220> FEATURE:
<223> OTHER INFORMATION: HB227-AJ556657

<400> SEQUENCE: 43

```
Gln Val Gln Leu Glu Glu Ser Gly Gly Gly Val Val Arg Pro Gly Arg
  1               5                  10                  15

Ser Leu Arg Leu Ser Cys Ala Ala Ser Gly Phe Thr Phe Asp Asp Tyr
             20                  25                  30

Gly Val Asn Trp Ile Arg Gln Ala Pro Gly Lys Gly Leu Glu Trp Val
         35                  40                  45

Thr Ile Ile Trp Gly Asp Gly Arg Thr Asp Tyr Asn Ser Ala Leu Lys
     50                  55                  60

Ser Arg Phe Thr Val Ser Arg Asn Asn Ser Asn Thr Leu Ser Leu
 65                  70                  75                  80

Gln Met Asn Ser Leu Thr Thr Glu Asp Thr Ala Val Tyr Tyr Cys Val
                 85                  90                  95

Arg Ala Pro Gly Asn Arg Ala Met Glu Tyr Trp Gly Gln Gly Val Leu
            100                 105                 110

Val Thr Val Ser
        115
```

<210> SEQ ID NO 44
<211> LENGTH: 408
<212> TYPE: DNA
<213> ORGANISM: Artificial Sequence
<220> FEATURE:
<223> OTHER INFORMATION: HB227-AJ556657 WITH VH3-30 LEADER

<400> SEQUENCE: 44

```
atggagtttg ggctgagctg ggttttcctc gttgctcttt taagaggtgt ccagtgtcag    60
gtgcagttgg aagaatctgg ggaggcgtg gtccggcctg ggaggtccct gaggctctcc    120
tgtgcagcct ctggattcac cttcgatgac tatggtgtaa actggatccg ccaggctcca    180 ggcaagggc tagagtgggt gacaataata tggggtgatg gaaggacaga ctataattca    240
gctctcaaat cccgattcac cgtctccaga aacaactcca acaacacact gagtctccaa    300
atgaacagcc tgacaactga ggacacggct gtctattatt gtgtgaggc ccccggtaat    360 agggctatgg agtactgggg ccagggagtc ctggtcaccg tctcctct              408
```

<210> SEQ ID NO 45
<211> LENGTH: 135
<212> TYPE: PRT
<213> ORGANISM: Artificial Sequence
<220> FEATURE:
<223> OTHER INFORMATION: HB227-AJ556657 WITH VH3-30 LEADER

<400> SEQUENCE: 45

```
Met Glu Phe Gly Leu Ser Trp Val Phe Leu Val Ala Leu Leu Arg Gly
  1               5                  10                  15

Val Gln Cys Gln Val Gln Leu Glu Glu Ser Gly Gly Gly Val Val Arg
             20                  25                  30

Pro Gly Arg Ser Leu Arg Leu Ser Cys Ala Ala Ser Gly Phe Thr Phe
         35                  40                  45

Asp Asp Tyr Gly Val Asn Trp Ile Arg Gln Ala Pro Gly Lys Gly Leu
```

```
                50                  55                  60
Glu Trp Val Thr Ile Ile Trp Gly Asp Gly Arg Thr Asp Tyr Asn Ser
 65                  70                  75                  80

Ala Leu Lys Ser Arg Phe Thr Val Ser Arg Asn Asn Ser Asn Asn Thr
                 85                  90                  95

Leu Ser Leu Gln Met Asn Ser Leu Thr Thr Glu Asp Thr Ala Val Tyr
                100                 105                 110

Tyr Cys Val Arg Ala Pro Gly Asn Arg Ala Met Glu Tyr Trp Gly Gln
            115                 120                 125

Gly Val Leu Val Thr Val Ser
        130                 135

<210> SEQ ID NO 46
<211> LENGTH: 408
<212> TYPE: DNA
<213> ORGANISM: Artificial Sequence
<220> FEATURE:
<223> OTHER INFORMATION: HB227RHO - VH3-30 Backmutated

<400> SEQUENCE: 46
atggagtttg ggctgagctg ggttttcctc gttgctcttt taagaggtgt ccagtgtcag      60
gtgcagttgg aagaatctgg gggaggcgtg gtccggcctg ggaggtccct gaggctctcc     120
tgtgcagcct ctggattcac cttaagcgac tatggtgtaa actggatccg ccaggctcca     180
ggcaaggggc tagagtgggt gggaataata tggggtgatg gaaggacaga ctataattca     240
gctctcaaat cccgactgac cgtctccaga aacaactcca acaacacact gagtctccaa     300
atgaacagcc tgacaactga ggacacggct gtctattatt gtgtgagggc ccccggtaat     360
agggctatgg agtactgggg ccagggagtc ctggtcaccg tctcctct                  408

<210> SEQ ID NO 47
<211> LENGTH: 135
<212> TYPE: PRT
<213> ORGANISM: Artificial Sequence
<220> FEATURE:
<223> OTHER INFORMATION: HB227RHO - VH3-30 Backmutated

<400> SEQUENCE: 47

Met Glu Phe Gly Leu Ser Trp Val Phe Leu Val Ala Leu Leu Arg Gly
 1               5                  10                  15

Val Gln Cys Gln Val Gln Leu Glu Glu Ser Gly Gly Gly Val Val Arg
             20                  25                  30

Pro Gly Arg Ser Leu Arg Leu Ser Cys Ala Ala Ser Gly Phe Thr Leu
         35                  40                  45

Ser Asp Tyr Gly Val Asn Trp Ile Arg Gln Ala Pro Gly Lys Gly Leu
     50                  55                  60

Glu Trp Val Gly Ile Ile Trp Gly Asp Gly Arg Thr Asp Tyr Asn Ser
 65                  70                  75                  80

Ala Leu Lys Ser Arg Leu Thr Val Ser Arg Asn Asn Ser Asn Asn Thr
                 85                  90                  95

Leu Ser Leu Gln Met Asn Ser Leu Thr Thr Glu Asp Thr Ala Val Tyr
                100                 105                 110

Tyr Cys Val Arg Ala Pro Gly Asn Arg Ala Met Glu Tyr Trp Gly Gln
            115                 120                 125

Gly Val Leu Val Thr Val Ser
        130                 135

<210> SEQ ID NO 48
```

<211> LENGTH: 408
<212> TYPE: DNA
<213> ORGANISM: Artificial Sequence
<220> FEATURE:
<223> OTHER INFORMATION: HB227RHOv2 - VH2-V50

<400> SEQUENCE: 48

```
atggacacac tttgctccac gctcctgctg ctgaccatcc cttcatgggt cttgtcccag      60
gtgcagttgg aagaatctgg gggaggcgtg gtccggcctg gaggtccct gaggctctcc     120
tgtgcagcct ctggattcac cttaagcgac tatggtgtaa actggatccg ccaggctcca     180
ggcaaggggc tagagtgggt gggaataata tggggtgatg gaaggacaga ctataattca     240
gctctcaaat cccgactgac cgtctccaga aacaactcca acaacacact gagtctccaa     300
atgaacagcc tgacaactga ggacacggct gtctattatt gtgtgagagc ccccggtaat     360
agggctatgg agtactgggg ccagggagtc ctggtcaccg tctcctca                  408
```

<210> SEQ ID NO 49
<211> LENGTH: 135
<212> TYPE: PRT
<213> ORGANISM: Artificial Sequence
<220> FEATURE:
<223> OTHER INFORMATION: HB227RHOv2 - VH2-V50

<400> SEQUENCE: 49

```
Met Asp Thr Leu Cys Ser Thr Leu Leu Leu Thr Ile Pro Ser Trp
 1               5                  10                  15
Val Leu Ser Gln Val Gln Leu Glu Glu Ser Gly Gly Gly Val Val Arg
            20                  25                  30
Pro Gly Arg Ser Leu Arg Leu Ser Cys Ala Ala Ser Gly Phe Thr Leu
        35                  40                  45
Ser Asp Tyr Gly Val Asn Trp Ile Arg Gln Ala Pro Gly Lys Gly Leu
    50                  55                  60
Glu Trp Val Gly Ile Ile Trp Gly Asp Gly Arg Thr Asp Tyr Asn Ser
65                  70                  75                  80
Ala Leu Lys Ser Arg Leu Thr Val Ser Arg Asn Asn Ser Asn Asn Thr
                85                  90                  95
Leu Ser Leu Gln Met Asn Ser Leu Thr Thr Glu Asp Thr Ala Val Tyr
            100                 105                 110
Tyr Cys Val Arg Ala Pro Gly Asn Arg Ala Met Glu Tyr Trp Gly Gln
        115                 120                 125
Gly Val Leu Val Thr Val Ser
    130                 135
```

<210> SEQ ID NO 50
<211> LENGTH: 408
<212> TYPE: DNA
<213> ORGANISM: Artificial Sequence
<220> FEATURE:
<223> OTHER INFORMATION: HB227RHOv2A - VH2-V50

<400> SEQUENCE: 50

```
atggacacac tttgctccac gctcctgctg ctgaccatcc cttcatgggt cttgtcccag      60
gtgcagttgg aagaatctgg gggaggcgtg gtccggcctg gaggtccct gaggctctcc     120
tgtgcagcct ctggattcac cttcagcgac tatggtgtaa actggatccg ccaggctcca     180
ggcaaggggc tagagtgggt gggaataata tggggtgatg gaaggacaga ctataattca     240
gctctcaaat cccgactgac cgtctccaga aacaactcca acaacacact gagtctccaa     300
atgaacagcc tgacaactga ggacacggct gtctattatt gtgtgagagc ccccggtaat     360
```

```
agggctatgg agtactgggg ccagggagtc ctggtcaccg tctcctca            408
```

<210> SEQ ID NO 51
<211> LENGTH: 135
<212> TYPE: PRT
<213> ORGANISM: Artificial Sequence
<220> FEATURE:
<223> OTHER INFORMATION: HB227RHOv2A - VH2-V50

<400> SEQUENCE: 51

```
Met Asp Thr Leu Cys Ser Thr Leu Leu Leu Thr Ile Pro Ser Trp
 1               5                  10                  15

Val Leu Ser Gln Val Gln Leu Glu Glu Ser Gly Gly Gly Val Val Arg
            20                  25                  30

Pro Gly Arg Ser Leu Arg Leu Ser Cys Ala Ala Ser Gly Phe Thr Phe
        35                  40                  45

Ser Asp Tyr Gly Val Asn Trp Ile Arg Gln Ala Pro Gly Lys Gly Leu
    50                  55                  60

Glu Trp Val Gly Ile Ile Trp Gly Asp Gly Arg Thr Asp Tyr Asn Ser
65                  70                  75                  80

Ala Leu Lys Ser Arg Leu Thr Val Ser Arg Asn Asn Ser Asn Asn Thr
                85                  90                  95

Leu Ser Leu Gln Met Asn Ser Leu Thr Thr Glu Asp Thr Ala Val Tyr
            100                 105                 110

Tyr Cys Val Arg Ala Pro Gly Asn Arg Ala Met Glu Tyr Trp Gly Gln
        115                 120                 125

Gly Val Leu Val Thr Val Ser
    130                 135
```

<210> SEQ ID NO 52
<211> LENGTH: 408
<212> TYPE: DNA
<213> ORGANISM: Artificial Sequence
<220> FEATURE:
<223> OTHER INFORMATION: HB227RHOv2B - VH2-V50

<400> SEQUENCE: 52

```
atggacacac tttgctccac gctcctgctg ctgaccatcc cttcatgggt cttgtcccag    60
gtgcagttgg aagaatctgg gggaggcgtg gtccggcctg ggaggtccct gaggctctcc   120
tgtgcagcct ctggattcac cttagatgac tatggtgtaa actggatccg ccaggctcca   180
ggcaaggggc tagagtgggt gggaataata tggggtgatg gaaggacaga ctataattca   240
gctctcaaat cccgactgac cgtctccaga aacaactcca acaacacact gagtctccaa   300
atgaacagcc tgacaactga ggacacggct gtctattatt gtgtgagagc ccccggtaat   360
agggctatgg agtactgggg ccagggagtc ctggtcaccg tctcctca              408
```

<210> SEQ ID NO 53
<211> LENGTH: 135
<212> TYPE: PRT
<213> ORGANISM: Artificial Sequence
<220> FEATURE:
<223> OTHER INFORMATION: HB227RHOv2B - VH2-V50

<400> SEQUENCE: 53

```
Met Asp Thr Leu Cys Ser Thr Leu Leu Leu Thr Ile Pro Ser Trp
 1               5                  10                  15

Val Leu Ser Gln Val Gln Leu Glu Glu Ser Gly Gly Gly Val Val Arg
            20                  25                  30
```

```
Pro Gly Arg Ser Leu Arg Leu Ser Cys Ala Ala Ser Gly Phe Thr Leu
        35                  40                  45

Asp Asp Tyr Gly Val Asn Trp Ile Arg Gln Ala Pro Gly Lys Gly Leu
 50                  55                  60

Glu Trp Val Gly Ile Ile Trp Gly Asp Gly Arg Thr Asp Tyr Asn Ser
 65                  70                  75                  80

Ala Leu Lys Ser Arg Leu Thr Val Ser Arg Asn Asn Ser Asn Asn Thr
                 85                  90                  95

Leu Ser Leu Gln Met Asn Ser Leu Thr Thr Glu Asp Thr Ala Val Tyr
             100                 105                 110

Tyr Cys Val Arg Ala Pro Gly Asn Arg Ala Met Glu Tyr Trp Gly Gln
         115                 120                 125

Gly Val Leu Val Thr Val Ser
    130                 135

<210> SEQ ID NO 54
<211> LENGTH: 408
<212> TYPE: DNA
<213> ORGANISM: Artificial Sequence
<220> FEATURE:
<223> OTHER INFORMATION: HB227RHOv2C - VH2-V50

<400> SEQUENCE: 54
atggacacac tttgctccac gctcctgctg ctgaccatcc cttcatgggt cttgtcccag      60
gtgcagttgg aagaatctgg gggaggcgtg gtccggcctg ggaggtccct gaggctctcc     120
tgtgcagcct ctggattcac cttaagcgac tatggtgtaa actggatccg ccaggctcca     180
ggcaaggggc tagagtgggt gacaataata tggggtgatg gaaggacaga ctataattca     240
gctctcaaat cccgactgac cgtctccaga aacaactcca acaacacact gagtctccaa     300
atgaacagcc tgacaactga ggacacggct gtctattatt gtgtgagagc ccccggtaat     360
agggctatgg agtactgggg ccagggagtc ctggtcaccg tctcctca                  408

<210> SEQ ID NO 55
<211> LENGTH: 135
<212> TYPE: PRT
<213> ORGANISM: Artificial Sequence
<220> FEATURE:
<223> OTHER INFORMATION: HB227RHOv2C - VH2-V50

<400> SEQUENCE: 55

Met Asp Thr Leu Cys Ser Thr Leu Leu Leu Thr Ile Pro Ser Trp
 1               5                  10                  15

Val Leu Ser Gln Val Gln Leu Glu Glu Ser Gly Gly Gly Val Val Arg
             20                  25                  30

Pro Gly Arg Ser Leu Arg Leu Ser Cys Ala Ala Ser Gly Phe Thr Leu
         35                  40                  45

Ser Asp Tyr Gly Val Asn Trp Ile Arg Gln Ala Pro Gly Lys Gly Leu
 50                  55                  60

Glu Trp Val Thr Ile Ile Trp Gly Asp Gly Arg Thr Asp Tyr Asn Ser
 65                  70                  75                  80

Ala Leu Lys Ser Arg Leu Thr Val Ser Arg Asn Asn Ser Asn Asn Thr
                 85                  90                  95

Leu Ser Leu Gln Met Asn Ser Leu Thr Thr Glu Asp Thr Ala Val Tyr
             100                 105                 110

Tyr Cys Val Arg Ala Pro Gly Asn Arg Ala Met Glu Tyr Trp Gly Gln
         115                 120                 125

Gly Val Leu Val Thr Val Ser
```

<210> SEQ ID NO 56
<211> LENGTH: 408
<212> TYPE: DNA
<213> ORGANISM: Artificial Sequence
<220> FEATURE:
<223> OTHER INFORMATION: HB227RHOv2D - VH2-V50

<400> SEQUENCE: 56

```
atggacacac tttgctccac gctcctgctg ctgaccatcc cttcatgggt cttgtcccag      60
gtgcagttgg aagaatctgg gggaggcgtg gtccggcctg gaggtccct gaggctctcc     120
tgtgcagcct ctggattcac cttaagcgac tatggtgtaa actggatccg ccaggctcca    180
ggcaaggggc tagagtgggt gggaataata tggggtgatg gaaggacaga ctataattca    240
gctctcaaat cccgattcac cgtctccaga aacaactcca acaacacact gagtctccaa    300
atgaacagcc tgacaactga ggacacggct gtctattatt gtgtgagagc ccccggtaat    360
agggctatgg agtactgggg ccagggagtc ctggtcaccg tctcctca                 408
```

<210> SEQ ID NO 57
<211> LENGTH: 135
<212> TYPE: PRT
<213> ORGANISM: Artificial Sequence
<220> FEATURE:
<223> OTHER INFORMATION: HB227RHOv2D - VH2-V50

<400> SEQUENCE: 57

```
Met Asp Thr Leu Cys Ser Thr Leu Leu Leu Thr Ile Pro Ser Trp
  1               5                  10                  15
Val Leu Ser Gln Val Gln Leu Glu Glu Ser Gly Gly Gly Val Val Arg
             20                  25                  30
Pro Gly Arg Ser Leu Arg Leu Ser Cys Ala Ala Ser Gly Phe Thr Leu
         35                  40                  45
Ser Asp Tyr Gly Val Asn Trp Ile Arg Gln Ala Pro Gly Lys Gly Leu
     50                  55                  60
Glu Trp Val Gly Ile Ile Trp Gly Asp Gly Arg Thr Asp Tyr Asn Ser
 65                  70                  75                  80
Ala Leu Lys Ser Arg Phe Thr Val Ser Arg Asn Asn Ser Asn Asn Thr
                 85                  90                  95
Leu Ser Leu Gln Met Asn Ser Leu Thr Thr Glu Asp Thr Ala Val Tyr
            100                 105                 110
Tyr Cys Val Arg Ala Pro Gly Asn Arg Ala Met Glu Tyr Trp Gly Gln
        115                 120                 125
Gly Val Leu Val Thr Val Ser
    130                 135
```

<210> SEQ ID NO 58
<211> LENGTH: 408
<212> TYPE: DNA
<213> ORGANISM: Artificial Sequence
<220> FEATURE:
<223> OTHER INFORMATION: HB227RHOv2ACD - VH2-V50

<400> SEQUENCE: 58

```
atggacacac tttgctccac gctcctgctg ctgaccatcc cttcatgggt cttgtcccag      60
gtgcagttgg aagaatctgg gggaggcgtg gtccggcctg gaggtccct gaggctctcc     120
tgtgcagcct ctggattcac cttcagcgac tatggtgtaa actggatccg ccaggctcca    180
ggcaaggggc tagagtgggt gacaataata tggggtgatg gaaggacaga ctataattca    240
```

```
gctctcaaat cccgattcac cgtctccaga aacaactcca acaacacact gagtctccaa    300
atgaacagcc tgacaactga ggacacggct gtctattatt gtgtgagagc ccccggtaat    360
agggctatgg agtactgggg ccagggagtc ctggtcaccg tctcctca               408
```

```
<210> SEQ ID NO 59
<211> LENGTH: 135
<212> TYPE: PRT
<213> ORGANISM: Artificial Sequence
<220> FEATURE:
<223> OTHER INFORMATION: HB227RHOv2ACD - VH2-V50

<400> SEQUENCE: 59
```

```
Met Asp Thr Leu Cys Ser Thr Leu Leu Leu Thr Ile Pro Ser Trp
 1               5                  10                  15

Val Leu Ser Gln Val Gln Leu Glu Glu Ser Gly Gly Val Val Arg
            20                  25                  30

Pro Gly Arg Ser Leu Arg Leu Ser Cys Ala Ala Ser Gly Phe Thr Phe
         35                  40                  45

Ser Asp Tyr Gly Val Asn Trp Ile Arg Gln Ala Pro Gly Lys Gly Leu
    50                  55                  60

Glu Trp Val Thr Ile Ile Trp Gly Asp Gly Arg Thr Asp Tyr Asn Ser
65                  70                  75                  80

Ala Leu Lys Ser Arg Phe Thr Val Ser Arg Asn Asn Ser Asn Asn Thr
                85                  90                  95

Leu Ser Leu Gln Met Asn Ser Leu Thr Thr Glu Asp Thr Ala Val Tyr
            100                 105                 110

Tyr Cys Val Arg Ala Pro Gly Asn Arg Ala Met Glu Tyr Trp Gly Gln
        115                 120                 125

Gly Val Leu Val Thr Val Ser
    130                 135
```

```
<210> SEQ ID NO 60
<211> LENGTH: 408
<212> TYPE: DNA
<213> ORGANISM: Artificial Sequence
<220> FEATURE:
<223> OTHER INFORMATION: HB227RHOv2ABCD - VH2-V50

<400> SEQUENCE: 60
```

```
atggacacac tttgctccac gctcctgctg ctgaccatcc cttcatgggt cttgtcccag    60
gtgcagttgg aagaatctgg gggaggcgtg gtccggcctg ggaggtccct gaggctctcc   120
tgtgcagcct ctggattcac cttcgatgac tatggtgtaa actggatccg ccaggctcca   180
ggcaaggggc tagagtgggt gacaataata tggggtgatg gaaggacaga ctataattca   240
gctctcaaat cccgattcac cgtctccaga aacaactcca acaacacact gagtctccaa   300
atgaacagcc tgacaactga ggacacggct gtctattatt gtgtgagagc ccccggtaat   360
agggctatgg agtactgggg ccagggagtc ctggtcaccg tctcctca               408
```

```
<210> SEQ ID NO 61
<211> LENGTH: 135
<212> TYPE: PRT
<213> ORGANISM: Artificial Sequence
<220> FEATURE:
<223> OTHER INFORMATION: HB227RHOv2ABCD - VH2-V50

<400> SEQUENCE: 61
```

```
Met Asp Thr Leu Cys Ser Thr Leu Leu Leu Thr Ile Pro Ser Trp
 1               5                  10                  15
```

```
Val Leu Ser Gln Val Gln Leu Glu Glu Ser Gly Gly Gly Val Val Arg
            20                  25                  30

Pro Gly Arg Ser Leu Arg Leu Ser Cys Ala Ala Ser Gly Phe Thr Phe
        35                  40                  45

Asp Asp Tyr Gly Val Asn Trp Ile Arg Gln Ala Pro Gly Lys Gly Leu
    50                  55                  60

Glu Trp Val Thr Ile Ile Trp Gly Asp Gly Arg Thr Asp Tyr Asn Ser
65                  70                  75                  80

Ala Leu Lys Ser Arg Phe Thr Val Ser Arg Asn Asn Ser Asn Asn Thr
                85                  90                  95

Leu Ser Leu Gln Met Asn Ser Leu Thr Thr Glu Asp Thr Ala Val Tyr
            100                 105                 110

Tyr Cys Val Arg Ala Pro Gly Asn Arg Ala Met Glu Tyr Trp Gly Gln
        115                 120                 125

Gly Val Leu Val Thr Val Ser
    130                 135

<210> SEQ ID NO 62
<211> LENGTH: 5
<212> TYPE: PRT
<213> ORGANISM: Artificial Sequence
<220> FEATURE:
<223> OTHER INFORMATION: HB22.7 VH CDR1

<400> SEQUENCE: 62

Asp Tyr Gly Val Asn
1               5

<210> SEQ ID NO 63
<211> LENGTH: 16
<212> TYPE: PRT
<213> ORGANISM: Artificial Sequence
<220> FEATURE:
<223> OTHER INFORMATION: HB22.7 VH CDR2

<400> SEQUENCE: 63

Ile Ile Trp Gly Asp Gly Arg Thr Asp Tyr Asn Ser Ala Leu Lys Ser
1               5                   10                  15

<210> SEQ ID NO 64
<211> LENGTH: 9
<212> TYPE: PRT
<213> ORGANISM: Artificial Sequence
<220> FEATURE:
<223> OTHER INFORMATION: HB22.7 VH CDR3

<400> SEQUENCE: 64

Ala Pro Gly Asn Arg Ala Met Glu Tyr
1               5

<210> SEQ ID NO 65
<211> LENGTH: 11
<212> TYPE: PRT
<213> ORGANISM: Artificial Sequence
<220> FEATURE:
<223> OTHER INFORMATION: HB22.7 VK CDR1

<400> SEQUENCE: 65

Lys Ala Ser Gln Ser Val Thr Asn Asp Val Ala
1               5                   10

<210> SEQ ID NO 66
<211> LENGTH: 7
```

```
<212> TYPE: PRT
<213> ORGANISM: Artificial Sequence
<220> FEATURE:
<223> OTHER INFORMATION: HB22.7 VK CDR2

<400> SEQUENCE: 66

Tyr Ala Ser Asn Arg Tyr Thr
 1               5

<210> SEQ ID NO 67
<211> LENGTH: 9
<212> TYPE: PRT
<213> ORGANISM: Artificial Sequence
<220> FEATURE:
<223> OTHER INFORMATION: HB22.7 VK CDR 3

<400> SEQUENCE: 67

Gln Gln Asp Tyr Arg Ser Pro Trp Thr
 1               5

<210> SEQ ID NO 68
<211> LENGTH: 20
<212> TYPE: PRT
<213> ORGANISM: Artificial Sequence
<220> FEATURE:
<223> OTHER INFORMATION: leader sequence/leader peptide of the mouse
      PCG-1 VH gene

<400> SEQUENCE: 68

Met Lys Ser Gln Thr Gln Val Phe Val Phe Leu Leu Leu Cys Val Ser
 1               5                  10                  15

Gly Ala His Gly
            20

<210> SEQ ID NO 69
<211> LENGTH: 19
<212> TYPE: PRT
<213> ORGANISM: Artificial Sequence
<220> FEATURE:
<223> OTHER INFORMATION: leader sequence/leader peptide of the human
      VH2-05 gene

<400> SEQUENCE: 69

Met Asp Thr Leu Cys Ser Thr Leu Leu Leu Leu Thr Ile Pro Ser Trp
 1               5                  10                  15

Val Leu Ser

<210> SEQ ID NO 70
<211> LENGTH: 19
<212> TYPE: PRT
<213> ORGANISM: Artificial Sequence
<220> FEATURE:
<223> OTHER INFORMATION: leader sequence/leader peptide of the human
      VH2-05 gene

<400> SEQUENCE: 70

Met Glu Phe Gly Leu Ser Trp Val Phe Leu Val Ala Leu Leu Arg Gly
 1               5                  10                  15

Val Gln Cys

<210> SEQ ID NO 71
<211> LENGTH: 20
<212> TYPE: PRT
<213> ORGANISM: Artificial Sequence
<220> FEATURE:
<223> OTHER INFORMATION: leader sequence/leader peptide of the mouse
      SK/CamRK VH gene
```

```
<400> SEQUENCE: 71

Met Lys Ser Gln Thr Gln Val Phe Val Phe Leu Leu Leu Cys Val Ser
1               5                   10                  15

Gly Ala His Gly
            20

<210> SEQ ID NO 72
<211> LENGTH: 22
<212> TYPE: PRT
<213> ORGANISM: Artificial Sequence
<220> FEATURE:
<223> OTHER INFORMATION: leader sequence/leader peptide of the human
      DPK018 VH gene

<400> SEQUENCE: 72

Met Asp Met Arg Val Pro Ala Gln Leu Leu Gly Leu Leu Gln Leu Trp
1               5                   10                  15

Leu Ser Gly Ala Arg Cys
            20

<210> SEQ ID NO 73
<211> LENGTH: 30
<212> TYPE: PRT
<213> ORGANISM: Artificial Sequence
<220> FEATURE:
<223> OTHER INFORMATION: VH FW1

<400> SEQUENCE: 73

Gln Val Gln Leu Gln Glu Ser Gly Pro Ala Leu Val Lys Pro Thr Gln
1               5                   10                  15

Thr Leu Thr Leu Thr Cys Thr Phe Ser Gly Phe Ser Leu Ser
            20                  25                  30

<210> SEQ ID NO 74
<211> LENGTH: 30
<212> TYPE: PRT
<213> ORGANISM: Artificial Sequence
<220> FEATURE:
<223> OTHER INFORMATION: VH FW1

<400> SEQUENCE: 74

Gln Val Gln Leu Gln Glu Ser Gly Pro Ala Leu Val Lys Pro Thr Gln
1               5                   10                  15

Thr Leu Thr Leu Thr Cys Thr Val Ser Gly Phe Ser Leu Ser
            20                  25                  30

<210> SEQ ID NO 75
<211> LENGTH: 14
<212> TYPE: PRT
<213> ORGANISM: Artificial Sequence
<220> FEATURE:
<223> OTHER INFORMATION: VH FW2

<400> SEQUENCE: 75

Trp Ile Arg Gln Pro Pro Gly Lys Ala Leu Glu Trp Leu Ala
1               5                   10

<210> SEQ ID NO 76
<211> LENGTH: 14
<212> TYPE: PRT
<213> ORGANISM: Artificial Sequence
<220> FEATURE:
<223> OTHER INFORMATION: VH FW2

<400> SEQUENCE: 76
```

```
Trp Ile Arg Gln Pro Pro Gly Lys Ala Leu Glu Trp Leu Gly
 1               5                  10
```

<210> SEQ ID NO 77
<211> LENGTH: 32
<212> TYPE: PRT
<213> ORGANISM: Artificial Sequence
<220> FEATURE:
<223> OTHER INFORMATION: VH FW3

<400> SEQUENCE: 77

```
Arg Leu Ser Ile Ser Lys Asp Thr Ser Lys Asn Gln Val Val Leu Arg
 1               5                  10                  15

Met Thr Asn Val Asp Pro Val Asp Thr Ala Thr Tyr Phe Cys Ala Arg
            20                  25                  30
```

<210> SEQ ID NO 78
<211> LENGTH: 32
<212> TYPE: PRT
<213> ORGANISM: Artificial Sequence
<220> FEATURE:
<223> OTHER INFORMATION: VH FW3

<400> SEQUENCE: 78

```
Arg Leu Ser Ile Ser Lys Asp Asn Ser Lys Asn Gln Val Val Leu Arg
 1               5                  10                  15

Met Thr Asn Val Asp Pro Val Asp Thr Ala Thr Tyr Phe Cys Ala Arg
            20                  25                  30
```

<210> SEQ ID NO 79
<211> LENGTH: 11
<212> TYPE: PRT
<213> ORGANISM: Artificial Sequence
<220> FEATURE:
<223> OTHER INFORMATION: VH FW4

<400> SEQUENCE: 79

```
Trp Gly Gln Gly Thr Val Val Thr Val Ser Ser
 1               5                  10
```

<210> SEQ ID NO 80
<211> LENGTH: 30
<212> TYPE: PRT
<213> ORGANISM: Artificial Sequence
<220> FEATURE:
<223> OTHER INFORMATION: VH FW1

<400> SEQUENCE: 80

```
Gln Val Gln Leu Glu Glu Ser Gly Gly Gly Val Val Arg Pro Gly Arg
 1               5                  10                  15

Ser Leu Arg Leu Ser Cys Ala Ala Ser Gly Phe Thr Phe Asp
            20                  25                  30
```

<210> SEQ ID NO 81
<211> LENGTH: 30
<212> TYPE: PRT
<213> ORGANISM: Artificial Sequence
<220> FEATURE:
<223> OTHER INFORMATION: VH FW1

<400> SEQUENCE: 81

```
Gln Val Gln Leu Glu Glu Ser Gly Gly Gly Val Val Arg Pro Gly Arg
 1               5                  10                  15

Ser Leu Arg Leu Ser Cys Ala Ala Ser Gly Phe Thr Phe Ser
            20                  25                  30
```

```
<210> SEQ ID NO 82
<211> LENGTH: 30
<212> TYPE: PRT
<213> ORGANISM: Artificial Sequence
<220> FEATURE:
<223> OTHER INFORMATION: VH FW1

<400> SEQUENCE: 82

Gln Val Gln Leu Glu Glu Ser Gly Gly Gly Val Val Arg Pro Gly Arg
 1               5                  10                  15

Ser Leu Arg Leu Ser Cys Ala Ala Ser Gly Phe Thr Leu Asp
            20                  25                  30

<210> SEQ ID NO 83
<211> LENGTH: 30
<212> TYPE: PRT
<213> ORGANISM: Artificial Sequence
<220> FEATURE:
<223> OTHER INFORMATION: VH FW1

<400> SEQUENCE: 83

Gln Val Gln Leu Glu Glu Ser Gly Gly Gly Val Val Arg Pro Gly Arg
 1               5                  10                  15

Ser Leu Arg Leu Ser Cys Ala Ala Ser Gly Phe Thr Leu Ser
            20                  25                  30

<210> SEQ ID NO 84
<211> LENGTH: 14
<212> TYPE: PRT
<213> ORGANISM: Artificial Sequence
<220> FEATURE:
<223> OTHER INFORMATION: VH FW2

<400> SEQUENCE: 84

Trp Ile Arg Gln Ala Pro Gly Lys Gly Leu Glu Trp Val Thr
 1               5                  10

<210> SEQ ID NO 85
<211> LENGTH: 14
<212> TYPE: PRT
<213> ORGANISM: Artificial Sequence
<220> FEATURE:
<223> OTHER INFORMATION: VH FW2

<400> SEQUENCE: 85

Trp Ile Arg Gln Ala Pro Gly Lys Gly Leu Glu Trp Val Gly
 1               5                  10

<210> SEQ ID NO 86
<211> LENGTH: 32
<212> TYPE: PRT
<213> ORGANISM: Artificial Sequence
<220> FEATURE:
<223> OTHER INFORMATION: VH FW3

<400> SEQUENCE: 86

Arg Phe Thr Val Ser Arg Asn Asn Ser Asn Thr Leu Ser Leu Gln
 1               5                  10                  15

Met Asn Ser Leu Thr Thr Glu Asp Thr Ala Val Tyr Tyr Cys Val Arg
            20                  25                  30

<210> SEQ ID NO 87
<211> LENGTH: 32
<212> TYPE: PRT
<213> ORGANISM: Artificial Sequence
```

```
<220> FEATURE:
<223> OTHER INFORMATION: VH FW3

<400> SEQUENCE: 87

Arg Leu Thr Val Ser Arg Asn Asn Ser Asn Asn Thr Leu Ser Leu Gln
 1               5                  10                  15

Met Asn Ser Leu Thr Thr Glu Asp Thr Ala Val Tyr Tyr Cys Val Arg
            20                  25                  30

<210> SEQ ID NO 88
<211> LENGTH: 10
<212> TYPE: PRT
<213> ORGANISM: Artificial Sequence
<220> FEATURE:
<223> OTHER INFORMATION: VH FW4

<400> SEQUENCE: 88

Trp Gly Gln Gly Val Leu Val Thr Val Ser
 1               5                  10

<210> SEQ ID NO 89
<211> LENGTH: 32
<212> TYPE: PRT
<213> ORGANISM: Artificial Sequence
<220> FEATURE:
<223> OTHER INFORMATION: VH FW3

<400> SEQUENCE: 89

Arg Leu Ile Ile Ser Arg Asp Asn Tyr Lys Asn Thr Met Ser Leu Gln
 1               5                  10                  15

Met Tyr Ser Leu Ser Ala Ala Asp Thr Ala Ile Tyr Phe Cys Val Lys
            20                  25                  30

<210> SEQ ID NO 90
<211> LENGTH: 32
<212> TYPE: PRT
<213> ORGANISM: Artificial Sequence
<220> FEATURE:
<223> OTHER INFORMATION: VH FW3

<400> SEQUENCE: 90

Arg Phe Asn Ile Ser Arg Asp Asn Tyr Lys Asn Thr Met Ser Leu Gln
 1               5                  10                  15

Met Tyr Ser Leu Ser Ala Ala Asp Thr Ala Ile Tyr Phe Cys Val Lys
            20                  25                  30

<210> SEQ ID NO 91
<211> LENGTH: 32
<212> TYPE: PRT
<213> ORGANISM: Artificial Sequence
<220> FEATURE:
<223> OTHER INFORMATION: VH FW3

<400> SEQUENCE: 91

Arg Phe Ile Ile Ser Arg Asp Asn Tyr Lys Asn Thr Asn Ser Leu Gln
 1               5                  10                  15

Met Tyr Ser Leu Ser Ala Ala Asp Thr Ala Ile Tyr Phe Cys Val Lys
            20                  25                  30

<210> SEQ ID NO 92
<211> LENGTH: 32
<212> TYPE: PRT
<213> ORGANISM: Artificial Sequence
<220> FEATURE:
<223> OTHER INFORMATION: VH FW3
```

<400> SEQUENCE: 92

Arg Leu Asn Ile Ser Arg Asp Asn Tyr Lys Asn Thr Met Ser Leu Gln
1               5                   10                  15

Met Tyr Ser Leu Ser Ala Ala Asp Thr Ala Ile Tyr Phe Cys Val Lys
            20                  25                  30

<210> SEQ ID NO 93
<211> LENGTH: 32
<212> TYPE: PRT
<213> ORGANISM: Artificial Sequence
<220> FEATURE:
<223> OTHER INFORMATION: VH FW3

<400> SEQUENCE: 93

Arg Leu Ile Ile Ser Arg Asp Asn Tyr Lys Asn Thr Asn Ser Leu Gln
1               5                   10                  15

Met Tyr Ser Leu Ser Ala Ala Asp Thr Ala Ile Tyr Phe Cys Val Lys
            20                  25                  30

<210> SEQ ID NO 94
<211> LENGTH: 32
<212> TYPE: PRT
<213> ORGANISM: Artificial Sequence
<220> FEATURE:
<223> OTHER INFORMATION: VH FW3

<400> SEQUENCE: 94

Arg Phe Asn Ile Ser Arg Asp Asn Tyr Lys Asn Thr Asn Ser Leu Gln
1               5                   10                  15

Met Tyr Ser Leu Ser Ala Ala Asp Thr Ala Ile Tyr Phe Cys Val Lys
            20                  25                  30

<210> SEQ ID NO 95
<211> LENGTH: 32
<212> TYPE: PRT
<213> ORGANISM: Artificial Sequence
<220> FEATURE:
<223> OTHER INFORMATION: VH FW3

<400> SEQUENCE: 95

Arg Leu Asn Ile Ser Arg Asp Asn Tyr Lys Asn Thr Asn Ser Leu Gln
1               5                   10                  15

Met Tyr Ser Leu Ser Ala Ala Asp Thr Ala Ile Tyr Phe Cys Val Lys
            20                  25                  30

<210> SEQ ID NO 96
<211> LENGTH: 30
<212> TYPE: PRT
<213> ORGANISM: Artificial Sequence
<220> FEATURE:
<223> OTHER INFORMATION: VH FW1

<400> SEQUENCE: 96

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser
            20                  25                  30

<210> SEQ ID NO 97
<211> LENGTH: 14
<212> TYPE: PRT
<213> ORGANISM: Artificial Sequence
<220> FEATURE:
<223> OTHER INFORMATION: VH FW2

```
<400> SEQUENCE: 97

Trp Val Arg Gln Ala Pro Gly Lys Gly Leu Glu Trp Ile Ser
 1               5                  10

<210> SEQ ID NO 98
<211> LENGTH: 32
<212> TYPE: PRT
<213> ORGANISM: Artificial Sequence
<220> FEATURE:
<223> OTHER INFORMATION: VH FW3

<400> SEQUENCE: 98

Arg Phe Ile Ile Ser Arg Asp Asn Tyr Lys Asn Thr Met Ser Leu Gln
 1               5                  10                  15

Met Tyr Ser Leu Ser Ala Ala Asp Thr Ala Ile Tyr Phe Cys Val Lys
             20                  25                  30

<210> SEQ ID NO 99
<211> LENGTH: 10
<212> TYPE: PRT
<213> ORGANISM: Artificial Sequence
<220> FEATURE:
<223> OTHER INFORMATION: VH FW4

<400> SEQUENCE: 99

Trp Gly Gln Gly Thr Met Val Thr Val Ser
 1               5                  10

<210> SEQ ID NO 100
<211> LENGTH: 32
<212> TYPE: PRT
<213> ORGANISM: Artificial Sequence
<220> FEATURE:
<223> OTHER INFORMATION: VH FW3

<400> SEQUENCE: 100

Arg Phe Thr Ile Ser Arg Asn Asn Ser Asn Thr Leu Ser Leu Gln
 1               5                  10                  15

Met Asn Ser Leu Thr Thr Glu Asp Thr Ala Val Tyr Tyr Cys Val Arg
             20                  25                  30

<210> SEQ ID NO 101
<211> LENGTH: 32
<212> TYPE: PRT
<213> ORGANISM: Artificial Sequence
<220> FEATURE:
<223> OTHER INFORMATION: VH FW3

<400> SEQUENCE: 101

Arg Leu Thr Ile Ser Arg Asn Asn Ser Asn Thr Leu Ser Leu Gln
 1               5                  10                  15

Met Asn Ser Leu Thr Thr Glu Asp Thr Ala Val Tyr Tyr Cys Val Arg
             20                  25                  30

<210> SEQ ID NO 102
<211> LENGTH: 30
<212> TYPE: PRT
<213> ORGANISM: Artificial Sequence
<220> FEATURE:
<223> OTHER INFORMATION: VH FW1

<400> SEQUENCE: 102

Glu Leu Gln Leu Val Glu Ser Gly Gly Gly Phe Val Gln Pro Gly Gly
 1               5                  10                  15

Ser Leu Arg Leu Ser Cys Ala Ala Ser Gly Phe Pro Phe Arg
```

```
                20                  25                  30

<210> SEQ ID NO 103
<211> LENGTH: 30
<212> TYPE: PRT
<213> ORGANISM: Artificial Sequence
<220> FEATURE:
<223> OTHER INFORMATION: VH FW1

<400> SEQUENCE: 103

Glu Leu Gln Leu Val Glu Ser Gly Gly Gly Phe Val Gln Pro Gly Gly
  1               5                  10                  15

Ser Leu Arg Leu Ser Cys Ala Ala Ser Gly Phe Pro Leu Arg
                20                  25                  30

<210> SEQ ID NO 104
<211> LENGTH: 30
<212> TYPE: PRT
<213> ORGANISM: Artificial Sequence
<220> FEATURE:
<223> OTHER INFORMATION: VH FW1

<400> SEQUENCE: 104

Glu Leu Gln Leu Val Glu Ser Gly Gly Gly Phe Val Gln Pro Gly Gly
  1               5                  10                  15

Ser Leu Arg Leu Ser Cys Ala Ala Ser Gly Phe Pro Phe Ser
                20                  25                  30

<210> SEQ ID NO 105
<211> LENGTH: 30
<212> TYPE: PRT
<213> ORGANISM: Artificial Sequence
<220> FEATURE:
<223> OTHER INFORMATION: VH FW1

<400> SEQUENCE: 105

Glu Leu Gln Leu Val Glu Ser Gly Gly Gly Phe Val Gln Pro Gly Gly
  1               5                  10                  15

Ser Leu Arg Leu Ser Cys Ala Ala Ser Gly Phe Pro Leu Ser
                20                  25                  30

<210> SEQ ID NO 106
<211> LENGTH: 32
<212> TYPE: PRT
<213> ORGANISM: Artificial Sequence
<220> FEATURE:
<223> OTHER INFORMATION: VH FW3

<400> SEQUENCE: 106

Arg Val Thr Ile Ser Arg Asp Asn Ala Lys Lys Met Val Tyr Pro Gln
  1               5                  10                  15

Met Asn Ser Leu Arg Ala Glu Asp Thr Ala Met Tyr Tyr Cys His Cys
                20                  25                  30

<210> SEQ ID NO 107
<211> LENGTH: 32
<212> TYPE: PRT
<213> ORGANISM: Artificial Sequence
<220> FEATURE:
<223> OTHER INFORMATION: VH FW3

<400> SEQUENCE: 107

Arg Val Thr Ile Ser Arg Asp Asn Ala Lys Lys Met Val Tyr Pro Gln
  1               5                  10                  15

Met Asn Ser Leu Arg Ala Glu Asp Thr Ala Met Tyr Tyr Cys His Arg
```

```
                20                  25                  30

<210> SEQ ID NO 108
<211> LENGTH: 32
<212> TYPE: PRT
<213> ORGANISM: Artificial Sequence
<220> FEATURE:
<223> OTHER INFORMATION: VH FW3

<400> SEQUENCE: 108

Arg Val Thr Ile Ser Arg Asp Asn Ala Lys Lys Met Val Tyr Pro Gln
 1               5                  10                  15

Met Asn Ser Leu Arg Ala Glu Asp Thr Ala Met Tyr Tyr Cys His Lys
                20                  25                  30

<210> SEQ ID NO 109
<211> LENGTH: 32
<212> TYPE: PRT
<213> ORGANISM: Artificial Sequence
<220> FEATURE:
<223> OTHER INFORMATION: VH FW3

<400> SEQUENCE: 109

Arg Val Thr Ile Ser Arg Asp Asn Ala Lys Lys Met Val Tyr Pro Gln
 1               5                  10                  15

Met Asn Ser Leu Arg Ala Glu Asp Thr Ala Met Tyr Tyr Cys Val Cys
                20                  25                  30

<210> SEQ ID NO 110
<211> LENGTH: 32
<212> TYPE: PRT
<213> ORGANISM: Artificial Sequence
<220> FEATURE:
<223> OTHER INFORMATION: VH FW3

<400> SEQUENCE: 110

Arg Val Thr Ile Ser Arg Asp Asn Ala Lys Lys Met Val Tyr Pro Gln
 1               5                  10                  15

Met Asn Ser Leu Arg Ala Glu Asp Thr Ala Met Tyr Tyr Cys Val Arg
                20                  25                  30

<210> SEQ ID NO 111
<211> LENGTH: 32
<212> TYPE: PRT
<213> ORGANISM: Artificial Sequence
<220> FEATURE:
<223> OTHER INFORMATION: VH FW3

<400> SEQUENCE: 111

Arg Val Thr Ile Ser Arg Asp Asn Ala Lys Lys Met Val Tyr Pro Gln
 1               5                  10                  15

Met Asn Ser Leu Arg Ala Glu Asp Thr Ala Met Tyr Tyr Cys Val Lys
                20                  25                  30

<210> SEQ ID NO 112
<211> LENGTH: 32
<212> TYPE: PRT
<213> ORGANISM: Artificial Sequence
<220> FEATURE:
<223> OTHER INFORMATION: VH FW3

<400> SEQUENCE: 112

Arg Val Thr Ile Ser Arg Asp Asn Ala Lys Lys Met Val Tyr Pro Gln
 1               5                  10                  15

Met Asn Ser Leu Arg Ala Glu Asp Thr Ala Met Tyr Tyr Cys Ala Cys
```

```
                    20                  25                  30
```

<210> SEQ ID NO 113
<211> LENGTH: 32
<212> TYPE: PRT
<213> ORGANISM: Artificial Sequence
<220> FEATURE:
<223> OTHER INFORMATION: VH FW3

<400> SEQUENCE: 113

```
Arg Val Thr Ile Ser Arg Asp Asn Ala Lys Lys Met Val Tyr Pro Gln
1               5                   10                  15

Met Asn Ser Leu Arg Ala Glu Asp Thr Ala Met Tyr Tyr Cys Ala Arg
                20                  25                  30
```

<210> SEQ ID NO 114
<211> LENGTH: 32
<212> TYPE: PRT
<213> ORGANISM: Artificial Sequence
<220> FEATURE:
<223> OTHER INFORMATION: VH FW3

<400> SEQUENCE: 114

```
Arg Val Thr Ile Ser Arg Asp Asn Ala Lys Lys Met Val Tyr Pro Gln
1               5                   10                  15

Met Asn Ser Leu Arg Ala Glu Asp Thr Ala Met Tyr Tyr Cys Ala Lys
                20                  25                  30
```

<210> SEQ ID NO 115
<211> LENGTH: 10
<212> TYPE: PRT
<213> ORGANISM: Artificial Sequence
<220> FEATURE:
<223> OTHER INFORMATION: VH FW4

<400> SEQUENCE: 115

```
Trp Gly Gln Gly Thr Leu Val Thr Val Ser
1               5                   10
```

<210> SEQ ID NO 116
<211> LENGTH: 14
<212> TYPE: PRT
<213> ORGANISM: Artificial Sequence
<220> FEATURE:
<223> OTHER INFORMATION: VH FW2

<400> SEQUENCE: 116

```
Trp Val Arg Gln Gly Pro Gly Lys Gly Leu Val Trp Val Ser
1               5                   10
```

<210> SEQ ID NO 117
<211> LENGTH: 23
<212> TYPE: PRT
<213> ORGANISM: Artificial Sequence
<220> FEATURE:
<223> OTHER INFORMATION: VK FW1

<400> SEQUENCE: 117

```
Asp Ile Val Met Thr Gln Ser Pro Ser Ser Leu Ser Ala Ser Val Gly
1               5                   10                  15

Asp Arg Val Thr Ile Thr Cys
                20
```

<210> SEQ ID NO 118
<211> LENGTH: 15
<212> TYPE: PRT

<213> ORGANISM: Artificial Sequence
<220> FEATURE:
<223> OTHER INFORMATION: VK FW2

<400> SEQUENCE: 118

Trp Tyr Gln Gln Lys Pro Gly Lys Ala Pro Lys Leu Leu Ile Tyr
1               5                   10                  15

<210> SEQ ID NO 119
<211> LENGTH: 32
<212> TYPE: PRT
<213> ORGANISM: Artificial Sequence
<220> FEATURE:
<223> OTHER INFORMATION: VK FW3

<400> SEQUENCE: 119

Gly Val Pro Ser Arg Phe Ser Gly Ser Gly Ser Gly Thr Asp Phe Thr
1               5                   10                  15

Leu Thr Ile Ser Ser Leu Gln Pro Glu Asp Phe Ala Thr Tyr Tyr Cys
            20                  25                  30

<210> SEQ ID NO 120
<211> LENGTH: 32
<212> TYPE: PRT
<213> ORGANISM: Artificial Sequence
<220> FEATURE:
<223> OTHER INFORMATION: VK FW3

<400> SEQUENCE: 120

Gly Val Pro Asp Arg Phe Ser Gly Ser Gly Ser Gly Thr Asp Phe Thr
1               5                   10                  15

Leu Thr Ile Ser Ser Leu Gln Pro Glu Asp Phe Ala Thr Tyr Tyr Cys
            20                  25                  30

<210> SEQ ID NO 121
<211> LENGTH: 32
<212> TYPE: PRT
<213> ORGANISM: Artificial Sequence
<220> FEATURE:
<223> OTHER INFORMATION: VK FW3

<400> SEQUENCE: 121

Gly Val Pro Ser Arg Phe Ser Gly Ser Gly Tyr Gly Thr Asp Phe Thr
1               5                   10                  15

Leu Thr Ile Ser Ser Leu Gln Pro Glu Asp Phe Ala Thr Tyr Tyr Cys
            20                  25                  30

<210> SEQ ID NO 122
<211> LENGTH: 32
<212> TYPE: PRT
<213> ORGANISM: Artificial Sequence
<220> FEATURE:
<223> OTHER INFORMATION: VK FW3

<400> SEQUENCE: 122

Gly Val Pro Ser Arg Phe Ser Gly Ser Gly Ser Gly Thr Asp Phe Thr
1               5                   10                  15

Leu Thr Ile Ser Ser Leu Gln Pro Glu Asp Phe Ala Thr Tyr Phe Cys
            20                  25                  30

<210> SEQ ID NO 123
<211> LENGTH: 32
<212> TYPE: PRT
<213> ORGANISM: Artificial Sequence
<220> FEATURE:
<223> OTHER INFORMATION: VK FW3

```
<400> SEQUENCE: 123

Gly Val Pro Asp Arg Phe Ser Gly Ser Gly Tyr Gly Thr Asp Phe Thr
1               5                   10                  15

Leu Thr Ile Ser Ser Leu Gln Pro Glu Asp Phe Ala Thr Tyr Tyr Cys
            20                  25                  30

<210> SEQ ID NO 124
<211> LENGTH: 32
<212> TYPE: PRT
<213> ORGANISM: Artificial Sequence
<220> FEATURE:
<223> OTHER INFORMATION: VK FW3

<400> SEQUENCE: 124

Gly Val Pro Asp Arg Phe Ser Gly Ser Gly Ser Gly Thr Asp Phe Thr
1               5                   10                  15

Leu Thr Ile Ser Ser Leu Gln Pro Glu Asp Phe Ala Thr Tyr Phe Cys
            20                  25                  30

<210> SEQ ID NO 125
<211> LENGTH: 32
<212> TYPE: PRT
<213> ORGANISM: Artificial Sequence
<220> FEATURE:
<223> OTHER INFORMATION: VK FW3

<400> SEQUENCE: 125

Gly Val Pro Ser Arg Phe Ser Gly Ser Gly Tyr Gly Thr Asp Phe Thr
1               5                   10                  15

Leu Thr Ile Ser Ser Leu Gln Pro Glu Asp Phe Ala Thr Tyr Phe Cys
            20                  25                  30

<210> SEQ ID NO 126
<211> LENGTH: 32
<212> TYPE: PRT
<213> ORGANISM: Artificial Sequence
<220> FEATURE:
<223> OTHER INFORMATION: VK FW3

<400> SEQUENCE: 126

Gly Val Pro Asp Arg Phe Ser Gly Ser Gly Tyr Gly Thr Asp Phe Thr
1               5                   10                  15

Leu Thr Ile Ser Ser Leu Gln Pro Glu Asp Phe Ala Thr Tyr Phe Cys
            20                  25                  30

<210> SEQ ID NO 127
<211> LENGTH: 12
<212> TYPE: PRT
<213> ORGANISM: Artificial Sequence
<220> FEATURE:
<223> OTHER INFORMATION: VK FW4

<400> SEQUENCE: 127

Phe Gly Gly Gly Thr Lys Val Glu Ile Lys Arg Thr
1               5                   10

<210> SEQ ID NO 128
<211> LENGTH: 30
<212> TYPE: PRT
<213> ORGANISM: Artificial Sequence
<220> FEATURE:
<223> OTHER INFORMATION: VH FW1

<400> SEQUENCE: 128
```

-continued

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Leu Ser
            20                  25                  30

<210> SEQ ID NO 129
<211> LENGTH: 14
<212> TYPE: PRT
<213> ORGANISM: Artificial Sequence
<220> FEATURE:
<223> OTHER INFORMATION: VH FW1

<400> SEQUENCE: 129

Trp Val Arg Gln Ala Pro Gly Lys Gly Leu Glu Trp Ile Gly
1               5                   10

<210> SEQ ID NO 130
<211> LENGTH: 22
<212> TYPE: PRT
<213> ORGANISM: Artificial Sequence
<220> FEATURE:
<223> OTHER INFORMATION: Human HB22.7 VH VCI Resiudes

<400> SEQUENCE: 130

Val Val Gly Phe Ser Leu Ser Val Gln Leu Trp Leu Gly Leu Ile Lys
1               5                   10                  15

Asn Val Tyr Ala Arg Trp
            20

<210> SEQ ID NO 131
<211> LENGTH: 22
<212> TYPE: PRT
<213> ORGANISM: Artificial Sequence
<220> FEATURE:
<223> OTHER INFORMATION: Human 673 VH VCI Resiudes

<400> SEQUENCE: 131

Val Ala Gly Phe Thr Phe Ser Val Gln Leu Trp Val Ala Phe Ile Arg
1               5                   10                  15

Asn Leu Tyr Ala Arg Trp
            20

<210> SEQ ID NO 132
<211> LENGTH: 22
<212> TYPE: PRT
<213> ORGANISM: Artificial Sequence
<220> FEATURE:
<223> OTHER INFORMATION: Human AJ556657 VH VCI Resiudes

<400> SEQUENCE: 132

Val Ala Gly Phe Thr Phe Asp Ile Gln Leu Trp Val Thr Phe Val Arg
1               5                   10                  15

Asn Leu Tyr Val Arg Trp
            20

<210> SEQ ID NO 133
<211> LENGTH: 22
<212> TYPE: PRT
<213> ORGANISM: Artificial Sequence
<220> FEATURE:
<223> OTHER INFORMATION: Human AJ556703 VH VCI Resiudes

<400> SEQUENCE: 133

Val Gly Gly Phe Thr Phe Ser Val Gln Leu Trp Leu Ala Leu Ile Arg
1               5                   10                  15

Asn Leu Tyr Ala Lys Trp
            20

<210> SEQ ID NO 134
<211> LENGTH: 22
<212> TYPE: PRT
<213> ORGANISM: Artificial Sequence
<220> FEATURE:
<223> OTHER INFORMATION: Human AJ556712 VH VCI Resiudes

<400> SEQUENCE: 134

Val Gly Gly Phe Thr Phe Ser Val Gln Leu Trp Leu Ala Leu Ile Arg
1               5                   10                  15

Asn Leu Tyr Ala Lys Trp
            20

<210> SEQ ID NO 135
<211> LENGTH: 22
<212> TYPE: PRT
<213> ORGANISM: Artificial Sequence
<220> FEATURE:
<223> OTHER INFORMATION: Human AJ556713 VH VCI Resiudes

<400> SEQUENCE: 135

Val Gly Gly Phe Thr Phe Ser Val Gln Leu Trp Leu Ala Leu Ile Arg
1               5                   10                  15

Asn Leu Tyr Ala Lys Trp
            20

<210> SEQ ID NO 136
<211> LENGTH: 22
<212> TYPE: PRT
<213> ORGANISM: Artificial Sequence
<220> FEATURE:
<223> OTHER INFORMATION: Human 25354 VH VCI Resiudes

<400> SEQUENCE: 136

Val Ser Gly Phe Thr Phe Asn Val Gln Leu Trp Val Ser Phe Ile Arg
1               5                   10                  15

Asn Leu Tyr Ala Arg Trp
            20

<210> SEQ ID NO 137
<211> LENGTH: 22
<212> TYPE: PRT
<213> ORGANISM: Artificial Sequence
<220> FEATURE:
<223> OTHER INFORMATION: Humna AF376954 VH VCI Resiudes

<400> SEQUENCE: 137

Leu Ala Gly Phe Pro Phe Arg Val Gln Leu Trp Val Ser Val Ile Arg
1               5                   10                  15

Asn Val Tyr His Cys Trp
            20

<210> SEQ ID NO 138
<211> LENGTH: 22
<212> TYPE: PRT
<213> ORGANISM: Artificial Sequence
<220> FEATURE:
<223> OTHER INFORMATION: Human AF376955 VH VCI Resiudes

<400> SEQUENCE: 138

Val Ala Gly Phe Arg Phe Gly Val Gln Leu Trp Val Ser Phe Ile Arg
1               5                   10                  15

Asn Leu Tyr Ala Thr Trp
            20

<210> SEQ ID NO 139
<211> LENGTH: 22
<212> TYPE: PRT
<213> ORGANISM: Artificial Sequence
<220> FEATURE:
<223> OTHER INFORMATION: Human AY052532 VH VCI Resiudes

<400> SEQUENCE: 139

Gly Ala Gly Phe Thr Phe Ser Val Gln Leu Trp Val Ser Phe Ile Arg
1               5                   10                  15

Asn Leu Tyr Ala Arg Trp
            20

<210> SEQ ID NO 140
<211> LENGTH: 22
<212> TYPE: PRT
<213> ORGANISM: Artificial Sequence
<220> FEATURE:
<223> OTHER INFORMATION: Human M23691 VH VCI Resiudes

<400> SEQUENCE: 140

Val Ala Gly Phe Thr Phe Ser Ile Gln Leu Trp Val Ala Phe Ile Arg
1               5                   10                  15

Asn Leu Tyr Ala Arg Trp
            20

<210> SEQ ID NO 141
<211> LENGTH: 22
<212> TYPE: PRT
<213> ORGANISM: Artificial Sequence
<220> FEATURE:
<223> OTHER INFORMATION: Human 44977 VH VCI Resiudes

<400> SEQUENCE: 141

Val Ala Gly Ile Pro Phe Ser Val Gln Leu Trp Val Ala Phe Ile Arg
1               5                   10                  15

Asn Val Tyr Ala Arg Trp
            20

<210> SEQ ID NO 142
<211> LENGTH: 22
<212> TYPE: PRT
<213> ORGANISM: Artificial Sequence
<220> FEATURE:
<223> OTHER INFORMATION: Human AB067248 VH VCI Resiudes

<400> SEQUENCE: 142

Val Ala Gly Phe Thr Phe Ser Val Gln Leu Trp Ile Ser Phe Ile Arg
1               5                   10                  15

Asn Met Phe Val Lys Trp
            20

<210> SEQ ID NO 143
<211> LENGTH: 22
<212> TYPE: PRT
<213> ORGANISM: Artificial Sequence
<220> FEATURE:
<223> OTHER INFORMATION: Human AJ556642 VH VCI Resiudes

<400> SEQUENCE: 143

Val Ala Gly Phe Thr Phe Asp Ile Gln Leu Trp Val Thr Phe Ile Arg
1               5                   10                  15

Asn Leu Tyr Val Arg Trp
            20

<210> SEQ ID NO 144
<211> LENGTH: 22
<212> TYPE: PRT
<213> ORGANISM: Artificial Sequence
<220> FEATURE:
<223> OTHER INFORMATION: Human AJ556644 VH VCI Resiudes

<400> SEQUENCE: 144

Val Ala Gly Phe Thr Phe Asp Ile Gln Leu Trp Val Thr Phe Val Arg
1               5                   10                  15

Asn Leu Tyr Val Arg Trp
            20

<210> SEQ ID NO 145
<211> LENGTH: 22
<212> TYPE: PRT
<213> ORGANISM: Artificial Sequence
<220> FEATURE:
<223> OTHER INFORMATION: Human 40394 VH VCI Resiudes

<400> SEQUENCE: 145

Val Val Gly Gly Ser Phe Arg Ile Gln Leu Trp Ile Gly Val Ile Val
1               5                   10                  15

Thr Phe Tyr Ala Arg Trp
            20

<210> SEQ ID NO 146
<211> LENGTH: 22
<212> TYPE: PRT
<213> ORGANISM: Artificial Sequence
<220> FEATURE:
<223> OTHER INFORMATION: Human 40570 VH VCI Resiudes

<400> SEQUENCE: 146

Ile Val Gly Gly Pro Leu Ser Ile Gln Leu Trp Ile Gly Val Ile Ile
1               5                   10                  15

Met Phe Phe Ala Arg Trp
            20

<210> SEQ ID NO 147
<211> LENGTH: 22
<212> TYPE: PRT
<213> ORGANISM: Artificial Sequence
<220> FEATURE:
<223> OTHER INFORMATION: Human 40903 VH VCI Resiudes

<400> SEQUENCE: 147

Val Val Gly Gly Ser Phe Asn Ile Gln Leu Trp Ile Gly Val Ile Val
1               5                   10                  15

Lys Phe Tyr Ala Arg Trp
            20

<210> SEQ ID NO 148
<211> LENGTH: 22
<212> TYPE: PRT
<213> ORGANISM: Artificial Sequence
<220> FEATURE:
<223> OTHER INFORMATION: Human AX167737 VH VCI Resiudes

<400> SEQUENCE: 148

Val Val Gly Ala Ser Leu Asp Ile Gln Leu Trp Ile Ala Val Ile Met
1               5                   10                  15

```
Thr Leu Tyr Ala Arg Trp
            20

<210> SEQ ID NO 149
<211> LENGTH: 22
<212> TYPE: PRT
<213> ORGANISM: Artificial Sequence
<220> FEATURE:
<223> OTHER INFORMATION: hUMAN U68224 VH VCI Resiudes

<400> SEQUENCE: 149

Ile Val Gly Gly Pro Leu Ser Ile Gln Leu Trp Ile Gly Val Ile Ile
1               5                   10                  15

Met Phe Phe Ala Arg Trp
            20

<210> SEQ ID NO 150
<211> LENGTH: 22
<212> TYPE: PRT
<213> ORGANISM: Artificial Sequence
<220> FEATURE:
<223> OTHER INFORMATION: Human 117 VH VCI Resiudes

<400> SEQUENCE: 150

Val Gly Gly Tyr Ser Phe Thr Val Gln Leu Trp Met Gly Val Ile Ala
1               5                   10                  15

Lys Ala Tyr Ala Arg Trp
            20

<210> SEQ ID NO 151
<211> LENGTH: 22
<212> TYPE: PRT
<213> ORGANISM: Artificial Sequence
<220> FEATURE:
<223> OTHER INFORMATION: Human 165 VH VCI Resiudes

<400> SEQUENCE: 151

Val Gly Gly Tyr Thr Phe Asn Val Gln Leu Trp Met Gly Val Ile Ala
1               5                   10                  15

Lys Ala Tyr Ala Arg Trp
            20

<210> SEQ ID NO 152
<211> LENGTH: 22
<212> TYPE: PRT
<213> ORGANISM: Artificial Sequence
<220> FEATURE:
<223> OTHER INFORMATION: Human 602 VH VCI Resiudes

<400> SEQUENCE: 152

Met Ala Gly Phe Asn Phe Ser Val Gln Leu Trp Val Gly Phe Ile Arg
1               5                   10                  15

Asp Ala Tyr Thr Pro Trp
            20

<210> SEQ ID NO 153
<211> LENGTH: 22
<212> TYPE: PRT
<213> ORGANISM: Artificial Sequence
<220> FEATURE:
<223> OTHER INFORMATION: Human 667 VH VCI Resiudes

<400> SEQUENCE: 153

Val Ala Gly Phe Thr Val Ser Val Gln Leu Trp Val Ser Phe Ile Arg
1               5                   10                  15
```

```
Asp Val Tyr Ala Arg Phe
            20

<210> SEQ ID NO 154
<211> LENGTH: 22
<212> TYPE: PRT
<213> ORGANISM: Artificial Sequence
<220> FEATURE:
<223> OTHER INFORMATION: Human 723 VH VCI Resiudes

<400> SEQUENCE: 154

Val Gly Gly Phe Ser Phe Thr Val Gln Leu Trp Val Gly Val Ile Ala
1               5                   10                  15

Lys Ala Tyr Ala Arg Trp
            20

<210> SEQ ID NO 155
<211> LENGTH: 22
<212> TYPE: PRT
<213> ORGANISM: Artificial Sequence
<220> FEATURE:
<223> OTHER INFORMATION: Human 747 VH VCI Resiudes

<400> SEQUENCE: 155

Val Gly Gly Phe Ser Phe Thr Val Gln Leu Trp Val Gly Val Ile Ala
1               5                   10                  15

Lys Ala Tyr Ala Arg Trp
            20

<210> SEQ ID NO 156
<211> LENGTH: 22
<212> TYPE: PRT
<213> ORGANISM: Artificial Sequence
<220> FEATURE:
<223> OTHER INFORMATION: Human 25893 VH VCI Resiudes

<400> SEQUENCE: 156

Val Gly Gly Tyr Thr Phe Ser Val Gln Leu Trp Met Gly Val Ile Val
1               5                   10                  15

Lys Ala Tyr Ala Arg Trp
            20

<210> SEQ ID NO 157
<211> LENGTH: 22
<212> TYPE: PRT
<213> ORGANISM: Artificial Sequence
<220> FEATURE:
<223> OTHER INFORMATION: Human 29976 VH VCI Resiudes

<400> SEQUENCE: 157

Val Gly Gly Tyr Ser Ile Ser Val Gln Leu Trp Leu Gly Val Ile Ala
1               5                   10                  15

Lys Ala Tyr Ala Thr Trp
            20

<210> SEQ ID NO 158
<211> LENGTH: 22
<212> TYPE: PRT
<213> ORGANISM: Artificial Sequence
<220> FEATURE:
<223> OTHER INFORMATION: Human 29979 VH VCI Resiudes

<400> SEQUENCE: 158

Val Gly Gly Tyr Ser Phe Ser Val Gln Leu Trp Met Gly Val Ile Ala
1               5                   10                  15
```

```
Lys Ala Tyr Ala Lys Trp
            20

<210> SEQ ID NO 159
<211> LENGTH: 22
<212> TYPE: PRT
<213> ORGANISM: Artificial Sequence
<220> FEATURE:
<223> OTHER INFORMATION: Human 30001 VH VCI Resiudes

<400> SEQUENCE: 159

Val Gly Gly Tyr Ser Phe Thr Val Gln Leu Trp Met Gly Val Ile Ala
1               5                   10                  15

Lys Ala Tyr Ala Arg Trp
            20

<210> SEQ ID NO 160
<211> LENGTH: 22
<212> TYPE: PRT
<213> ORGANISM: Artificial Sequence
<220> FEATURE:
<223> OTHER INFORMATION: Human AB063882 VH VCI Resiudes

<400> SEQUENCE: 160

Val Ala Gly Tyr Thr Phe Thr Val Gln Leu Trp Met Gly Phe Phe Leu
1               5                   10                  15

Thr Ala Tyr Ala Arg Trp
            20

<210> SEQ ID NO 161
<211> LENGTH: 22
<212> TYPE: PRT
<213> ORGANISM: Artificial Sequence
<220> FEATURE:
<223> OTHER INFORMATION: Human AB066958 VH VCI Resiudes

<400> SEQUENCE: 161

Val Ala Gly Tyr Ser Phe Thr Val Gln Leu Trp Val Gly Phe Phe Leu
1               5                   10                  15

Thr Ala Tyr Ala Arg Trp
            20

<210> SEQ ID NO 162
<211> LENGTH: 22
<212> TYPE: PRT
<213> ORGANISM: Artificial Sequence
<220> FEATURE:
<223> OTHER INFORMATION: Human AB066964 VH VCI Resiudes

<400> SEQUENCE: 162

Val Ala Gly Tyr Ser Phe Thr Val Gln Leu Trp Val Gly Phe Phe Leu
1               5                   10                  15

Thr Ala Tyr Ala Arg Trp
            20

<210> SEQ ID NO 163
<211> LENGTH: 22
<212> TYPE: PRT
<213> ORGANISM: Artificial Sequence
<220> FEATURE:
<223> OTHER INFORMATION: Human AB067138 VH VCI Resiudes

<400> SEQUENCE: 163

Val Ala Gly Gly His Phe Thr Val Gln Leu Trp Ile Gly Val Leu Ile
1               5                   10                  15
```

Thr Phe Tyr Ala Arg Trp
            20

<210> SEQ ID NO 164
<211> LENGTH: 22
<212> TYPE: PRT
<213> ORGANISM: Artificial Sequence
<220> FEATURE:
<223> OTHER INFORMATION: Human 38277 VH VCI Resiudes

<400> SEQUENCE: 164

Val Ala Gly Phe Thr Phe Lys Val Gln Leu Trp Val Ser Phe Ile Arg
1               5                   10                  15

Asn Leu Tyr Val Lys Trp
            20

<210> SEQ ID NO 165
<211> LENGTH: 22
<212> TYPE: PRT
<213> ORGANISM: Artificial Sequence
<220> FEATURE:
<223> OTHER INFORMATION: Human S65761 VH VCI Resiudes

<400> SEQUENCE: 165

Val Ala Gly Phe Thr Phe Ser Val Gln Leu Trp Val Ala Phe Val Arg
1               5                   10                  15

Asp Val Tyr Thr Thr Trp
            20

<210> SEQ ID NO 166
<211> LENGTH: 22
<212> TYPE: PRT
<213> ORGANISM: Artificial Sequence
<220> FEATURE:
<223> OTHER INFORMATION: Human 748 VH VCI Resiudes

<400> SEQUENCE: 166

Glu Gly Gly Tyr Arg Phe Thr Val Gln Leu Trp Met Gly Val Ile Val
1               5                   10                  15

Lys Ala Tyr Ala Arg Trp
            20

<210> SEQ ID NO 167
<211> LENGTH: 22
<212> TYPE: PRT
<213> ORGANISM: Artificial Sequence
<220> FEATURE:
<223> OTHER INFORMATION: Human 878 VH VCI Resiudes

<400> SEQUENCE: 167

Ile Phe Gly Phe Ser Leu Ser Ile Gln Leu Trp Leu Ala Leu Gly Lys
1               5                   10                  15

Thr Val Phe Ala His Trp
            20

<210> SEQ ID NO 168
<211> LENGTH: 22
<212> TYPE: PRT
<213> ORGANISM: Artificial Sequence
<220> FEATURE:
<223> OTHER INFORMATION: Human 29973 VH VCI Resiudes

<400> SEQUENCE: 168

Val Asp Gly Asn Ser Phe Thr Val Gln Leu Trp Met Gly Val Ile Ala
1               5                   10                  15

Arg Ala Phe Ala Ser Trp
            20

<210> SEQ ID NO 169
<211> LENGTH: 22
<212> TYPE: PRT
<213> ORGANISM: Artificial Sequence
<220> FEATURE:
<223> OTHER INFORMATION: Human 46911 VH VCI Resiudes

<400> SEQUENCE: 169

Ser Leu Gly Phe Ser Leu Thr Phe Gln Leu Trp Leu Ala Leu Ile Arg
1               5                   10                  15

Thr Val Tyr Ala Arg Trp
            20

<210> SEQ ID NO 170
<211> LENGTH: 22
<212> TYPE: PRT
<213> ORGANISM: Artificial Sequence
<220> FEATURE:
<223> OTHER INFORMATION: Human AB004303 VH VCI Resiudes

<400> SEQUENCE: 170

Val Ala Gly Phe Thr Val Ser Val Gln Leu Trp Val Ser Phe Ile Arg
1               5                   10                  15

Ile Leu Tyr Ala Thr Trp
            20

<210> SEQ ID NO 171
<211> LENGTH: 22
<212> TYPE: PRT
<213> ORGANISM: Artificial Sequence
<220> FEATURE:
<223> OTHER INFORMATION: Human 40569 VH VCI Resiudes

<400> SEQUENCE: 171

Val Val Gly Gly Ser Val Ser Ile Lys Leu Glu Trp Val Ile Val
1               5                   10                  15

Thr Phe Tyr Ala Arg Trp
            20

<210> SEQ ID NO 172
<211> LENGTH: 22
<212> TYPE: PRT
<213> ORGANISM: Artificial Sequence
<220> FEATURE:
<223> OTHER INFORMATION: Human 32035 VH VCI Resiudes

<400> SEQUENCE: 172

Leu Val Gly Gly Ser Ile Ser Gly Ile Lys Leu Leu Glu Val Ile Val
1               5                   10                  15

Thr Phe Tyr Ala Ser Trp
            20

<210> SEQ ID NO 173
<211> LENGTH: 22
<212> TYPE: PRT
<213> ORGANISM: Artificial Sequence
<220> FEATURE:
<223> OTHER INFORMATION: Human 44473 VH VCI Resiudes

<400> SEQUENCE: 173

Leu Val Gly Gly Ser Ile Ser Gly Ile Lys Leu Glu Trp Val Ile Val
1               5                   10                  15

```
Thr Phe Tyr Ala Arg Trp
            20

<210> SEQ ID NO 174
<211> LENGTH: 22
<212> TYPE: PRT
<213> ORGANISM: Artificial Sequence
<220> FEATURE:
<223> OTHER INFORMATION: Human 329 VH VCI Resiudes

<400> SEQUENCE: 174

Leu Val Gly Gly Ser Ile Ser Gly Ile Lys Leu Glu Trp Val Ile Val
1               5                   10                  15

Thr Ile Tyr Ala Arg Trp
            20

<210> SEQ ID NO 175
<211> LENGTH: 22
<212> TYPE: PRT
<213> ORGANISM: Artificial Sequence
<220> FEATURE:
<223> OTHER INFORMATION: Human 23961 VH VCI Resiudes

<400> SEQUENCE: 175

Leu Val Gly Gly Ser Ile Ser Gly Ile Lys Leu Glu Trp Val Ile Val
1               5                   10                  15

Thr Phe Tyr Ala Ser Trp
            20

<210> SEQ ID NO 176
<211> LENGTH: 22
<212> TYPE: PRT
<213> ORGANISM: Artificial Sequence
<220> FEATURE:
<223> OTHER INFORMATION: Human AJ555264 VH VCI Resiudes

<400> SEQUENCE: 176

Leu Val Gly Gly Ser Ile Ser Gly Ile Lys Leu Glu Trp Val Ile Val
1               5                   10                  15

Thr Phe Tyr Ala Arg Trp
            20

<210> SEQ ID NO 177
<211> LENGTH: 22
<212> TYPE: PRT
<213> ORGANISM: Artificial Sequence
<220> FEATURE:
<223> OTHER INFORMATION: Human 25069 VH VCI Resiudes

<400> SEQUENCE: 177

Val Val Gly Gly Ser Ile Ser Ser Ile Lys Leu Glu Tyr Val Ile Val
1               5                   10                  15

Thr Phe Tyr Ala Arg Trp
            20

<210> SEQ ID NO 178
<211> LENGTH: 22
<212> TYPE: PRT
<213> ORGANISM: Artificial Sequence
<220> FEATURE:
<223> OTHER INFORMATION: Human AJ519242 VH VCI Resiudes

<400> SEQUENCE: 178

Ile Ala Gly Phe Thr Phe Ser Val Gln Pro Trp Val Ser Phe Ile Arg
1               5                   10                  15
```

```
Asp Leu Tyr Val Lys Trp
            20

<210> SEQ ID NO 179
<211> LENGTH: 22
<212> TYPE: PRT
<213> ORGANISM: Artificial Sequence
<220> FEATURE:
<223> OTHER INFORMATION: Human AJ556676 VH VCI Resiudes

<400> SEQUENCE: 179

Leu Val Gly Gly Ser Ile Ser Gly Ile Lys Leu Glu Trp Val Ile Val
 1               5                  10                  15

Thr Phe Tyr Ala Arg Trp
            20

<210> SEQ ID NO 180
<211> LENGTH: 22
<212> TYPE: PRT
<213> ORGANISM: Artificial Sequence
<220> FEATURE:
<223> OTHER INFORMATION: Human AJ556683 VCI Resiudes

<400> SEQUENCE: 180

Val Val Gly Gly Ser Val Ser Thr Val Lys Leu Glu Trp Val Ile Val
 1               5                  10                  15

Thr Phe Phe Ala Ser Trp
            20

<210> SEQ ID NO 181
<211> LENGTH: 22
<212> TYPE: PRT
<213> ORGANISM: Artificial Sequence
<220> FEATURE:
<223> OTHER INFORMATION: Human AJ556687 VH VCI Resiudes

<400> SEQUENCE: 181

Val Val Gly Gly Ser Ile Ser Ser Val Lys Leu Glu Trp Ala Ile Val
 1               5                  10                  15

Lys Phe Tyr Ala Arg Trp
            20

<210> SEQ ID NO 182
<211> LENGTH: 22
<212> TYPE: PRT
<213> ORGANISM: Artificial Sequence
<220> FEATURE:
<223> OTHER INFORMATION: Human AJ556750 VH VCI Resiudes

<400> SEQUENCE: 182

Val Val Gly Ala Ser Ile Thr Ser Ile Lys Leu Glu Trp Val Ile Leu
 1               5                  10                  15

Pro Phe Phe Ala Arg Trp
            20

<210> SEQ ID NO 183
<211> LENGTH: 22
<212> TYPE: PRT
<213> ORGANISM: Artificial Sequence
<220> FEATURE:
<223> OTHER INFORMATION: Human AJ556763 VH VCI Resiudes

<400> SEQUENCE: 183

Val Val Gly Asp Ser Val Thr Ser Ile Gln Leu Glu Trp Leu Ile Glu
 1               5                  10                  15
```

Thr Phe Tyr Ala Ser Trp
            20

<210> SEQ ID NO 184
<211> LENGTH: 22
<212> TYPE: PRT
<213> ORGANISM: Artificial Sequence
<220> FEATURE:
<223> OTHER INFORMATION: Human AJ556770 VH VCI Resiudes

<400> SEQUENCE: 184

Val Val Gly Asp Ser Val Thr Ser Ile Gln Leu Glu Trp Leu Ile Glu
1               5                   10                  15

Thr Phe Tyr Ala Ser Trp
            20

<210> SEQ ID NO 185
<211> LENGTH: 22
<212> TYPE: PRT
<213> ORGANISM: Artificial Sequence
<220> FEATURE:
<223> OTHER INFORMATION: Human U80123 VH VCI Resiudes

<400> SEQUENCE: 185

Val Val Gly Gly Ser Ile Ser Ser Ile Lys Leu Glu Trp Val Ile Val
1               5                   10                  15

Thr Phe Tyr Ala Arg Trp
            20

<210> SEQ ID NO 186
<211> LENGTH: 22
<212> TYPE: PRT
<213> ORGANISM: Artificial Sequence
<220> FEATURE:
<223> OTHER INFORMATION: Human U80175 VH VCI Resiudes

<400> SEQUENCE: 186

Val Val Gly Gly Ser Ile Ser Ser Ile Lys Leu Glu Trp Val Ile Val
1               5                   10                  15

Thr Phe Tyr Ala Arg Trp
            20

<210> SEQ ID NO 187
<211> LENGTH: 22
<212> TYPE: PRT
<213> ORGANISM: Artificial Sequence
<220> FEATURE:
<223> OTHER INFORMATION: Human AJ556768 VH VCI Resiudes

<400> SEQUENCE: 187

Val Val Gly Asp Ser Val Thr Ser Val Gln Leu Glu Trp Leu Ile Glu
1               5                   10                  15

Thr Phe Tyr Ala Ser Trp
            20

<210> SEQ ID NO 188
<211> LENGTH: 22
<212> TYPE: PRT
<213> ORGANISM: Artificial Sequence
<220> FEATURE:
<223> OTHER INFORMATION: Human AJ556769 VH VCI Resiudes

<400> SEQUENCE: 188

Val Val Gly Asp Ser Val Thr Ser Ile Gln Leu Glu Trp Leu Ile Glu
1               5                   10                  15

Thr Phe Tyr Ala Ser Trp
            20

<210> SEQ ID NO 189
<211> LENGTH: 22
<212> TYPE: PRT
<213> ORGANISM: Artificial Sequence
<220> FEATURE:
<223> OTHER INFORMATION: Human U84183 VH VCI Resiudes

<400> SEQUENCE: 189

Val Val Gly Gly Ser Ile Ser Ser Ile Lys Leu Glu Trp Val Ile Val
1               5                   10                  15

Thr Phe Tyr Ala Arg Trp
            20

<210> SEQ ID NO 190
<211> LENGTH: 22
<212> TYPE: PRT
<213> ORGANISM: Artificial Sequence
<220> FEATURE:
<223> OTHER INFORMATION: Human X95746 VH VCI Resiudes

<400> SEQUENCE: 190

Val Val Gly Gly Ser Ile Ser Ser Ile Lys Leu Glu Trp Val Ile Val
1               5                   10                  15

Thr Phe Tyr Ala Arg Trp
            20

<210> SEQ ID NO 191
<211> LENGTH: 22
<212> TYPE: PRT
<213> ORGANISM: Artificial Sequence
<220> FEATURE:
<223> OTHER INFORMATION: Human Y12437 VH VCI Resiudes

<400> SEQUENCE: 191

Val Val Gly Gly Ser Ile Ser Ser Ile Lys Leu Glu Trp Val Ile Val
1               5                   10                  15

Thr Phe Tyr Ala Arg Trp
            20

<210> SEQ ID NO 192
<211> LENGTH: 22
<212> TYPE: PRT
<213> ORGANISM: Artificial Sequence
<220> FEATURE:
<223> OTHER INFORMATION: Human AF376955 VH VCI Resiudes

<400> SEQUENCE: 192

Val Ala Gly Phe Arg Phe Gly Val Gln Leu Trp Val Ser Phe Ile Arg
1               5                   10                  15

Asn Leu Tyr Ala Thr Trp
            20

<210> SEQ ID NO 193
<211> LENGTH: 22
<212> TYPE: PRT
<213> ORGANISM: Artificial Sequence
<220> FEATURE:
<223> OTHER INFORMATION: Human 44497 VH VCI Resiudes

<400> SEQUENCE: 193

Val Ala Gly Phe Thr Phe Ser Val Gln Leu Tyr Ile Ser Val Ile Arg
1               5                   10                  15

Asn Leu Tyr Ala Arg Trp
            20

<210> SEQ ID NO 194
<211> LENGTH: 22
<212> TYPE: PRT
<213> ORGANISM: Artificial Sequence
<220> FEATURE:
<223> OTHER INFORMATION: Human AJ555272 VH VCI Resiudes

<400> SEQUENCE: 194

Ile Phe Gly Phe Ser Leu Ser Ile Gln Leu Trp Leu Ala Leu Ile Lys
1               5                   10                  15

Thr Val Tyr Ala His Trp
            20

<210> SEQ ID NO 195
<211> LENGTH: 22
<212> TYPE: PRT
<213> ORGANISM: Artificial Sequence
<220> FEATURE:
<223> OTHER INFORMATION: Human 29989 VH VCI Resiudes

<400> SEQUENCE: 195

Val Asp Gly Asn Ser Phe Ser Val Gln Leu Trp Met Gly Val Ile Val
1               5                   10                  15

Lys Ala Tyr Ala Arg Trp
            20

<210> SEQ ID NO 196
<211> LENGTH: 22
<212> TYPE: PRT
<213> ORGANISM: Artificial Sequence
<220> FEATURE:
<223> OTHER INFORMATION: Human D11016 VH VCI Resiudes

<400> SEQUENCE: 196

Glu Ala Gly Phe Thr Phe Ser Val Gln Leu Trp Val Gly Phe Ile Arg
1               5                   10                  15

Asp Leu Tyr Thr Thr Trp
            20

<210> SEQ ID NO 197
<211> LENGTH: 22
<212> TYPE: PRT
<213> ORGANISM: Artificial Sequence
<220> FEATURE:
<223> OTHER INFORMATION: Human 40088 VH VCI Resiudes

<400> SEQUENCE: 197

Ala Ala Arg Phe Thr Phe Arg Ile Gln Leu Trp Val Ser Phe Ile Arg
1               5                   10                  15

Asn Leu Tyr Ala Arg Trp
            20

<210> SEQ ID NO 198
<211> LENGTH: 22
<212> TYPE: PRT
<213> ORGANISM: Artificial Sequence
<220> FEATURE:
<223> OTHER INFORMATION: Human 25351 VH VCI Resiudes

<400> SEQUENCE: 198

Leu Val Val Gly Ser Ile Ser Gly Ile Lys Leu Glu Trp Val Ile Val
1               5                   10                  15

```
Thr Phe Phe Ala Arg Trp
                20

<210> SEQ ID NO 199
<211> LENGTH: 118
<212> TYPE: PRT
<213> ORGANISM: Artificial Sequence
<220> FEATURE:
<223> OTHER INFORMATION: AB067248 Acceptor sequence (HB22.7 RHN)

<400> SEQUENCE: 199

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Ser His
            20                  25                  30

Ala Met Gly Trp Val Arg Gln Ala Pro Gly Lys Gly Leu Glu Trp Ile
        35                  40                  45

Ser Gly Val Ser Arg Ser Gly Glu Tyr Thr Phe Tyr Glu Gly Ser Val
    50                  55                  60

Arg Gly Arg Phe Ile Ile Ser Arg Asp Asn Tyr Lys Asn Thr Met Ser
65                  70                  75                  80

Leu Gln Met Tyr Ser Leu Ser Ala Ala Asp Thr Ala Ile Tyr Phe Cys
                85                  90                  95

Val Lys Tyr Asp Thr Asp Pro Val Met Gly Ser Asp Trp Gly Gln Gly
            100                 105                 110

Thr Met Val Thr Val Ser
        115

<210> SEQ ID NO 200
<211> LENGTH: 122
<212> TYPE: PRT
<213> ORGANISM: Artificial Sequence
<220> FEATURE:
<223> OTHER INFORMATION: AJ556642 Acceptor sequence (HB22.7 RHM)

<400> SEQUENCE: 200

Gln Val Gln Leu Glu Glu Ser Gly Gly Gly Val Val Arg Pro Gly Arg
 1               5                  10                  15

Ser Leu Arg Leu Ser Cys Ala Ala Ser Gly Phe Thr Phe Asp Gln Tyr
            20                  25                  30

Ala Ile His Trp Ile Arg Gln Ala Pro Gly Lys Gly Leu Glu Trp Val
        35                  40                  45

Thr Val Ile Ser Pro Val Gly Asn Glu Gln His Tyr Ala Ala Ser Val
    50                  55                  60

Lys Gly Arg Phe Thr Ile Ser Arg Asn Asn Ser Asn Asn Thr Leu Ser
65                  70                  75                  80

Leu Gln Met Asn Ser Leu Thr Thr Glu Asp Thr Ala Val Tyr Tyr Cys
                85                  90                  95

Val Arg Gly Asp Val Val Thr Val Thr Thr Gly Tyr Phe Asp Tyr
            100                 105                 110

Trp Gly Gln Gly Val Leu Val Thr Val Ser
        115                 120

<210> SEQ ID NO 201
<211> LENGTH: 122
<212> TYPE: PRT
<213> ORGANISM: Artificial Sequence
<220> FEATURE:
<223> OTHER INFORMATION: AJ556644 Acceptor sequence (HB22.7 RHL)

<400> SEQUENCE: 201
```

```
Gln Val Gln Leu Glu Glu Ser Gly Gly Val Val Arg Pro Gly Arg
  1               5                  10                  15

Ser Leu Arg Leu Ser Cys Ala Ala Ser Gly Phe Thr Phe Asp Gln Tyr
             20                  25                  30

Ala Ile His Trp Ile Arg Gln Ala Pro Gly Lys Gly Leu Glu Trp Val
         35                  40                  45

Thr Val Ile Ser Pro Val Gly Asn Glu Gln His Tyr Ala Ala Ser Val
     50                  55                  60

Lys Gly Arg Phe Thr Val Ser Arg Asn Asn Ser Asn Asn Thr Leu Ser
 65                  70                  75                  80

Leu Gln Met Asn Ser Leu Thr Thr Glu Asp Thr Ala Val Tyr Tyr Cys
                 85                  90                  95

Val Arg Gly Asp Val Val Thr Thr Val Thr Thr Gly Tyr Phe Asp Tyr
             100                 105                 110

Trp Gly Gln Gly Val Leu Val Thr Val Ser
            115                 120

<210> SEQ ID NO 202
<211> LENGTH: 121
<212> TYPE: PRT
<213> ORGANISM: Artificial Sequence
<220> FEATURE:
<223> OTHER INFORMATION: AF376954 Acceptor Sequence (HB22.7 RHK)

<400> SEQUENCE: 202

Glu Leu Gln Leu Val Glu Ser Gly Gly Gly Phe Val Gln Pro Gly Gly
  1               5                  10                  15

Ser Leu Arg Leu Ser Cys Ala Ala Ser Gly Phe Pro Phe Arg Asn Tyr
             20                  25                  30

Asn Met His Trp Val Arg Gln Gly Pro Gly Lys Gly Leu Val Trp Val
         35                  40                  45

Ser Arg Ile Val Ser Asp Gly Ser Ser Ala Asn Tyr Ala Asp Ser Val
     50                  55                  60

Lys Gly Arg Val Thr Ile Ser Arg Asp Asn Ala Lys Lys Met Val Tyr
 65                  70                  75                  80

Pro Gln Met Asn Ser Leu Arg Ala Glu Asp Thr Ala Met Tyr Tyr Cys
                 85                  90                  95

His Cys Tyr Gly Ser Thr Glu Ser Ser Asp Tyr Tyr Phe Asp Tyr Trp
             100                 105                 110

Gly Gln Gly Thr Leu Val Thr Val Ser
            115                 120
```

US 8,664,363 B2

HUMANIZED ANTI-CD22 ANTIBODIES AND THEIR USE IN TREATMENT OF ONCOLOGY, TRANSPLANTATION AND AUTOIMMUNE DISEASE

This application is a divisional of U.S. application Ser. No. 11/715,307, filed Mar. 6, 2007, now U.S. Pat. No. 8,389,688, which claims priority benefit under 35 U.S.C. §119(e) to U.S. Provisional Application No. 60/779,804 (filed on Mar. 6, 2006), each of which is incorporated by reference herein in its entirety.

One or more inventions disclosed herein were made, in part, with government support under contract number N01-CO-12400 awarded by the National Cancer Institute, National Institutes of Health. The United States Government has certain rights in one or more of the presently disclosed inventions.

1. INTRODUCTION

The present invention relates to human, humanized, or chimeric anti-CD22 antibodies that bind to the human CD22 antigen. The present invention is also directed to compositions comprising human, humanized, or chimeric anti-CD22 antibodies that mediate one or more of the following: complement-dependent cell-mediated cytotoxicity (CDC), antibody-dependent cell-mediated cytotoxicity (ADCC), and programmed cell death (apoptosis). The present invention is further directed to compositions comprising human, humanized, or chimeric anti-CD22 antibodies of the IgG1 and/or IgG3 human isotype, as well as to compositions comprising human, humanized, or chimeric anti-CD22 antibodies of the IgG2 and/or IgG4 human isotype that preferably mediate human ADCC, CDC, or apoptosis.

The present invention is further directed to methods for the treatment of B cell disorders or diseases in human subjects, including B cell malignancies, using the therapeutic human, humanized, or chimeric anti-CD22 antibodies that bind to the human CD22 antigen. The present invention is directed to methods for the treatment and prevention of autoimmune disease as well as the treatment and prevention of graft-versus-host disease (GVHD), humoral rejection, and post-transplantation lymphoproliferative disorder in human transplant recipients using the therapeutic human, humanized, or chimeric anti-CD22 antibodies of the invention that bind to the human CD22 antigen.

2. BACKGROUND OF THE INVENTION

The proliferation and differentiation of B cells is a complex process directed and regulated through interactions with many other cell types. In this context, B cell surface markers have been generally suggested as targets for the treatment of B cell disorders or diseases, autoimmune disease, and transplantation rejection. Examples of B cell surface markers include CD10, CD19, CD20, CD21, CD22, CD23, CD24, CD37, CD53, CD72, CD74, CD75, CD77, CD79a, CD79b, CD80, CD81, CD82, CD83, CD84, CD85, and CD86 leukocyte surface markers. Antibodies that specifically bind these markers have been developed, and some have been tested for the treatment of diseases and disorders.

For example, chimeric or radiolabeled monoclonal antibody (mAb)-based therapies directed against the CD20 cell surface molecule specific for mature B cells and their malignant counterparts have been shown to be an effective in vivo treatment for non-Hodgkin's lymphoma (Tedder et al., *Immunol. Today* 15:450-454 (1994); Press et al., *Hematology:* 221-240 (2001); Kaminski et al., *N. Engl. J. Med.* 329:459-465 (1993); Weiner, *Semin. Oncol.* 26:43-51 (1999); Onrust et al., *Drugs* 58:79-88 (1999); McLaughlin et al., *Oncology* 12:1763-1769 (1998); Reff et al., *Blood* 83:435-445 (1994); Maloney et al., *Blood* 90:2188-2195 (1997); Malone et al., *J. Clin. Oncol.* 15:3266-3274 (1997); Anderson et al., *Biochem. Soc. Transac.* 25:705-708 (1997)). Anti-CD20 monoclonal antibody therapy has also been found to be partially effective in attenuating the manifestations of rheumatoid arthritis, systemic lupus erythematosus, idiopathic thrombocytopenic purpura and hemolytic anemia, as well as other immune-mediated diseases (Silverman et al., *Arthritis Rheum.* 48:1484-1492 (2002); Edwards et al., *Rheumatology* 40:1-7 (2001); De Vita et al., *Arthritis Rheumatism* 46:2029-2033 (2002); Leandro et al., *Ann. Rheum. Dis.* 61:883-888 (2002); Leandro et al., *Arthritis Rheum.* 46:2673-2677 (2001)). The anti-CD20 (IgG1) antibody, RITUXAN™, has successfully been used in the treatment of certain diseases such as adult immune thrombocytopenic purpura, rheumatoid arthritis, and autoimmune hemolytic anemia (Cured et al., WO 00/67796). Despite the effectiveness of these therapies, B cell depletion is less effective where B cells do not express or express CD20 at low levels, (e.g., on pre-B cells or immature B cells) or have lost CD20 expression following CD20 immunotherapy (Smith et al., *Oncogene* 22:7359-7368 (2003)).

Anti-CD22 antibodies have been described, for example, in U.S. Pat. Nos. 5,484,892; 6,183,744; 6,187,287; 6,254,868; 6,306,393, and in Tuscano et al., *Blood* 94(4):1382-92 (1999) (each of which is incorporated herein in its entirety by reference). The use of monoclonal antibodies, including anti-CD22 antibodies, in the treatment of non-Hodgkin's lymphoma is reviewed, for example, by Renner et al., *Leukemia* 11(Suppl. 2):S5509 (1997).

The use of humanized CD22 antibodies has been described for the treatment of autoimmune disorders (see, Tedder U.S. Patent Application Publication No. US2003/0202975) and for the treatment of B cell malignancies, such as lymphomas and leukemia (see, Tuscano U.S. Patent Application Publication No. U.S. 2004/0001828). Humanized CD22 antibodies that target specific epitopes on CD22 have been described for use in immunoconjugates for therapeutic uses in cancer (see U.S. Pat. Nos. 5,789,554 and 6,187,287 to Leung).

Epratuzumab (LymoCide™ Immunomedics, Inc.), a humanized version of the murine LL2, is under development for the treatment of non-Hodgkin's lymphomas (Coleman, Clin. Cancer Res. 9:39915-45 (2003)). A DOTA-conjugated $^{90}$Y-radiolabeled form of Epratuzumab is currently in Phase III clinical trials for the treatment of indolent and aggressive forms of non-Hodgkin's lymphomas (Linden et al., *Clin Cancer Res II* (14):5215-5222 (2005)). Epratuzumab in combination with Rituximab is currently in Phase II clinical trials for the same indication.

Despite recent advances in cancer therapy, B cell malignancies, such as the B cell subtypes of non-Hodgkin's lymphomas, and chronic lymphocytic leukemia, are major contributors of cancer-related deaths. Accordingly, there is a great need for further, improved therapeutic regimens for the treatment of B cell malignancies.

Both cellular (T cell-mediated) and humoral (antibody, B cell-mediated) immunity are now known to play significant roles in graft rejection. While the importance of T cell-mediated immunity in graft rejection is well established, the critical role of humoral immunity in acute and chronic rejection has only recently become evident. Consequently, most of the advances in the treatment and prevention of graft rejection have developed from therapeutic agents that target T cell activation. The first therapeutic monoclonal antibody that was FDA approved for the treatment of graft rejection was the murine monoclonal antibody ORTHOCLONE-OKT3™ (muromonab-CD3), directed against the CD3 receptor of T cells. OKT3 has been joined by a number of other anti-lymphocyte directed antibodies, including the monoclonal anti-CD52 CAMPATH™ antibodies, CAMPATH-1G, CAMPATH-1H (alemtuzumab), and CAMPATH-1M), and polyclonal anti-thymocyte antibody preparations (referred to as anti-thymocyte globulin, or "ATG," also called "thymoglobin" or "thymoglobulin"). Other T cell antibodies approved for the prevention of transplant rejection include the chimeric monoclonal antibody SIMULECTT™ (basiliximab) and the humanized monoclonal antibody ZENAPAX™ (daclizumab), both of which target the high-affinity IL-2 receptor of activated T cells.

The importance of humoral immunity in graft rejection was initially thought to be limited to hyperacute rejection, in which the graft recipient possesses anti-donor HLA antibodies prior to transplantation, resulting in rapid destruction of the graft in the absence of an effective therapeutic regimen of antibody suppression. Recently, it has become evident that humoral immunity is also an important factor mediating both acute and chronic rejection. For example, clinical observations demonstrated that graft survival in patients capable of developing class I or class II anti-HLA alloantibodies (also referred to as "anti-MHC alloantibodies") was reduced compared to graft survival in patients that could not develop such antibodies. Clinical and experimental data also indicate that other donor-specific alloantibodies and autoantibodies are critical mediators of rejection. For a current review of the evidence supporting a role for donor-specific antibodies in allograft rejection, see Rifle et al., *Transplantation,* 79:S14-S18 (2005). Thus, due to the relatively recent appreciation of the role of humoral immunity in acute and chronic graft rejection, current therapeutic agents and strategies for targeting humoral immunity are less well developed than those for targeting cellular immunity. Accordingly, there is a need in the art for improved reagents and methods for treating and preventing graft rejection, i.e. graft-versus-host disease (GVHD), humoral rejection, and post-transplantation lymphoproliferative disorder in human transplant recipients.

Autoimmune diseases as a whole cause significant morbidity and disability. Based on incidence data collected from 1965 to 1995, it has been estimated that approximately 1.2 million persons will develop a new autoimmune disease over the next five years. Jacobsen et al. (*Clin Immunol. Immunopathol.* 84:223 (1997)) evaluated over 130 published studies and estimated that in 1996, 8.5 million people in the United States (3.2% of the population) had at least one of the 24 autoimmune diseases examined in these studies. Considering the major impact of autoimmune diseases on public health, effective and safe treatments are needed to address the burden of these disorders. Thus, there is a need in the art for improved reagents and methods for treating autoimmune disease.

3. SUMMARY OF THE INVENTION

The invention relates to chimeric, human, and humanized anti-CD22 monoclonal antibodies that comprise a heavy chain and a light chain, wherein the heavy chain variable region comprises three complementarity determining regions, CDR1, CDR2, and CDR3, and four framework regions, FW1, FW2, FW3, and FW4, in the order FW1-CDR1-FW2-CDR2-FW3-CDR3-FW4, and wherein CDR1 comprises the amino acid sequence DYGVN (SEQ ID NO:62), CDR2 comprises the amino acid sequence IIWGDGRTDYNSALKS (SEQ ID NO:63), and CDR3 comprises the amino acid sequence APGNRAMEY (SEQ ID NO:64).

In certain embodiments, FW1 of the heavy chain variable region of the monoclonal antibodies of the present invention comprises the amino acid sequence QVQLQESGPALVKPTQTLTLTCTFSGFSLS (SEQ ID NO:73) or QVQLQESGPALVKPTQTLTLTCTVSGFSLS (SEQ ID NO:74), FW2 comprises the amino acid sequence WIRQPPGKALEWLA (SEQ ID NO:75) or WIRQPPGKALEWLG (SEQ ID NO:76), FW3 comprises the amino acid sequence RLSISKDTSKNQVVLRMTNVDPVDTATYFCAR (SEQ ID NO:77) or RLSISKDNSKNQVVLRMTNVDPVDTATYFCAR (SEQ ID NO:78). In a particular aspect of each of theses embodiments, FW4 comprises the amino acid sequence WGQGTVVTVSS (SEQ ID NO:79).

The present invention is also directed in one aspect to a humanized anti-CD22 monoclonal antibody in which CDR1 comprises the amino acid sequence DYGVN (SEQ ID NO:62), CDR2 comprises the amino acid sequence IIWGDGRTDYNSALKS (SEQ ID NO:63), and CDR3 comprises the amino acid sequence APGNRAMEY (SEQ ID NO:64), while FW1 comprises the amino acid sequence QVQLQESGPALVKPTQTLTLTCTVSGFSLS (SEQ ID NO:74), FW2 comprises the amino acid sequence WIRQPPGKALEWLG (SEQ ID NO:76), FW3 comprises the amino acid RLSISKDNSKNQVVLRMTNVDPVDTATYFCAR (SEQ ID NO:78), and FW4 comprises the amino acid sequence WGQGTVVTVSS (SEQ ID NO:79).

In certain embodiments, FW1 of the heavy chain variable region of the monoclonal antibodies of the present invention comprises the amino acid sequence QVQLEESGGGVVRPGRSLRLSCAASGFTFD (SEQ ID NO:80), QVQLEESGGGVVRPGRSLRLSCAASGFTFS (SEQ ID NO:81), QVQLEESGGGVVRPGRSLRLSCAASGFTLD (SEQ ID NO:82), or QVQLEESGGGVVRPGRSLRLSCAASGFTLS (SEQ ID NO:83), FW2 comprises an amino acid sequence WIRQAPGKGLEWVT (SEQ ID NO:84) or WIRQAPGKGLEWVG (SEQ ID NO:85), FW3 comprises the amino acid sequence RFTVSRNNSNNTLSLQMNSLTTEDTAVYYCVR (SEQ ID NO:86) or RLTVSRNNSNNTLSLQMNSLTTEDTAVYYCVR (SEQ ID NO:87). In a particular aspect of each of theses embodiments, FW4 comprises the amino acid sequence WGQGVLVTVS (SEQ ID NO:88).

The present invention is further directed in one aspect to a humanized anti-CD22 monoclonal antibody in which CDR1 comprises the amino acid sequence DYGVN (SEQ ID NO:62), CDR2 comprises the amino acid sequence IIWGDGRTDYNSALKS (SEQ ID NO:63), and CDR3 comprises the amino acid sequence APGNRAMEY (SEQ ID NO:64), while FW1 comprises the amino acid sequence QVQLEESGGGVVRPGRSLRLSCAASGFTLS (SEQ ID NO:83), FW2 comprises the amino acid sequence WIRQAPGKGLEWVG (SEQ ID NO:85), FW3 comprises the amino acid RLTVSRNNSNNTLSLQMNSLTTEDTAVYYCVR (SEQ ID NO:87), and FW4 comprises the amino acid sequence WGQGVLVTVS (SEQ ID NO:88).

In still another aspect of this embodiment, the present invention is further directed in one aspect to a humanized anti-CD22 monoclonal antibody in which CDR1 comprises the amino acid sequence DYGVN (SEQ ID NO:62), CDR2 comprises the amino acid sequence IIWGDGRTDYNSALKS (SEQ ID NO:63), and CDR3 comprises the amino acid sequence APGNRAMEY (SEQ ID NO:64), while FW1 comprises the amino acid sequence QVQLEESGGGVVRPGRSLRLSCAASGFTFS (SEQ ID NO:81), FW2 comprises the amino acid sequence WIRQAPGKGLEWVT (SEQ ID NO:84), FW3 comprises the amino acid RFTVSRNNSNNTLSLQMNSLTTEDTAVYYCVR (SEQ ID NO:86), and FW4 comprises the amino acid sequence WGQGVLVTVS (SEQ ID NO:88).

The humanized anti-CD22 monoclonal antibodies of the present invention also include those in which FW3 of the heavy chain variable region of the monoclonal antibodies of the present invention comprises the amino acid sequence of RLIISRDNYKNTMSLQMYSLSAADTAIYFCVK (SEQ ID NO:89), RFNISRDNYKNTMSLQMYSLSAADTAIYFCVK (SEQ ID NO:90), RFIISRDNYKNTNSLQMYSLSAADTAIYFCVK (SEQ ID NO:91), RLNISRDNYKNTMSLQMYSLSAADTAIYFCVK (SEQ ID NO:92), RLIISRDNYKNTNSLQMYSLSAADTAIYFCVK (SEQ ID NO:93), RFNISRDNYKNTNSLQMYSLSAADTAIYFCVK (SEQ ID NO:94), or RLNISRDNYKNTNSLQMYSLSAADTAIYFCVK (SEQ ID NO:95). The humanized anti-CD22 monoclonal antibodies of the invention therefore include a humanized monoclonal antibody in which the heavy chain variable regions includes FW1 comprises the amino acid sequence EVQLVESGGGLVQPGGSLRLSCAASGFTFS (SEQ ID NO:96), FW2 comprises the amino acid sequence WVRQAPGKGLEWIS (SEQ ID NO:97), FW3 comprises the amino acid sequence RFIISRDNYKNTMSLQMYSLSAADTAIYFCVK (SEQ ID NO:98), and FW4 comprises the amino acid sequence WGQGTMVTVS (SEQ ID NO:99).

The humanized anti-CD22 monoclonal antibodies of the present invention also include those in which FW1 of the heavy chain variable region of the monoclonal antibodies of the present invention comprises the amino acid sequence QVQLEESGGGVVRPGRSLRLSCAASGFTFD (SEQ ID NO:80), QVQLEESGGGVVRPGRSLRLSCAASGFTLD (SEQ ID NO:82), QVQLEESGGGVVRPGRSLRLSCAASGFTFS (SEQ ID NO:81), or QVQLEESGGGVVRPGRSLRLSCAASGFTLS (SEQ ID NO:83); FW2 comprises the amino acid sequence WIRQAPGKGLEWVT (SEQ ID NO:84) or WIRQAPGKGLEWVG (SEQ ID NO:85); FW3 comprises the amino acid sequence RFTISRNNSNNTLSLQMNSLTTEDTAVYYCVR (SEQ ID NO:100) or RLTISRNNSNNTLSLQMNSLTTEDTAVYYCVR (SEQ ID NO:101). In a particular aspect of each of theses embodiments, FW4 comprises the amino acid sequence WGQGVLVTVS (SEQ ID NO:88).

The humanized anti-CD22 monoclonal antibodies of the invention therefore include a humanized monoclonal antibody in which the heavy chain variable region includes framework regions in which FW1 comprises the amino acid sequence QVQLEESGGGVVRPGRSLRLSCAASGFTFS (SEQ ID NO:81), FW2 comprises the amino acid sequence WIRQAPGKGLEWVT (SEQ ID NO:84), FW3 comprises the amino acid sequence RFTISRNNSNNTLSLQMNSLTTEDTAVYYCVR (SEQ ID NO:100), and FW4 comprises the amino acid sequence WGQGVLVTVS (SEQ ID NO:88).

The humanized anti-CD22 monoclonal antibodies of the present invention also include those in which FW1 of the heavy chain variable region of the monoclonal antibodies of the present invention comprises the amino acid sequence QVQLEESGGGVVRPGRSLRLSCAASGFTFD (SEQ ID NO:80), QVQLEESGGGVVRPGRSLRLSCAASGFTLD (SEQ ID NO:82), QVQLEESGGGVVRPGRSLRLSCAASGFTFS (SEQ ID NO:81), or QVQLEESGGGVVRPGRSLRLSCAASGFTLS (SEQ ID NO:83); FW2 comprises the amino acid sequence WIRQAPGKGLEWVT (SEQ ID NO:84) or WIRQAPGKGLEWVG (SEQ ID NO:85); FW3 comprises the amino acid sequence RFTVSRNNSNNTLSLQMNSLTTEDTAVYYCVR (SEQ ID NO:86) or RLTVSRNNSNNTLSLQMNSLTTEDTAVYYCVR (SEQ ID NO:87). In a particular aspect of each of theses embodiments, FW4 comprises the amino acid sequence WGQGVLVTVS (SEQ ID NO:88).

The humanized anti-CD22 monoclonal antibodies of the invention therefore include a humanized monoclonal antibody in which the heavy chain variable region includes FW1 which comprises the amino acid sequence QVQLEESGGGVVRPGRSLRLSCAASGFTFS (SEQ ID NO:81), FW2 comprises the amino acid sequence WIRQAPGKGLEWVT (SEQ ID NO:84), FW3 comprises the amino acid sequence RFTVSRNNSNNTLSLQMNSLTTEDTAVYYCVR (SEQ ID NO:86), and FW4 comprises the amino acid sequence WGQGVLVTVS (SEQ ID NO:88).

The humanized anti-CD22 monoclonal antibodies of the present invention also include those in which FW1 of the heavy chain variable region of the monoclonal antibodies of the present invention comprises the amino acid sequence ELQLVESGGGFVQPGGSLRLSCAASGFPFR (SEQ ID NO:102), ELQLVESGGGFVQPGGSLRLSCAASGFPLR (SEQ ID NO:103), ELQLVESGGGFVQPGGSLRLSCAASGFPFS (SEQ ID NO:104), or ELQLVESGGGFVQPGGSLRLSCAASGFPLS (SEQ ID NO:105); FW2 comprises the amino acid sequence WVRQGPGKGLVWVS (SEQ ID NO:116); FW3 comprises the amino acid sequence RVTISRDNAKKMVYPQMNSLRAEDTAMYYCHC (SEQ ID NO:106), RVTISRDNAKKMVYPQMNSLRAEDTAMYYCHR (SEQ ID NO:107), RVTISRDNAKKMVYPQMNSLRAEDTAMYYCHK (SEQ ID NO:108), RVTISRDNAKKMVYPQMNSLRAEDTAMYYCVC (SEQ ID NO:109), RVTISRDNAKKMVYPQMNSLRAEDTAMYYCVR (SEQ ID NO:110), RVTISRDNAKKMVYPQMNSLRAEDTAMYYCVK (SEQ ID NO:111), RVTISRDNAKKMVYPQMNSLRAEDTAMYYCAC (SEQ ID NO:112), RVTISRDNAKKMVYPQMNSLRAEDTAMYYCAR (SEQ ID NO:113), or RVTISRDNAKKMVYPQMNSLRAEDTAMYYCAK (SEQ ID NO:114). In a particular aspect of each of theses embodiments, FW4 comprises the amino acid sequence WGQGTLVTVS (SEQ ID NO:115).

The humanized anti-CD22 monoclonal antibodies of the invention therefore include a humanized monoclonal antibody in which the heavy chain variable region includes FW1 which comprises the amino acid sequence ELQLVESGGGFVQPGGSLRLSCAASGFPFS (SEQ ID NO:104), FW2 comprises the amino acid sequence WVRQGPGKGLVWVS (SEQ ID NO:116), FW3 comprises the amino acid sequence RVTISRDNAKKMVYPQMNSLRAEDTAMYYCHC (SEQ ID NO:106), and FW4 comprises the amino acid sequence WGQGTLVTVS (SEQ ID NO:115).

The present invention also relates to chimeric, human, and humanized anti-CD22 monoclonal antibodies in which the light chain variable region comprises three complementarity determining regions, CDR1, CDR2, and CDR3, and four framework regions, FW1, FW2, FW3, and FW4, in the order FW1-CDR1-FW2-CDR2-FW3-CDR3-FW4, wherein CDR1 comprises the amino acid sequence KASQSVTNDVA (SEQ ID NO:65), CDR2 comprises the amino acid sequence YASNRYT (SEQ ID NO:66), and CDR3 comprises the amino acid sequence QQDYRSPWT (SEQ ID NO:67). In particular aspects, humanized anti-CD22 monoclonal antibodies of the invention include a light chain variable region in which FW1 comprises the amino acid sequence DIVMTQSPSSLSASVGDRVTITC (SEQ ID NO:117); those in which FW2 comprises the amino acid sequence WYQQKPGKAPKLLIY (SEQ ID NO:118); those in which FW3 comprises the amino acid sequence GVPSRFSGSGSGTDFTLTISSLQPEDFA-TYYC (SEQ ID NO:119), GVPDRFSGSGSGTDFTLTISSLQPEDFATYYC (SEQ ID NO:120), GVPSRFSGSGYGTDFTLTISSLQPEDFATYYC (SEQ ID NO:121), GVPSRFSGSGSGTDFTLTISSLQPEDFATYFC (SEQ ID NO:122), GVPDRFSGSGYGTDFTLTISSLQPEDFATYYC (SEQ ID NO:123), GVPDRFSGSGSGTDFTLTISSLQPEDFATYFC (SEQ ID NO:124), GVPSRFSGSGYGTDFTLTISSLQPEDFATYFC (SEQ ID NO:125), or GVPDRFSGSGYGTDFTLTISSLQPEDFATYFC (SEQ ID NO:126); and those in which FW4 comprises the amino acid sequence FGGGTKVEIKRT (SEQ ID NO:127).

The present invention further relates to a humanized anti-CD22 monoclonal antibody in which the light chain variable region comprises three complementarity determining regions, CDR1, CDR2, and CDR3, and four framework regions, FW1, FW2, FW3, and FW4, in the order FW1-CDR1-FW2-CDR2-FW3-CDR3-FW4, wherein CDR1 comprises the amino acid sequence KASQSVTNDVA (SEQ ID NO:65), CDR2 comprises the amino acid sequence YASNRYT (SEQ ID NO:66), and CDR3 comprises the amino acid sequence QQDYRSPWT (SEQ ID NO:67), while FW1 comprises the amino acid sequence DIVMTQSPSSLSASVGDRVTITC (SEQ ID NO:117), FW2 comprises the amino acid sequence WYQQKPGKAPKLLIY (SEQ ID NO:118); FW3 comprises the amino acid sequence GVPSRFSGSGSGTDFTLTISSLQPEDFATYYC (SEQ ID NO:119), and FW4 comprises the amino acid sequence FGGGTKVEIKRT (SEQ ID NO:127).

The present invention also relates to a humanized anti-CD22 monoclonal antibody in which the light chain variable region comprises three complementarity determining regions, CDR1, CDR2, and CDR3, and four framework regions, FW1, FW2, FW3, and FW4, in the order FW1-CDR1-FW2-CDR2-FW3-CDR3-FW4, wherein CDR1 comprises the amino acid sequence KASQSVTNDVA (SEQ ID NO:65), CDR2 comprises the amino acid sequence YASNRYT (SEQ ID NO:66), and CDR3 comprises the amino acid sequence QQDYRSPWT (SEQ ID NO:67), while FW1 comprises the amino acid sequence DIVMTQSPSSLSASVGDRVTITC (SEQ ID NO:117), FW2 comprises the amino acid sequence WYQQKPGKAPKLLIY (SEQ ID NO:118); FW3 comprises the amino acid sequence GVPSRFSGSGSGTDFTLTISSLQPEDFATYFC (SEQ ID NO:122), and FW4 comprises the amino acid sequence FGGGTKVEIKRT (SEQ ID NO:127).

The present invention still further relates to a humanized anti-CD22 monoclonal antibody in which the light chain variable region comprises three complementarity determining regions, CDR1, CDR2, and CDR3, and four framework regions, FW1, FW2, FW3, and FW4, in the order FW1-CDR1-FW2-CDR2-FW3-CDR3-FW4, wherein CDR1 comprises the amino acid sequence KASQSVTNDVA (SEQ ID NO:65), CDR2 comprises the amino acid sequence YASNRYT (SEQ ID NO:66), and CDR3 comprises the amino acid sequence QQDYRSPWT (SEQ ID NO:67), while FW1 comprises the amino acid sequence DIVMTQSPSSLSASVGDRVTITC (SEQ ID NO:117), FW2 comprises the amino acid sequence WYQQKPGKAPKLLIY (SEQ ID NO:118); FW3 comprises the amino acid sequence GVPDRFSGSGYGTDFTLTISSLQPEDFATYFC (SEQ ID NO:126), and FW4 comprises the amino acid sequence FGGGTKVEIKRT (SEQ ID NO:127).

The present invention also relates to humanized anti-CD22 monoclonal antibodies comprising a heavy chain and a light chain, in which the heavy chain variable region includes CDR1, comprising the amino acid sequence DYGVN (SEQ ID NO:62); CDR2, comprising the amino acid sequence IIWGDGRTDYNSALKS (SEQ ID NO:63); CDR3, comprising the amino acid sequence APGNRAMEY (SEQ ID NO:64), and heavy chain framework regions FW1-FW4 selected from those disclosed above; and a light chain, in which the light chain variable region includes CDR1, comprising the amino acid sequence KASQSVTNDVA (SEQ ID NO:65); CDR2, comprising the amino acid sequence YASNRYT (SEQ ID NO:66); CDR3, comprising the amino acid sequence QQDYRSPWT (SEQ ID NO:67); and light chain framework regions FW1-FW4 selected from those disclosed above.

The chimeric, human, and humanized anti-CD22 monoclonal antibodies of the present invention include those of the IgG1, IgG2, IgG3, or IgG4 human isotype.

The present invention further relates to pharmaceutical compositions comprising the chimeric, human, and humanized anti-CD22 antibodies of the invention.

In still another other aspect, the present invention is directed toward a method of treating a B cell malignancy in a human, comprising administering to a human in need thereof a therapeutically-effective amount of a chimeric, human, or humanized anti-CD22 monoclonal antibody of the invention.

In a further aspect, the present invention relates to a method of treating an autoimmune disease or disorder in a human, comprising administering to a human in need thereof a therapeutically-effective amount of a chimeric, human, or humanized anti-CD22 monoclonal antibody of the invention.

The present invention further relates to a method of treating or preventing humoral rejection in a human transplant patient, comprising administering to a human in need thereof a therapeutically-effective amount of a chimeric, human, or humanized anti-CD22 monoclonal antibody of the invention.

3.1. Definitions

As used herein, the terms "antibody" and "antibodies" (immunoglobulins) refer to monoclonal antibodies (including full-length monoclonal antibodies), polyclonal antibodies, multispecific antibodies (e.g., bispecific antibodies) formed from at least two intact antibodies, human antibodies, humanized antibodies, camelised antibodies, chimeric antibodies, single-chain Fvs (scFv), single-chain antibodies, single domain antibodies, domain antibodies, Fab fragments, F(ab')$_2$ fragments, antibody fragments that exhibit the desired biological activity, disulfide-linked Fvs (sdFv), and anti-idiotypic (anti-Id) antibodies (including, e.g., anti-Id antibodies to antibodies of the invention), intrabodies, and epitope-binding fragments of any of the above. In particular, antibodies include immunoglobulin molecules and immunologically active fragments of immunoglobulin molecules, i.e., molecules that contain an antigen-binding site. Immunoglobulin molecules can be of any type (e.g., IgG, IgE, IgM, IgD, IgA and IgY), class (e.g., IgG1, IgG2, IgG3, IgG4, IgA1 and IgA2) or subclass.

Native antibodies are usually heterotetrameric glycoproteins of about 150,000 daltons, composed of two identical light (L) chains and two identical heavy (H) chains. Each light chain is linked to a heavy chain by one covalent disulfide bond, while the number of disulfide linkages varies between the heavy chains of different immunoglobulin isotypes. Each heavy and light chain also has regularly spaced intrachain disulfide bridges. Each heavy chain has at one end a variable domain (VH) followed by a number of constant domains. Each light chain has a variable domain at one end (VL) and a constant domain at its other end; the constant domain of the light chain is aligned with the first constant domain of the heavy chain, and the light chain variable domain is aligned with the variable domain of the heavy chain. Particular amino acid residues are believed to form an interface between the light and heavy chain variable domains. Such antibodies may be derived from any mammal, including, but not limited to, humans, monkeys, pigs, horses, rabbits, dogs, cats, mice, etc.

The term "variable" refers to the fact that certain portions of the variable domains differ extensively in sequence among antibodies and are responsible for the binding specificity of each particular antibody for its particular antigen. However, the variability is not evenly distributed through the variable domains of antibodies. It is concentrated in segments called Complementarity Determining Regions (CDRs) both in the light chain and the heavy chain variable domains. The more highly conserved portions of the variable domains are called the framework regions (FW). The variable domains of native heavy and light chains each comprise four FW regions, largely adopting a β-sheet configuration, connected by three CDRs, which form loops connecting, and in some cases forming part of, the β-sheet structure. The CDRs in each chain are held together in close proximity by the FW regions and, with the CDRs from the other chain, contribute to the formation of the antigen-binding site of antibodies (see, Kabat et al., *Sequences of Proteins of Immunological Interest,* 5th Ed. Public Health Service, National Institutes of Health, Bethesda, Md. (1991)). The constant domains are generally not involved directly in antigen binding, but may influence antigen binding affinity and may exhibit various effector functions, such as participation of the antibody in ADCC, CDC, and/or apoptosis.

The term "hypervariable region" when used herein refers to the amino acid residues of an antibody which are associated with its binding to antigen. The hypervariable regions encompass the amino acid residues of the "complementarity determining regions" or "CDRs" (e.g., residues 24-34 (L1), 50-56 (L2) and 89-97 (L3) of the light chain variable domain and residues 31-35 (H1), 50-65 (H2) and 95-102 (H3) of the heavy chain variable domain; Kabat et al., *Sequences of Proteins of Immunological Interest,* 5th Ed. Public Health Service, National Institutes of Health, Bethesda, Md. (1991)) and/or those residues from a "hypervariable loop" (e.g., residues 26-32 (L1), 50-52 (L2) and 91-96 (L3) in the light chain variable domain and 26-32 (H1), 53-55 (H2) and 96-101 (H3) in the heavy chain variable domain; Chothia and Lesk, *J. Mol. Biol.,* 196:901-917 (1987)). "Framework" or "FW" residues are those variable domain residues flanking the CDRs. FW residues are present in chimeric, humanized, human, domain antibodies, diabodies, vaccibodies, linear antibodies, and bispecific antibodies.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations which typically include different antibodies directed against different determinants (epitopes), each monoclonal antibody is directed against a single determinant on the antigen. In addition to their specificity, the monoclonal antibodies are advantageous in that they are synthesized by hybridoma cells that are uncontaminated by other immunoglobulin producing cells. Alternatively, the monoclonal antibody may be produced by cells stably or transiently transfected with the heavy and light chain genes encoding the monoclonal antibody.

The modifier "monoclonal" indicates the character of the antibody as being obtained from a substantially homogeneous population of antibodies, and is not to be construed as requiring engineering of the antibody by any particular method. The term "monoclonal" is used herein to refer to an antibody that is derived from a clonal population of cells, including any eukaryotic, prokaryotic, or phage clone, and not the method by which the antibody was engineered. For example, the monoclonal antibodies to be used in accordance with the present invention may be made by the hybridoma method first described by Kohler et al., *Nature,* 256:495 (1975), or may be made by any recombinant DNA method (see, e.g., U.S. Pat. No. 4,816,567), including isolation from phage antibody libraries using the techniques described in Clackson et al., *Nature,* 352:624-628 (1991) and Marks et al., *J. Mol. Biol.,* 222:581-597 (1991), for example. These methods can be used to produce monoclonal mammalian, chimeric, humanized, human, domain antibodies, diabodies, vaccibodies, linear antibodies, and bispecific antibodies.

The term "chimeric" antibodies includes antibodies in which at least one portion of the heavy and/or light chain is identical with or homologous to corresponding sequences in antibodies derived from a particular species or belonging to a particular antibody class or subclass, and at least one other portion of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; Morrison et al., *Proc. Natl. Acad. Sci. USA,* 81:6851-6855 (1984)). Chimeric antibodies of interest herein include "primatized" antibodies comprising variable domain antigen-binding sequences derived from a nonhuman primate (e.g., Old World Monkey, such as baboon, rhesus or cynomolgus monkey) and human constant region sequences (U.S. Pat. No. 5,693,780).

"Humanized" forms of nonhuman (e.g., murine) antibodies are chimeric antibodies that contain minimal sequence derived from nonhuman immunoglobulin. For the most part, humanized antibodies are human immunoglobulins (recipient antibody) in which the native CDR residues are replaced by residues from the corresponding CDR of a nonhuman species (donor antibody) such as mouse, rat, rabbit or nonhuman primate having the desired specificity, affinity, and capacity. In some instances, one or more FW region residues of the human immunoglobulin are replaced by corresponding nonhuman residues. Furthermore, humanized antibodies may comprise residues that are not found in the recipient antibody or in the donor antibody. These modifications are made to further refine antibody performance. In general, a humanized antibody heavy or light chain will comprise substantially all of at least one or more variable domains, in which all or substantially all of the CDRs correspond to those of a non-human immunoglobulin and all or substantially all of the FWs are those of a human immunoglobulin sequence. In certain embodiments, the humanized antibody will comprise at least a portion of an immunoglobulin constant region (Fc), typically that of a human immunoglobulin. For further details, see, Jones et al., *Nature,* 321:522-525 (1986); Riechmann et al., *Nature,* 332:323-329 (1988); and Presta, *Curr. Op. Struct. Biol.,* 2:593-596 (1992).

A "human antibody" can be an antibody derived from a human or an antibody obtained from a transgenic organism that has been "engineered" to produce specific human antibodies in response to antigenic challenge and can be produced by any method known in the art. In certain techniques, elements of the human heavy and light chain loci are introduced into strains of the organism derived from embryonic stem cell lines that contain targeted disruptions of the endogenous heavy chain and light chain loci. The transgenic organism can synthesize human antibodies specific for human antigens, and the organism can be used to produce human antibody-secreting hybridomas. A human antibody can also be an antibody wherein the heavy and light chains are encoded by a nucleotide sequence derived from one or more sources of human DNA. A fully human antibody also can be constructed by genetic or chromosomal transfection methods, as well as phage display technology, or in vitro activated B cells, all of which are known in the art.

"Antibody-dependent cell-mediated cytotoxicity" and "ADCC" refer to a cell-mediated reaction in which non-specific cytotoxic cells (e.g., Natural Killer (NK) cells, neutrophils, and macrophages) recognize bound antibody on a target cell and subsequently cause lysis of the target cell. In one embodiment, such cells are human cells. While not wishing to be limited to any particular mechanism of action, these cytotoxic cells that mediate ADCC generally express Fc receptors (FcRs). The primary cells for mediating ADCC, NK cells, express FcγRIII, whereas monocytes express FcγRI, FcγRII, FcγRIII and/or FcγRIV. FcR expression on hematopoietic cells is summarized in Ravetch and Kinet, *Annu. Rev. Immunol.*, 9:457-92 (1991). To assess ADCC activity of a molecule, an in vitro ADCC assay, such as that described in U.S. Pat. No. 5,500,362 or 5,821,337 may be performed. Useful effector cells for such assays include peripheral blood mononuclear cells (PBMC) and Natural Killer (NK) cells. Alternatively, or additionally, ADCC activity of the molecules of interest may be assessed in vivo, e.g., in an animal model such as that disclosed in Clynes et al., *Proc. Natl. Acad. Sci.* (USA), 95:652-656 (1998).

"Complement dependent cytotoxicity" or "CDC" refers to the ability of a molecule to initiate complement activation and lyse a target in the presence of complement. The complement activation pathway is initiated by the binding of the first component of the complement system (C1q) to a molecule (e.g., an antibody) complexed with a cognate antigen. To assess complement activation, a CDC assay, e.g., as described in Gazzano-Santaro et al., *J. Immunol. Methods*, 202:163 (1996), may be performed.

"Effector cells" are leukocytes which express one or more FcRs and perform effector functions. Preferably, the cells express at least FcγRI, FCγRII, FcγRIII and/or FcγRIV and carry out ADCC effector function. Examples of human leukocytes which mediate ADCC include peripheral blood mononuclear cells (PBMC), natural killer (NK) cells, monocytes, cytotoxic T cells and neutrophils. In certain embodiments of the invention, PBMCs and NK cells are used. In one embodiment, the effector cells are human cells.

The terms "Fc receptor" or "FcR" are used to describe a receptor that binds to the Fc region of an antibody. In one embodiment, the FcR is a native sequence human FcR. Moreover, in certain embodiments, the FcR is one which binds an IgG antibody (a gamma receptor) and includes receptors of the FcγRI, FcγRII, FcγRIII, and FcγRIV subclasses, including allelic variants and alternatively spliced forms of these receptors. FCγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain. Inhibiting receptor FcγRIIB contains an immunoreceptor tyrosine-based inhibition motif (ITIM) in its cytoplasmic domain. (See, Daëron, *Annu. Rev. Immunol.*, 15:203-234 (1997)). FcRs are reviewed in Ravetech and Kinet, *Annu. Rev. Immunol.*, 9:457-92 (1991); Capel et al., *Immunomethods*, 4:25-34 (1994); and de Haas et al., *J. Lab. Clin. Med.*, 126:330-41 (1995). Other FcRs, including those to be identified in the future, are encompassed by the term "FcR" herein. The term also includes the neonatal receptor, FcRn, which is responsible for the transfer of maternal IgGs to the fetus (Guyer et al., *Immunol.*, 117:587 (1976) and Kim et al., *J. Immunol.*, 24:249 (1994)).

"Fv" is the minimum antibody fragment which contains a complete antigen-recognition and binding site. This region consists of a dimer of one heavy and one light chain variable domain in tight, non-covalent or covalent association. It is in this configuration that the three CDRs of each variable domain interact to define an antigen-binding site on the surface of the $V_H$-$V_L$ dimer. Collectively, the six CDRs confer antigen-binding specificity to the antibody. However, even a single variable domain (or half of an Fv comprising only three CDRs specific for an antigen) has the ability to recognize and bind antigen, although at a lower affinity than the entire binding site.

"Affinity" of an antibody for an epitope to be used in the treatment(s) described herein is a term well understood in the art and means the extent, or strength, of binding of antibody to epitope. Affinity may be measured and/or expressed in a number of ways known in the art, including, but not limited to, equilibrium dissociation constant (KD or Kd), apparent equilibrium dissociation constant (KD' or Kd'), and IC50 (amount needed to effect 50% inhibition in a competition assay). It is understood that, for purposes of this invention, an affinity is an average affinity for a given population of antibodies which bind to an epitope. Values of KD reported herein in terms of mg IgG per mL or mg/mL indicate mg Ig per mL of serum, although plasma can be used. When antibody affinity is used as a basis for administration of the treatment methods described herein, or selection for the treatment methods described herein, antibody affinity can be measured before and/or during treatment, and the values obtained can be used by a clinician in assessing whether a human patient is an appropriate candidate for treatment.

An "epitope" is a term well understood in the art and means any chemical moiety that exhibits specific binding to an antibody. An "antigen" is a moiety or molecule that contains an epitope, and, as such, also specifically binds to antibody.

A "B cell surface marker" as used herein is an antigen expressed on the surface of a B cell which can be targeted with an agent which binds thereto. Exemplary B cell surface markers include the CD10, CD22, CD20, CD21, CD22, CD23, CD24, CD25, CD37, CD53, CD72, CD73, CD74, CD75, CD77, CD79a, CD79b, CD80, CD81, CD82, CD83, CD84, CD85, and CD86 leukocyte surface markers. The B cell surface marker of particular interest is preferentially expressed on B cells compared to other non-B cell tissues of a mammal and may be expressed on both precursor B cells and mature B-lineage cells. In one embodiment, the marker is CD22, which is found on B cells at various stages of differentiation.

The term "antibody half-life" as used herein means a pharmacokinetic property of an antibody that is a measure of the mean survival time of antibody molecules following their administration. Antibody half-life can be expressed as the time required to eliminate 50 percent of a known quantity of immunoglobulin from the patient's body or a specific compartment thereof, for example, as measured in serum or plasma, i.e., circulating half-life, or in other tissues. Half-life may vary from one immunoglobulin or class of immunoglobulin to another. In general, an increase in antibody half-life results in an increase in mean residence time (MRT) in circulation for the antibody administered.

The term "isotype" refers to the classification of an antibody's heavy or light chain constant region. The constant domains of antibodies are not involved in binding to antigen, but exhibit various effector functions. Depending on the amino acid sequence of the heavy chain constant region, a given human antibody or immunoglobulin can be assigned to one of five major classes of immunoglobulins: IgA, IgD, IgE, IgG, and IgM. Several of these classes may be further divided into subclasses (isotypes), e.g., IgG1 (gamma 1), IgG2 (gamma 2), IgG3 (gamma 3), and IgG4 (gamma 4), and IgA1 and IgA2. The heavy chain constant regions that correspond to the different classes of immunoglobulins are called α, δ, ε, γ, and μ, respectively. The structures and three-dimensional configurations of different classes of immunoglobulins are well-known. Of the various human immunoglobulin classes, only human IgG1, IgG2, IgG3, IgG4, and IgM are known to activate complement. Human IgG1 and IgG3 are known to mediate ADCC in humans. Human light chain constant regions may be classified into two major classes, kappa and lambda As used herein, the term "immunogenicity" means that a compound is capable of provoking an immune response (stimulating production of specific antibodies and/or proliferation of specific T cells).

As used herein, the term "antigenicity" means that a compound is recognized by an antibody or may bind to an antibody and induce an immune response.

As used herein, the term "avidity" is a measure of the overall binding strength (i.e., both antibody arms) with which an antibody binds an antigen. Antibody avidity can be determined by measuring the dissociation of the antigen-antibody bond in antigen excess using any means known in the art, such as, but not limited to, by the modification of indirect fluorescent antibody as described by Gray et al., *J. Virol. Meth.*, 44:11-24. (1993).

By the terms "treat," "treating" or "treatment of" (or grammatically equivalent terms) it is meant that the severity of the subject's condition is reduced or at least partially improved or ameliorated and/or that some alleviation, mitigation or decrease in at least one clinical symptom is achieved and/or there is an inhibition or delay in the progression of the condition and/or prevention or delay of the onset of a disease or illness. Thus, the terms "treat," "treating" or "treatment of" (or grammatically equivalent terms) refer to both prophylactic and therapeutic treatment regimes.

As used herein, a "sufficient amount" or "an amount sufficient to" achieve a particular result refers to an amount of an antibody or composition of the invention that is effective to produce a desired effect, which is optionally a therapeutic effect (i.e., by administration of a therapeutically effective amount). For example, a "sufficient amount" or "an amount sufficient to" can be an amount that is effective to deplete B cells.

A "therapeutically effective" amount as used herein is an amount that provides some improvement or benefit to the subject. Alternatively stated, a "therapeutically effective" amount is an amount that provides some alleviation, mitigation, and/or decrease in at least one clinical symptom. Clinical symptoms associated with the disorders that can be treated by the methods of the invention are well-known to those skilled in the art. Further, those skilled in the art will appreciate that the therapeutic effects need not be complete or curative, as long as some benefit is provided to the subject.

4. BRIEF DESCRIPTION OF THE DRAWINGS

FIG. 1A-B: (A) Nucleotide [SEQ ID NO:1] and amino acid [SEQ ID NO:2] of the chimeric HB22.7 variable heavy (VH) chain. The Kozak sequence, leader sequence, and 5' fragment of the human gamma 1 constant region up to the natural ApaI restriction site are indicated. The vector encoding this sequence is designated HB22.7Hc.pG1D20. (B) Nucleotide and amino acid sequences of chHB227 and the HB227 variable heavy chain (VH) region [SEQ ID NO:5 and SEQ ID NO:7]. CDRs are underlined. Leader sequences are italicized. The Kabat numbering system is used to identify specific residues.

FIG. 2: Nucleotide [SEQ ID NO: 3] and amino acid [SEQ ID NO:4] sequence of the chimeric HB22.7 variable light (VK) chain. The Kozak sequence, leader sequence, and 5' splice donor site are indicated. The vector encoding this sequence is designated HB22.7Kc.pKN10. (B) Nucleotide and amino acid sequences of chHB227 and HB227 variable light chain region (VL) [SEQ ID NO:26 and SEQ ID NO:27]. CDRs are underlined. Leader sequences are italicized. The Kabat numbering system is used to identify specific residues.

Figure 3:
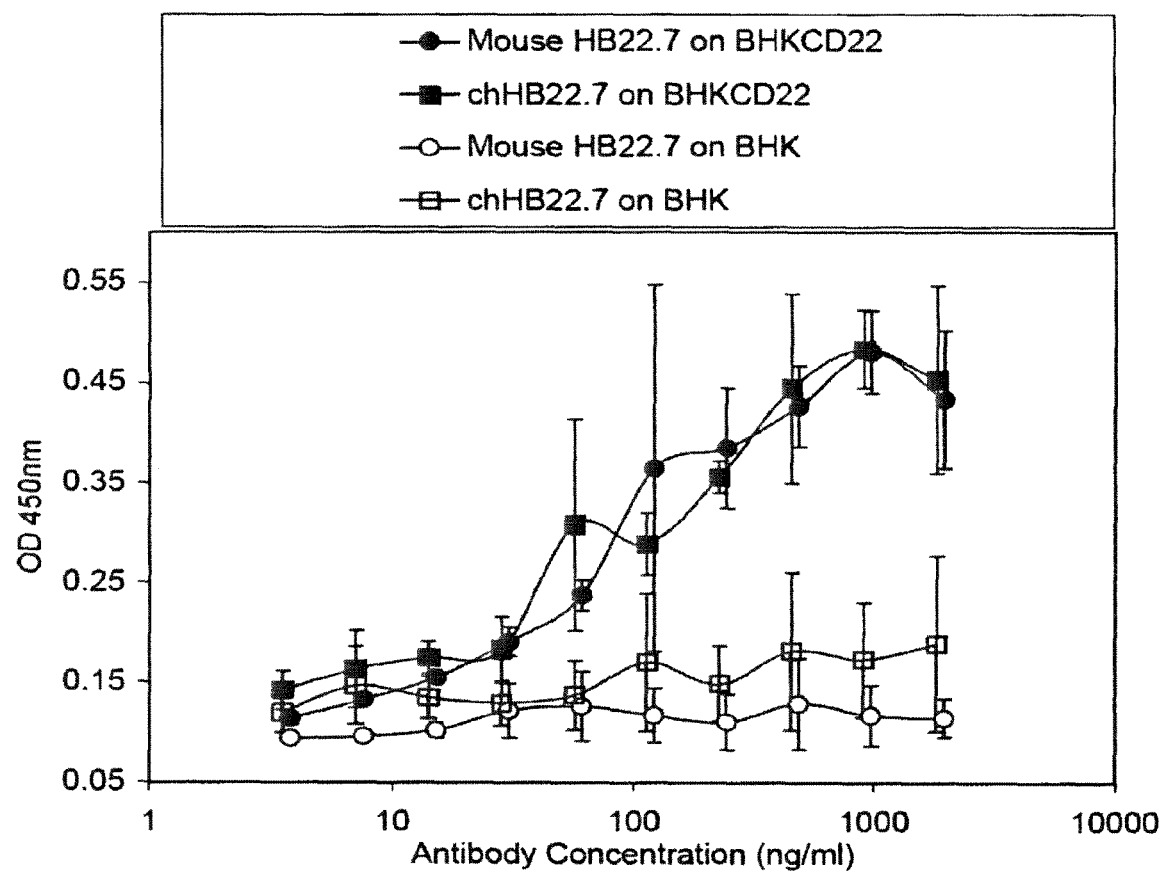

FIG. 3: Binding of the chimeric HB22.7 antibody (chHB227) to CD22-expressing BHK cells. The parental mouse HB22.7 antibody (closed circles) was used as a reference standard. The binding profile of the chHB227 (closed squares) closely matches that of the mouse parental control. As a negative control, the binding of each antibody to BHK cells not expressing CD22 is also shown, mouse HB22.7 (open circles), chHB227 (open squares).

FIG. 4: Amino acid sequence of parental mouse HB22.7 VH [SEQ ID NO:7] and high homology acceptor VH (VH46898) [SEQ ID NO:6]. Canonical (c), Vernier (v), Interface (i), and residues within the 200% Van der Waal's radius (*) of are shown in the context of the Kabat numbering system.

FIG. 5A-G: Generation of humanized variants of mouse VH, HB22.7 [SEQ ID NO: 5 and 7]. (A and B) Generation of HB227-(V2-70+IC4) heavy chain variant. Germline human FW1, FW2 and FW3 from human V2-70 VH [SEQ ID NO:8 and 9], and FW4 from human IC4 [SEQ ID NO: 10 and 11] were used as acceptor sequences for the parental mouse HB22.7 VH CDR1, CDR2, and CDR3 sequences. The resulting humanized VH construct was termed HB227-(V2-70+ IC4) [SEQ ID NO: 12 and 13]. CDR sequences are underlined. (C and D) Generation of HB227-VH46898 [SEQ ID NO: 14 and 15] and HB227RHB [SEQ ID NO: 16 and 17] high homology variants. Single nucleotide substitutions were introduced in the HB227-(V2-70+IC4) FW sequence so as to recreate the HB227-VH46898 FW coding sequence [SEQ ID NO: 14 and 15]. The addition of the V2-50 leader sequence resulted in the HB227RHB humanized construct [SEQ ID NO: 16 and 17]. CDR sequences are underlined. Leader sequences are italicized. (E-G) Generation of RHC, RHD, RHE, and RHF variants of HB227RHB. In an effort to increase binding activity of HB227RHB, the mismatched Vernier residues at Kabat positions 73 and 49 were backmutated to the corresponding mouse residues individually or simultaneously to generate HB227RHE [SEQ ID NO:22 and 23], HB227RHD [SEQ ID NO:20 and 21], and HB227RHC [SEQ ID NO:18 and 19] respectively. The HB227RHF construct [SEQ ID NO:24 and 25] was derived from HB227RHC by backmutation of a mismatched mouse canonical residue at Kabat position 24. CDR sequences are underlined. Leader sequences are italicized.

FIG. 6: Alignment of human light chain framework acceptor genes with HB22.7 variable light chain (VL) sequence. Among the human variable kappa light chains (VK) with homology to the parental mouse HB22.7 VK [SEQ ID NO:26 and 27], the VL Clone 47 human sequence was chosen as the acceptor for the mouse HB22.7 VK CDRs. Because Clone 47 DNA sequence information was not available, a closely related human VK gene, AJ388641 [SEQ ID NO: 28 and 29], was mutated by replacing single nucleotides so as to recreate the Clone 47 FW regions. The resulting construct was referred to as AJ388641+Clone 47 FW [SEQ ID NO: 30 and 31]. Canonical (c), Vernier (v), Interface (i), and residues are shown in the context of the Kabat numbering system. CDR sequences are underlined.

FIG. 7A-D: Generation of humanized VK light chain from parental mouse HB22.7 VK sequence. (A and B) The humanized version of the HB22.7 VK gene was generated by PCR cloning of the HB22.7 VK CDRs into the human Clone 47 FW regions. The Clone 47 FW regions were generated by mutating a closely related human VK gene (AJ3888641 [SEQ ID NO: 28 and 29] CDR sequences are underlined. (C and D) Addition of DPK018 leader sequence to HB227-Clone 47 resulting in the HB227-RKA humanized VK chain [SEQ ID NO: 34 and 35]. HB227-RKB variant [SEQ ID NO: 36 and 37] of HB227-RKA was generated by backmutation (human to mouse) of a single interface residue at Kabat position 87 (Y87F). HB227-RKC [SEQ ID NO: 38 and 39] was generated by backmutating two additional residues, S60D and S67Y which were potential binding residues. CDR sequences are underlined. Leader sequences are italicized.

Figure 8:
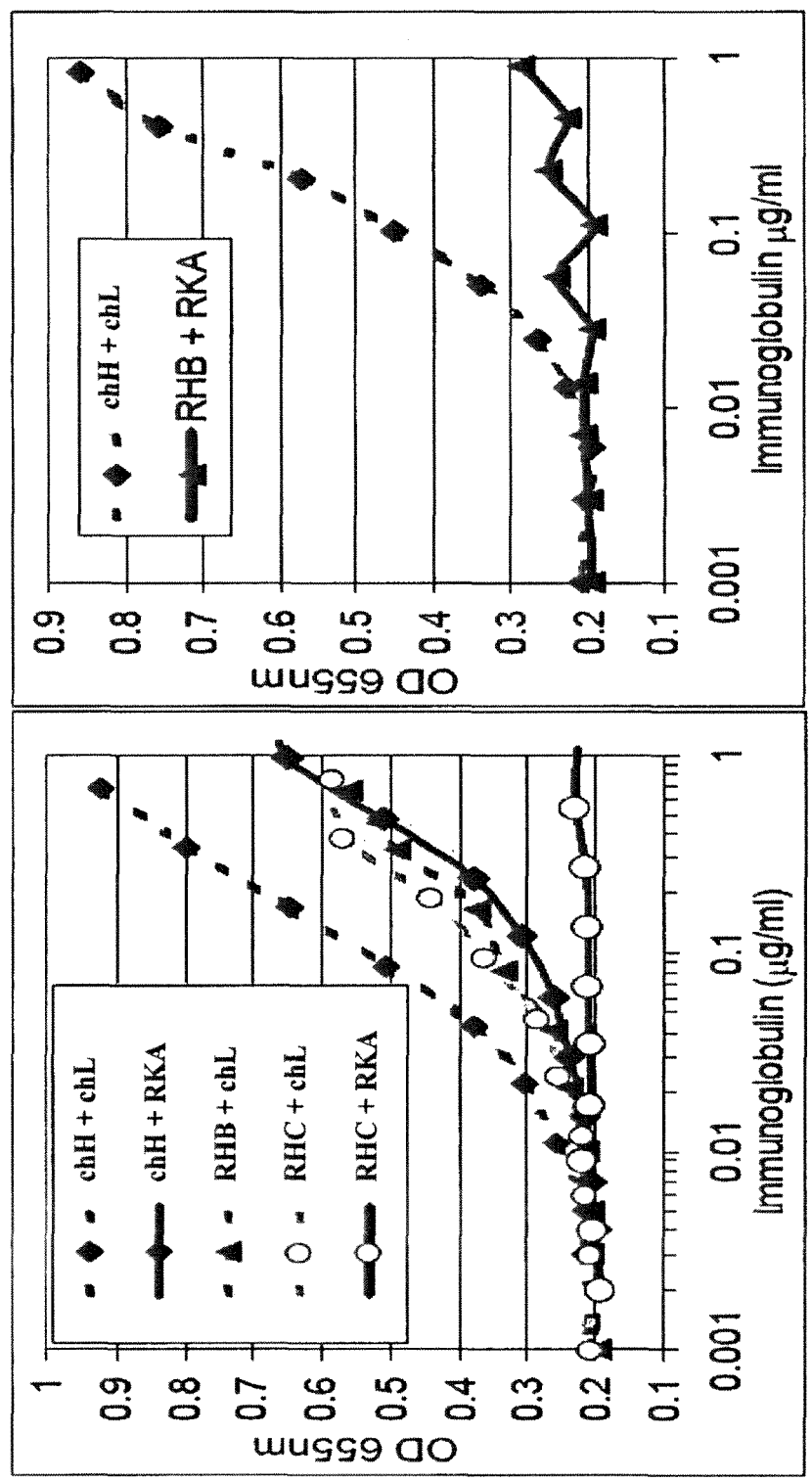

FIG. 8: CD22-binding of antibodies comprising HB227RHB, RHC, or chimeric HB22.7 heavy chain (chH) with chimeric HB22.7 light chain (chL) or HB227RKA light chain.

Figure 9:
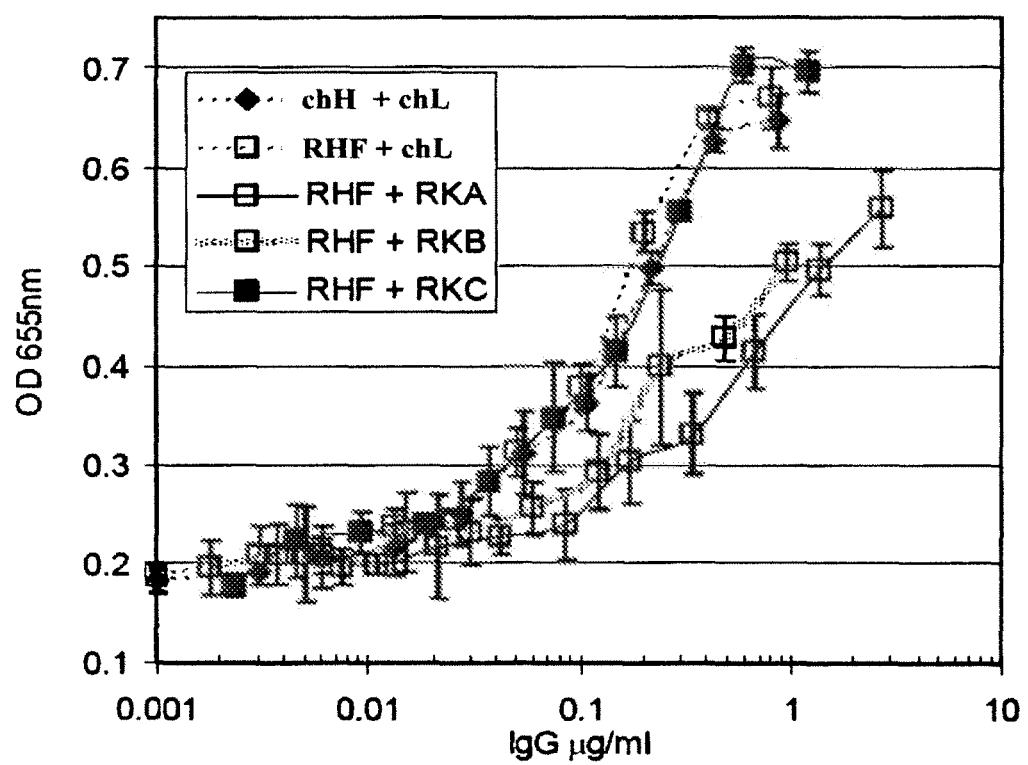

FIG. 9: CD22-binding of antibodies comprising chHB227 (chH+chL) and HB227RHF heavy chain associated with chL, HB227RKA, HB227RKB, or HB227RKC light chains.

Figure 10:
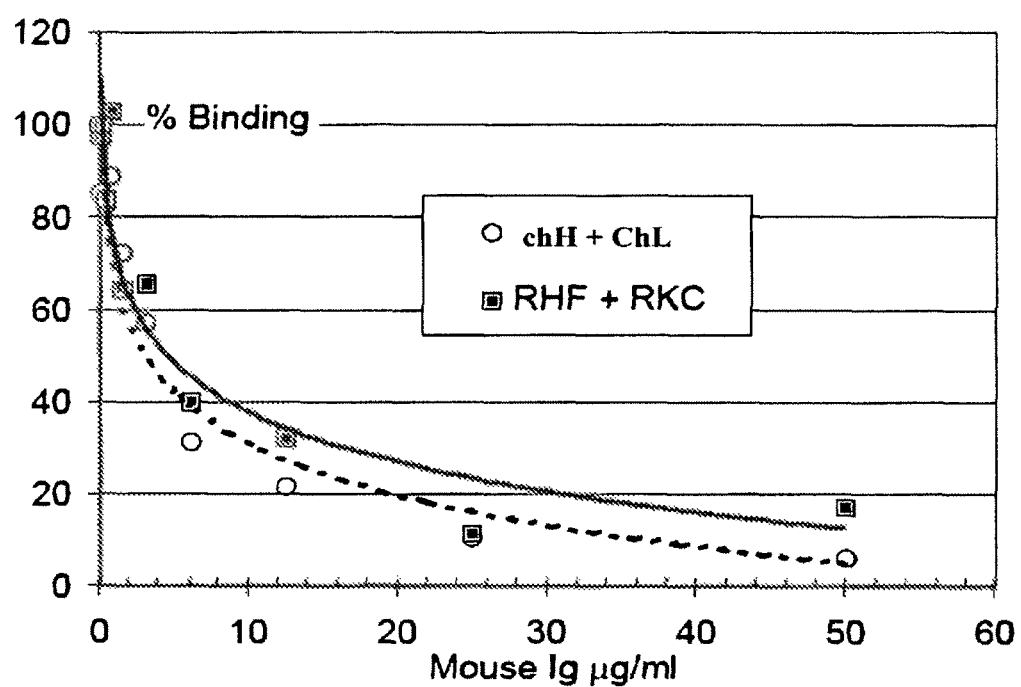

FIG. 10: chHB227 antibody and the humanized HB227RHF+HB227RKC antibody each compete similarly with the parental mouse antibody HB22.7 for binding to CD22. The figure shows the percentage binding to CD22 by the chHB227 antibody or the humanized (RHF+RKC) antibody in the presence of increasing concentrations of the parental mouse HB22.7 antibody. Fifty percent inhibition ($IC_{50}$) is achieved at about 4 µg/ml of the chimeric antibody (grey rectangle).

Figure 11:
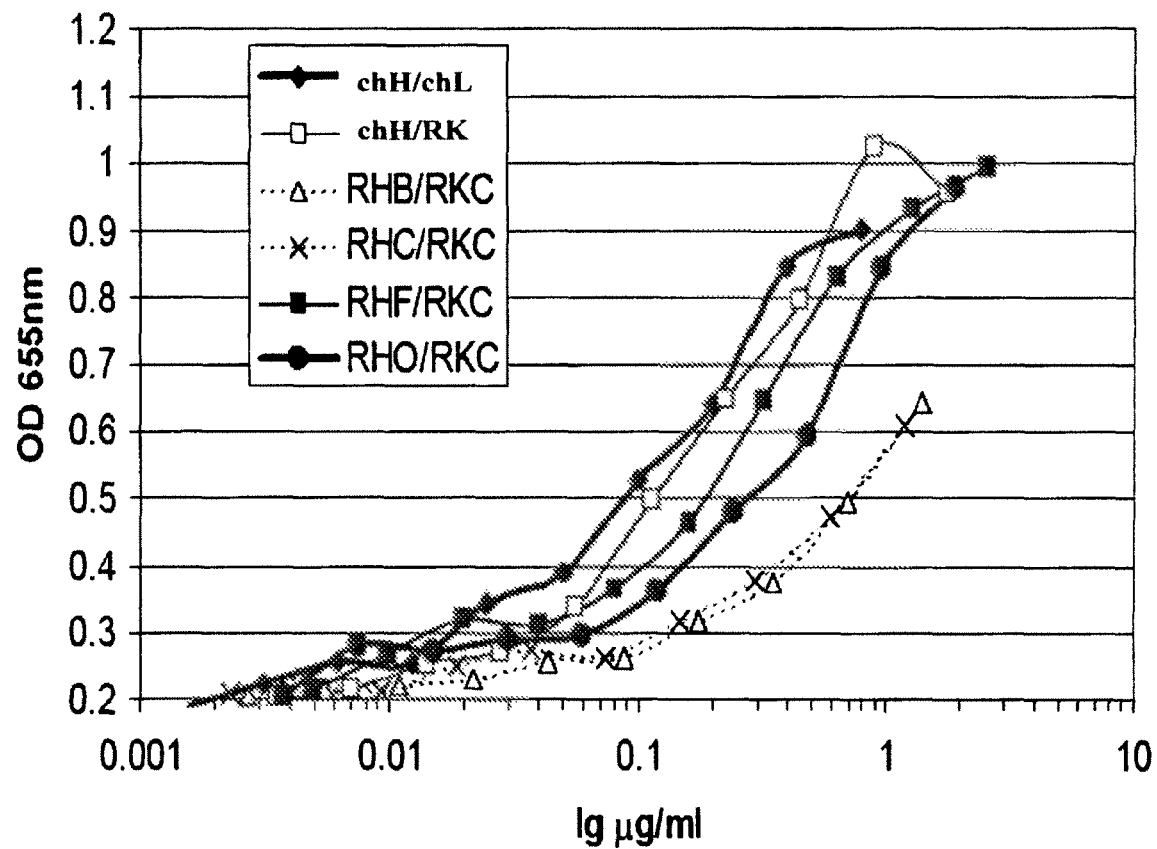

FIG. 11: CD22 binding of antibodies comprising HB227RKC or the chL, paired with either the chH or one of the humanized HB227 heavy chains, RHB, RHC, RHF, or RHO.

FIG. 12: Identification of human VH acceptor sequence. The Canonical (c), Vernier (v), and Interface (i) residues within HB227 VH [SEQ ID NO: 5 and 7] are denoted in the context of the Kabat numbering system. Those residues within the 200% Van der Waal's radius envelope (*) are also depicted. Three canonical residues, V24, G26, F27; one Vernier, N73; and the VL interaction residues V37, Q39, L45, and Y91 lie outside the 200% VdW envelope and thus were not targeted for backmutation to the parental residue. Human VH gene databases were searched for VH sequences that conserved these residues but had low framework homology with HB22.7. Five such sequences were identified with AJ556657 sequence [SEQ ID NO: 40 and 41] being selected as the low identity acceptor VH for the HB227 VH CDRs. CDR sequences are underlined.

FIG. 13A-G: Generation of humanized, FW variants of HB22.7 VH. (A-B) Generation of HB227-AJ556657. The HB227-AJ556657 VH [SEQ ID NO: 42 and 43] was accomplished by inserting the HB22.7 CDRs into the FW regions of AJ556657 [SEQ ID NO: 40 and 41]. (C-D) Generation of HB227RHO and HB227RHOv2. The HB227RHO [SEQ ID NO: 46 and 47] and H227RHOv2 [SEQ ID NO: 48 and 49] were generated by sequential backmutation of four residues within the 200% VdW radius (F29L, D30S, T49G, and F67L) and replacement of the VH3-30 leader sequence [SEQ ID NO: 44 and 45] with the VH2-50 leader sequence. (E-G) HB227RHOv2 variants were generated by selectively reversing one or more of the backmutations at Kabat positions 29, 30, 49, and 67. The resulting variants, HB227RHOv2A [SEQ ID NO: 50 and 51], HB227RHOv2B [SEQ ID NO: 52 and 53], HB227RHOv2C [SEQ ID NO: 54 and 55], HB227RHOv2D [SEQ ID NO: 56 and 57], HB227RHOv2ACD [SEQ ID NO: 58 and 59], and HB227RHOv2ABCD [SEQ ID NO: 60 and 61] were subsequently screened for hCD22 binding activity. CDR sequences are underlined. Leader sequences are italicized.

FIG. 14A-E: CD22 binding by RHOv2A, -B, -C and D, each expressed with the humanized RKC light chain. In each panel, the binding of CD22 by the chH+chL antibody is shown for comparison (filled squares) (A) RHOv2. (B) RHOv2A. (C) RHOv2B. (D) RHOv2C. (E) RHOv2D. The A-D designations refer to the removal of one of the four back mutations, F29L (A), D30S (B), T49G (C), and F67L (D) from the RHOv2 sequence. RHOv2 contains all four mutations. In each of RHOv2A-D, the single back mutation indicated by the letter A, B, C, or D, has been removed, leaving the other three back mutations intact.

FIG. 15A-E: CD22 binding by RHOv2ACD and RHOv2ABCD. In each panel, the binding of CD22 by the chH+chL antibody is shown for comparison (filled circles). (A) CD22 binding by the humanized antibody comprising the heavy chain sequence, RHF, and the light chain sequence, RKC, (open circles) is comparable to that of the fully chimeric antibody (filled circles). CD22 binding by RHOv2ACD (B) and RHOv2ABCD (C), each paired with the humanized light chain, RKA. CD22 binding by RHOv2ACD (D) and RHOv2ABCD (E), each paired with the humanized light chain, RKC. The A-D designations refer to the removal of one of the four back mutations, F29L (A), D30S (B), T49G (C), and F67L (D). RHOv2ACD contains only the D30S back mutation; RHOv2ABCD contains no back mutations.

FIG. 16A-C: provides a compilation of human VH amino acid sequences (SEQ ID NOs:130-198) with overall low FW sequence identity relative to HB22.7 VH but which comprise conserved residues at positions 24, 26, 39, 45, and 73.

FIG. 17: depicts the amino acid sequence of five potential, overall low sequence identity VH acceptor sequences (SEQ ID NOs:7, 41, 199-202) selected from among those depicted in FIG. 16. In particular, the VH acceptor sequences of HB22.7 (SEQ ID NO:7), AJ556657 (SEQ ID NO:41), AB067248 (SEQ ID NO:199), AJ556642 (SEQ ID NO:200), AJ556644 (SEQ ID NO:201), and AF376954 (SEQ ID NO:202) are shown with the corresponding humanized version names.

Figure 18:
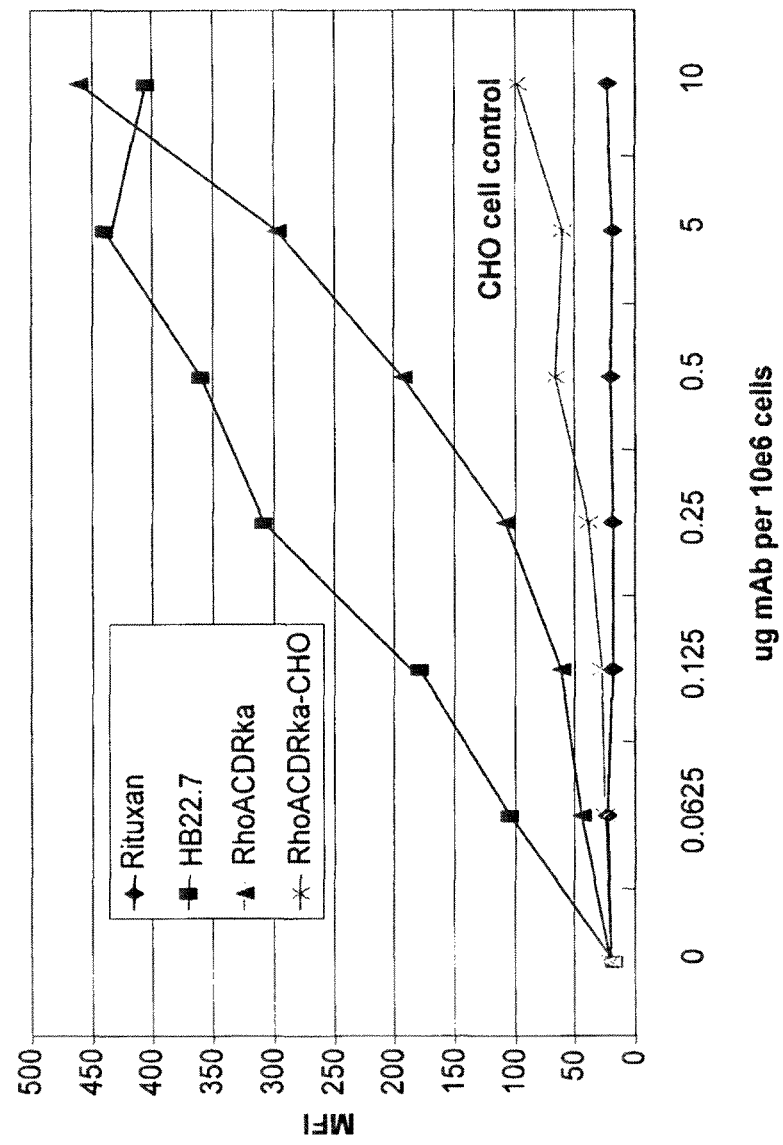

FIG. 18: provides binding affinity of murine antibody HB22.7 and humanized antibody RHOv2ACD/RKA to CD22-transfected CHO cells.

Figure 19:
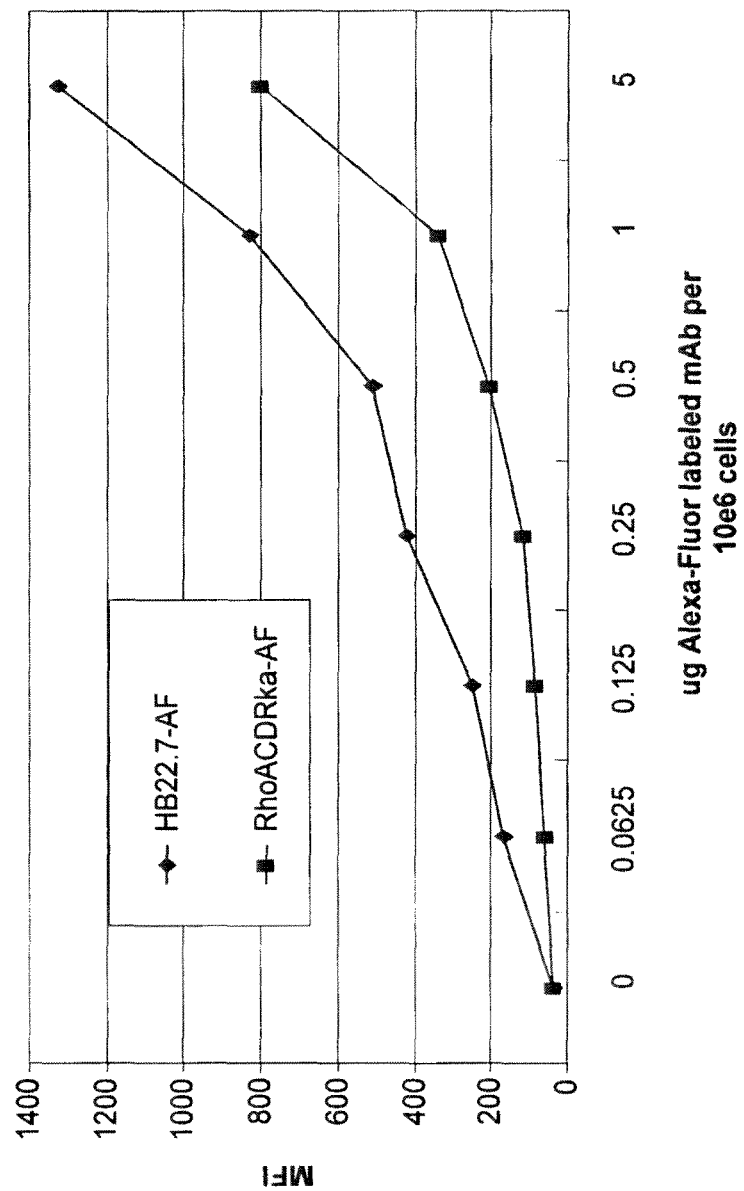

FIG. 19: provides binding affinity of Alexa-fluor labeled murine HB22.7 and humanized RHOv2ACD/RKA antibodies by FACS on Daudi cells.

Figure 20A:
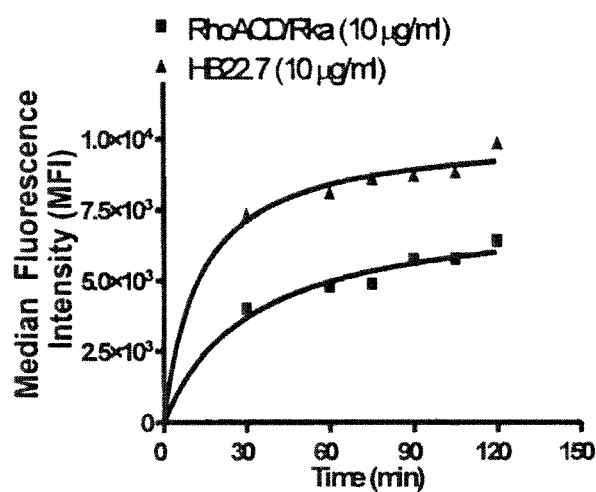

FIGS. 20A and B: provides cell surface binding and CD22 internalization of murine HB22.7 and humanized RHOv2ACD/RKA antibodies on Daudi lymphoma B cells. (A) provides the kinetics of binding activity and (B) provides internalization of each antibody on the Daudi lymphoma B cells.

Figure 21A:
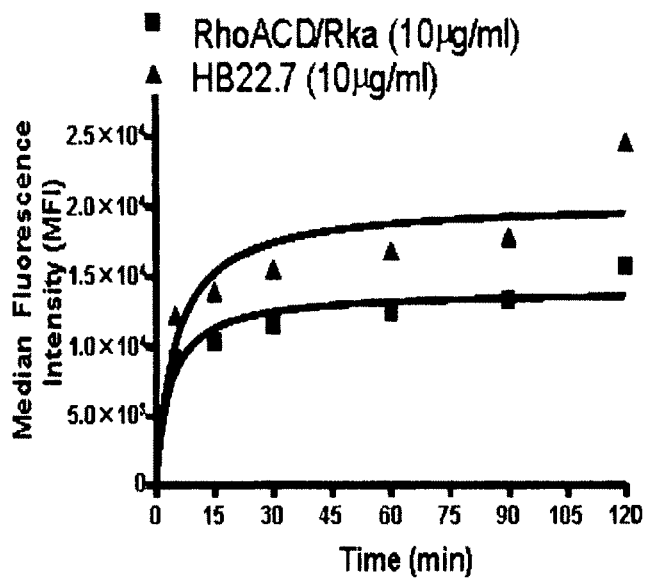

FIGS. 21A and B: provides cell surface binding and CD22 internalization of murine HB22.7 and humanized RHOv2ACD/RKA antibodies on human tonsillar B cells. (A) provides the kinetics of binding activity and (B) provides internalization of each antibody on human tonsillar B cells.

Figure 22A:
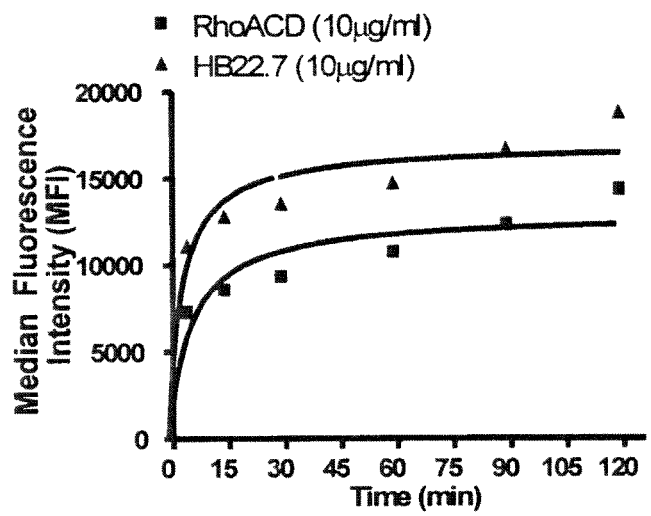
Figure 22B:
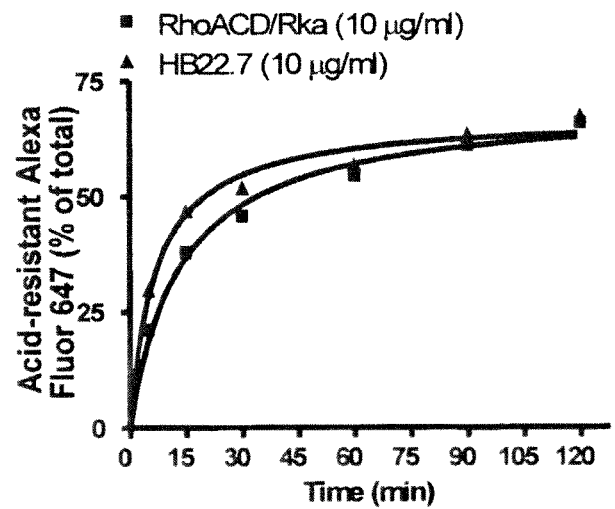

FIGS. 22 A and B: provides cell surface binding and CD22 internalization of murine HB22.7 and humanized RHOv2ACD/RKA antibodies on human peripheral blood B cells. (A) provides the kinetics of binding activity and (B) provides internalization of each antibody on human peripheral blood B cells.

Figure 23:
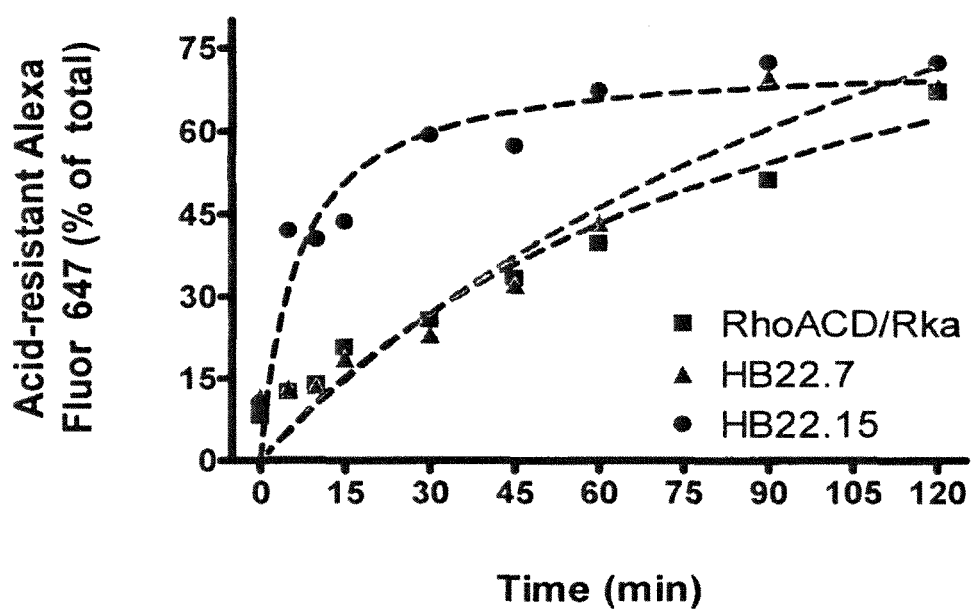

FIG. 23: compares CD22 internalization by blocking (HB22.7 and RHOv2ACD/RKA) and non-blocking (HB22.15) anti-hCD22 antibodies using Daudi lymphoma cell lines.

Figure 24:
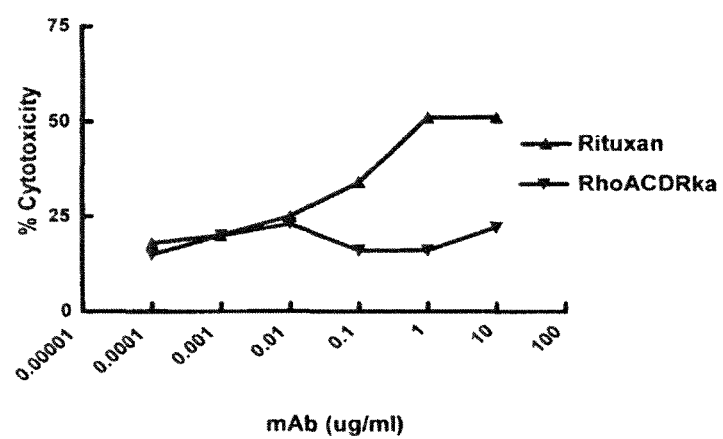

FIG. 24: provides ADCC effector function of humanized anti-hCD22 antibody RHOv2ACD/RKA on Raji lymphoma cells.

Figure 25A:
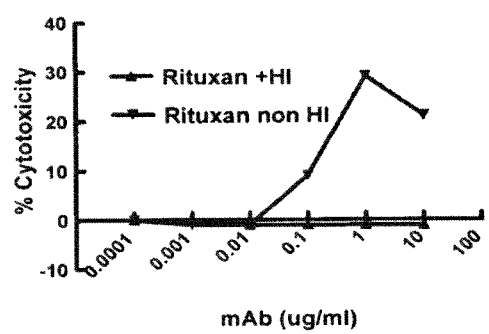

FIGS. 25A and B: provides CDC effector function of humanized anti-hCD22 antibody RHOv2ACD/RKA on Raji lymphoma cells. (A) shows effect of Rituxan; and (B) shows effect of RHOv2ACD/RKA on CDC on Raji cells.

FIG. 26A-D: shows that each of HB22.7 and RHOv2ACD/RKA block binding of Daudi cells to hCD22-expressing COS cells. (A) co-culture of COS and Daudi cells; (B) co-culture of COS cells expressing hCD22 and Daudi cells; (C) co-culture of COS cells expressing hCD22 and Daudi cells, the COS cells expressing hCD22 were pre-incubated with HB22.7; (D) co-culture of COS cells expressing hCD22 and Daudi cells, the COS cells expressing hCD22 were pre-incubated with RHOv2ACD/RKA.

Figure 27A:
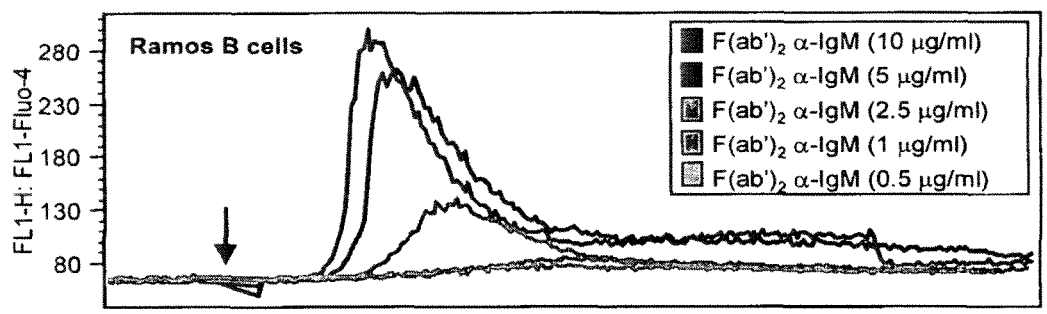

FIGS. 27A and B: provides effect of humanized anti-hCD22 antibody RHOv2ACD/RKA on CD22 signaling activity, Ca-flux, in Ramos B cells. (A) provides a Ca-flux dose response of Ramos B cells to B cell receptor crosslinking; (B) provides Ca-flux response of Ramos B cells to hCD22 antibody RHOv2ACD/RKA.

Figure 28A:
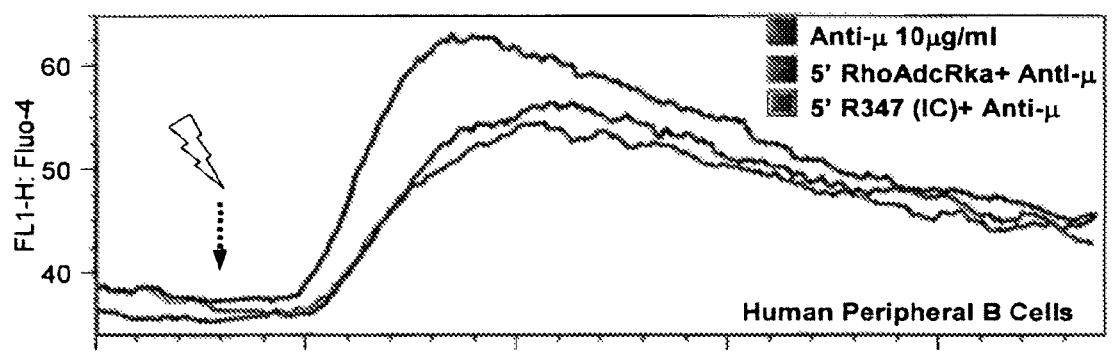

FIGS. 28A and B: shows that anti-IgM-induced Ca-flux in human peripheral B cells is enhanced by ligand blocking anti-hCD22 antibodies, HB22.7 and RHOv2ACD/RKA, but not non-ligand blocking anti-hCD22 antibody, HB22.15. (A) provides Ca-flux in human peripheral B cells contacted with anti-μ, RHOv2ACD/RKA+anti-μ, and isotype control antibody R347+anti-μ antibodies; (B) provides Ca-flux in human peripheral B cells bound by anti-μ, HB22.7+anti-μ, and HB22.15 (a non-ligand binding hCD22 antibody)+anti-μ antibodies.

FIG. 29A-H: provides the effect of anti-IgM with or without anti-CD22 antibodies, HB22.7 and RHOv2ACD/RKA, on Ramos B cell survival. Treatment of Ramos B cells was as follows: (A) no antibody; (B) 10 μg/ml HB22.7; (C) 10 μg/ml RHOv2ACD/RKA; (D) 3.3 μg/ml anti-IgM; (E) 3.3 μg/ml anti-IgM+10 μg/ml HB22.7; (F) 3.3 μg/ml anti-IgM+10 μg/ml RHOv2ACD/RKA; (G) 10 μg/ml anti-IgM; (H) 10 μg/ml anti-IgM+10 μg/ml HB22.7. Analysis was performed by forward and side scatter.

Figure 30:
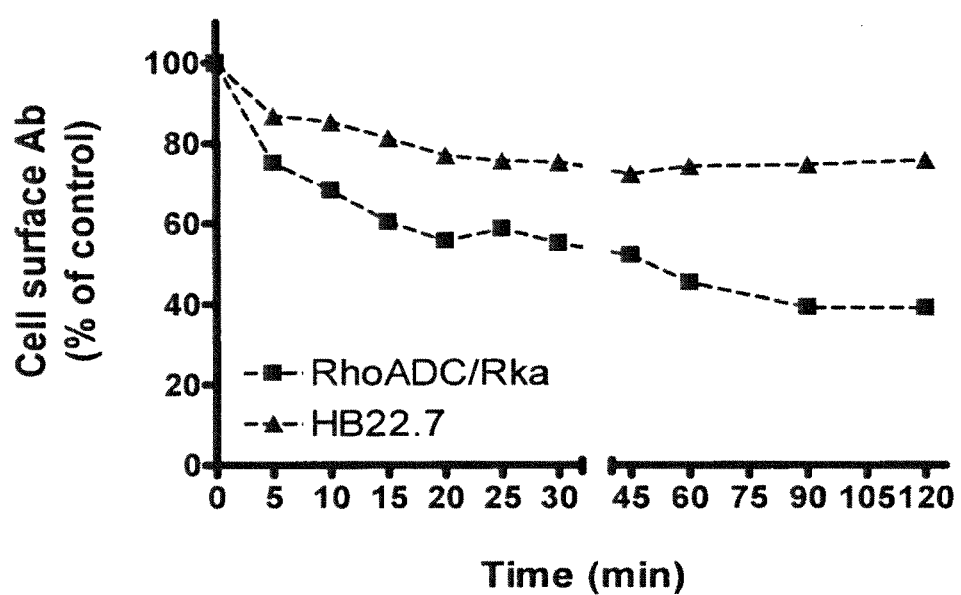

FIG. 30: provides dissociation of murine antibody HB22.7 and humanized RHOv2ACD/RKA antibody from Daudi cells.

5. DETAILED DESCRIPTION OF THE INVENTION

The present invention relates to human, humanized, or chimeric anti-CD22 antibodies that bind to the human CD22 antigen, as well as to compositions comprising those antibodies. In certain embodiments the human, humanized, or chimeric anti-CD22 antibodies of the invention are those that mediate antigen-dependent-cell-mediated-cytotoxicity (ADCC). In particular embodiments, the present invention is directed toward compositions comprising human, humanized, or chimeric anti-CD22 antibodies of the invention are of the IgG1 and/or IgG3 human isotype, as well as to human, humanized, or chimeric anti-CD22 antibodies of the IgG2 and/or IgG4 human isotype, that preferably mediate human ADCC, CDC, and/or apoptosis.

The present invention provides chimeric and humanized versions of anti-CD22 mouse monoclonal antibody, HB22.7. In one embodiment, the humanized anti-CD22 antibodies bind to human CD22 with an affinity comparable to that of the mouse monoclonal antibody designated HB22.7 or comparable to that of the chHB227 antibody. The anti-CD22 antibodies of the invention comprise four human or humanized framework regions of the immunoglobulin heavy chain variable region ("VH") and four human or humanized framework regions of the immunoglobulin light chain variable region ("VK"). The invention further comprises heavy and/or light chain FW regions that contain one or more backmutations in which a human FW residue is exchanged for the corresponding residue present in the parental mouse heavy or light chain. The invention comprises anti-CD22 antibodies having one or more CDRs present in the heavy and light chains of the antibody produced by the parental mouse hybridoma HB22.7. and deposited with the American Type Culture Collection ("ATCC") under accession no. ATCC Designation: HB11347. The amino acid sequences for CDR1, CDR2, and CDR3 of the heavy chain are identified as SEQ ID NO:62, SEQ ID NO:63, and SEQ ID NO: 64 respectively. The amino acid sequences for CDR1, CDR2 and CDR3 of the light chain are identified as SEQ ID NO:65, SEQ ID NO:66, and SEQ ID NO:67 respectively.

In other embodiments, the human or humanized VH framework regions of antibodies of the invention comprise one or more of the following residues: a valine (V) at position 24 of framework region 1, a glycine (G) at position 49 of framework region 2, and an asparagine (N) at position 73 of framework region 3, numbered according to Kabat. Kabat numbering is based on the seminal work of Kabat et al. (1991) *Sequences of Proteins of Immunological Interest*, Publication No. 91-3242, published as a three volume set by the National Institutes of Health, National Technical Information Service (hereinafter "Kabat"). Kabat provides multiple sequence alignments of immunoglobulin chains from numerous species antibody isotypes. The aligned sequences are numbered according to a single numbering system, the Kabat numbering system. The Kabat sequences have been updated since the 1991 publication and are available as an electronic sequence database (latest downloadable version 1997). Any immunoglobulin sequence can be numbered according to Kabat by performing an alignment with the Kabat reference sequence. Accordingly, the Kabat numbering system provides a uniform system for numbering immunoglobulin chains. Unless indicated otherwise, all immunoglobulin amino acid sequences described herein are numbered according to the Kabat numbering system. Similarly, all single amino acid positions referred to herein are numbered according to the Kabat numbering system.

Exemplary VH and VK antibody regions of the invention were deposited with the American Type Culture Collection (ATCC). In particular, a plasmid encoding the humanized anti-CD22 VH sequence of the invention designated RHOv2 (SEQ ID NO:48 and SEQ ID NO:49), was deposited under ATCC deposit no. PTA-7372, on Feb. 9, 2006. A plasmid encoding the humanized anti-CD22 VH sequence of the invention designated RHOv2ACD (SEQ ID NO:58 and SEQ ID NO:59), was deposited under ATCC deposit no. PTA-7373, on Feb. 9, 2006. A plasmid encoding the humanized anti-CD22 VK sequence of the invention, RKA (SEQ ID NO:34 and SEQ ID NO:35), was deposited under ATCC deposit no. PTA-7370, on Feb. 9, 2006. A plasmid encoding the humanized anti-CD22 VK sequence of the invention, RKC (SEQ ID NO:38 and SEQ ID NO:39), was deposited under ATCC deposit no. PTA-7371, on Feb. 9, 2006.

In one embodiment of the invention, the human or humanized VH framework regions of antibodies of the invention have an amino acid sequence identity with the HB22.7 antibody VH within the range of from about 64% to about 100%. In certain aspects of this embodiment, the human or humanized VH framework regions of antibodies of the invention have an amino acid sequence identity with the HB22.7 antibody VH that is at least 64%, at least 65%, at least 70%, at least 75%, at least 80%, at least 85%, at least 90%, or at least 95%.

In particular embodiments, the human or humanized VH framework regions of antibodies of the invention have an amino acid sequence identity with the HB22.7 antibody VH of at least 56 out of 87 amino acids (56/87) In particular embodiments, the VH framework amino acid sequence identity is at least 56/87, 57/87, 58/87, 59/87, 60/87, 61/87, 62/87, 63/87, 64/87, 65/87, 66/87, 67/87, 68/87, 69/87, 70/87, 71, 87, 72/87, 73/87m 74/87, 75/87, 76/87, 77.87, 78/87, 79/87, 80/87, 81/87, 82/87, 83/87, 84/87, 85/87, 86/87, or 87/87 amino acids. Preferably, the VH sequences have high sequence identity among the Vernier amino acid residues of HB22.7 (see FIG. 4), for example a Vernier sequence identity of at least 10 out of 16 (10/16), at least 11/16, at least 12/16, at least 13/16, at least 14/16, or at least 15/16 Vernier residues. In another embodiment, the mismatch of a Vernier amino acid residue is a conservative amino acid substitution. A mismatch that is a conservative amino acid substitution is one in which the mismatched amino acid has physical and chemical properties similar to the Vernier amino acid, e.g., the mismatched residue has similar characteristics of polarity (polar or nonpolar), acidity (acidic or basic), side chain structure (e.g., branched or straight, or comprising a phenyl ring, a hydroxyl moiety, or a sulfur moiety) to the Vernier residue.

In other embodiments, the mismatch of a Vernier amino acid residue is a non-conservative amino acid substitution. A mismatch that is a non-conservative amino acid substitution is one in which the mismatched amino acid does not have physical and chemical properties similar to the Vernier amino acid, e.g., the mismatched residue may have a different polarity, acidity, or side chain structure (e.g., branched or straight, or comprising a phenyl ring, a hydroxyl moiety, or a sulfur moiety) as compared to the Vernier residue to be replaced.

In further particular embodiments, the human or humanized VH framework regions of antibodies of the invention have framework regions selected for identity or conservative mismatches at one or more of the following Vernier, Interface or Canonical residue positions: 24, 26, 27, 37, 39, 45, 73, and 91, all of which are located outside the 200% van der Waal's ("VdW") envelope described by Winter in U.S. Pat. No. 6,548,640. One or more of the mismatched Vernier, Interface and Canonical residues within the 200% van der Waal's ("VdW") envelope as described by Winter in U.S. Pat. No. 6,548,640 are changed, e.g., by mutagenesis, to match the corresponding Vernier or canonical amino acid residue of the HB22.7 framework region.

In other embodiments, the human or humanized VK framework regions comprise one or more of the following residues: an aspartate (D) at position 60 of framework region 3, a tyrosine (Y) at position 67 of framework region 3, and a phenylalanine (F) at position 87 of framework region 3.

In particular embodiments, a humanized VH is expressed with a humanized VK to produce a humanized anti-CD22 antibody. In another embodiment, a humanized anti-CD22 antibody of the invention comprises a VH sequence selected from the group comprising the sequence designated HB22.7RHF (SEQ ID NO:24 and 25), HB227RHO (SEQ ID NO:46 and 47), HB227RHOv2, (SEQ ID NO:48 and 49), HB227RHOv2A, (SEQ ID NO:50 and 51), HB227RHOv2B, (SEQ ID NO:52 and 53), HB227RHOv2C, (SEQ ID NO:54 and 55), HB227RHOv2D, (SEQ ID NO:56 and 57), HB227RHOv2ACD (SEQ ID NO:58-59) and HB227RHOv2ABCD, (SEQ ID NO:60 and 61). Any of the aforementioned VH sequences may be paired with the VK sequence designated HB227RKA (SEQ ID NO:34 and 35) HB227RKB (SEQ ID NO:36 and 37, or HB227RKC (SEQ ID NO:38 and 39) ("RKA", "RKB", or "RKC"). In a particular embodiment, the humanized anti-CD22 antibody comprises the VH sequence RHF and the VK sequence RKC, the VH sequence RHO and the VK sequence RKC, the VH sequence RHOv2 and the VK sequence RKC, or the VH sequence RHOv2ACD and the VK sequence RKC.

In other embodiments, the humanized anti-CD22 antibody comprises the VH sequence RHF and the VK sequence RKA, or the VH sequence RHF and the VK sequence RKB. In further embodiments, the humanized anti-CD22 antibody comprises the VH sequence RHO and the VK sequence RKA, or the VH sequence RHO and the VK sequence RKB. In still other embodiments, the humanized anti-CD22 antibody comprises the VH sequence RHOv2A and the VK sequence RKA, the VH sequence RHOv2A and the VK sequence RKB, or the VH sequence RHOv2A and the VK sequence RKC. In further embodiments, the humanized anti-CD22 antibody comprises the VH sequence RHOv2B and the VK sequence RKA, the VH sequence RHOv2B and the VK sequence RKB, or the VH sequence RHOv2B and the VK sequence RKC. In additional embodiments, the humanized anti-CD22 antibody comprises the VH sequence RHOv2C and the VK sequence RKA, the VH sequence RHOv2C and the VK sequence RKB, or the VH sequence RHOv2C and the VK sequence RKC. In another other embodiment, the humanized anti-CD22 antibody comprises the VH sequence RHOv2D and the VK sequence RKA, the VH sequence RHOv2D and the VK sequence RKB, or the VH sequence RHOv2D and the VK sequence RKC. In still another embodiment, the humanized anti-CD22 antibody comprises the VH sequence RHOv2ABCD and the VK sequence RKA, the VH sequence RHOv2ABCD and the VK sequence RKB, or the VH sequence RHOv2ABCD and the VK sequence RKC. In a still further embodiment, the humanized anti-CD22 antibody comprises the VH sequence RHOv2ACD and the VK sequence RKA, or the VH sequence RHOv2ACD and the VK sequence RKB.

In certain embodiments, a humanized VH or VK derived from the parental HB22.7 hybridoma is expressed as a chimeric immunoglobulin light chain or a immunoglobulin heavy chain to produce a chimeric anti-CD22 antibody. In a particular embodiment, a humanized VH is expressed as a chimeric comprising the chVK sequence of (SEQ ID NO:3 or SEQ ID NO:4). In another particular embodiment, a humanized VK is expressed as a chimeric comprising the chVH sequence of (SEQ ID NO: SEQ ID NO:1 or SEQ ID NO:2). In another embodiment, the invention provides a chimeric anti-CD22 antibody comprising the chVK sequence of (SEQ ID NO:3 or SEQ ID NO:4) and the chVH sequence of (SEQ ID NO:1 or SEQ ID NO:2).

In certain embodiments, the humanized VH further comprises a leader sequence which is selected, for example, on the basis of sequence homology to the leader associated with the native human FW acceptor VH. In one embodiment, a leader is selected based on the basis of sequence homology to the leader associated with the VH expressed by HB22.7 hybridoma. High homology leader sequences are embodiments of the invention.

In certain embodiments, the humanized VL further comprises a leader sequence which is selected on the basis of sequence homology to the leader associated with the native human FW acceptor VL. In one embodiment, a leader is selected based on the basis of sequence homology to the leader associated with the VL expressed by HB22.7 hybridoma. High homology leader sequences are used in certain embodiments of the invention.

In a particular embodiment, the humanized VH further comprises a leader sequence MKSQTQVFVFLLLCVSGAHG (SEQ ID NO:68) selected from the leader peptide of the mouse PCG-1 VH gene, or the leader sequence MDTLCSTLLLLTIPSWVLS (SEQ ID NO:69) selected from the leader peptide of the human VH2-05 gene, or the leader peptide MEFGLSWVFLVALLRGVQC (SEQ ID NO:70) selected from the leader peptide of the human VH3-30 gene.

In another embodiment, the humanized VL further comprises a leader sequence MKSQTQVFVFLLLCVSGAHG (SEQ ID NO:71) selected from the leader peptide of the mouse SK/CamRK VH gene, or the leader sequence MDMRVPAQLLGLLQLWLSGARC (SEQ ID NO:72) selected from the leader peptide of the human DPK018 VH gene.

In one embodiment, the humanized anti-CD22 monoclonal antibody comprises a VH and a VK, wherein the VH comprises the four framework regions, FW1, FW2, FW3, and FW4 of the sequence designated AJ556657 (SEQ ID NO:40 and 41) (Colombo, M. M. et al., (2003) *Eur. J. Immunol.* 33:3422-3438); and the three VH CDR sequences of the HB22.7 antibody, CDR1 (SEQ ID NO:62), CDR2 (SEQ ID NO:63), and CDR3 (SEQ ID NO:64); and the VK comprises the four framework regions, FW1, FW2, FW3, and FW4, of the sequence designated AJ388641 CDRs with predicted VL clone 47 FW regions (SEQ ID NO:30 and 31) (Welschof, M. et al., (1995) *J. Immunol. Methods* 179:203-214); and the three VK CDR1 (SEQ ID NO:65), CDR2 (SEQ ID NO:66), and CDR3 (SEQ ID NO:67). In one embodiment, this antibody further comprises one or more of the following VH and VK framework mutations: the VH mutations selected from the group consisting of F29L, D30S, T49G, and F67L; and the VK mutations selected from the group consisting of S60D, S67Y and Y87F. In one embodiment, the VH framework regions contain each of the point mutations F29L, D30S, T49G, and F67L; and the VK framework comprises each of the point mutations S60D, S67Y and Y87F. In another embodiment, the VH framework regions contain only the D30S point mutation and the VK framework comprises each of the point mutations S60D, S67Y and Y87F.

The present invention also provides polynucleotide sequences encoding the VH and VK framework regions and CDRs of the antibodies of the invention as well as expression vectors for their efficient expression in mammalian cells.

The present invention also relates to a method of treating a B cell malignancy in a human comprising administering to a human in need thereof, a human, humanized or chimeric anti-CD22 antibody of the invention, particularly a human, humanized or chimeric anti-CD22 antibody that mediates human antibody-dependent cell-mediated cytotoxicity (ADCC), complement-dependent cell-mediated cytotoxicity (CDC), and/or apoptosis in an amount sufficient to deplete circulating B cells. In a particular aspect, the present invention also concerns methods of treating a B cell malignancy in a human comprising administration of a therapeutically effective regimen of a human, humanized, or chimeric anti-CD22 antibody of the invention, which is of the IgG1 or IgG3 human isotype. In another aspect, the present invention also concerns methods of treating a B cell malignancy in a human comprising administration of a therapeutically effective regimen of a human, humanized, or chimeric anti-CD22 antibody of the invention, which is of the IgG2 or IgG4 human isotype.

The present invention further relates to a method of treating an autoimmune disease or disorder in a human comprising administering to a human in need thereof a human, humanized, or chimeric anti-CD22 antibody of the invention that mediates human ADCC, CDC, and/or apoptosis in an amount sufficient to deplete circulating B cells. In a particular aspect, the present invention also concerns methods of treating autoimmune disorders comprising administration of a therapeutically effective regimen of a human, humanized, or chimeric anti-CD22 antibody of the invention, which is of the IgG1 or IgG3 human isotype.

The present invention also provides methods for treating or preventing humoral rejection in a human transplant recipient in need thereof comprising administering to the recipient a human, humanized, or chimeric anti-CD22 antibody of the invention in an amount sufficient to deplete circulating B cells, or circulating immunoglobulin, or both. In other embodiments, the invention provides methods for preventing graft rejection or graft versus host disease in a human transplant recipient in need thereof comprising contacting a graft prior to transplantation with an amount of a human, humanized, or chimeric anti-CD22 antibody of the invention sufficient to deplete B cells from the graft.

5.1. Production of Humanized Anti-CD22 Antibodies

The humanized antibodies provided by the invention can be produced using a variety of techniques known in the art, including, but not limited to, CDR-grafting (see e.g., European Patent No. EP 239,400; International Publication No. WO 91/09967; and U.S. Pat. Nos. 5,225,539, 5,530,101, and 5,585,089, each of which is incorporated herein in its entirety by reference), veneering or resurfacing (see, e.g., European Patent Nos. EP 592,106 and EP 519,596; Padlan, 1991, *Molecular Immunology* 28(4/5):489-498; Studnicka et al., 1994, *Protein Engineering,* 7(6):805-814; and Roguska et al., 1994, *Proc. Natl. Acad. Sci.,* 91:969-973, each of which is incorporated herein by its entirety by reference), chain shuffling (see, e.g., U.S. Pat. No. 5,565,332, which is incorporated herein in its entirety by reference), and techniques disclosed in, e.g., U.S. Pat. No. 6,407,213, U.S. Pat. No. 5,766,886, International Publication No. WO 9317105, Tan et al., *Immunol.,* 169:1119-25 (2002), Caldas et al., *Protein Eng.,* 13(5): 353-60 (2000), Morea et al., *Methods,* 20(3):267-79 (2000), Baca et al., *J. Biol. Chem.,* 272(16):10678-84 (1997), Roguska et al., *Protein Eng.,* 9(10):895-904 (1996), Couto et al., *Cancer Res.,* 55 (23 Supp):5973s-5977s (1995), Couto et al., *Cancer Res.,* 55(8):1717-22 (1995), Sandhu J S, *Gene,* 150(2):409-10 (1994), and Pedersen et al., *J. Mol. Biol.,* 235 (3):959-73 (1994), each of which is incorporated herein in its entirety by reference. Often, FW residues in the FW regions will be substituted with the corresponding residue from the CDR donor antibody to alter, preferably improve, antigen binding. These FW substitutions are identified by methods well-known in the art, e.g., by modeling of the interactions of the CDR and FW residues to identify FW residues important for antigen binding and sequence comparison to identify unusual FW residues at particular positions. (See, e.g., Queen et al., U.S. Pat. No. 5,585,089; and Riechmann et al., 1988, *Nature,* 332:323, which are incorporated herein by reference in their entireties.)

A humanized anti-CD22 antibody has one or more amino acid residues introduced into it from a source which is nonhuman. These nonhuman amino acid residues are often referred to as "import" residues, which are typically taken from an "import" variable domain. Thus, humanized antibodies comprise one or more CDRs from nonhuman immunoglobulin molecules and framework regions from human. Humanization of antibodies is well-known in the art and can essentially be performed following the method of Winter and co-workers (Jones et al., *Nature,* 321:522-525 (1986); Riechmann et al., *Nature,* 332:323-327 (1988); Verhoeyen et al., *Science,* 239:1534-1536 (1988)), by substituting rodent CDRs or CDR sequences for the corresponding sequences of a human antibody, i.e., CDR-grafting (EP 239,400; PCT Publication No. WO 91/09967; and U.S. Pat. Nos. 4,816,567; 6,331,415; 5,225,539; 5,530,101; 5,585,089; 6,548,640, the contents of which are incorporated herein by reference herein in their entirety). In such humanized chimeric antibodies, substantially less than an intact human variable domain has been substituted by the corresponding sequence from a nonhuman species. In practice, humanized antibodies are typically human antibodies in which some CDR residues and possibly some FW residues are substituted by residues from analogous sites in rodent antibodies. Humanization of anti-CD22 antibodies can also be achieved by veneering or resurfacing (EP 592,106; EP 519,596; Padlan, 1991, *Molecular Immunology* 28(4/5):489-498; Studnicka et al., *Protein Engineering,* 7(6):805-814 (1994); and Roguska et al., *Proc. Natl. Acad. Sci.,* 91:969-973 (1994)) or chain shuffling (U.S. Pat. No. 5,565,332), the contents of which are incorporated herein by reference herein in their entirety.

The choice of human variable domains, both light and heavy, to be used in making the humanized antibodies is to reduce antigenicity. According to the so-called "best-fit" method, the sequence of the variable domain of a rodent antibody is screened against the entire library of known human variable-domain sequences. The human sequences which are most closely related to that of the rodent are then screened for the presences of specific residues that may be critical for antigen binding, appropriate structural formation and/or stability of the intended humanized mAb (Sims et al., *J. Immunol.,* 151:2296 (1993); Chothia et al., *J. Mol. Biol.,* 196:901 (1987), the contents of which are incorporated herein by reference herein in their entirety). The resulting FW sequences matching the desired criteria are then be used as the human donor FW regions for the humanized antibody.

Another method uses a particular FW derived from the consensus sequence of all human antibodies of a particular subgroup of light or heavy chains. The same FW may be used for several different humanized anti-CD22 antibodies (Carter et al., *Proc. Natl. Acad. Sci. USA,* 89:4285 (1992); Presta et al., *J. Immunol.,* 151:2623 (1993), the contents of which are incorporated herein by reference herein in their entirety).

Anti-CD22 antibodies can be humanized with retention of high affinity for CD22 and other favorable biological properties. According to one aspect of the invention, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind CD22. In this way, FW residues can be selected and combined from the recipient and import sequences so that the desired antibody characteristic, such as increased affinity for CD22, is achieved. In general, the CDR residues are directly and most substantially involved in influencing antigen binding.

A "humanized" antibody retains a similar antigenic specificity as the original antibody, i.e., in the present invention, the ability to bind human CD22 antigen. However, using certain methods of humanization, the affinity and/or specificity of binding of the antibody for human CD22 antigen may be increased using methods of "directed evolution," as described by Wu et al., *J. Mol. Biol.,* 294:151 (1999), the contents of which are incorporated herein by reference herein in their entirety.

The humanized anti-CD22 antibodies provided by the invention were constructed by the selection of distinct human framework regions for grafting of the HB22.7 complementarity determining regions, or "CDR's" as described in the sections that follow. The invention provides a number of humanized versions of the mouse HB22.7 antibody as well as a chimeric version, designated chHB227.

5.2. Monoclonal Anti-CD22 Antibodies

The monoclonal anti-CD22 antibodies of the invention exhibit binding specificity to human CD22 antigen and can preferably mediate human ADCC and/or apoptotic mechanisms. These antibodies can be generated using a wide variety of techniques known in the art including the use of hybridoma, recombinant, and phage display technologies, or a combination thereof. Antibodies are highly specific, being directed against a single antigenic site. An engineered anti-CD22 antibody can be produced by any means known in the art, including, but not limited to, those techniques described below and improvements to those techniques. Large-scale high-yield production typically involves culturing a host cell that produces the engineered anti-CD22 antibody and recovering the anti-CD22 antibody from the host cell culture.

5.2.1. Hybridoma Technique

Monoclonal antibodies can be produced using hybridoma techniques including those known in the art and taught, for example, in Harlow et al., *Antibodies: A Laboratory Manual,* (Cold Spring Harbor Laboratory Press, 2nd ed. 1988); Hammerling et al., in *Monoclonal Antibodies and T Cell Hybridomas,* 563-681 (Elsevier, N.Y., 1981) (said references incorporated by reference in their entireties). For example, in the hybridoma method, a mouse or other appropriate host animal, such as a hamster or macaque monkey, is immunized to elicit lymphocytes that produce or are capable of producing antibodies that will specifically bind to the protein used for immunization. Alternatively, lymphocytes may be immunized in vitro. Lymphocytes then are fused with myeloma cells using a suitable fusing agent, such as polyethylene glycol, to form a hybridoma cell (Goding, *Monoclonal Antibodies: Principles and Practice,* pp. 59-103 (Academic Press, 1986)).

The hybridoma cells thus prepared are seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

Specific embodiments employ myeloma cells that fuse efficiently, support stable high-level production of antibody by the selected antibody-producing cells, and are sensitive to a medium such as HAT medium. Among these myeloma cell lines are murine myeloma lines, such as those derived from MOPC-21 and MPC-11 mouse tumors available from the Salk Institute Cell Distribution Center, San Diego, Calif., USA, and SP-2 or X63-Ag8.653 cells available from the American Type Culture Collection, Rockville, Md., USA. Human myeloma and mouse-human heteromyeloma cell lines also have been described for the production of human monoclonal antibodies (Kozbor, *J. Immunol.*, 133:3001 (1984); Brodeur et al., *Monoclonal Antibody Production Techniques and Applications*, pp. 51-63 (Marcel Dekker, Inc., New York, 1987)).

Culture medium in which hybridoma cells are growing is assayed for production of monoclonal antibodies directed against the human CD22 antigen. Preferably, the binding specificity of monoclonal antibodies produced by hybridoma cells is determined by immunoprecipitation or by an in vitro binding assay, such as radioimmunoassay (RIA) or enzyme-linked immunoabsorbent assay (ELISA).

After hybridoma cells are identified that produce antibodies of the desired specificity, affinity, and/or activity, the clones may be subcloned by limiting dilution procedures and grown by standard methods (Goding, *Monoclonal Antibodies: Principles and Practice*, pp. 59-103 (Academic Press, 1986)). Suitable culture media for this purpose include, for example, D-MEM or RPMI 1640 medium. In addition, the hybridoma cells may be grown in vivo as ascites tumors in an animal.

The monoclonal antibodies secreted by the subclones are suitably separated from the culture medium, ascites fluid, or serum by conventional immunoglobulin purification procedures such as, for example, protein A-Sepharose, hydroxylapatite chromatography, gel electrophoresis, dialysis, or affinity chromatography.

5.2.2. Recombinant DNA Techniques

DNA encoding the anti-CD22 antibodies of the invention is readily isolated and sequenced using conventional procedures (e.g., by using oligonucleotide probes that are capable of binding specifically to genes encoding the heavy and light chains of the anti-CD22 antibodies). The hybridoma cells serve as a source of such DNA. Once isolated, the DNA may be placed into expression vectors, which are then transfected into host cells such as *E. coli* cells, simian COS cells, Chinese hamster ovary (CHO) cells, or myeloma cells that do not otherwise produce immunoglobulin protein, to obtain the synthesis of anti-CD22 antibodies in the recombinant host cells.

In phage display methods, functional antibody domains are displayed on the surface of phage particles which carry the polynucleotide sequences encoding them. In particular, DNA sequences encoding $V_H$ and $V_L$ domains are amplified from animal cDNA libraries (e.g., human or murine cDNA libraries of affected tissues). The DNA encoding the $V_H$ and $V_L$ domains are recombined together with an scFv linker by PCR and cloned into a phagemid vector. The vector is electroporated in *E. coli* and the *E. coli* is infected with helper phage. Phage used in these methods are typically filamentous phage including fd and M13 and the $V_H$ and $V_L$ domains are usually recombinantly fused to either the phage gene III or gene VIII. Phage expressing an antigen-binding domain that binds to a particular antigen can be selected or identified with antigen, e.g., using labeled antigen or antigen bound or captured to a solid surface or bead. Examples of phage display methods that can be used to make the antibodies of the present invention include those disclosed in Brinkman et al., 1995, *J. Immunol. Methods*, 182:41-50; Ames et al., 1995, *J. Immunol. Methods*, 184:177-186; Kettleborough et al., 1994, *Eur. J. Immunol.*, 24:952-958; Persic et al., 1997, *Gene*, 187:9-18; Burton et al., 1994, *Advances in Immunology*, 57:191-280; International Application No. PCT/GB91/O1 134; International Publication Nos. WO 90/02809, WO 91/10737, WO 92/01047, WO 92/18619, WO 93/11236, WO 95/15982, WO 95/20401, and WO97/13844; and U.S. Pat. Nos. 5,698,426, 5,223,409, 5,403,484, 5,580,717, 5,427,908, 5,750,753, 5,821,047, 5,571,698, 5,427,908, 5,516,637, 5,780,225, 5,658,727, 5,733,743, and 5,969,108; each of which is incorporated herein by reference in its entirety.

As described in the above references, after phage selection, the antibody coding regions from the phage can be isolated and used to generate whole antibodies, including human antibodies, or any other desired antigen-binding fragment, and expressed in any desired host, including mammalian cells, insect cells, plant cells, yeast, and bacteria, e.g., as described below. Techniques to recombinantly produce Fab, Fab' and F(ab')$_2$ fragments can also be employed using methods known in the art such as those disclosed in PCT Publication No. WO 92/22324; Mullinax et al., 1992, *BioTechniques*, 12(6):864-869; Sawai et al., 1995, *AJRI*, 34:26-34; and Better et al., 1988, *Science*, 240:1041-1043 (said references incorporated by reference in their entireties).

Antibodies may be isolated from antibody phage libraries generated using the techniques described in McCafferty et al., *Nature*, 348:552-554 (1990). Clackson et al., *Nature*, 352: 624-628 (1991). Marks et al., *J. Mol. Biol.*, 222:581-597 (1991) describe the isolation of murine and human antibodies, respectively, using phage libraries. Chain shuffling can be used in the production of high affinity (nM range) human antibodies (Marks et al., *Bio/Technology*, 10:779-783 (1992)), as well as combinatorial infection and in vivo recombination as a strategy for constructing very large phage libraries (Waterhouse et al., *Nuc. Acids. Res.*, 21:2265-2266 (1993)). Thus, these techniques are viable alternatives to traditional monoclonal antibody hybridoma techniques for isolation of anti-CD22 antibodies.

To generate whole antibodies, PCR primers including VH or VL nucleotide sequences, a restriction site, and a flanking sequence to protect the restriction site can be used to amplify the VH or VL sequences in scFv clones. Utilizing cloning techniques known to those of skill in the art, the PCR amplified VH domains can be cloned into vectors expressing a heavy chain constant region, e.g., the human gamma 4 constant region, and the PCR amplified VL domains can be cloned into vectors expressing a light chain constant region, e.g., human kappa or lambda constant regions. Preferably, the vectors for expressing the VH or VL domains comprise an EF-1α promoter, a secretion signal, a cloning site for the variable domain, constant domains, and a selection marker such as neomycin. The VH and VL domains may also be cloned into one vector expressing the necessary constant regions. The heavy chain conversion vectors and light chain conversion vectors are then co-transfected into cell lines to generate stable or transient cell lines that express full-length antibodies, e.g., IgG, using techniques known to those of skill in the art.

The DNA also may be modified, for example, by substituting the coding sequence for human heavy and light chain constant domains in place of the homologous murine sequences (U.S. Pat. No. 4,816,567; Morrison et al., *Proc. Natl. Acad. Sci. USA*, 81:6851 (1984)), or by covalently joining to the immunoglobulin coding sequence all or part of the coding sequence for a non-immunoglobulin polypeptide.

5.3. Chimeric Antibodies

The anti-CD22 antibodies herein specifically include chimeric antibodies (immunoglobulins) in which a portion of the heavy and/or light chain is identical with or homologous to corresponding sequences in antibodies derived from a particular species or belonging to a particular antibody class or subclass, while another portion of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; Morrison et al., *Proc. Natl. Acad. Sci. USA,* 81:6851-6855 (1984)). Chimeric antibodies of interest herein include "primatized" antibodies comprising variable domain antigen-binding sequences derived from a nonhuman primate (e.g., Old World Monkey, such as baboon, rhesus or cynomolgus monkey) and human constant region sequences (U.S. Pat. No. 5,693,780).

The present invention provides for antibodies that have a high binding affinity for the hCD22 antigen. In a specific embodiment, an antibody of the present invention has an association rate constant or $k_{on}$ rate (antibody (Ab)+antigen (Ag)$^{k_{on}}$→Ab-Ag) of at least $2\times10^5$ $M^{-1}s^{-1}$, at least $5\times10^5 M^{-1}s^{-1}$, at least $10^6 M^{-1}s^{-1}$, at least $5\times10^6 M^{-1}$ $s^{-1}$, at least $10^7 M^{-1}s^{-1}$, at least $5\times10^7 M^{-1}s^{-1}$, or at least $10^8 M^{-1}s^{-1}$. In a preferred embodiment, an antibody of the present invention has a $k_{on}$ of at least $2\times10^5 M^{-1}s^{-1}$, at least $5\times10^5 M^{-1}s^{-1}$, at least $10^6 M^{-1}s^{-1}$, at least $5\times10^6 M^{-1}s^{-1}$, at least $10^7 M^{-1}s^{-1}$, at least $5\times10^7 M^{-1}s^{-1}$, or at least $10^8 M^{-1}s^{-1}$.

In another embodiment, an antibody of the invention has a $k_{off}$ rate ((Ab-Ag)$^{k_{off}}$→antibody (Ab)+antigen) of less than $10^{-1}s^{-1}$, less than $5\times10^{-1}s^{-1}$, less than $10^{-2}s^{-1}$, less than $5\times10^{-2}s^{-1}$, less than $10^{-3}s^{-1}$, less than $5\times10^{-4}s^{-1}$, less than $10^{-4}s^{-1}$, less than $5\times10^{-4}s^{-1}$, less than $10^{-5}s^{-1}$, less than $5\times10^{-5}s^1$, less than $10^{-6}s^{-1}$, less than $5\times10^{-6}s^{-1}$, less than $10^{-7}s^{-1}$, less than $5\times10^{-7}s^{-1}$, less than $10^{-8}s^{-1}$, less than $5\times10^{-8}s^{-1}$, less than $10^{-9}s^{-1}$, less than $5\times10^{-9}s^{-1}$, or less than $10^{-10}s^{-1}$. In a preferred embodiment, an antibody of the invention has a $k_{on}$ of less than $5\times10^{-4}s^{-1}$, less than $10^{-5}s^{-1}$, less than $5\times10^{-5}s^{-1}$, less than $10^{-6}s^{-1}$, less than $5\times10^{-6}s^{-1}$, less than $10^{-7}s^{-1}$, less than $5\times10^{-7}s^{-1}$, less than $10^{-8}s^{-1}$, less than $5\times10^{-8}s^{-1}$, less than $10^{-9}s^{-1}$, less than $5\times10^{-9}s^{-1}$, or less than $10^{-10}s^{-1}$.

In another embodiment, an antibody of the invention has an affinity constant or $K_a$ ($k_{on}/k_{off}$) of at least $10^2$ $M^{-1}$, at least $5\times10^2$ $M^{-1}$, at least $10^3$ $M^{-1}$, at least $5\times10^3$ $M^{-1}$, at least $10^4$ $M^{-1}$, at least $5\times10^4 M^{-1}$, at least $10^5$ $M^{-1}$, at least $5\times10^5$ $M^{-1}$, at least $10^6$ $M^{-1}$, at least $5\times10^6$ $M^{-1}$, at least $10^7$ $M^{-1}$, at least $5\times10^7 M^{-1}$, at least $10^8$ $M^{-1}$, at least $5\times10^8$ $M^{-1}$, at least $10^9$ $M^{-1}$, at least $5\times10^9$ $M^{-1}$, at least $10^{10}$ $M^{-1}$, at least $5\times10^{10}$ $M^{-1}$, at least $10^{11}$ $M^{-1}$, at least $5\times10^{11}$ $M^{-1}$, at least $10^{12}$ $M^{-1}$, at least $5\times10^{12}$ $M^{-1}$, at least $10^{13}$ $M^{-1}$, at least $5\times10^{13}$ $M^{-1}$, at least $10^{14}$ $M^{-1}$, at least $5\times10^{14}$ $M^{-1}$, at least $10^{15}$ $M^{-1}$, or at least $5\times10^{15}$ $M^{-1}$. In yet another embodiment, an antibody has a dissociation constant or $k_d$ ($k_{off}/k_{on}$) of less than $10^{-2}$ M, less than $5\times10^{-2}$ M, less than $10^{-3}$ M, less than $5\times10^{-3}$ M, less than $10^{-4}$ M, less than $5\times10^{-4}$ M, less than $10^{-5}$ M, less than $5\times10^{-5}$ M, less than $10^{-6}$ M, less than $5\times10^{-6}$ M, less than $10^{-7}$ M, less than $5\times10^{-7}$M, less than $10^{-8}$ M, less than $5\times10^{-8}$ M, less than $10^{-9}$ M, less than $5\times10^{-9}$ M, less than $10^{-10}$ M, less than $5\times10^{-10}$ M, less than $10^{-11}$ M, less than $5\times10^{-11}$ M, less than $10^{-12}$ M, less than $5\times10^{-12}$ M, less than $10^{-13}$ M, less than $5\times10^{-13}$ M, less than $10^{-14}$ M, less than $5\times10^{-14}$ M, less than $10^{-15}$ M, or less than $5\times10^{-15}$ M.

The antibodies used in accordance with the methods of the invention immunospecifically bind to hCD22 and have a dissociation constant ($K_D$) of less than 3000 pM, less than 2500 pM, less than 2000 pM, less than 1500 pM, less than 1000 pM, less than 750 pM, less than 500 pM, less than 250 pM, less than 200 pM, less than 150 pM, less than 100 pM, less than 75 pM as assessed using an described herein or known to one of skill in the art (e.g., a BIAcore assay) (Biacore International AB, Uppsala, Sweden). In a specific embodiment, the antibodies used in accordance with the methods of the invention immunospecifically bind to human CD22 antigen and have a dissociation constant ($K_D$) of between 25 to 3400 pM, 25 to 3000 pM, 25 to 2500 pM, 25 to 2000 pM, 25 to 1500 pM, 25 to 1000 pM, 25 to 750 pM, 25 to 500 pM, 25 to 250 pM, 25 to 100 pM, 25 to 75 pM, 25 to 50 pM as assessed using methods described herein or known to one of skill in the art (e.g., a BIAcore assay). In another embodiment, the antibodies used in accordance with the methods of the invention immunospecifically bind to hCD22 and have a dissociation constant ($K_D$) of 500 pM, preferably 100 pM, more preferably 75 pM and most preferably 50 pM as assessed using an described herein or known to one of skill in the art (e.g., a BIAcore assay).

5.4. Altered/Mutant Antibodies

The anti-CD22 antibodies of the compositions and methods of the invention can be mutant antibodies. As used herein, "antibody mutant" or "altered antibody" refers to an amino acid sequence variant of an anti-CD22 antibody wherein one or more of the amino acid residues of an anti-CD22 antibody have been modified. The modifications to the amino acid sequence of the anti-CD22 antibody, include modifications to the sequence to improve affinity or avidity of the antibody for its antigen, and/or modifications to the Fc portion of the antibody to improve or to modulate effector function.

The present invention, therefore relates to the human, humanized, and chimeric anti-CD22 antibodies disclosed herein as well as altered/mutant derivatives thereof exhibiting improved human CD22 binding characteristics; e.g. including altered association constants $K_{ON}$, dissociation constants $K_{OFF}$, and/or altered equilibrium constant or binding affinity, $K_a$. In certain embodiments the $K_a$ of an antibody of the present invention, or an altered/mutant derivative thereof, for human CD22 is no more than about $10^{-6}$M, $10^{-7}$M, $10^{-8}$M, or a $10^{-9}$M. Methods and reagents suitable for determination of such binding characteristics of an antibody of the present invention, or an altered/mutant derivative thereof, are known in the art and/or are commercially available (se above and, e.g., U.S. Pat. No. 6,849,425, U.S. Pat. No. 6,632,926, U.S. Pat. No. 6,294,391, and U.S. Pat. No. 6,143,574, each of which is hereby incorporated by reference in its entirety). Moreover, equipment and software designed for such kinetic analyses are commercially available (e.g. Biacore® A100, and Biacore® 2000 instruments; Biacore International AB, Uppsala, Sweden).

The modifications may be made to any known anti-CD22 antibodies or anti-CD22 antibodies identified as described herein. Such altered antibodies necessarily have less than 100% sequence identity or similarity with a known anti-CD22 antibody. In certain embodiments, the altered antibody will have an amino acid sequence that is within the range of from about 25% to about 95% identical or similar to the amino acid sequence of either the heavy or light chain variable domain of an anti-CD22 antibody of the invention. In particular embodiments, the altered antibody will have an amino acid sequence having at least 25%, 35%, 45%, 55%, 65%, or 75% amino acid sequence identity or similarity with the amino acid sequence of either the heavy or light chain variable domain of an anti-CD22 antibody of the invention, more preferably at least 80%, more preferably at least 85%, more preferably at least 90%, and most preferably at least 95%. In another embodiment, the altered antibody will have an amino acid sequence having at least 5%, 35%, 45%, 55%, 65%, or 75% amino acid sequence identity or similarity with the amino acid sequence of the heavy chain CDR1, CDR2, or CDR3 of an anti-CD22 antibody of the invention, more preferably at least 80%, more preferably at least 85%, more preferably at least 90%, and most preferably at least 95%. In one embodiment, the altered antibody will maintain human CD22 binding capability. In certain embodiments, anti-CD22 antibodies of the invention comprises a VH that is at least or about 10%, 15%, 20%, 25%, 30%, 35%, 40%, 45%, 50%, 55%, 60%, 65%, 70%, 75%, 80%, 85%, 90%, 95% or more identical to an amino acid sequence of HB227 VH (SEQ ID NO:7), HB227-(V2-70+IC4) (SEQ ID NO:13), HB227-VH46898 (SEQ ID NO:15), HB227RHB (SEQ ID NO:17), HB227RHC (SEQ ID NO:19), HB227RHD (SEQ ID NO:21), HB227RHE (SEQ ID NO:23), HB227RHF (SEQ ID NO:25), HB227-AJ556657 (SEQ ID NO:43), HB227RHO-V3-30 backmutated (SEQ ID NO:47), HB227RHOv2-VH2-50 (SEQ ID NO:49), HB227RHOv2A VH2-50 (SEQ ID NO:51), HB227RHOv2B-VH2-50 (SEQ ID NO:53), HB227RHOv2C-VH2-50 (SEQ ID NO:55), HB227RHOv2D-VH2-50 (SEQ ID NO:57), HB227RHOv2ACD-VH2-50 (SEQ ID NO:59), or HB227RHOv2-VH2-50 (SEQ ID NO:61) (see FIGS. 5A-G and 13A-G).

In certain embodiments, the anti-CD22 antibody of the invention comprises a VL that is at least or about 10%, 15%, 20%, 25%, 30%, 35%, 40%, 45%, 50%, 55%, 60%, 65%, 70%, 75%, 80%, 85%, 90%, 95% or more identical to an amino acid sequence of HB227 VK (SEQ ID NO:27), HB227-Clone 47 (SEQ ID NO:33), HB227RKA (SEQ ID NO:35), HB227RKB (SEQ ID NO:37), or HB227RKC (SEQ ID NO:39) (see FIG. 7A-D).

The mouse hybridoma HB22.7 producing anti-CD22 antibodies has been deposited under ATCC deposit nos. HB11347 deposited on May 14, 1993.

Identity or similarity with respect to a sequence is defined herein as the percentage of amino acid residues in the candidate sequence that are identical (i.e., same residue) or similar (i.e., amino acid residue from the same group based on common side-chain properties, see below) with anti-CD22 antibody residues, after aligning the sequences and introducing gaps, if necessary, to achieve the maximum percent sequence identity. None of N-terminal, C-terminal, or internal extensions, deletions, or insertions into the antibody sequence outside of the variable domain shall be construed as affecting sequence identity or similarity.

"% identity," as known in the art, is a measure of the relationship between two polynucleotides or two polypeptides, as determined by comparing their nucleotide or amino acid sequences, respectively. In general, the two sequences to be compared are aligned to give a maximum correlation between the sequences. The alignment of the two sequences is examined and the number of positions giving an exact amino acid or nucleotide correspondence between the two sequences determined, divided by the total length of the alignment and multiplied by 100 to give a % identity figure. This % identity figure may be determined over the whole length of the sequences to be compared, which is particularly suitable for sequences of the same or very similar length and which are highly homologous, or over shorter defined lengths, which is more suitable for sequences of unequal length or which have a lower level of homology.

For example, sequences can be aligned with the software CLUSTALW under Unix which generates a file with an ".aln" extension, this file can then be imported into the Bioedit program (Hall, T. A. 1999, *BioEdit: a user-friendly biological sequence alignment editor and analysis program for Windows 95/98/NT. Nucl. Acids. Symp. Ser.* 41:95-98) which opens the .aln file. In the Bioedit window, one can choose individual sequences (two at a time) and alignment them. This method allows for comparison of the entire sequence.

Methods for comparing the identity of two or more sequences are well-known in the art. Thus for instance, programs are available in the Wisconsin Sequence Analysis Package, version 9.1 (Devereux J. et al., *Nucleic Acids Res.*, 12:387-395, 1984, available from Genetics Computer Group, Madison, Wis., USA). The determination of percent identity between two sequences can be accomplished using a mathematical algorithm. For example, the programs BESTFIT and GAP, may be used to determine the % identity between two polynucleotides and the % identity between two polypeptide sequences. BESTFIT uses the "local homology" algorithm of Smith and Waterman (*Advances in Applied Mathematics,* 2:482-489, 1981) and finds the best single region of similarity between two sequences. BESTFIT is more suited to comparing two polynucleotide or two polypeptide sequences which are dissimilar in length, the program assuming that the shorter sequence represents a portion of the longer. In comparison, GAP aligns two sequences finding a "maximum similarity" according to the algorithm of Neddleman and Wunsch (*J. Mol. Biol.,* 48:443-354, 1970). GAP is more suited to comparing sequences which are approximately the same length and an alignment is expected over the entire length. Preferably the parameters "Gap Weight" and "Length Weight" used in each program are 50 and 3 for polynucleotides and 12 and 4 for polypeptides, respectively. Preferably % identities and similarities are determined when the two sequences being compared are optimally aligned.

Other programs for determining identity and/or similarity between sequences are also known in the art, for instance the BLAST family of programs (Karlin & Altschul, 1990, *Proc. Natl. Acad. Sci. USA,* 87:2264-2268, modified as in Karlin & Altschul, 1993, *Proc. Natl. Acad. Sci. USA,* 90:5873-5877, available from the National Center for Biotechnology Information (NCB), Bethesda, Md., USA and accessible through the home page of the NCBI at www.ncbi.nlm.nih.gov). These programs are non-limiting examples of a mathematical algorithm utilized for the comparison of two sequences. Such an algorithm is incorporated into the NBLAST and XBLAST programs of Altschul et al., 1990, *J. Mol. Biol.,* 215:403-410. BLAST nucleotide searches can be performed with the NBLAST program, score=100, wordlength=12 to obtain nucleotide sequences homologous to a nucleic acid molecule encoding all or a portion if an anti-CD22 antibody of the invention. BLAST protein searches can be performed with the XBLAST program, score=50, wordlength=3 to obtain amino acid sequences homologous to a protein molecule of the invention. To obtain gapped alignments for comparison purposes, Gapped BLAST can be utilized as described in Altschul et al., 1997, *Nucleic Acids Res.,* 25:3389-3402. Alternatively, PSI-Blast can be used to perform an iterated search which detects distant relationships between molecules (Id.). When utilizing BLAST, Gapped BLAST, and PSI-Blast programs, the default parameters of the respective programs (e.g., XBLAST and NBLAST) can be used. See, http://www.ncbi.nlm.nih.gov. Another, non-limiting example of a mathematical algorithm utilized for the comparison of sequences is the algorithm of Myers and Miller, 1988, *CABIOS* 4:11-17. Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used.

Another non-limiting example of a program for determining identity and/or similarity between sequences known in the art is FASTA (Pearson W. R. and Lipman D. J., *Proc. Natl. Acad. Sci. USA,* 85:2444-2448, 1988, available as part of the Wisconsin Sequence Analysis Package). Preferably the BLOSUM62 amino acid substitution matrix (Henikoff S. and Henikoff J. G., *Proc. Natl. Acad. Sci. USA,* 89:10915-10919, 1992) is used in polypeptide sequence comparisons including where nucleotide sequences are first translated into amino acid sequences before comparison.

Yet another non-limiting example of a program known in the art for determining identity and/or similarity between amino acid sequences is SeqWeb Software (a web-based interface to the GCG Wisconsin Package: Gap program) which is utilized with the default algorithm and parameter settings of the program: blosum62, gap weight 8, length weight 2.

The percent identity between two sequences can be determined using techniques similar to those described above, with or without allowing gaps. In calculating percent identity, typically exact matches are counted.

Preferably the program BESTFIT is used to determine the % identity of a query polynucleotide or a polypeptide sequence with respect to a polynucleotide or a polypeptide sequence of the present invention, the query and the reference sequence being optimally aligned and the parameters of the program set at the default value.

To generate an altered antibody, one or more amino acid alterations (e.g., substitutions) are introduced in one or more of the hypervariable regions of the species-dependent antibody. Alternatively, or in addition, one or more alterations (e.g., substitutions) of framework region residues may be introduced in an anti-CD22 antibody where these result in an improvement in the binding affinity of the antibody mutant for the antigen from the second mammalian species. Examples of framework region residues to modify include those which non-covalently bind antigen directly (Amit et al., *Science,* 233:747-753 (1986)); interact with/effect the conformation of a CDR (Chothia et al., *J. Mol. Biol.,* 196:901-917 (1987)); and/or participate in the $V_L$-$V_H$ interface (EP 239 400B1). In certain embodiments, modification of one or more of such framework region residues results in an enhancement of the binding affinity of the antibody for the antigen from the second mammalian species. For example, from about one to about five framework residues may be altered in this embodiment of the invention. Sometimes, this may be sufficient to yield an antibody mutant suitable for use in preclinical trials, even where none of the hypervariable region residues have been altered. Normally, however, an altered antibody will comprise additional hypervariable region alteration(s).

The hypervariable region residues which are altered may be changed randomly, especially where the starting binding affinity of an anti-CD22 antibody for the antigen from the second mammalian species is such that such randomly produced altered antibody can be readily screened.

One useful procedure for generating such an altered antibody is called "alanine scanning mutagenesis" (Cunningham and Wells, *Science,* 244:1081-1085 (1989)). Here, one or more of the hypervariable region residue(s) are replaced by alanine or polyalanine residue(s) to affect the interaction of the amino acids with the antigen from the second mammalian species. Those hypervariable region residue(s) demonstrating functional sensitivity to the substitutions then are refined by introducing additional or other mutations at or for the sites of substitution. Thus, while the site for introducing an amino acid sequence variation is predetermined, the nature of the mutation per se need not be predetermined. The Ala-mutants produced this way are screened for their biological activity as described herein.

Another procedure for generating such an altered antibody involves affinity maturation using phage display (Hawkins et al., *J. Mol. Biol.,* 254:889-896 (1992) and Lowman et al., *Biochemistry,* 30(45):10832-10837 (1991)). Briefly, several hypervariable region sites (e.g., 6-7 sites) are mutated to generate all possible amino acid substitutions at each site. The antibody mutants thus generated are displayed in a monovalent fashion from filamentous phage particles as fusions to the gene III product of M13 packaged within each particle. The phage-displayed mutants are then screened for their biological activity (e.g., binding affinity) as herein disclosed.

Mutations in antibody sequences may include substitutions, deletions, including internal deletions, additions, including additions yielding fusion proteins, or conservative substitutions of amino acid residues within and/or adjacent to the amino acid sequence, but that result in a "silent" change, in that the change produces a functionally equivalent anti-CD22 antibody. Conservative amino acid substitutions may be made on the basis of similarity in polarity, charge, solubility, hydrophobicity, hydrophilicity, and/or the amphipathic nature of the residues involved. For example, non-polar (hydrophobic) amino acids include alanine, leucine, isoleucine, valine, proline, phenylalanine, tryptophan, and methionine; polar neutral amino acids include glycine, serine, threonine, cysteine, tyrosine, asparagine, and glutamine; positively charged (basic) amino acids include arginine, lysine, and histidine; and negatively charged (acidic) amino acids include aspartic acid and glutamic acid. In addition, glycine and proline are residues that can influence chain orientation. Non-conservative substitutions will entail exchanging a member of one of these classes for another class. Furthermore, if desired, non-classical amino acids or chemical amino acid analogs can be introduced as a substitution or addition into the antibody sequence. Non-classical amino acids include, but are not limited to, the D-isomers of the common amino acids, α-amino isobutyric acid, 4-aminobutyric acid, Abu, 2-amino butyric acid, γ-Abu, ε-Ahx, 6-amino hexanoic acid, Aib, 2-amino isobutyric acid, 3-amino propionic acid, ornithine, norleucine, norvaline, hydroxyproline, sarcosine, citrulline, cysteic acid, t-butylglycine, t-butylalanine, phenylglycine, cyclohexylalanine, β-alanine, fluoro-amino acids, designer amino acids such as β-methyl amino acids, Cα-methyl amino acids, Nα-methyl amino acids, and amino acid analogs in general.

In another embodiment, the sites selected for modification are affinity matured using phage display (see above).

Any technique for mutagenesis known in the art can be used to modify individual nucleotides in a DNA sequence, for purposes of making amino acid substitution(s) in the antibody sequence, or for creating/deleting restriction sites to facilitate further manipulations. Such techniques include, but are not limited to, chemical mutagenesis, in vitro site-directed mutagenesis (Kunkel, *Proc. Natl. Acad. Sci. USA,* 82:488 (1985); Hutchinson, C. et al., *J. Biol. Chem.,* 253:6551 (1978)), oligonucleotide-directed mutagenesis (Smith, *Ann. Rev. Genet.,* 19:423-463 (1985); Hill et al., *Methods Enzymol.,* 155:558-568 (1987)), PCR-based overlap extension (Ho et al., *Gene,* 77:51-59 (1989)), PCR-based megaprimer mutagenesis (Sarkar et al., *Biotechniques,* 8:404-407 (1990)), etc. Modifications can be confirmed by double-stranded dideoxy DNA sequencing.

In certain embodiments of the invention the anti-CD22 antibodies can be modified to produce fusion proteins; i.e., the antibody, or a fragment fused to a heterologous protein, polypeptide or peptide. In certain embodiments, the protein fused to the portion of an anti-CD22 antibody is an enzyme component of Antibody-Directed Enzyme Prodrug Therapy (ADEPT). Examples of other proteins or polypeptides that can be engineered as a fusion protein with an anti-CD22 antibody include, but are not limited to toxins such as ricin, abrin, ribonuclease, DNase I, *Staphylococcal* enterotoxin-A, pokeweed anti-viral protein, gelonin, diphtherin toxin, *Pseudomonas* exotoxin, and *Pseudomonas* endotoxin. See, for example, Pastan et al., *Cell,* 47:641 (1986), and Goldenberg et al., *Cancer Journal for Clinicians,* 44:43 (1994). Enzymatically active toxins and fragments thereof which can be used include diphtheria A chain, non-binding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *momordica charantia* inhibitor, curcin, crotin, *sapaonaria officinalis* inhibitor, gelonin, mitogellin, restrictocin, phenomycin, enomycin and the tricothecenes. See, for example, WO 93/21232 published Oct. 28, 1993.

Additional fusion proteins may be generated through the techniques of gene-shuffling, motif-shuffling, exon-shuffling, and/or codon-shuffling (collectively referred to as "DNA shuffling"). DNA shuffling may be employed to alter the activities of SYNAGIS® or fragments thereof (e.g., an antibody or a fragment thereof with higher affinities and lower dissociation rates). See, generally, U.S. Pat. Nos. 5,605, 793; 5,811,238; 5,830,721; 5,834,252; and 5,837,458, and Patten et al., 1997, *Curr. Opinion Biotechnol.,* 8:724-33; Harayama, 1998, *Trends Biotechnol.* 16(2):76-82; Hansson et al., 1999, *J. Mol. Biol.,* 287:265-76; and Lorenzo and Blasco, 1998, *Biotechniques* 24(2):308-313 (each of these patents and publications are hereby incorporated by reference in its entirety). The antibody can further be a binding-domain immunoglobulin fusion protein as described in U.S. Publication 20030118592, U.S. Publication 200330133939, and PCT Publication WO 02/056910, all to Ledbetter et al., which are incorporated herein by reference in their entireties.

5.5. Domain Antibodies

The anti-CD22 antibodies of the compositions and methods of the invention can be domain antibodies, e.g., antibodies containing the small functional binding units of antibodies, corresponding to the variable regions of the heavy ($V_H$) or light ($V_L$) chains of human antibodies. Examples of domain antibodies include, but are not limited to, those available from Domantis Limited (Cambridge, UK) and Domantis Inc. (Cambridge, Mass., USA) that are specific to therapeutic targets (see, for example, WO04/058821; WO04/003019; U.S. Pat. Nos. 6,291,158; 6,582,915; 6,696,245; and 6,593,081). Commercially available libraries of domain antibodies can be used to identify anti-CD22 domain antibodies. In certain embodiments, the anti-CD22 antibodies of the invention comprise a CD22 functional binding unit and a Fc gamma receptor functional binding unit.

5.6. Diabodies

The term "diabodies" refers to small antibody fragments with two antigen-binding sites, which fragments comprise a heavy chain variable domain ($V_H$) connected to a light chain variable domain ($V_L$) in the same polypeptide chain ($V_H$-$V_L$). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger et al., *Proc. Natl. Acad. Sci. USA,* 90:6444-6448 (1993).

5.7. Vaccibodies

In certain embodiments of the invention, the anti-CD22 antibodies are Vaccibodies. Vaccibodies are dimeric polypeptides. Each monomer of a vaccibody consists of a scFv with specificity for a surface molecule on APC connected through a hinge region and a Cγ3 domain to a second scFv. In other embodiments of the invention, vaccibodies containing as one of the scFv's an anti-CD22 antibody fragment may be used to juxtapose those B cells to be destroyed and an effector cell that mediates ADCC. For example, see, Bogen et al., U.S. Patent Application Publication No. 20040253238.

5.8. Linear Antibodies

In certain embodiments of the invention, the anti-CD22 antibodies are linear antibodies. Linear antibodies comprise a pair of tandem Fd segments ($V_H$-$C_{H1}$-$V_H$-$C_{H1}$) which form a pair of antigen-binding regions. Linear antibodies can be bispecific or monospecific. See, Zapata et al., *Protein Eng.,* 8(10):1057-1062 (1995).

5.9. Parent Antibody

In certain embodiments of the invention, the anti-CD22 antibody is a parent antibody. A "parent antibody" is an antibody comprising an amino acid sequence which lacks, or is deficient in, one or more amino acid residues in or adjacent to one or more hypervariable regions thereof compared to an altered/mutant antibody as herein disclosed. Thus, the parent antibody has a shorter hypervariable region than the corresponding hypervariable region of an antibody mutant as herein disclosed. The parent polypeptide may comprise a native sequence (i.e., a naturally occurring) antibody (including a naturally occurring allelic variant) or an antibody with pre-existing amino acid sequence modifications (such as other insertions, deletions and/or substitutions) of a naturally occurring sequence. Preferably the parent antibody is a humanized antibody or a human antibody.

5.10. Antibody Fragments

"Antibody fragments" comprise a portion of a full-length antibody, generally the antigen binding or variable region thereof. Examples of antibody fragments include Fab, Fab', $F(ab')_2$, and Fv fragments; diabodies; linear antibodies; single-chain antibody molecules; and multispecific antibodies formed from antibody fragments.

Traditionally, these fragments were derived via proteolytic digestion of intact antibodies (see, e.g., Morimoto et al., *Journal of Biochemical and Biophysical Methods,* 24:107-117 (1992) and Brennan et al., *Science,* 229:81 (1985)). However, these fragments can now be produced directly by recombinant host cells. For example, the antibody fragments can be isolated from the antibody phage libraries discussed above. Alternatively, Fab'-SH fragments can be directly recovered from *E. coli* and chemically coupled to form $F(ab')_2$ fragments (Carter et al., *Bio/Technology,* 10:163-167 (1992)). According to another approach, $F(ab')_2$ fragments can be isolated directly from recombinant host cell culture. Other techniques for the production of antibody fragments will be apparent to the skilled practitioner. In other embodiments, the antibody of choice is a single-chain Fv fragment (scFv). See, for example, WO 93/16185. In certain embodiments, the antibody is not a Fab fragment.

5.11. Bispecific Antibodies

Bispecific antibodies are antibodies that have binding specificities for at least two different epitopes. Exemplary bispecific antibodies may bind to two different epitopes of the B cell surface marker. Other such antibodies may bind a first B cell marker and further bind a second B cell surface marker. Alternatively, an anti-B cell marker binding arm may be combined with an arm which binds to a triggering molecule on a leukocyte such as a T cell receptor molecule (e.g., CD2 or CD3), or Fc receptors for IgG (FcγR), so as to focus cellular defense mechanisms to the B cell. Bispecific antibodies may also be used to localize cytotoxic agents to the B cell. These antibodies possess a B cell marker-binding arm and an arm which binds the cytotoxic agent (e.g., saporin, anti-interferon-α, vinca alkaloid, ricin A chain, methola-exate or radioactive isotope hapten). Bispecific antibodies can be prepared as full-length antibodies or antibody fragments (e.g., F(ab'): bispecific antibodies).

Methods for making bispecific antibodies are known in the art. (See, for example, Milistein et al., *Nature,* 305:537-539 (1983); Traunecker et al., *EMBO J.,* 10:3655-3659 (1991); Suresh et al., *Methods in Enzymology,* 121:210 (1986); Kostelny et al., *J. Immunol.,* 148(5):1547-1553 (1992); Hollinger et al., *Proc. Natl. Acad. Sci. USA,* 90:6444-6448 (1993); Gruber et al., *J. Immunol.,* 152:5368 (1994); U.S. Pat. Nos. 4,474,893; 4,714,681; 4,925,648; 5,573,920; 5,601,81; 95,731,168; 4,676,980; and 4,676,980, WO 94/04690; WO 91/00360; WO 92/200373; WO 93/17715; WO 92/08802; and EP 03089.)

In one embodiment, where the anti-CD22 antibody of the compositions and methods of the invention is bispecific, the anti-CD22 antibody is human or humanized and has specificity for human CD22 and an epitope on a T cell or is capable of binding to a human effector cell such as, for example, a monocyte/macrophage and/or a natural killer cell to effect cell death.

5.12. Variant Fc Regions

The present invention provides formulation of proteins comprising a variant Fc region. That is, a non-naturally occurring Fc region, for example an Fc region comprising one or more non-naturally occurring amino acid residues. Also encompassed by the variant Fc regions of present invention are Fc regions which comprise amino acid deletions, additions and/or modifications.

It will be understood that Fc region as used herein includes the polypeptides comprising the constant region of an antibody excluding the first constant region immunoglobulin domain. Thus Fc refers to the last two constant region immunoglobulin domains of IgA, IgD, and IgG, and the last three constant region immunoglobulin domains of IgE and IgM, and the flexible hinge N-terminal to these domains. For IgA and IgM Fc may include the J chain. For IgG, Fc comprises immunoglobulin domains Cgamma2 and Cgamma3 (Cγ2 and Cγ3) and the hinge between Cgamma1 (Cγ1) and Cgamma2 (Cγ2). Although the boundaries of the Fc region may vary, the human IgG heavy chain Fc region is usually defined to comprise residues C226 or P230 to its carboxyl-terminus, wherein the numbering is according to the EU index as in Kabat et al. (1991, NIH Publication 91-3242, National Technical Information Service, Springfield, Va.). The "EU index as set forth in Kabat" refers to the residue numbering of the human IgG1 EU antibody as described in Kabat et. al. supra. Fc may refer to this region in isolation, or this region in the context of an antibody, antibody fragment, or Fc fusion protein. An Fc variant protein may be an antibody, Fc fusion, or any protein or protein domain that comprises an Fc region. Particularly preferred are proteins comprising variant Fc regions, which are non-naturally occurring variants of an Fc. Note: Polymorphisms have been observed at a number of Fc positions, including but not limited to Kabat 270, 272, 312, 315, 356, and 358, and thus slight differences between the presented sequence and sequences in the prior art may exist.

The present invention encompasses Fc variant proteins which have altered binding properties for an Fc ligand (e.g., an Fc receptor, C1q) relative to a comparable molecule (e.g., a protein having the same amino acid sequence except having a wild type Fc region). Examples of binding properties include but are not limited to, binding specificity, equilibrium dissociation constant (KD), dissociation and association rates ($K_{off}$ and $K_{on}$ respectively), binding affinity and/or avidity. It is generally understood that a binding molecule (e.g., a Fc variant protein such as an antibody) with a low KD is preferable to a binding molecule with a high KD. However, in some instances the value of the kon or koff may be more relevant than the value of the KD. One skilled in the art can determine which kinetic parameter is most important for a given antibody application.

The affinities and binding properties of an Fc domain for its ligand, may be determined by a variety of in vitro assay methods (biochemical or immunological based assays) known in the art for determining Fc-FcγR interactions, i.e., specific binding of an Fc region to an FcγR including but not limited to, equilibrium methods (e.g., enzyme-linked immunoabsorbent assay (ELISA), or radioimmunoassay (RIA)), or kinetics (e.g., BIACORE® analysis), and other methods such as indirect binding assays, competitive inhibition assays, fluorescence resonance energy transfer (FRET), gel electrophoresis and chromatography (e.g., gel filtration). These and other methods may utilize a label on one or more of the components being examined and/or employ a variety of detection methods including but not limited to chromogenic, fluorescent, luminescent, or isotopic labels. A detailed description of binding affinities and kinetics can be found in Paul, W. E., ed., Fundamental Immunology, 4th Ed., Lippincott-Raven, Philadelphia (1999), which focuses on antibody-immunogen interactions.

In one embodiment, the Fc variant protein has enhanced binding to one or more Fc ligand relative to a comparable molecule. In another embodiment, the Fc variant protein has an affinity for an Fc ligand that is at least 2 fold, or at least 3 fold, or at least 5 fold, or at least 7 fold, or a least 10 fold, or at least 20 fold, or at least 30 fold, or at least 40 fold, or at least 50 fold, or at least 60 fold, or at least 70 fold, or at least 80 fold, or at least 90 fold, or at least 100 fold, or at least 200 fold greater than that of a comparable molecule. In a specific embodiment, the Fc variant protein has enhanced binding to an Fc receptor. In another specific embodiment, the Fc variant protein has enhanced binding to the Fc receptor FcγRIIIA. In still another specific embodiment, the Fc variant protein has enhanced binding to the Fc receptor FcRn. In yet another specific embodiment, the Fc variant protein has enhanced binding to C1q relative to a comparable molecule.

The serum half-life of proteins comprising Fc regions may be increased by increasing the binding affinity of the Fc region for FcRn. In one embodiment, the Fc variant protein has enhanced serum half life relative to comparable molecule.

"Antibody-dependent cell-mediated cytotoxicity" or "ADCC" refers to a form of cytotoxicity in which secreted Ig bound onto Fc receptors (FcRs) present on certain cytotoxic cells (e.g., Natural Killer (NK) cells, neutrophils, and macrophages) enables these cytotoxic effector cells to bind specifically to an antigen-bearing target cell and subsequently kill the target cell with cytotoxins. Specific high-affinity IgG antibodies directed to the surface of target cells "arm" the cytotoxic cells and are absolutely required for such killing. Lysis of the target cell is extracellular, requires direct cell-to-cell contact, and does not involve complement. It is contemplated that, in addition to antibodies, other proteins comprising Fc regions, specifically Fc fusion proteins, having the capacity to bind specifically to an antigen-bearing target cell will be able to effect cell-mediated cytotoxicity. For simplicity, the cell-mediated cytotoxicity resulting from the activity of an Fc fusion protein is also referred to herein as ADCC activity.

The ability of any particular Fc variant protein to mediate lysis of the target cell by ADCC can be assayed. To assess ADCC activity an Fc variant protein of interest is added to target cells in combination with immune effector cells, which may be activated by the antigen antibody complexes resulting in cytolysis of the target cell. Cytolysis is generally detected by the release of label (e.g. radioactive substrates, fluorescent dyes or natural intracellular proteins) from the lysed cells. Useful effector cells for such assays include peripheral blood mononuclear cells (PBMC) and Natural Killer (NK) cells. Specific examples of in vitro ADCC assays are described in Wisecarver et al., 1985 79:277-282; Bruggemann et al., 1987, *J Exp. Med.* 166:1351-1361; Wilkinson et al., 2001, *J Immunol. Methods* 258:183-191; Patel et al., 1995 *J Immunol. Methods* 184:29-38. Alternatively, or additionally, ADCC activity of the Fc variant protein of interest may be assessed in vivo, e.g., in a animal model such as that disclosed in Clynes et al., 1998, *Proc. Natl. Acad. Sci. USA* 95:652-656.

In one embodiment, an Fc variant protein has enhanced ADCC activity relative to a comparable molecule. In a specific embodiment, an Fc variant protein has ADCC activity that is about at least 1.5 fold, or at least 2 fold, or at least 3 fold, or at least 4 fold, or at least 5 fold, or at least 10 fold, or at least 15 fold, or at least 20 fold, or at least 25 fold, or at least 30 fold, or at least 35 fold, or at least 40 fold, or at least 45 fold, or at least 50 fold or at least 100 fold greater than that of a comparable molecule. In another specific embodiment, an Fc variant protein has enhanced binding to the Fc receptor FcγRIIIA and has enhanced ADCC activity relative to a comparable molecule. In other embodiments, the Fc variant protein has both enhanced ADCC activity and enhanced serum half life relative to a comparable molecule.

"Complement dependent cytotoxicity" and "CDC" refer to the lysing of a target cell in the presence of complement. The complement activation pathway is initiated by the binding of the first component of the complement system (C1q) to a molecule, an antibody for example, complexed with a cognate antigen. To assess complement activation, a CDC assay, e.g. as described in Gazzano-Santoro et al., 1996, J. Immunol. Methods, 202:163, may be performed. In one embodiment, an Fc variant protein has enhanced CDC activity relative to a comparable molecule. In a specific embodiment, an Fc variant protein has CDC activity that is at least 2 fold, or at least 3 fold, or at least 5 fold or at least 10 fold or at least 50 fold or at least 100 fold greater than that of a comparable molecule. In other embodiments, the Fc variant protein has both enhanced CDC activity and enhanced serum half life relative to a comparable molecule.

In one embodiment, the present invention provides formulations, wherein the Fc region comprises a non-naturally occurring amino acid residue at one or more positions selected from the group consisting of 234, 235, 236, 239, 240, 241, 243, 244, 245, 247, 252, 254, 256, 262, 263, 264, 265, 266, 267, 269, 296, 297, 298, 299, 313, 325, 326, 327, 328, 329, 330, 332, 333, and 334 as numbered by the EU index as set forth in Kabat. Optionally, the Fc region may comprise a non-naturally occurring amino acid residue at additional and/or alternative positions known to one skilled in the art (see, e.g., U.S. Pat. Nos. 5,624,821; 6,277,375; 6,737,056; PCT Patent Publications WO 01/58957; WO 02/06919; WO 04/016750; WO 04/029207; WO 04/035752 and WO 05/040217).

In a specific embodiment, the present invention provides an Fc variant protein formulation, wherein the Fc region comprises at least one non-naturally occurring amino acid residue selected from the group consisting of 234D, 234E, 234N, 234Q, 234T, 234H, 234Y, 234I, 234V, 234F, 235A, 235D, 235R, 235W, 235P, 235S, 235N, 235Q, 235T, 235H, 235Y, 235I, 235V, 235F, 236E, 239D, 239E, 239N, 239Q, 239F, 239T, 239H, 239Y, 240I, 240A, 240T, 240M, 241W, 241L, 241Y, 241E, 241 R. 243W, 243L 243Y, 243R, 243Q, 244H, 245A, 247V, 247G, 252Y, 254T, 256E, 262I, 262A, 262T, 262E, 263I, 263A, 263T, 263M, 264L, 264I, 264W, 264T, 264R, 264F, 264M, 264Y, 264E, 265G, 265N, 265Q, 265Y, 265F, 265V, 265I, 265L, 265I1, 265T, 266I, 266A, 266T, 266M, 267Q, 267L, 269H, 269Y, 269F, 269R, 296E, 296Q, 296D, 296N, 296S, 296T, 296L, 296I, 296H, 269G, 297S, 297D, 297E, 298H, 298I, 298T, 298F, 299I, 299L, 299A, 299S, 299V, 299I1, 299F, 299E, 313F, 325Q, 325L, 325I, 325D, 325E, 325A, 325T, 325V, 325H, 327G, 327W, 327N, 327L, 328S, 328M, 328D, 328E, 328N, 328Q, 328F, 328I, 328V, 328T, 328H, 328A, 329F, 329H, 329Q, 330K, 330G, 330T, 330C, 330L, 330Y, 330V, 330I, 330F, 330R, 330H, 332D, 332S, 332W, 332F, 332E, 332N, 332Q, 332T, 332H, 332Y, and 332A as numbered by the EU index as set forth in Kabat. Optionally, the Fc region may comprise additional and/or alternative non-naturally occurring amino acid residues known to one skilled in the art (see, e.g., U.S. Pat. Nos. 5,624,821; 6,277,375; 6,737,056; PCT Patent Publications WO 01/58957; WO 02/06919; WO 04/016750; WO 04/029207; WO 04/035752 and WO 05/040217).

In another embodiment, the present invention provides an Fc variant protein formulation, wherein the Fc region comprises at least a non-naturally occurring amino acid at one or more positions selected from the group consisting of 239, 330 and 332, as numbered by the EU index as set forth in Kabat. In a specific embodiment, the present invention provides an Fc variant protein formulation, wherein the Fc region comprises at least one non-naturally occurring amino acid selected from the group consisting of 239D, 330L and 332E, as numbered by the EU index as set forth in Kabat. Optionally, the Fc region may further comprise additional non-naturally occurring amino acid at one or more positions selected from the group consisting of 252, 254, and 256, as numbered by the EU index as set forth in Kabat. In a specific embodiment, the present invention provides an Fc variant protein formulation, wherein the Fc region comprises at least one non-naturally occurring amino acid selected from the group consisting of 239D, 330L and 332E, as numbered by the EU index as set forth in Kabat and at least one non-naturally occurring amino acid at one or more positions are selected from the group consisting of 252Y, 254T and 256E, as numbered by the EU index as set forth in Kabat.

In one embodiment, the Fc variants of the present invention may be combined with other known Fc variants such as those disclosed in Ghetie et al., 1997, Nat. Biotech. 15:637-40; Duncan et al, 1988, Nature 332:563-564; Lund et al., 1991, J. Immunol 147:2657-2662; Lund et al, 1992, Mol Immunol 29:53-59; Alegre et al, 1994, Transplantation 57:1537-1543; Hutchins et al., 1995, *Proc Natl. Acad Sci USA* 92:11980-11984; Jefferis et al, 1995, Immunol Lett. 44:111-117; Lund et al., 1995, Faseb J 9:115-119; Jefferis et al, 1996, Immunol Lett 54:101-104; Lund et al, 1996, J Immunol 157:4963-4969; Armour et al., 1999, Eur J Immunol 29:2613-2624; Idusogie et al, 2000, J Immunol 164:4178-4184; Reddy et al, 2000, J Immunol 164:1925-1933; Xu et al., 2000, Cell Immunol 200:16-26; Idusogie et al, 2001, J Immunol 166:2571-2575; Shields et al., 2001, J Biol Chem 276:6591-6604; Jefferis et al, 2002, Immunol Lett 82:57-65; Presta et al., 2002, Biochem Soc Trans 30:487-490); U.S. Pat. Nos. 5,624,821; 5,885,573; 5,677,425; 6,165,745; 6,277,375; 5,869,046; 6,121,022; 5,624,821; 5,648,260; 6,528,624; 6,194,551; 6,737,056; 6,821,505; 6,277,375; U.S. Patent Publication Nos. 2004/0002587 and PCT Publications WO 94/29351; WO 99/58572; WO 00/42072; WO 02/060919; WO 04/029207; WO 04/099249; WO 04/063351. Also encompassed by the present invention are Fc regions which comprise deletions, additions and/or modifications. Still other modifications/substitutions/additions/deletions of the Fc domain will be readily apparent to one skilled in the art.

Methods for generating non-naturally occurring Fc regions are known in the art. For example, amino acid substitutions and/or deletions can be generated by mutagenesis methods, including, but not limited to, site-directed mutagenesis (Kunkel, *Proc. Natl. Acad. Sci.* USA 82:488-492 (1985)), PCR mutagenesis (Higuchi, in "PCR Protocols: A Guide to Methods and Applications", Academic Press, San Diego, pp. 177-183 (1990)), and cassette mutagenesis (Wells et al., Gene 34:315-323 (1985)). Preferably, site-directed mutagenesis is performed by the overlap-extension PCR method (Higuchi, in "PCR Technology: Principles and Applications for DNA Amplification", Stockton Press, New York, pp. 61-70 (1989)). Alternatively, the technique of overlap-extension PCR (Higuchi, ibid.) can be used to introduce any desired mutation(s) into a target sequence (the starting DNA). For example, the first round of PCR in the overlap-extension method involves amplifying the target sequence with an outside primer (primer 1) and an internal mutagenesis primer (primer 3), and separately with a second outside primer (primer 4) and an internal primer (primer 2), yielding two PCR segments (segments A and B). The internal mutagenesis primer (primer 3) is designed to contain mismatches to the target sequence specifying the desired mutation(s). In the second round of PCR, the products of the first round of PCR (segments A and B) are amplified by PCR using the two outside primers (primers 1 and 4). The resulting full-length PCR segment (segment C) is digested with restriction enzymes and the resulting restriction fragment is cloned into an appropriate vector. As the first step of mutagenesis, the starting DNA (e.g., encoding an Fc fusion protein, an antibody or simply an Fc region), is operably cloned into a mutagenesis vector. The primers are designed to reflect the desired amino acid substitution. Other methods useful for the generation of variant Fc regions are known in the art (see, e.g., U.S. Pat. Nos. 5,624,821; 5,885,573; 5,677,425; 6,165,745; 6,277,375; 5,869,046; 6,121,022; 5,624,821; 5,648,260; 6,528,624; 6,194,551; 6,737,056; 6,821,505; 6,277,375; U.S. Patent Publication Nos. 2004/0002587 and PCT Publications WO 94/29351; WO 99/58572; WO 00/42072; WO 02/060919; WO 04/029207; WO 04/099249; WO 04/063351).

In some embodiments, an Fc variant protein comprises one or more engineered glycoforms, i.e., a carbohydrate composition that is covalently attached to the molecule comprising an Fc region. Engineered glycoforms may be useful for a variety of purposes, including but not limited to enhancing or reducing effector function. Engineered glycoforms may be generated by any method known to one skilled in the art, for example by using engineered or variant expression strains, by co-expression with one or more enzymes, for example DI N-acetylglucosaminyltransferase III (GnTI11), by expressing a molecule comprising an Fc region in various organisms or cell lines from various organisms, or by modifying carbohydrate(s) after the molecule comprising Fc region has been expressed. Methods for generating engineered glycoforms are known in the art, and include but are not limited to those described in Umana et al, 1999, Nat. Biotechnol 17:176-180; Davies et al., 20017 Biotechnol Bioeng 74:288-294; Shields et al, 2002, J Biol Chem 277:26733-26740; Shinkawa et al., 2003, J Biol Chem 278:3466-3473) U.S. Pat. No. 6,602,684; U.S. Ser. No. 10/277,370; U.S. Ser. No. 10/113,929; PCT WO 00/61739A1; PCT WO 01/292246A1; PCT WO 02/311140A1; PCT WO 02/30954A1; Potillegent™ technology (Biowa, Inc. Princeton, N.J.); GlycoMAb™ glycosylation engineering technology (GLYCART biotechnology AG, Zurich, Switzerland). See, e.g., WO 00061739; EA01229125; US 20030115614; Okazaki et al., 2004, JMB, 336: 1239-49.

5.13. Glycosylation of Antibodies

In still another embodiment, the glycosylation of antibodies utilized in accordance with the invention is modified. For example, an aglycoslated antibody can be made (i.e., the antibody lacks glycosylation). Glycosylation can be altered to, for example, increase the affinity of the antibody for a target antigen. Such carbohydrate modifications can be accomplished by, for example, altering one or more sites of glycosylation within the antibody sequence. For example, one or more amino acid substitutions can be made that result in elimination of one or more variable region framework glycosylation sites to thereby eliminate glycosylation at that site. Such aglycosylation may increase the affinity of the antibody for antigen. Such an approach is described in further detail in U.S. Pat. Nos. 5,714,350 and 6,350,861. Alternatively, one or more amino acid substitutions can be made that result in elimination of a glycosylation site present in the Fc region (e.g., Asparagine 297 of IgG). Furthermore, a glycosylated antibodies may be produced in bacterial cells which lack the necessary glycosylation machinery.

Additionally or alternatively, an antibody can be made that has an altered type of glycosylation, such as a hypofucosylated antibody having reduced amounts of fucosyl residues or an antibody having increased bisecting GlcNAc structures. Such altered glycosylation patterns have been demonstrated to increase the ADCC ability of antibodies. Such carbohydrate modifications can be accomplished by, for example, expressing the antibody in a host cell with altered glycosylation machinery. Cells with altered glycosylation machinery have been described in the art and can be used as host cells in which to express recombinant antibodies of the invention to thereby produce an antibody with altered glycosylation. See, for example, Shields, R. L. et al. (2002) J. Biol. Chem. 277: 26733-26740; Umana et al. (1999) Nat. Biotech. 17:176-1, as well as, European Patent No: EP 1,176,195; PCT Publications WO 03/035835; WO 99/54342.

5.14. Engineering Effector Function

It may be desirable to modify the anti-CD22 antibody of the invention with respect to effector function, so as to enhance the effectiveness of the antibody in treating B cell malignancies, for example. For example, cysteine residue(s) may be introduced in the Fc region, thereby allowing interchain disulfide bond formation in this region. The homodimeric antibody thus generated may have improved internalization capability and/or increased complement-mediated cell killing and/or antibody-dependent cellular cytotoxicity (ADCC). See, Caron et al., *J. Exp Med.*, 176:1191-1195 (1992) and Shopes, B., *J. Immunol.*, 148:2918-2922 (1992). Homodimeric antibodies with enhanced anti-tumor activity may also be prepared using heterobifunctional cross-linkers as described in Wolff et al., *Cancer Research*, 53:2560-2565 (1993). Alternatively, an antibody can be engineered which has dual Fc regions and may thereby have enhanced complement lysis and ADCC capabilities. See, Stevenson et al., *Anti-Cancer Drug Design*, 3:219-230 (1989).

Other methods of engineering Fc regions of antibodies so as to alter effector functions are known in the art (e.g., U.S. Patent Publication No. 20040185045 and PCT Publication No. WO 2004/016750, both to Koenig et al., which describe altering the Fc region to enhance the binding affinity for FcγRIIB as compared with the binding affinity for FCγRIIA; see, also, PCT Publication Nos. WO 99/58572 to Armour et al., WO 99/51642 to Idusogie et al., and U.S. Pat. No. 6,395,272 to Deo et al.; the disclosures of which are incorporated herein in their entireties). Methods of modifying the Fc region to decrease binding affinity to FcγRIIB are also known in the art (e.g., U.S. Patent Publication No. 20010036459 and PCT Publication No. WO 01/79299, both to Ravetch et al., the disclosures of which are incorporated herein in their entireties). Modified antibodies having variant Fc regions with enhanced binding affinity for FcγRIIIA and/or FcγRIIA as compared with a wildtype Fc region have also been described (e.g., PCT Publication Nos. WO 2004/063351, to Stavenhagen et al., the disclosure of which is incorporated herein in its entirety).

In vitro assays known in the art can be used to determine whether the anti-CD22 antibodies used in the compositions and methods of the invention are capable of mediating ADCC, such as those described herein.

5.15. Manufacture/Production of Anti-CD22 Antibodies

Once a desired anti-CD22 antibody is engineered, the anti-CD22 antibody can be produced on a commercial scale using methods that are well-known in the art for large scale manufacturing of antibodies. For example, this can be accomplished using recombinant expressing systems such as, but not limited to, those described below.

5.16. Recombinant Expression Systems

Recombinant expression of an antibody of the invention or variant thereof, generally requires construction of an expression vector containing a polynucleotide that encodes the antibody. Once a polynucleotide encoding an antibody molecule or a heavy or light chain of an antibody, or portion thereof (preferably, but not necessarily, containing the heavy or light chain variable domain), of the invention has been obtained, the vector for the production of the antibody molecule may be produced by recombinant DNA technology using techniques well-known in the art. See, e.g., U.S. Pat. No. 6,331,415, which is incorporated herein by reference in its entirety. Thus, methods for preparing a protein by expressing a polynucleotide containing an antibody encoding nucleotide sequence are described herein. Methods which are well-known to those skilled in the art can be used to construct expression vectors containing antibody coding sequences and appropriate transcriptional and translational control signals. These methods include, for example, in vitro recombinant DNA techniques, synthetic techniques, and in vivo genetic recombination. The invention, thus, provides replicable vectors comprising a nucleotide sequence encoding an antibody molecule of the invention, a heavy or light chain of an antibody, a heavy or light chain variable domain of an antibody or a portion thereof, or a heavy or light chain CDR, operably linked to a promoter. Such vectors may include the nucleotide sequence encoding the constant region of the antibody molecule (see, e.g., International Publication Nos. WO 86/05807 and WO 89/01036; and U.S. Pat. No. 5,122,464) and the variable domain of the antibody may be cloned into such a vector for expression of the entire heavy, the entire light chain, or both the entire heavy and light chains.

In an alternate embodiment, the anti-CD22 antibodies of the compositions and methods of the invention can be made using targeted homologous recombination to produce all or portions of the anti-CD22 antibodies (see, U.S. Pat. Nos. 6,063,630, 6,187,305, and 6,692,737). In certain embodiments, the anti-CD22 antibodies of the compositions and methods of the invention can be made using random recombination techniques to produce all or portions of the anti-CD22 antibodies (see, U.S. Pat. Nos. 6,361,972, 6,524,818, 6,541,221, and 6,623,958). Anti-CD22 antibodies can also be produced in cells expressing an antibody from a genomic sequence of the cell comprising a modified immunoglobulin locus using Cre-mediated site-specific homologous recombination (see, U.S. Pat. No. 6,091,001). Where human or humanized antibody production is desired, the host cell line may be derived from human or nonhuman species including mouse, and Chinese hampster. should be a human cell line. These methods may advantageously be used to engineer stable cell lines which permanently express the antibody molecule.

Once the expression vector is transferred to a host cell by conventional techniques, the transfected cells are then cultured by conventional techniques to produce an antibody of the invention. Thus, the invention includes host cells containing a polynucleotide encoding an antibody of the invention or fragments thereof, or a heavy or light chain thereof, or portion thereof, or a single-chain antibody of the invention, operably linked to a heterologous promoter. In certain embodiments for the expression of double-chained antibodies, vectors encoding both the heavy and light chains may be co-expressed in the host cell for expression of the entire immunoglobulin molecule, as detailed below.

A variety of host-expression vector systems may be utilized to express the anti-CD22 antibodies of the invention and portions thereof that can be used in the engineering and generation of anti-CD22 antibodies (see, e.g., U.S. Pat. No. 5,807,715). For example, mammalian cells such as Chinese hamster ovary cells (CHO), in conjunction with a vector such as the major intermediate early gene promoter element from human cytomegalovirus is an effective expression system for antibodies (Foecking et al., *Gene,* 45:101 (1986); and Cockett et al., *Bio/Technology,* 8:2 (1990)). In addition, a host cell strain may be chosen which modulates the expression of inserted antibody sequences, or modifies and processes the antibody gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins and gene products. Appropriate cell lines or host systems can be chosen to ensure the correct modification and processing of the antibody or portion thereof expressed. To this end, eukaryotic host cells which possess the cellular machinery for proper processing of the primary transcript, glycosylation, and phosphorylation of the gene product may be used. Such mammalian host cells include but are not limited to CHO, VERY, BHK, Hela, COS, MDCK, 293, 3T3, W138, BT483, Hs578T, HTB2, BT2O and T47D, NS0 (a murine myeloma cell line that does not endogenously produce any functional immunoglobulin chains), CRL7O3O and HsS78Bst cells.

In one embodiment, human cell lines developed by immortalizing human lymphocytes can be used to recombinantly produce monoclonal human anti-CD22 antibodies. In one embodiment, the human cell line PER.C6. (Crucell, Netherlands) can be used to recombinantly produce monoclonal human anti-CD22 antibodies.

In bacterial systems, a number of expression vectors may be advantageously selected depending upon the use intended for the antibody molecule being expressed. For example, when a large quantity of such an antibody is to be produced, for the generation of pharmaceutical compositions comprising an anti-CD22 antibody, vectors which direct the expression of high levels of fusion protein products that are readily purified may be desirable. Such vectors include, but are not limited to, the *E. coli* expression vector pUR278 (Ruther et al., *EMBO,* 12:1791 (1983)), in which the antibody coding sequence may be ligated individually into the vector in frame with the lac Z coding region so that a fusion protein is produced; pIN vectors (Inouye & Inouye, 1985, *Nucleic Acids Res.* 13:3101-3109 (1985); Van Heeke & Schuster, 1989, *J. Biol. Chem.*, 24:5503-5509 (1989)); and the like. pGEX vectors may also be used to express foreign polypeptides as fusion proteins with glutathione 5-transferase (GST). In general, such fusion proteins are soluble and can easily be purified from lysed cells by adsorption and binding to matrix glutathione agarose beads followed by elution in the presence of free glutathione. The pGEX vectors are designed to include thrombin or factor Xa protease cleavage sites so that the cloned target gene product can be released from the GST moiety.

In an insect system, *Autographa californica* nuclear polyhedrosis virus (AcNPV) is used as a vector to express foreign genes. The virus grows in *Spodoptera frugiperda* cells. The antibody coding sequence may be cloned individually into non-essential regions (for example, the polyhedrin gene) of the virus and placed under control of an AcNPV promoter (for example, the polyhedrin promoter).

In mammalian host cells, a number of viral-based expression systems may be utilized. In cases where an adenovirus is used as an expression vector, the antibody coding sequence of interest may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing the antibody molecule in infected hosts (e.g., see, Logan & Shenk, *Proc. Natl. Acad. Sci. USA*, 81:355-359 (1984)). Specific initiation signals may also be required for efficient translation of inserted antibody coding sequences. These signals include the ATG initiation codon and adjacent sequences. Furthermore, the initiation codon should generally be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see, e.g., Bittner et al., *Methods in Enzymol.*, 153:51-544 (1987)).

Stable expression can be used for long-term, high-yield production of recombinant proteins. For example, cell lines which stably express the antibody molecule may be engineered. Rather than transient expression systems that use replicating expression vectors which contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells may be allowed to grow for 1-2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. Plasmids that encode the anti-CD22 antibody can be used to introduce the gene/cDNA into any cell line suitable for production in culture. Alternatively, plasmids called "targeting vectors" can be used to introduce expression control elements (e.g., promoters, enhancers, etc.) into appropriate chromosomal locations in the host cell to "activate" the endogenous gene for anti-CD22 antibodies.

A number of selection systems may be used, including, but not limited to, the herpes simplex virus thymidine kinase (Wigler et al., *Cell*, 11:223 (1977)), hypoxanthineguanine phosphoribosyltransferase (Szybalska & Szybalski, *Proc. Natl. Acad. Sci. USA*, 48:202 (1992)), and adenine phosphoribosyltransferase (Lowy et al., *Cell*, 22:8-17 (1980)) genes can be employed in tk$^-$, hgprt$^-$ or aprT$^-$ cells, respectively. Also, antimetabolite resistance can be used as the basis of selection for the following genes: dhfr, which confers resistance to methotrexate (Wigler et al., *Natl. Acad. Sci. USA*, 77:357 (1980); O'Hare et al., *Proc. Natl. Acad. Sci. USA*, 78:1527 (1981)); gpt, which confers resistance to mycophenolic acid (Mulligan & Berg, *Proc. Natl. Acad. Sci. USA*, 78:2072 (1981)); neo, which confers resistance to the aminoglycoside G-418 (Wu and Wu, *Biotherapy* 3:87-95 (1991); Tolstoshev, *Ann. Rev. Pharmacol. Toxicol.* 32:573-596 (1993); Mulligan, *Science* 260:926-932 (1993); and Morgan and Anderson, *Ann. Rev. Biochem.* 62:191-217 (1993); May, TIB TECH 11(5):155-2 15 (1993)); and hygro, which confers resistance to hygromycin (Santerre et al., *Gene*, 30:147 (1984)). Methods commonly known in the art of recombinant DNA technology may be routinely applied to select the desired recombinant clone, and such methods are described, for example, in Ausubel et al. (eds.), *Current Protocols in Molecular Biology*, John Wiley & Sons, NY (1993); Kriegler, *Gene Transfer and Expression, A Laboratory Manual*, Stockton Press, NY (1990); and in Chapters 12 and 13, Dracopoli et al. (eds.), *Current Protocols in Human Genetics*, John Wiley & Sons, NY (1994); Colberre-Garapin et al., 1981, *J. Mol. Biol.*, 150:1, which are incorporated by reference herein in their entireties.

The expression levels of an antibody molecule can be increased by vector amplification (for a review, see, Bebbington and Hentschel, *The use of vectors based on gene amplification for the expression of cloned genes in mammalian cells in DNA cloning*, Vol. 3. Academic Press, New York (1987)). When a marker in the vector system expressing antibody is amplifiable, increase in the level of inhibitor present in culture of host cell will increase the number of copies of the marker gene. Since the amplified region is associated with the antibody gene, production of the antibody will also increase (Crouse et al., *Mol. Cell. Biol.*, 3:257 (1983)). Antibody expression levels may be amplified through the use recombinant methods and tools known to those skilled in the art of recombinant protein production, including technologies that remodel surrounding chromatin and enhance transgene expression in the form of an active artificial transcriptional domain.

The host cell may be co-transfected with two expression vectors of the invention, the first vector encoding a heavy chain derived polypeptide and the second vector encoding a light chain derived polypeptide. The two vectors may contain identical selectable markers which enable equal expression of heavy and light chain polypeptides. Alternatively, a single vector may be used which encodes, and is capable of expressing, both heavy and light chain polypeptides. In such situations, the light chain should be placed before the heavy chain to avoid an excess of toxic free heavy chain (Proudfoot, *Nature* 322:562-65 (1986); and Kohler, 1980, *Proc. Natl. Acad. Sci. USA*, 77:2197 (1980)). The coding sequences for the heavy and light chains may comprise cDNA or genomic DNA.

Once an antibody molecule of the invention has been produced by recombinant expression, it may be purified by any method known in the art for purification of an immunoglobulin molecule, for example, by chromatography (e.g., ion exchange, affinity, particularly by affinity for the specific antigen after Protein A, and sizing column chromatography), centrifugation, differential solubility, or by any other standard technique for the purification of proteins. Further, the antibodies of the present invention or fragments thereof may be fused to heterologous polypeptide sequences described herein or otherwise known in the art to facilitate purification.

5.16.1. Antibody Purification and Isolation

When using recombinant techniques, the antibody can be produced intracellularly, in the periplasmic space, or directly secreted into the medium. If the antibody is produced intracellularly, as a first step, the particulate debris, either host cells or lysed fragments, is removed, for example, by centrifugation or ultrafiltration. Carter et al., *Bio/Technology*, 10:163-167 (1992) describe a procedure for isolating antibodies which are secreted into the periplasmic space of *E. coli*. Briefly, cell paste is thawed in the presence of sodium acetate (pH 15), EDTA, and phenylmethylsulfonylfluoride (PMSF) over about 30 min. Cell debris can be removed by centrifugation. Where the antibody mutant is secreted into the medium, supernatants from such expression systems are generally first concentrated using a commercially available protein concentration filter, for example, an Amicon or Millipore Pellicon ultrafiltration unit. A protease inhibitor such as PMSF may be included in any of the foregoing steps to inhibit proteolysis and antibiotics may be included to prevent the growth of adventitious contaminants.

The antibody composition prepared from the cells can be purified using, for example, hydroxylapatite chromatography, hydrophobic interaction chromatography, ion exchange chromatography, gel electrophoresis, dialysis, and/or affinity chromatography either alone or in combination with other purification steps. The suitability of protein A as an affinity ligand depends on the species and isotype of any immunoglobulin Fc domain that is present in the antibody mutant. Protein A can be used to purify antibodies that are based on human γ1, γ2, or γ4 heavy chains (Lindmark et al., *J. Immunol. Methods*, 62:1-13 (1983)). Protein G is recommended for all mouse isotypes and for human γ3 (Guss et al., *EMBO* 5:15671575 (1986)). The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. Where the antibody comprises a $CH_3$ domain, the Bakerbond ABX resin (J. T. Baker, Phillipsburg, N.J.) is useful for purification. Other techniques for protein purification such as fractionation on an ion-exchange column, ethanol precipitation, Reverse Phase HPLC, chromatography on silica, chromatography on heparin, SEPHAROSE chromatography on an anion or cation exchange resin (such as a polyaspartic acid column), chromatofocusing, SDS-PAGE, and ammonium sulfate precipitation are also available depending on the antibody to be recovered.

Following any preliminary purification step(s), the mixture comprising the antibody of interest and contaminants may be subjected to low pH hydrophobic interaction chromatography using an elution buffer at a pH between about 2.5-4.5, preferably performed at low salt concentrations (e.g., from about 0-0.25 M salt).

5.17. Therapeutic Anti-CD22 Antibodies

The anti-CD22 antibody used in the compositions and methods of the invention is preferably a human antibody or a humanized antibody that preferably mediates B lineage cell apoptosis and/or human ADCC, or is selected from known anti-CD22 antibodies that preferably mediate B lineage cell apoptosis and/or human ADCC. In certain embodiments, the anti-CD22 antibodies can be chimeric antibodies. In certain embodiments, anti-CD22 antibody is a monoclonal human, humanized, or chimeric anti-CD22 antibody. The anti-CD22 antibody used in the compositions and methods of the invention is preferably a human antibody or a humanized antibody of the IgG1 or IgG3 human isotype or any IgG1 or IgG3 allele found in the human population. In other embodiments, the anti-CD22 antibody used in the compositions and methods of the invention is preferably a human antibody or a humanized antibody of the IgG2 or IgG4 human isotype or any IgG2 or IgG4 allele found in the human population.

While such antibodies can be generated using the techniques described above, in other embodiments of the invention, the murine antibodies HB22.7 as described herein or other commercially available anti-CD22 antibodies can be chimerized, humanized, or made into human antibodies.

For example, known anti-CD22 antibodies that can be used include, but are not limited to, HB22.2, HB22.5, HB22.12, HB22.13, HB22.15, HB22.17, HB22.18, HB22.19, HB22.22, HB22.23, HB22.25, HB22.26, HB22.27, HB22.28, HB22.33, 196-9, (Engel et al. 1993. J. Immunol. 150:4719-4732 and Engel et al 1995. J. Exp. Med. 181:1581-1586.), HD37 (IgG1) (DAKO, Carpinteria, Calif.), BU12 (G. D. Johnson, University of Birmingham, Birmingham, United Kingdom), 4G7 (IgG1) (Becton-Dickinson, Heidelberg, Germany), J4.119 (Beckman Coulter, Krefeld, Germany), B43 (PharMingen, San Diego, Calif.), SJ25C1 (BD PharMingen, San Diego, Calif.), FMC63 (IgG2a) (Chemicon Int'l., Temecula, Calif.) (Nicholson et al., *Mol. Immunol.*, 34:1157-1165 (1997); Pietersz et al., *Cancer Immunol. Immunotherapy*, 41:53-60 (1995); and Zola et al., *Immunol. Cell Biol.*, 69:411-422 (1991)), B4 (IgG1) (Beckman Coulter, Miami, Fla.) Nadler et al., *J. Immunol.*, 131:244-250 (1983), and/or HD237 (IgG2b) (Fourth International Workshop on Human Leukocyte Differentiation Antigens, Vienna, Austria, 1989; and Pezzutto et al., *J. Immunol.*, 138:2793-2799 (1987)).

In certain embodiments, the anti-CD22 antibody of the invention comprises the VH domain sequence of the humanized VH designated HB22.7RHOv2ACD, which comprises an amino acid sequence of SEQ ID NO:59. In other embodiments, the anti-CD22 antibody of the invention comprises the VH domain sequence of the humanized VH designated HB22.7RHF, which comprises the amino acid sequence of SEQ ID NO:25.

In certain embodiments, the anti-CD22 antibody of the invention comprise a heavy chain variable region, VH, comprising at least one CDR sequence selected from DYGVN (SEQ ID NO: 62), IIWGDGRTDYNSALKS (SEQ ID NO: 63), or APGNRAMEY (SEQ ID NO: 64); and at least one FW region selected from QVQLQESGPALVKPTQTLTLTCTF-SGFSLS (SEQ ID NO:73), QVQLQESG-PALVKPTQTLTLTCTVSGFSLS (SEQ ID NO:74), WIRQPPGKALEWLA (SEQ ID NO:75), WIRQP-PGKALEWLG (SEQ ID NO:76), RLSISKDTSKNQVVL-RMTNVDPVDTATYFCAR (SEQ ID NO:77), RLSISKDN-SKNQVVLRMTNVDPVDTATYFCAR (SEQ ID NO:78), or WGQGTVVTVSS(SEQ ID NO:79).

In another embodiments, the anti-CD22 antibody of the invention comprise a heavy chain variable region, VH, comprising at least one CDR sequence selected from DYGVN (SEQ ID NO: 62), IIWGDGRTDYNSALKS (SEQ ID NO: 63), or APGNRAMEY (SEQ ID NO: 64); and at least one FW region selected from QVQLEESGGGVVRPGRSL-RLSCAASGFTFD (SEQ ID NO:80), QVQLEESGGGV-VRPGRSLRLSCAASGFTFS (SEQ ID NO:81), QVQLEESGGGVVRPGRSLRLSCAASGFTLD (SEQ ID NO:82), QVQLEESGGGVVRPGRSLRLSCAASGFTLS (SEQ ID NO:83), WIRQAPGKGLEWVT (SEQ ID NO:84), WIRQAPGKGLEWVG (SEQ ID NO:85), RFTVS-RNNSNNTLSLQMNSLTTEDTAVYYCVR (SEQ ID NO:86), RLTVSRNNSNNTLSLQMNSLTTED-TAVYYCVR (SEQ ID NO:87), or WGQGVLVTVS (SEQ ID NO:88).

In another embodiments, the anti-CD22 antibody of the invention comprise a heavy chain variable region, VH, comprising at least one CDR sequence selected from DYGVN (SEQ ID NO: 62), IIWGDGRTDYNSALKS (SEQ ID NO: 63), or APGNRAMEY (SEQ ID NO: 64); and at least one FW region selected from EVQLVESGGGLVQPGGSL-RLSCAASGFTFS (SEQ ID NO:96), EVQLVESGGGLVQPGGSLRLSCAASGFTLS (SEQ ID NO:128), WVRQAPGKGLEWIS (SEQ ID NO:97), WVRQAPGKGLEWIG (SEQ ID NO:129), RLIISRD-NYKNTMSLQMYSLSAADTAIYFCVK (SEQ ID NO:89), RFNISRDNYKNTMSLQMYSLSAADTAIYFCVK (SEQ ID NO:90), RFIISRDNYKNTNSLQMYSLSAADTAIY-FCVK (SEQ ID NO:91), RLNISRDNYKNTMSLQMYSL-SAADTAIYFCVK (SEQ ID NO:92), RLIISRDNYKNT-NSLQMYSLSAADTAIYFCVK (SEQ ID NO:93), RFNISRDNYKNTNSLQMYSLSAADTAIYFCVK (SEQ ID NO:94), RLNISRDNYKNTNSLQMYSLSAADTAIY-FCVK (SEQ ID NO:95), or WGQGTMVTVS (SEQ ID NO:99).

In another embodiment, the anti-CD22 antibody of the invention comprise a heavy chain variable region, VH, comprising at least one CDR sequence selected from DYGVN (SEQ ID NO: 62), IIWGDGRTDYNSALKS (SEQ ID NO: 63), or APGNRAMEY (SEQ ID NO: 64); and at least one FW region selected from QVQLEESGGGVVRPGRSL-RLSCAASGFTFD (SEQ ID NO:80), QVQLEESGGGV-VRPGRSLRLSCAASGFTLD (SEQ ID NO:82), QVQLEESGGGVVRPGRSLRLSCAASGFTFS (SEQ ID NO:81), QVQLEESGGGVVRPGRSLRLSCAASGFTLS (SEQ ID NO:83), WIRQAPGKGLEWVT (SEQ ID NO:84), WIRQAPGKGLEWVG (SEQ ID NO:85), RFTIS-RNNSNNTLSLQMNSLTTEDTAVYYCVR (SEQ ID NO:100), RLTISRNNSNNTLSLQMNSLTTED-TAVYYCVR (SEQ ID NO:101), or WGQGVLVTVS (SEQ ID NO:88).

In another embodiments, the anti-CD22 antibody of the invention comprise a heavy chain variable region, VH, comprising at least one CDR sequence selected from DYGVN (SEQ ID NO: 62), IIWGDGRTDYNSALKS (SEQ ID NO: 63), or APGNRAMEY (SEQ ID NO: 64); and at least one FW region selected from QVQLEESGGGVVRPGRSL-RLSCAASGFTFD (SEQ ID NO:80), QVQLEESGGGV-VRPGRSLRLSCAASGFTLD (SEQ ID NO:82), QVQLEESGGGVVRPGRSLRLSCAASGFTFS (SEQ ID NO:81), QVQLEESGGGVVRPGRSLRLSCAASGFTLS (SEQ ID NO:83), WIRQAPGKGLEWVT (SEQ ID NO:84), WIRQAPGKGLEWVG (SEQ ID NO:85), RFTVS-RNNSNNTLSLQMNSLTTEDTAVYYCVR (SEQ ID NO:86), RLTVSRNNSNNTLSLQMNSLTTED-TAVYYCVR (SEQ ID NO:87), or WGQGVLVTVS (SEQ ID NO:88).

In another embodiments, the anti-CD22 antibody of the invention comprise a heavy chain variable region, VH, comprising at least one CDR sequence selected from DYGVN (SEQ ID NO: 62), IIWGDGRTDYNSALKS (SEQ ID NO: 63), or APGNRAMEY (SEQ ID NO: 64); and at least one FW region selected from ELQLVESGGGFVQPGGSL-RLSCAASGFPFR (SEQ ID NO:102), ELQLVESGGG-FVQPGGSLRLSCAASGFPLR (SEQ ID NO:103), ELQLVESGGGFVQPGGSLRLSCAASGFPFS (SEQ ID NO:104), ELQLVESGGGFVQPGGSLRLSCAASGFPLS (SEQ ID NO:105), WVRQGPGKGLVWVS (SEQ ID NO:116), RVTISRDNAKKMVYPQMNSLRAED-TAMYYCHC (SEQ ID NO:106), RVTISRDNAKKM-VYPQMNSLRAEDTAMYYCHR (SEQ ID NO:107), RVTISRDNAKKMVYPQMNSLRAEDTAMYYCHK (SEQ ID NO:108), RVTISRDNAKKMVYPQMNSL-RAEDTAMYYCVC (SEQ ID NO:109), RVTISRDNAKK-MVYPQMNSLRAEDTAMYYCVR (SEQ ID NO:110), RVTISRDNAKKMVYPQMNSLRAEDTAMYYCVK (SEQ ID NO:111), RVTISRDNAKKMVYPQMNSL-RAEDTAMYYCAC (SEQ ID NO:112), RVTISRDNAKK-MVYPQMNSLRAEDTAMYYCAR (SEQ ID NO:113), RVTISRDNAKKMVYPQMNSLRAEDTAMYYCAK (SEQ ID NO:114), or WGQGTLVTV (SEQ ID NO:129).

In further embodiments, the anti-CD22 antibody of the invention comprise a light chain variable region, VK, comprising at least one CDR sequence selected from KASQSVT-NDVA (SEQ ID NO: 65), YASNRYT (SEQ ID NO: 66), or QQDYRSPWT (SEQ ID NO: 67); and at least one FW region selected from DIVMTQSPSSLSASVGDRVTITC (SEQ ID NO:117), WYQQKPGKAPKLLIY (SEQ ID NO:118), GVPSRFSGSGSGTDFTLTISSLQPEDFATYYC (SEQ ID NO:119), GVPDRFSGSGSGTDFTLTISSLQPEDFATYYC (SEQ ID NO:120), GVPSRFSGSGYGTDFTLTISSLQPED-FATYYC (SEQ ID NO:121), GVPSRFSGSGSGTD-FTLTISSLQPEDFATYFC (SEQ ID NO:122), GVPDRF-SGSGYGTDFTLTISSLQPEDFATYYC (SEQ ID NO:123), GVPDRFSGSGSGTDFTLTISSLQPEDFATYFC (SEQ ID NO:124), GVPSRFSGSGYGTDFTLTISSLQPEDFATYFC (SEQ ID NO:125), GVPDRFSGSGYGTDFTLTISS-LQPEDFATYFC (SEQ ID NO:126), or FGGGTKVEIKRT (SEQ ID NO:127).

In certain embodiments, the anti-CD22 antibody of the invention further comprises the VK domain sequence of the humanized VK designated HB22.7RKC, which comprises an amino acid sequence of SEQ ID NO:39. In other embodiments, the anti-CD22 antibody of the invention comprises the VK domain sequence of the humanized VK designated HB22.7RKA, which comprises an amino acid sequence of SEQ ID NO:35.

In certain embodiments, the antibody is an isotype switched variant of a known antibody (e.g., to an IgG1 or IgG3 human isotype) such as those described above.

The anti-CD22 antibodies used in the compositions and methods of the invention can be naked antibodies, immunoconjugates or fusion proteins. Preferably the anti-CD22 antibodies described above for use in the compositions and methods of the invention are able to reduce or deplete B cells and circulating immunoglobulin in a human treated therewith. Depletion of B cells can be in circulating B cells, or in particular tissues such as, but not limited to, bone marrow, spleen, gut-associated lymphoid tissues, and/or lymph nodes. Such depletion may be achieved via various mechanisms such as antibody-dependent cell-mediated cytotoxicity (ADCC), and/or by blocking of CD22 interaction with its intended ligand, and/or complement dependent cytotoxicity (CDC), inhibition of B cell proliferation and/or induction of B cell death (e.g., via apoptosis). By "depletion" of B cells it is meant a reduction in circulating B cells and/or B cells in particular tissue(s) by at least about 10%, 15%, 20%, 25%, 30%, 35%, 40%, 45%, 50%, 55%, 60%, 65%, 70%, 75%, 80%, 85%, 90%, 95% or more. In particular embodiments, virtually all detectable B cells are depleted from the circulation and/or particular tissue(s). By "depletion" of circulating immunoglobulin (Ig) it is meant a reduction by at least about 25%, 40%, 50%, 65%, 75%, 80%, 85%, 90%, 95% or more. In particular embodiments, virtually all detectable Ig is depleted from the circulation.

5.17.1. Screening of Antibodies for Human CD22 Binding

Binding assays can be used to identify antibodies that bind the human CD22 antigen. Binding assays may be performed either as direct binding assays or as competition-binding assays. Binding can be detected using standard ELISA or standard Flow Cytometry assays. In a direct binding assay, a candidate antibody is tested for binding to human CD22 antigen. In certain embodiments, the screening assays comprise, in a second step, determining the ability to cause cell death or apoptosis of B cells expressing human CD22. Competition-binding assays, on the other hand, assess the ability of a candidate antibody to compete with a known anti-CD22 antibody or other compound that binds human CD22.

In a direct binding assay, the human CD22 antigen is contacted with a candidate antibody under conditions that allow binding of the candidate antibody to the human CD22 antigen. The binding may take place in solution or on a solid surface. Preferably, the candidate antibody is previously labeled for detection. Any detectable compound may be used for labeling, such as but not limited to, a luminescent, fluorescent, or radioactive isotope or group containing same, or a nonisotopic label, such as an enzyme or dye. After a period of incubation sufficient for binding to take place, the reaction is exposed to conditions and manipulations that remove excess or non-specifically bound antibody. Typically, it involves washing with an appropriate buffer. Finally, the presence of a CD22-antibody complex is detected.

In a competition-binding assay, a candidate antibody is evaluated for its ability to inhibit or displace the binding of a known anti-CD22 antibody (or other compound) to the human CD22 antigen. A labeled known binder of CD22 may be mixed with the candidate antibody, and placed under conditions in which the interaction between them would normally occur, with and without the addition of the candidate antibody. The amount of labeled known binder of CD22 that binds the human CD22 may be compared to the amount bound in the presence or absence of the candidate antibody.

In one embodiment, the binding assay is carried out with one or more components immobilized on a solid surface to facilitate antibody antigen complex formation and detection. In various embodiments, the solid support could be, but is not restricted to, polycarbonate, polystyrene, polypropylene, polyethylene, glass, nitrocellulose, dextran, nylon, polyacrylamide and agarose. The support configuration can include beads, membranes, microparticles, the interior surface of a reaction vessel such as a microtiter plate, test tube or other reaction vessel. The immobilization of human CD22, or other component, can be achieved through covalent or non-covalent attachments. In one embodiment, the attachment may be indirect, i.e., through an attached antibody. In another embodiment, the human CD22 antigen and negative controls are tagged with an epitope, such as glutathione S-transferase (GST) so that the attachment to the solid surface can be mediated by a commercially available antibody such as anti-GST (Santa Cruz Biotechnology).

For example, such an affinity binding assay may be performed using the human CD22 antigen which is immobilized to a solid support. Typically, the non-mobilized component of the binding reaction, in this case the candidate anti-CD22 antibody, is labeled to enable detection. A variety of labeling methods are available and may be used, such as luminescent, chromophore, fluorescent, or radioactive isotope or group containing same, and nonisotopic labels, such as enzymes or dyes. In one embodiment, the candidate anti-CD22 antibody is labeled with a fluorophore such as fluorescein isothiocyanate (FITC, available from Sigma Chemicals, St. Louis). Such an affinity binding assay may be performed using the human CD22 antigen immobilized on a solid surface. Anti-CD22 antibodies are then incubated with the antigen and the specific binding of antibodies is detected by methods known in the art including, but not limited to, BiaCore Analyses, ELISA, FMET and RIA methods.

Finally, the label remaining on the solid surface may be detected by any detection method known in the art. For example, if the candidate anti-CD22 antibody is labeled with a fluorophore, a fluorimeter may be used to detect complexes.

Preferably, the human CD22 antigen is added to binding assays in the form of intact cells that express human CD22 antigen, or isolated membranes containing human CD22 antigen. Thus, direct binding to human CD22 antigen may be assayed in intact cells in culture or in animal models in the presence and absence of the candidate anti-CD22 antibody. A labeled candidate anti-CD22 antibody may be mixed with cells that express human CD22 antigen, or with crude extracts obtained from such cells, and the candidate anti-CD22 antibody may be added. Isolated membranes may be used to identify candidate anti-CD22 antibodies that interact with human CD22. For example, in a typical experiment using isolated membranes, cells may be genetically engineered to express human CD22 antigen. Membranes can be harvested by standard techniques and used in an in vitro binding assay. Labeled candidate anti-CD22 antibody (e.g., fluorescent labeled antibody) is bound to the membranes and assayed for specific activity; specific binding is determined by comparison with binding assays performed in the presence of excess unlabeled (cold) candidate anti-CD22 antibody. Alternatively, soluble human CD22 antigen may be recombinantly expressed and utilized in non-cell based assays to identify antibodies that bind to human CD22 antigen. The recombinantly expressed human CD22 polypeptides can be used in the non-cell based screening assays. Alternatively, peptides corresponding to one or more of the binding portions of human CD22 antigen, or fusion proteins containing one or more of the binding portions of human CD22 antigen can be used in non-cell based assay systems to identify antibodies that bind to portions of human CD22 antigen. In non-cell based assays the recombinantly expressed human CD22 is attached to a solid substrate such as a test tube, microtiter well or a column, by means well-known to those in the art (see, Ausubel et al., supra). The test antibodies are then assayed for their ability to bind to human CD22 antigen.

Alternatively, the binding reaction may be carried out in solution. In this assay, the labeled component is allowed to interact with its binding partner(s) in solution. If the size differences between the labeled component and its binding partner(s) permit such a separation, the separation can be achieved by passing the products of the binding reaction through an ultrafilter whose pores allow passage of unbound labeled component but not of its binding partner(s) or of labeled component bound to its partner(s). Separation can also be achieved using any reagent capable of capturing a binding partner of the labeled component from solution, such as an antibody against the binding partner and so on.

In one embodiment, for example, a phage library can be screened by passing phage from a continuous phage display library through a column containing purified human CD22 antigen, or derivative, analog, fragment, or domain, thereof, linked to a solid phase, such as plastic beads. By altering the stringency of the washing buffer, it is possible to enrich for phage that express peptides with high affinity for human CD22 antigen. Phage isolated from the column can be cloned and affinities can be measured directly. Knowing which antibodies and their amino acid sequences confer the strongest binding to human CD22 antigen, computer models can be used to identify the molecular contacts between CD22 antigen and the candidate antibody.

In another specific embodiment of this aspect of the invention, the solid support is membrane containing human CD22 antigen attached to a microtiter dish. Candidate antibodies, for example, can bind cells that express library antibodies cultivated under conditions that allow expression of the library members in the microliter dish. Library members that bind to the human CD22 are harvested. Such methods, are generally described by way of example in Parmley and Smith, 1988, *Gene,* 73:305-318; Fowlkes et al., 1992, *Bio Techniques,* 13:422-427; PCT Publication No. WO94/18318; and in references cited hereinabove. Antibodies identified as binding to human CD22 antigen can be of any of the types or modifications of antibodies described above.

5.17.2. Screening of Antibodies for Human ADCC Effector Function

Antibodies of the human IgG class, which have functional characteristics such a long half-life in serum and the ability to mediate various effector functions are used in certain embodiments of the invention (*Monoclonal Antibodies: Principles and Applications,* Wiley-Liss, Inc., Chapter 1 (1995)). The human IgG class antibody is further classified into the following 4 subclasses: IgG1, IgG2, IgG3 and IgG4. A large number of studies have so far been conducted for ADCC and CDC as effector functions of the IgG class antibody, and it has been reported that among antibodies of the human IgG class, the IgG1 subclass has the highest ADCC activity and CDC activity in humans (*Chemical Immunology,* 65, 88 (1997)).

Expression of ADCC activity and CDC activity of the human IgG1 subclass antibodies generally involves binding of the Fc region of the antibody to a receptor for an antibody (hereinafter referred to as "FcγR") existing on the surface of effector cells such as killer cells, natural killer cells or activated macrophages. Various complement components can be bound. Regarding the binding, it has been suggested that several amino acid residues in the hinge region and the second domain of C region (hereinafter referred to as "Cγ2 domain") of the antibody are important (*Eur. J. Immunol.,* 23, 1098 (1993), *Immunology,* 86, 319 (1995), *Chemical Immunology,* 65, 88 (1997)) and that a sugar chain in the Cγ2 domain (*Chemical Immunology,* 65, 88 (1997)) is also important.

The anti-CD22 antibodies of the invention can be modified with respect to effector function, e.g., so as to enhance ADCC and/or complement dependent cytotoxicity (CDC) of the antibody. This may be achieved by introducing one or more amino acid substitutions in the Fc region of an antibody. Alternatively or additionally, cysteine residue(s) may be introduced in the Fc region, allowing for interchain disulfide bond formation in this region. In this way a homodimeric antibody can be generated that may have improved internalization capability and or increased complement-mediated cell killing and ADCC (Caron et al., *J. Exp. Med.,* 176:1191-1195 (1992) and Shopes, *J. Immunol.,* 148:2918-2922 (1992)). Heterobifunctional cross-linkers can also be used to generate homodimeric antibodies with enhanced anti-tumor activity (Wolff et al., *Cancer Research,* 53:2560-2565 (1993)). Antibodies can also be engineered to have two or more Fc regions resulting in enhanced complement lysis and ADCC capabilities (Stevenson et al., *Anti-Cancer Drug Design,* (3)219-230 (1989)).

Other methods of engineering Fc regions of antibodies so as to alter effector functions are known in the art (e.g., U.S. Patent Publication No. 20040185045 and PCT Publication No. WO 2004/016750, both to Koenig et al., which describe altering the Fc region to enhance the binding affinity for FcγRIIB as compared with the binding affinity for FCγRIIA; see also PCT Publication Nos. WO 99/58572 to Armour et al., WO 99/51642 to Idusogie et al., and U.S. Pat. No. 6,395,272 to Deo et al.; the disclosures of which are incorporated herein in their entireties). Methods of modifying the Fc region to decrease binding affinity to FcγRIIB are also known in the art (e.g., U.S. Patent Publication No. 20010036459 and PCT Publication No. WO 01/79299, both to Ravetch et al., the disclosures of which are incorporated herein in their entireties). Modified antibodies having variant Fc regions with enhanced binding affinity for FcγRIIIA and/or FcγRIIA as compared with a wildtype Fc region have also been described (e.g., PCT Publication No. WO 2004/063351, to Stavenhagen et al.; the disclosure of which is incorporated herein in its entirety).

At least four different types of FcγR have been found, which are respectively called FcγRI (CD64), FcγRII (CD32), FcγRIII (CD16), and FcγRIV. In human, FcγRII and FcγRIII are further classified into FcγRIIa and FcγRIIb, and FcγRIIIa and FcγRIIIb, respectively. FcγR is a membrane protein belonging to the immunoglobulin superfamily, FcγRII, FcγRIII, and FcγRIV have an α chain having an extracellular region containing two immunoglobulin-like domains, FcγRI has an α chain having an extracellular region containing three immunoglobulin-like domains, as a constituting component, and the α chain is involved in the IgG binding activity. In addition, FcγRI and FcγRIII have a γ chain or ζ chain as a constituting component which has a signal transduction function in association with the α chain (*Annu. Rev. Immunol.,* 18, 709 (2000), *Annu. Rev. Immunol.,* 19, 275 (2001)). FcγRIV has been described by Bruhns et al., *Clin. Invest. Med.,* (Canada) 27:3 D (2004).

To assess ADCC activity of an anti-CD22 antibody of interest, an in vitro ADCC assay can be used, such as that described in U.S. Pat. No. 5,500,362 or 5,821,337. Useful effector cells for such assays include peripheral blood mononuclear cells (PBMC) and Natural Killer (NK) cells. For example, the ability of any particular antibody to mediate lysis of the target cell by complement activation and/or ADCC can be assayed. The cells of interest are grown and labeled in vitro; the antibody is added to the cell culture in combination with immune cells which may be activated by the antigen-antibody complexes; i.e., effector cells involved in the ADCC response. The antibody can also be tested for complement activation. In either case, cytolysis of the target cells is detected by the release of label from the lysed cells. In fact, antibodies can be screened using the patient's own serum as a source of complement and/or immune cells. The antibodies that are capable of mediating human ADCC in the in vitro test can then be used therapeutically in that particular patient. Alternatively, or additionally, ADCC activity of the molecule of interest may be assessed in vivo, e.g., in an animal model such as that disclosed in Clynes et al., *Proc. Natl. Acad. Sci.* (USA) 95:652-656 (1998). Moreover, techniques for modulating (i.e., increasing or decreasing) the level of ADCC, and optionally CDC activity, of an antibody are well-known in the art. See, e.g., U.S. Pat. No. 6,194,551. Antibodies of the present invention preferably are capable or have been modified to have the ability of inducing ADCC and/or CDC. Preferably, such assays to determined ADCC function are practiced using humans effector cells to assess human ADCC function. Such assays may also include those intended to screen for antibodies that induce, mediate, enhance, block cell death by necrotic and/or apoptotic mechanisms. Such methods include assays utilizing viable dyes, methods of detecting and analyzing caspase activity or cytochrome c release from the mitochondria, and assays measuring DNA breaks can be used to assess the apoptotic activity of cells cultured in vitro with an anti-CD22 antibody of interest.

For example, Annexin V or TdT-mediated dUTP nick-end labeling (TUNEL) assays can be carried out as described in Decker et al., *Blood* (USA) 103:2718-2725 (2004) to detect apoptotic activity. The TUNEL assay involves culturing the cells of interest (e.g., B cells cultured in the presence or absence of anti-CD22 antibodies) with fluorescein-labeled dUTP for incorporation into DNA strand breaks. The cells are then processed for analysis by flow cytometry. The Annexin V assay detects the exposure of phosphatidylserine (PS) on the outside of the plasma membrane using a fluorescein-conjugated antibody that specifically recognizes the exposed PS on the surface of apoptotic cells. Concurrently, a viable dye such as propidium iodide can be used to exclude late apoptotic cells. The cells are stained with the antibody and are analyzed by flow cytometry. Moreover, techniques for assaying cells undergoing apoptosis are well-known in the art. See, e.g., Chaouchi et al., *J. Immunol.*, 154(7): 3096-104 (1995); Pedersen et al., *Blood,* 99(4): 1314-1318 (2002); Alberts et al., *Molecular Biology of the Cell*; Steensma et al., *Methods Mol Med.,* 85: 323-32, (2003)).

5.17.3. Immunoconjugates and Fusion Proteins

According to certain aspects of the invention, therapeutic agents or toxins can be conjugated to chimerized, human, or humanized anti-CD22 antibodies for use in the compositions and methods of the invention. In certain embodiments, these conjugates can be generated as fusion proteins. Examples of therapeutic agents and toxins include, but are not limited to, members of the enediyne family of molecules, such as calicheamicin and esperamicin. Chemical toxins can also be taken from the group consisting of duocarmycin (see, e.g., U.S. Pat. No. 5,703,080 and U.S. Pat. No. 4,923,990), methotrexate, doxorubicin, melphalan, chlorambucil, ARA-C, vindesine, mitomycin C, cis-platinum, etoposide, bleomycin and 5-fluorouracil. Examples of chemotherapeutic agents also include Adriamycin, Doxorubicin, 5-Fluorouracil, Cytosine arabinoside (Ara-C), Cyclophosphamide, Thiotepa, Taxotere (docetaxel), Busulfan, Cytoxin, Taxol, Methotrexate, Cisplatin, Melphalan, Vinblastine, Bleomycin, Etoposide, Ifosfamide, Mitomycin C, Mitoxantrone, Vincreistine, Vinorelbine, Carboplatin, Teniposide, Daunomycin, Caminomycin, Aminopterin, Dactinomycin, Mitomycins, Esperamicins (see, U.S. Pat. No. 4,675,187), Melphalan, and other related nitrogen mustards.

Other toxins that can be used in the immunoconjugates of the invention include poisonous lectins, plant toxins such as ricin, abrin, modeccin, botulina, and diphtheria toxins. Of course, combinations of the various toxins could also be coupled to one antibody molecule thereby accommodating variable cytotoxicity. Illustrative of toxins which are suitably employed in the combination therapies of the invention are ricin, abrin, ribonuclease, DNase I, *Staphylococcal* enterotoxin-A, pokeweed anti-viral protein, gelonin, diphtherin toxin, *Pseudomonas* exotoxin, and *Pseudomonas* endotoxin. See, for example, Pastan et al., *Cell,* 47:641 (1986), and Goldenberg et al., *Cancer Journal for Clinicians,* 44:43 (1994). Enzymatically active toxins and fragments thereof which can be used include diphtheria A chain, non-binding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *Momordica charantia* inhibitor, curcin, crotin, *Sapaonaria officinalis* inhibitor, gelonin, mitogellin, restrictocin, phenomycin, enomycin and the tricothecenes. See, for example, WO 93/21232 published Oct. 28, 1993.

Suitable toxins and chemotherapeutic agents are described in Remington's Pharmaceutical Sciences, 19th Ed. (Mack Publishing Co. 1995), and in Goodman And Gilman's The Pharmacological Basis of Therapeutics, 7th Ed. (MacMillan Publishing Co. 1985). Other suitable toxins and/or chemotherapeutic agents are known to those of skill in the art.

The anti-CD22 antibody of the present invention may also be used in ADEPT by conjugating the antibody to a prodrug-activating enzyme which converts a prodrug (e.g., a peptidyl chemotherapeutic agent, see, WO 81/01145) to an active anti-cancer drug. See, for example, WO 88/07378 and U.S. Pat. No. 4,975,278. The enzyme component of the immunoconjugate useful for ADEPT includes any enzyme capable of acting on a prodrug in such a way so as to covert it into its more active, cytotoxic form.

Enzymes that are useful in the method of this invention include, but are not limited to, alkaline phosphatase useful for converting phosphate-containing prodrugs into free drugs; arylsulfatase useful for converting sulfate-containing prodrugs into free drugs; cytosine deaminase useful for converting non-toxic 5-fluorocytosine into the anti-cancer drug, 5-fluorouracil; proteases, such as *serratia* protease, thermolysin, subtilisin, carboxypeptidases and cathepsins (such as cathepsins B and L), that are useful for converting peptide-containing prodrugs into free drugs; D-alanylcarboxypeptidases, useful for converting prodrugs that contain D-amino acid substituents; carbohydrate-cleaving enzymes such as β-galactosidase and neuraminidase useful for converting glycosylated prodrugs into free drugs; β-lactamase useful for converting drugs derivatized with α-lactams into free drugs; and penicillin amidases, such as penicillin V amidase or penicillin G amidase, useful for converting drugs derivatized at their amine nitrogens with phenoxyacetyl or phenylacetyl groups, respectively, into free drugs. Alternatively, antibodies with enzymatic activity, also known in the art as "abzymes," can be used to convert the prodrugs of the invention into free active drugs (see, e.g., Massey, *Nature* 328:457-458 (1987)). Antibody-abzyme conjugates can be prepared as described herein for delivery of the abzyme as desired to portions of a human affected by a B cell malignancy.

The enzymes of this invention can be covalently bound to the antibody by techniques well-known in the art such as the use of the heterobifunctional crosslinking reagents discussed above. Alternatively, fusion proteins comprising at least the antigen-binding region of an antibody of the invention linked to at least a functionally active portion of an enzyme of the invention can be constructed using recombinant DNA techniques well-known in the art (see, e.g., Neuberger et al., *Nature,* 312:604-608 (1984)).

Covalent modifications of the anti-CD22 antibody of the invention are included within the scope of this invention. They may be made by chemical synthesis or by enzymatic or chemical cleavage of the antibody, if applicable. Other types of covalent modifications of the anti-CD22 antibody are introduced into the molecule by reacting targeted amino acid residues of the antibody with an organic derivatizing agent that is capable of reacting with selected side chains or the N- or C-terminal residues.

Cysteinyl residues most commonly are reacted with α-haloacetates (and corresponding amines), such as chloroacetic acid or chloroacetamide, to give carboxymethyl or carboxyamidomethyl derivatives. Similarly, iodo-reagents may also be used. Cysteinyl residues also are derivatized by reaction with bromotrifluoroacetone, α-bromo-β-(5-imidozoyl)propionic acid, chloroacetyl phosphate, N-alkylmaleimides, 3-nitro-2- pyridyl disulfide, methyl 2-pyridyl disulfide, p-chloromercuribenzoate, 2-chloromercuri-4-nitrophenol, or chloro-7-nitrobenzo-2-oxa-1,3-diazole.

Histidyl residues are derivatized by reaction with diethylpyrocarbonate at pH 5.5-7.0 because this agent is relatively specific for the histidyl side chain. Para-bromophenacyl bromide also is useful; the reaction is preferably performed in 0.1 M sodium cacodylate at pH 6.0.

Lysyl and amino-terminal residues are reacted with succinic or other carboxylic acid anhydrides. Derivatization with these agents has the effect of reversing the charge of the lysinyl residues. Other suitable reagents for derivatizing α-amino-containing residues and/or ε-amino-containing residues include imidoesters such as methyl picolinimidate, pyridoxal phosphate, pyridoxal, chloroborohydride, trinitrobenzenesulfonic acid, 0-methylisourea, 2,4-pentanedione, and transaminase-catalyzed reaction with glyoxylate.

Arginyl residues are modified by reaction with one or several conventional reagents, among them phenylglyoxal, 2,3-butanedione, 1,2-cyclohexanedione, and ninhydrin. Derivatization of arginyl residues generally requires that the reaction be performed in alkaline conditions because of the high pKa of the guanidine functional group. Furthermore, these reagents may react with the ε-amino groups of lysine as well as the arginine epsilon-amino group.

The specific modification of tyrosyl residues may be made, with particular interest in introducing spectral labels into tyrosyl residues by reaction with aromatic diazonium compounds or tetranitromethane. Most commonly, N-acetylimidizole and tetranitromethane are used to form O-acetyl tyrosyl species and 3-nitro derivatives, respectively. Tyrosyl residues are iodinated using $^{125}$I or $^{131}$I to prepare labeled proteins for use in radioimmunoassay.

Carboxyl side groups (aspartyl or glutamyl) are selectively modified by reaction with carbodiimides (R—N=C=N—R'), where R and R' are different alkyl groups, such as 1-cyclohexyl-3-(2-morpholinyl-4-ethyl) carbodiimide or 1-ethyl-3-(4-azonia-4,4-dimethylpentyl)carbodiimide. Furthermore, aspartyl and glutamyl residues are converted to asparaginyl and glutaminyl residues by reaction with ammonium ions.

Glutaminyl and asparaginyl residues are frequently deamidated to the corresponding glutamyl and aspartyl residues, respectively. These residues are deamidated under neutral or basic conditions. The deamidated form of these residues falls within the scope of this invention.

Other modifications include hydroxylation of proline and lysine, phosphorylation of hydroxyl groups of seryl or threonyl residues, methylation of the α-amino groups of lysine, arginine, and histidine side chains (T. E. Creighton, *Proteins: Structure and Molecular Properties*, W.H. Freeman & Co., San Francisco, pp. 79-86 (1983)), acetylation of the N-terminal amine, and amidation of any C-terminal carboxyl group.

Another type of covalent modification involves chemically or enzymatically coupling glycosides to the antibody. These procedures are advantageous in that they do not require production of the antibody in a host cell that has glycosylation capabilities for N- or O-linked glycosylation. Depending on the coupling mode used, the sugar(s) may be attached to (a) arginine and histidine, (b) free carboxyl groups, (c) free sulfhydryl groups such as those of cysteine, (d) free hydroxyl groups such as those of serine, threonine, or hydroxyproline, (e) aromatic residues such as those of phenylalanine, tyrosine, or tryptophan, or (f) the amide group of glutamine. These methods are described in WO 87/05330 published 11 Sep. 1987, and in Aplin and Wriston, *CRC Crit. Rev. Biochem.*, pp. 259-306 (1981).

5.18. Chemotherapeutic Combinations

In other embodiments, the anti-CD22 mAb of the invention can be administered in combination with one or more additional chemotherapeutic agents. For example, "CVB" (1.5 g/m$^2$ cyclophosphamide, 200-400 mg/m$^2$ etoposide, and 150-200 mg/m$^2$ carmustine) can be used in the combination therapies of the invention. CVB is a regimen used to treat non-Hodgkin's lymphoma (Patti et al., *Eur. J. Haematol.*, 51:18 (1993)). Other suitable combination chemotherapeutic regimens are well-known to those of skill in the art. See, for example, Freedman et al., "*Non-Hodgkin's Lymphomas*," in Cancer Medicine, Volume 2, 3rd Edition, Holland et al. (eds.), pp. 2028-2068 (Lea & Febiger 1993). As an illustration, first generation chemotherapeutic regimens for treatment of intermediate-grade non-Hodgkin's lymphoma include C-MOPP (cyclophosphamide, vincristine, procarbazine and prednisone) and CHOP (cyclophosphamide, doxorubicin, vincristine, and prednisone). A useful second generation chemotherapeutic regimen is m-BACOD (methotrexate, bleomycin, doxorubicin, cyclophosphamide, vincristine, dexamethasone, and leucovorin), while a suitable third generation regimen is MACOP-B (methotrexate, doxorubicin, cyclophosphamide, vincristine, prednisone, bleomycin, and leucovorin). Additional useful drugs include phenyl butyrate and brostatin-1.

According to the invention, cancer or one or more symptoms thereof may be prevented, treated, managed or ameliorated by the administration of an anti-CD22 mAb of the invention in combination with the administration of one or more therapies such as, but not limited to, chemotherapies, radiation therapies, hormonal therapies, and/or biological therapies/immunotherapies.

In a specific embodiment, the methods of the invention encompass the administration of one or more angiogenesis antagonists such as but not limited to: Angiostatin (plasminogen fragment); antiangiogenic antithrombin III; Angiozyme; ABT-627; Bay 12-9566; Benefin; Bevacizumab; BMS-275291; cartilage-derived inhibitor (CDI); CAI; CD59 complement fragment; CEP-7055; Col 3; Combretastatin A-4; Endostatin (collagen XVIII fragment); Fibronectin fragment; Gro-beta; Halofuginone; Heparinases; Heparin hexasaccharide fragment; HMV833; Human chorionic gonadotropin (hCG); IM-862; Interferon alpha/beta/gamma; Interferon inducible protein (IP-10); Interleukin-12; Kringle 5 (plasminogen fragment); Marimastat; Metalloproteinase inhibitors (TIMPs); 2-Methoxyestradiol; MMI 270 (CGS 27023A); MoAb IMC-1C11; Neovastat; NM-3; Panzem; PI-88; Placental ribonuclease inhibitor; Plasminogen activator inhibitor; Platelet factor-4 (PF4); Prinomastat; Prolactin 16 kD fragment; Proliferin-related protein (PRP); PTK 787/ZK 222594; Retinoids; Solimastat; Squalamine; SS 3304; SU 5416; SU6668; SU11248; Tetrahydrocortisol-S; tetrathiomolybdate; thalidomide; Thrombospondin-1 (TSP-1); TNP-470; Transforming growth factor-beta (TGF-b); Vasculostatin; Vasostatin (calreticulin fragment); ZD6126; ZD 6474; farnesyl transferase inhibitors (FTI); and bisphosphonates (such as but are not limited to, alendronate, clodronate, etidronate, ibandronate, pamidronate, risedronate, tiludronate, and zoledronate).

In a specific embodiment, the methods of the invention encompass the administration of one or more immunomodulatory agents, such as but not limited to, chemotherapeutic agents and non-chemotherapeutic immunomodulatory agents. Non-limiting examples of chemotherapeutic agents include methotrexate, cyclosporin A, leflunomide, cisplatin, ifosfamide, taxanes such as taxol and paclitaxel, topoisomerase I inhibitors (e.g., CPT-11, topotecan, 9-AC, and GG-211), gemcitabine, vinorelbine, oxaliplatin, 5-fluorouracil (5-FU), leucovorin, vinorelbine, temodal, cytochalasin B, gramicidin D, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin homologs, and cytoxan. Examples of non-chemotherapeutic immunomodulatory agents include, but are not limited to, anti-T cell receptor antibodies (e.g., anti-CD4 antibodies (e.g., cM-T412 (Boeringer), IDEC-CE9.1® (IDEC and SKB), mAB 4162W94, Orthoclone and OKTcdr4a (Janssen-Cilag)), anti-CD3 antibodies (e.g., Nuvion (Product Design Labs), OKT3 (Johnson & Johnson), or Rituxan (IDEC)), anti-CD5 antibodies (e.g., an anti-CD5 ricin-linked immunoconjugate), anti-CD7 antibodies (e.g., CHH-380 (Novartis)), anti-CD8 antibodies, anti-CD40 ligand monoclonal antibodies (e.g., IDEC-131 (IDEC)), anti-CD52 antibodies (e.g., CAMPATH 1H (Ilex)), anti-CD2 antibodies (e.g., MEDI-507 (MedImmune, Inc., International Publication Nos. WO 02/098370 and WO 02/069904), anti-CD11a antibodies (e.g., Xanelim (Genentech)), and anti-B7 antibodies (e.g., IDEC-114) (IDEC)); anti-cytokine receptor antibodies (e.g., anti-IFN receptor antibodies, anti-IL-2 receptor antibodies (e.g., Zenapax (Protein Design Labs)), anti-IL-4 receptor antibodies, anti-IL-6 receptor antibodies, anti-IL-10 receptor antibodies, and anti-IL-12 receptor antibodies), anti-cytokine antibodies (e.g., anti-IFN antibodies, anti-TNF-α antibodies, anti-IL-1β antibodies, anti-IL-6 antibodies, anti-IL-8 antibodies (e.g., ABX-IL-8 (Abgenix)), anti-IL-12 antibodies and anti-IL-23 antibodies)); CTLA4-immunoglobulin; LFA-3TIP (Biogen, International Publication No. WO 93/08656 and U.S. Pat. No. 6,162,432); soluble cytokine receptors (e.g., the extracellular domain of a TNF-α receptor or a fragment thereof, the extracellular domain of an IL-1β receptor or a fragment thereof, and the extracellular domain of an IL-6 receptor or a fragment thereof); cytokines or fragments thereof (e.g., interleukin (IL)-2, IL-3, IL-4, IL-5, IL-6, IL-7, IL-8, IL-9, IL-10, IL-11, IL-12, IL-15, IL-23, TNF-α, TNF-β, interferon (IFN)-α, IFN-γ, and GM-CSF); and anti-cytokine antibodies (e.g., anti-IL-2 antibodies, anti-IL-4 antibodies, anti-IL-6 antibodies, anti-IL-10 antibodies, anti-IL-12 antibodies, anti-IL-15 antibodies, anti-TNF-α antibodies, and anti-IFN-γ antibodies), and antibodies that immunospecifically bind to tumor-associated antigens (e.g., Herceptine). In certain embodiments, an immunomodulatory agent is an immunomodulatory agent other than a chemotherapeutic agent. In other embodiments an immunomodulatory agent is an immunomodulatory agent other than a cytokine or hemapoietic such as IL-1, IL-2, IL-4, IL-12, IL-15, TNF, IFN-α, IFN-β, M-CSF, G-CSF, IL-3 or erythropoietin. In yet other embodiments, an immunomodulatory agent is an agent other than a chemotherapeutic agent and a cytokine or hemapoietic factor.

In a specific embodiment, the methods of the invention encompass the administration of one or more anti-inflammatory agents, such as but not limited to, nonsteroidal anti-inflammatory drugs (NSAIDs), steroidal anti-inflammatory drugs, beta-agonists, anticholingeric agents, and methyl xanthines. Examples of NSAIDs include, but are not limited to, aspirin, ibuprofen, celecoxib (CELEBREX™), diclofenac (VOLTAREN™), etodolac (LODINE™), fenoprofen (NALFON™), indomethacin (INDOCIN™), ketoralac (TORADOL™), oxaprozin (DAYPRO™), nabumentone (RELAFEN™), sulindac (CLINORIL™), tolmentin (TOLECTINT™), rofecoxib (VIOXX™), naproxen (ALEVE™, NAPROSYN™), ketoprofen (ACTRON™) and nabumetone (RELAFEN™). Such NSAIDs function by inhibiting a cyclooxygenase enzyme (e.g., COX-1 and/or COX-2). Examples of steroidal anti-inflammatory drugs include, but are not limited to, glucocorticoids, dexamethasone (DECADRON™), cortisone, hydrocortisone, prednisone (DELTASONE™), prednisolone, triamcinolone, azulfidine, and eicosanoids such as prostaglandins, thromboxanes, and leukotrienes.

In another specific embodiment, the methods of the invention encompass the administration of one or more antiviral agents (e.g., amantadine, ribavirin, rimantadine, acyclovir, famciclovir, foscarnet, ganciclovir, trifluridine, vidarabine, didanosine, stavudine, zalcitabine, zidovudine, interferon), antibiotics (e.g., dactinomycin (formerly actinomycin), bleomycin, mithramycin, and anthramycin (AMC)), anti-emetics (e.g., alprazolam, dexamethoasone, domperidone, dronabinol, droperidol, granisetron, haloperidol, haloperidol, iorazepam, methylprednisolone, metoclopramide, nabilone, ondansetron, prochlorperazine), anti-fungal agents (e.g., amphotericin, clotrimazole, econazole, fluconazole, flucytosine, griseofulvin, itraconazole, ketoconazole, miconazole and nystatin), anti-parasite agents (e.g., dehydroemetine, diloxanide furoate, emetine, mefloquine, melarsoprol, metronidazole, nifurtimox, paromomycin, pentabidine, pentamidine isethionate, primaquine, quinacrine, quinidine) or a combination thereof.

Specific examples of anti-cancer agents that can be used in the various embodiments of the invention, including pharmaceutical compositions and dosage forms and kits of the invention, include, but are not limited to: acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cisplatin; cladribine; crisnatol mesylate; cyclophosphamide; cytarabine; dacarbazine; dactinomycin; daunorubicin hydrochloride; decitabine; dexormaplatin; dezaguanine; dezaguanine mesylate; diaziquone; docetaxel; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; fluorocitabine; fosquidone; fostriecin sodium; gemcitabine; gemcitabine hydrochloride; hydroxyurea; idarubicin hydrochloride; ifosfamide; ilmofosine; interleukin II (including recombinant interleukin II, or rIL2), interferon alpha-2a; interferon alpha-2b; interferon alpha-n1; interferon alpha-n3; interferon beta-I a; interferon gamma-I b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; paclitaxel; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride. Other anti-cancer drugs include, but are not limited to: 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; antidorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-aminotriazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; dihydrotaxol, 9-; dioxamycin; diphenyl spiromustine; docetaxel; docosanol; dolasetron; doxifluridine; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; HMG-CoA reductase inhibitor (such as but not limited to, Lovastatin, Pravastatin, Fluvastatin, Statin, Simvastatin, and Atorvastatin); loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; paclitaxel; paclitaxel analogues; paclitaxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen binding protein; sizofuran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium;

tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; Vitaxin®; vorozole; zanoterone; zeniplatin; zilascorb; and zinostatin stimalamer. Preferred additional anti-cancer drugs are 5-fluorouracil and leucovorin. These two agents are particularly useful when used in methods employing thalidomide and a topoisomerase inhibitor. In specific embodiments, a anti-cancer agent is not a chemotherapeutic agent.

In more particular embodiments, the present invention also comprises the administration of an anti-CD22 mAb of the invention in combination with the administration of one or more therapies such as, but not limited to anti-cancer agents such as those disclosed in Table 1, preferably for the treatment of breast, ovary, melanoma, prostate, colon and lung cancers as described above. When used in a combination therapy, the dosages and/or the frequency of administration listed in Table 1 may be decreased.

TABLE 1

| Therapeutic Agent | Dose/Administration/Formulation | | |
|---|---|---|---|
| doxorubicin hydrochloride (Adriamycin RDF ® and Adriamycin PFS ®) | Intravenous | 60-75 mg/m$^2$ on Day 1 | 21 day intervals |
| epirubicin hydrochloride (Ellence ™) | Intravenous | 100-120 mg/m$^2$ on Day 1 of each cycle or divided equally and given on Days 1-8 of the cycle | 3-4 week cycles |
| fluorousacil | Intravenous | How supplied: 5 mL and 10 mL vials (containing 250 and 500 mg flourouracil respectively) | |
| docetaxel (Taxotere ®) | Intravenous | 60-100 mg/m$^2$ over 1 hour | Once every 3 weeks |
| paclitaxel (Taxol ®) | Intravenous | 175 mg/m$^2$ over 3 hours | Every 3 weeks for 4 courses (administered sequentially to doxorubicin-containing combination chemotherapy) |
| tamoxifen citrate (Nolvadex ®) | Oral (tablet) | 20-40 mg Dosages greater than 20 mg should be given in divided doses (morning and evening) | Daily |
| leucovorin calcium for injection | intravenous or intramuscular injection | How supplied: 350 mg vial | Dosage is unclear from text. PDR 3610 |
| luprolide acetate Lupron ®) | single subcutaneous injection | 1 mg (0.2 mL or 20 unit mark) | Once a day |
| flutamide (Eulexin ®) | Oral (capsule) | 50 mg (capsules contain 125 mg flutamide each) | 3 times a day at 8 hour intervals (total daily dosage 750 mg) |
| nilutamide (Nilandron ®) | Oral (tablet) | 300 mg or 150 mg (tablets contain 50 or 150 mg nilutamide each) | 300 mg once a day for 30 days followed by 150 mg once a day |
| bicalutamide (Casodex ®) | Oral (tablet) | 50 mg (tablets contain 50 mg bicalutamide each) | Once a day |
| progesterone | Injection | USP in sesame oil 50 mg/mL | |
| ketoconazole (Nizoral ®) | Cream | 2% cream applied once or twice daily depending on symptoms | |
| prednisone | Oral (tablet) | Initial dosage may vary from 5 mg to 60 mg per day depending on the specific disease entity being treated. | |
| estramustine phosphate sodium (Emcyt ®) | Oral (capsule) | 14 mg/ kg of body weight (i.e. one 140 mg capsule for each 10 kg or 22 lb of body weight) | Daily given in 3 or 4 divided doses |
| etoposide or VP-16 | Intravenous | 5 mL of 20 mg/ mL solution (100 mg) | |
| dacarbazine | Intravenous | 2-4.5 mg/kg | Once a day for 10 days. |

TABLE 1-continued

| Therapeutic Agent | Dose/Administration/Formulation | | |
|---|---|---|---|
| (DTIC-Dome ®) | | | May be repeated at 4 week intervals |
| polifeprosan 20 with carmustine implant (BCNU) (nitrosourea) (Gliadel ®) | wafer placed in resection cavity | 8 wafers, each containing 7.7 mg of carmustine, for a total of 61.6 mg, if size and shape of resection cavity allows | |
| cisplatin | Injection | [n/a in PDR 861] How supplied: solution of 1 mg/mL in multi-dose vials of 50 mL and 100 mL | |
| mitomycin | Injection | supplied in 5 mg and 20 mg vials (containing 5 mg and 20 mg mitomycin) | |
| gemcitabine HCl (Gemzar ®) | Intravenous | For NSCLC- 2 schedules have been investigated and the optimum schedule has not been determined 4 week schedule- administration intravenously at 1000 mg/m² over 30 minutes on 3 week schedule- Gemzar administered intravenously at 1250 mg/m² over 30 minutes | 4 week schedule- Days 1,8 and 15 of each 28-day cycle. Cisplatin intravenously at 100 mg/m² on day 1 after the infusion of Gemzar. 3 week schedule- Days 1 and 8 of each 21 day cycle. Cisplatin at dosage of 100 mg/m² administered intravenously after administration of Gemzar on day 1. |
| carboplatin (Paraplatin ®) | Intravenous | Single agent therapy: 360 mg/m² I.V. on day 1 (infusion lasting 15 minutes or longer) Other dosage calculations: Combination therapy with cyclophosphamide, Dose adjustment recommendations, Formula dosing, etc. | Every 4 weeks |
| ifosamide (Ifex ®) | Intravenous | 1.2 g/m² daily | 5 consecutive days Repeat every 3 weeks or after recovery from hematologic toxicity |
| topotecan hydrochloride (Hycamtin ®) | Intravenous | 1.5 mg/m² by intravenous infusion over 30 minutes daily | 5 consecutive days, starting on day 1 of 21 day course |
| Bisphosphonates Pamidronate Alendronate Risedronate | Intravenous or Oral take with 6-8 oz water. | 60 mg or 90 mg single infusion over 4-24 hours to correct hypercalcemia in cancer patients 5 mg/d daily for 2 years and then 10 mg/d for 9 month to prevent or control bone resorption. 5.0 mg to prevent or control bone resorption. | |
| Lovastatin (Mevacor ™) | Oral 1 | 10-80 mg/day in single or two divided dose. | |

The invention also encompasses administration of an anti-CD22 mAb of the invention in combination with radiation therapy comprising the use of x-rays, gamma rays and other sources of radiation to destroy the cancer cells. In preferred embodiments, the radiation treatment is administered as external beam radiation or teletherapy wherein the radiation is directed from a remote source. In other preferred embodiments, the radiation treatment is administered as internal therapy or brachytherapy wherein a radioactive source is placed inside the body close to cancer cells or a tumor mass.

Cancer therapies and their dosages, routes of administration and recommended usage are known in the art and have been described in such literature as the *Physician's Desk Reference* (56th ed., 2002).

5.19. Pharmaceutical Compositions

The invention also relates to immunotherapeutic compositions and methods for the treatment of B cell diseases and disorders in human subjects, such as, but not limited to, B cell malignancies, to immunotherapeutic compositions and methods for the treatment and prevention of GVHD, graft rejection, and post-transplant lymphocyte proliferative disorder in human transplant recipients, and to immunotherapeutic compositions and methods for the treatment of autoimmune diseases and disorders in human subjects, using therapeutic antibodies that bind to the CD22 antigen and preferably mediate human ADCC.

The present invention relates to pharmaceutical compositions comprising human, humanized, or chimeric anti-CD22 antibodies of the IgG1 or IgG3 human isotype. The present invention also relates to pharmaceutical compositions comprising human or humanized anti-CD22 antibodies of the IgG2 or IgG4 human isotype that preferably mediate human ADCC. In certain embodiments, the present invention also relates to pharmaceutical compositions comprising monoclonal human, humanized, or chimerized anti-CD22 antibodies that can be produced by means known in the art.

Therapeutic formulations and regimens are described for treating human subjects diagnosed with B cell malignancies that derive from B cells and their precursors, including but not limited to, acute lymphoblastic leukemia (ALL), Hodgkin's lymphomas, non-Hodgkin's lymphomas, B cell chronic lymphocytic leukemia (CLL), multiple myeloma, follicular lymphoma, mantle cell lymphoma, pro-lymphocytic leukemia, hairy cell leukemia, common acute lymphocytic leukemia and some Null-acute lymphoblastic leukemia.

In other particular embodiments, the anti-CD22 antibodies of the invention mediate ADCC, complement-dependent cellular cytoxicity, or apoptosis. The compositions and methods of the present invention also have the advantage of targeting a wider population of B cells than other B cell directed immunotherapies. For example, anti-CD22 antibodies of the present invention are effective to target bone marrow cells, circulating B cells, and mature, antibody-secreting B cells. Accordingly, the methods and compositions of the invention are effective to reduce or deplete circulating B cells as well as circulating immunoglobulin.

Accordingly, in one aspect, the invention provides compositions and methods for the treatment and prevention of GVHD, graft rejection, and post-transplantation lymphoproliferative disorder, which are associated with fewer and/or less severe complications than less-targeted therapeutic agents and regimens. In one embodiment, the compositions and methods of the invention are used with lower doses of traditional therapeutic agents than would be possible in the absence of the methods and compositions of the invention. In another embodiment, the compositions and methods of the invention obviate the need for a more severe form of therapy, such as radiation therapy, high-dose chemotherapy, or splenectomy.

In certain embodiments, the anti-CD22 antibodies and compositions of the invention may be administered to a transplant recipient patient prior to or following transplantation, alone or in combination with other therapeutic agents or regimens for the treatment or prevention of GVHD and graft rejection. For example, the anti-CD22 antibodies and compositions of the invention may be used to deplete alloantibodies from a transplant recipient prior to or following transplantation of an allogeneic graft. The anti-CD22 antibodies and compositions of the invention may also be used to deplete antibody-producing cells from the graft ex vivo, prior to transplantation, or in the donor, or as prophylaxis against GVHD and graft rejection.

5.20. Pharmaceutical Formulations, Administration and Dosing

The pharmaceutical formulations of the invention contain as the active ingredient human, humanized, or chimeric anti-CD22 antibodies. The formulations contain naked antibody, immunoconjugate, or fusion protein in an amount effective for producing the desired response in a unit of weight or volume suitable for administration to a human patient, and are preferably sterile. The response can, for example, be measured by determining the physiological effects of the anti-CD22 antibody composition, such as, but not limited to, circulating B cell depletion, tissue B cell depletion, regression of a B cell malignancy, or decrease of disease symptoms. Other assays will be known to one of ordinary skill in the art and can be employed for measuring the level of the response.

5.20.1. Pharmaceutical Formulations

An anti-CD22 antibody composition may be formulated with a pharmaceutically acceptable carrier. The term "pharmaceutically acceptable" means one or more non-toxic materials that do not interfere with the effectiveness of the biological activity of the active ingredients. Such preparations may routinely contain salts, buffering agents, preservatives, compatible carriers, and optionally other therapeutic agents. Such pharmaceutically acceptable preparations may also routinely contain compatible solid or liquid fillers, diluents or encapsulating substances which are suitable for administration into a human. When used in medicine, the salts should be pharmaceutically acceptable, but non-pharmaceutically acceptable salts may conveniently be used to prepare pharmaceutically acceptable salts thereof and are not excluded from the scope of the invention. Such pharmacologically and pharmaceutically acceptable salts include, but are not limited to, those prepared from the following acids: hydrochloric, hydrobromic, sulfuric, nitric, phosphoric, maleic, acetic, salicylic, citric, boric, formic, malonic, succinic, and the like. Also, pharmaceutically acceptable salts can be prepared as alkaline metal or alkaline earth salts, such as sodium, potassium or calcium salts. The term "carrier" denotes an organic or inorganic ingredient, natural or synthetic, with which the active ingredient is combined to facilitate the application. The components of the pharmaceutical compositions also are capable of being co-mingled with the antibodies of the present invention, and with each other, in a manner such that there is no interaction which would substantially impair the desired pharmaceutical efficacy.

According to certain aspects of the invention, the anti-CD22 antibody compositions can be prepared for storage by mixing the antibody or immunoconjugate having the desired degree of purity with optional physiologically acceptable carriers, excipients or stabilizers (*Remington's Pharmaceutical Sciences,* 16th edition, Osol, A. Ed. (1999)), in the form of lyophilized formulations or aqueous solutions. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN, PLURONICS™ or polyethylene glycol (PEG).

The anti-CD22 antibody compositions also may contain, optionally, suitable preservatives, such as: benzalkonium chloride; chlorobutanol; parabens and thimerosal.

The anti-CD22 antibody compositions may conveniently be presented in unit dosage form and may be prepared by any of the methods well-known in the art of pharmacy. All methods include the step of bringing the active agent into association with a carrier which constitutes one or more accessory ingredients. In general, the compositions are prepared by uniformly and intimately bringing the active compound into association with a liquid carrier, a finely divided solid carrier, or both, and then, if necessary, shaping the product.

Compositions suitable for parenteral administration conveniently comprise a sterile aqueous or non-aqueous preparation of anti-CD22 antibody, which is preferably isotonic with the blood of the recipient. This preparation may be formulated according to known methods using suitable dispersing or wetting agents and suspending agents. The sterile injectable preparation also may be a sterile injectable solution or suspension in a non-toxic parenterally acceptable diluent or solvent, for example, as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or di-glycerides. In addition, fatty acids such as oleic acid may be used in the preparation of injectables. Carrier formulation suitable for oral, subcutaneous, intravenous, intramuscular, etc. administration can be found in *Remington's Pharmaceutical Sciences*, Mack Publishing Co., Easton, Pa. In certain embodiments, carrier formulation suitable for various routes of administration can be the same or similar to that described for RITUXAN™. See, *Physicians' Desk Reference* (Medical Economics Company, Inc., Montvale, N.J., 2005), pp. 958-960 and 1354-1357, which is incorporated herein by reference in its entirety. In certain embodiments of the invention, the anti-CD22 antibody compositions are formulated for intravenous administration with sodium chloride, sodium citrate dihydrate, polysorbate 80, and sterile water where the pH of the composition is adjusted to approximately 6.5. Those of skill in the art are aware that intravenous injection provides a useful mode of administration due to the thoroughness of the circulation in rapidly distributing antibodies. Intravenous administration, however, is subject to limitation by a vascular barrier comprising endothelial cells of the vasculature and the subendothelial matrix. Still, the vascular barrier is a more notable problem for the uptake of therapeutic antibodies by solid tumors. Lymphomas have relatively high blood flow rates, contributing to effective antibody delivery. Intralymphatic routes of administration, such as subcutaneous or intramuscular injection, or by catheterization of lymphatic vessels, also provide a useful means of treating B cell lymphomas. In preferred embodiments, anti-CD22 antibodies of the compositions and methods of the invention are self-administered subcutaneously. In such preferred embodiments, the composition is formulated as a lyophilized drug or in a liquid buffer (e.g., PBS and/or citrate) at about 50 mg/mL.

The formulation herein may also contain more than one active compound as necessary for the particular indication being treated, preferably those with complementary activities that do not adversely affect each other. For example, it may be desirable to further provide an immunosuppressive agent. Such molecules are suitably present in combination in amounts that are effective for the purpose intended.

The active ingredients may also be entrapped in microcapsule prepared, for example, by coacervation techniques or by interfacial polymerization, for example, hydroxymethylcellulose or gelatin-microcapsule and poly-(methylmethacylate) microcapsule, respectively, in colloidal drug delivery systems (for example, liposomes, albumin microspheres, microemulsions, nano-particles and nanocapsules) or in macroemulsions. Such techniques are disclosed in *Remington's Pharmaceutical Sciences* 16th edition, Osol, A. Ed. (1980).

The formulations to be used for in vivo administration are typically sterile. This is readily accomplished by filtration through sterile filtration membranes.

Sustained-release preparations may be prepared. Suitable examples of sustained-release preparations include semipermeable matrices of solid hydrophobic polymers containing the anti-CD22 antibody, which matrices are in the form of shaped articles, e.g., films, or microcapsule. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and γ-ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods. When encapsulated antibodies remain in the body for a long time, they may denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions. In certain embodiments, the pharmaceutically acceptable carriers used in the compositions of the invention do not affect human ADCC or CDC.

The anti-CD22 antibody compositions disclosed herein may also be formulated as immunoliposomes. A "liposome" is a small vesicle composed of various types of lipids, phospholipids and/or surfactant which is useful for delivery of a drug (such as the anti-CD22 antibodies disclosed herein) to a human. The components of the liposome are commonly arranged in a bilayer formation, similar to the lipid arrangement of biological membranes. Liposomes containing the antibodies of the invention are prepared by methods known in the art, such as described in Epstein et al., *Proc. Natl. Acad. Sci. USA*, 82:3688 (1985); Hwang et al., *Proc. Natl. Acad. Sci. USA*, 77:4030 (1980); and U.S. Pat. Nos. 4,485,045 and 4,544,545. Liposomes with enhanced circulation time are disclosed in U.S. Pat. No. 5,013,556. Particularly useful liposomes can be generated by the reverse phase evaporation method with a lipid composition comprising phosphatidylcholine, cholesterol and PEG-derivatized phosphatidylethanolamine (PEG-PE). Liposomes are extruded through filters of defined pore size to yield liposomes with the desired diameter. The antibody of the present invention can be conjugated to the liposomes as described in Martin et al., *J. Biol. Chem.*, 257:286-288 (1982) via a disulfide interchange reaction. A therapeutic agent can also be contained within the liposome. See, Gabizon et al., *J. National Cancer Inst.*, (19)1484 (1989).

Some of the preferred pharmaceutical formulations include, but are not limited to:

(a) a sterile, preservative-free liquid concentrate for intravenous (i.v.) administration of anti-CD22 antibody, supplied at a concentration of 10 mg/ml in either 100 mg (10 mL) or 500 mg (50 mL) single-use vials. The product can be formulated for i.v. administration using sodium chloride, sodium citrate dihydrate, polysorbate and sterile water for injection.

For example, the product can be formulated in 9.0 mg/mL sodium chloride, 7.35 mg/mL sodium citrate dihydrate, 0.7 mg/mL polysorbate 80, and sterile water for injection. The pH is adjusted to 6.5.

(b) A sterile, lyophilized powder in single-use glass vials for subcutaneous (s.c.) injection. The product can be formulated with sucrose, L-histidine hydrochloride monohydrate, L-histidine and polysorbate 20. For example, each single-use vial can contain 150 mg anti-CD22 antibody, 123.2 mg sucrose, 6.8 mg L-histidine hydrochloride monohydrate, 4.3 mg L-histidine, and 3 mg polysorbate 20. Reconstitution of the single-use vial with 1.3 ml sterile water for injection yields approximately 1.5 ml solution to deliver 125 mg per 1.25 ml (100 mg/ml) of antibody.

(c) A sterile, preservative-free lyophilized powder for intravenous (i.v.) administration. The product can be formulated with α-trehalose dihydrate, L-histidine HCl, histidine and polysorbate 20 USP. For example, each vial can contain 440 mg anti-CD22 antibody, 400 mg α,α-trehalose dihydrate, 9.9 mg L-histidine HCl, 6.4 mg L-histidine, and 1.8 mg polysorbate 20, USP. Reconstitution with 20 ml of bacteriostatic water for injection (BWFI), USP, containing 1.1% benzyl alcohol as a preservative, yields a multi-dose solution containing 21 mg/ml antibody at a pH of approximately 6.

(d) A sterile, lyophilized powder for intravenous infusion in which the anti-CD22 antibody is formulated with sucrose, polysorbate, monobasic sodium phosphate monohydrate, and dibasic sodium phosphate dihydrate. For example, each single-use vial can contain 100 mg antibody, 500 mg sucrose, 0.5 mg polysorbate 80, 2.2 mg monobasic sodium phosphate monohydrate, and 6.1 mg dibasic sodium phosphate dihydrate. No preservatives are present. Following reconstitution with 10 ml sterile water for injection, USP, the resulting pH is approximately 7.2.

(e) A sterile, preservative-free solution for subcutaneous administration supplied in a single-use, 1 ml pre-filled syringe. The product can be formulated with sodium chloride, monobasic sodium phosphate dihydrate, dibasic sodium phosphate dihydrate, sodium citrate, citric acid monohydrate, mannitol, polysorbate 80 and water for injection, USP. Sodium hydroxide may be added to adjust pH to about 5.2.

For example, each syringe can be formulated to deliver 0.8 ml (40 mg) of drug product. Each 0.8 ml contains 40 mg anti-CD22 antibody, 4.93 mg sodium chloride, 0.69 mg monobasic sodium phosphate dihydrate, 1.22 mg dibasic sodium phosphate dihydrate, 0.24 mg sodium citrate, 1.04 citric acid monohydrate, 9.6 mg mannitol, 0.8 mg polysorbate 80 and water for injection, USP.

(f) A sterile, preservative-free, lyophilized powder contained in a single-use vial that is reconstituted with sterile water for injection (SWFI), USP, and administered as a subcutaneous (s.c.) injection. The product can be formulated with sucrose, histidine hydrochloride monohydrate, L-histidine, and polysorbate. For example, a 75 mg vial can contain 129.6 mg or 112.5 mg of the anti-CD22 antibody, 93.1 mg sucrose, 1.8 mg L-histidine hydrochloride monohydrate, 1.2 mg L-histidine, and 0.3 mg polysorbate 20, and is designed to deliver 75 mg of the antibody in 0.6 ml after reconstitution with 0.9 ml SWFI, USP. A 150 mg vial can contain 202.5 mg or 175 mg anti-CD22 antibody, 145.5 mg sucrose, 2.8 mg L-histidine hydrochloride monohydrate, 1.8 mg L-histidine, and 0.5 mg polysorbate 20, and is designed to deliver 150 mg of the antibody in 1.2 ml after reconstitution with 1.4 ml SWFI, USP.

(g) A sterile, lyophilized product for reconstitution with sterile water for injection. The product can be formulated as single-use vials for intramuscular (IM) injection using mannitol, histidine and glycine. For example, each single-use vial can contain 100 mg anti-CD22 antibody, 67.5 mg of mannitol, 8.7 mg histidine and 0.3 mg glycine, and is designed to deliver 100 mg antibody in 1.0 ml when reconstituted with 1.0 ml sterile water for injection. Alternatively, each single-use vial can contain 50 mg anti-CD22 antibody, 40.5 mg mannitol, 5.2 mg histidine and 0.2 mg glycine, and is designed to deliver 50 mg of antibody when reconstituted with 0.6 ml sterile water for injection.

(h) A sterile, preservative-free solution for intramuscular (IM) injection, supplied at a concentration of 100 mg/ml. The product can be formulated in single-use vials with histidine, glycine, and sterile water for injection. For example, each single-use vial can be formulated with 100 mg antibody, 4.7 mg histidine, and 0.1 mg glycine in a volume of 1.2 ml designed to deliver 100 mg of antibody in 1 ml. Alternatively, each single-use vial can be formulated with 50 mg antibody, 2.7 mg histidine and 0.08 mg glycine in a volume of 0.7 ml or 0.5 ml designed to deliver 50 mg of antibody in 0.5 ml.

In certain embodiments, the pharmaceutical composition of the invention is stable at 4° C. In certain embodiments, the pharmaceutical composition of the invention is stable at room temperature.

5.20.2. Antibody Half-Life

In certain embodiments, the half-life of an anti-CD22 antibody of the compositions and methods of the invention is at least about 4 to 7 days. In certain embodiments, the mean half-life of the anti-CD22 antibody of the compositions and methods of the invention is at least about 2 to 5 days, 3 to 6 days, 4 to 7 days, 5 to 8 days, 6 to 9 days, 7 to 10 days, 8 to 11 days, 8 to 12, 9 to 13, 10 to 14, 11 to 15, 12 to 16, 13 to 17, 14 to 18, 15 to 19, or 16 to 20 days. In other embodiments, the mean half-life of the anti-CD22 antibody of the compositions and methods of the invention is at least about 17 to 21 days, 18 to 22 days, 19 to 23 days, 20 to 24 days, 21 to 25, days, 22 to 26 days, 23 to 27 days, 24 to 28 days, 25 to 29 days, or 26 to 30 days. In still further embodiments the half-life of an anti-CD22 antibody of the compositions and methods of the invention can be up to about 50 days. In certain embodiments, the half-lives of the antibodies of the compositions and methods of the invention can be prolonged by methods known in the art. Such prolongation can in turn reduce the amount and/or frequency of dosing of the antibody compositions of the invention. Antibodies with improved in vivo half-lives and methods for preparing them are disclosed in U.S. Pat. No. 6,277,375; and International Publication Nos. WO 98/23289 and WO 97/3461.

The serum circulation of the anti-CD22 antibodies of the invention in vivo may also be prolonged by attaching inert polymer molecules such as high molecular weight polyethyleneglycol (PEG) to the antibodies with or without a multifunctional linker either through site-specific conjugation of the PEG to the N- or C-terminus of the antibodies or via epsilon-amino groups present on lysyl residues. Linear or branched polymer derivatization that results in minimal loss of biological activity will be used. The degree of conjugation can be closely monitored by SDS-PAGE and mass spectrometry to ensure proper conjugation of PEG molecules to the antibodies. Unreacted PEG can be separated from antibody-PEG conjugates by size-exclusion or by ion-exchange chromatography. PEG-derivatized antibodies can be tested for binding activity as well as for in vivo efficacy using methods known to those of skill in the art, for example, by immunoassays described herein.

Further, the antibodies of the compositions and methods of the invention can be conjugated to albumin in order to make the antibody more stable in vivo or have a longer half-life in vivo. The techniques are well known in the art, see, e.g., International Publication Nos. WO 93/15199, WO 93/15200, and WO 01/77137; and European Patent No. EP 413, 622, all of which are incorporated herein by reference.

5.20.3. Administration and Dosing

Administration of the compositions of the invention to a human patient can be by any route, including but not limited to intravenous, intradermal, transdermal, subcutaneous, intramuscular, inhalation (e.g., via an aerosol), buccal (e.g., sub-lingual), topical (i.e., both skin and mucosal surfaces, including airway surfaces), intrathecal, intraarticular, intraplural, intracerebral, intra-arterial, intraperitoneal, oral, intralymphatic, intranasal, rectal or vaginal administration, by perfusion through a regional catheter, or by direct intralesional injection. In a preferred embodiment, the compositions of the invention are administered by intravenous push or intravenous infusion given over defined period (e.g., 0.5 to 2 hours). The compositions of the invention can be delivered by peristaltic means or in the form of a depot, although the most suitable route in any given case will depend, as is well known in the art, on such factors as the species, age, gender and overall condition of the subject, the nature and severity of the condition being treated and/or on the nature of the particular composition (i.e., dosage, formulation) that is being administered. In particular embodiments, the route of administration is via bolus or continuous infusion over a period of time, once or twice a week. In other particular embodiments, the route of administration is by subcutaneous injection, optionally once or twice weekly. In one embodiment, the compositions, and/or methods of the invention are administered on an outpatient basis.

In certain embodiments, the dose of a composition comprising anti-CD22 antibody is measured in units of mg/kg of patient body weight. In other embodiments, the dose of a composition comprising anti-CD22 antibody is measured in units of mg/kg of patient lean body weight (i.e., body weight minus body fat content). In yet other embodiments, the dose of a composition comprising anti-CD22 antibody is measured in units of mg/m² of patient body surface area. In yet other embodiments, the dose of a composition comprising anti-CD22 antibody is measured in units of mg per dose administered to a patient. Any measurement of dose can be used in conjunction with the compositions and methods of the invention and dosage units can be converted by means standard in the art.

Those skilled in the art will appreciate that dosages can be selected based on a number of factors including the age, sex, species and condition of the subject (e.g., stage of B cell malignancy), the desired degree of cellular depletion, the disease to be treated and/or the particular antibody or antigen-binding fragment being used and can be determined by one of skill in the art. For example, effective amounts of the compositions of the invention may be extrapolated from dose-response curves derived in vitro test systems or from animal model (e.g., the cotton rat or monkey) test systems. Models and methods for evaluation of the effects of antibodies are known in the art (Wooldridge et al., *Blood,* 89(8): 2994-2998 (1997)), incorporated by reference herein in its entirety). In certain embodiments, for particular B cell malignancies, therapeutic regimens standard in the art for antibody therapy can be used with the compositions and methods of the invention.

Examples of dosing regimens that can be used in the methods of the invention include, but are not limited to, daily, three times weekly (intermittent), weekly, or every 14 days. In certain embodiments, dosing regimens include, but are not limited to, monthly dosing or dosing every 6-8 weeks.

Those skilled in the art will appreciate that dosages are generally higher and/or frequency of administration greater for initial treatment as compared with maintenance regimens.

In embodiments of the invention, the anti-CD22 antibodies bind to B cells and, thus, can result in more efficient (i.e., at lower dosage) depletion of B cells (as described herein). Higher degrees of binding may be achieved where the density of human CD22 on the surface of a patient's B cells is high. In exemplary embodiments, dosages of the antibody (optionally in a pharmaceutically acceptable carrier as part of a pharmaceutical composition) are at least about 0.0005, 0.001, 0.05, 0.075, 0.1, 0.25, 0.375, 0.5, 1, 2.5, 5, 10, 20, 37.5, or 50 mg/m² and/or less than about 500, 475, 450, 425, 400, 375, 350, 325, 300, 275, 250, 225, 200, 175, 150, 125, 100, 75, 60, 50, 37.5, 20, 15, 10, 5, 2.5, 1, 0.5, 0.375, 0.1, 0.075 or 0.01 mg/m². In certain embodiments, the dosage is between about 0.0005 to about 200 mg/m², between about 0.001 and 150 mg/m², between about 0.075 and 125 mg/m², between about 0.375 and 100 mg/m², between about 2.5 and 75 mg/m², between about 10 and 75 mg/m², and between about 20 and 50 mg/m². In related embodiments, the dosage of anti-CD22 antibody used is at least about 0.1, 0.2, 0.3, 0.4, 0.5, 0.6, 0.7, 0.8, 0.9, 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20, 20.5 mg/kg of body weight of a patient. In certain embodiments, the dose of naked anti-CD22 antibody used is at least about 1 to 10, 5 to 15, 10 to 20, or 15 to 25 mg/kg of body weight of a patient. In certain embodiments, the dose of anti-CD22 antibody used is at least about 1 to 20, 3 to 15, or 5 to 10 mg/kg of body weight of a patient. In preferred embodiments, the dose of anti-CD22 antibody used is at least about 5, 6, 7, 8, 9, or 10 mg/kg of body weight of a patient. In certain embodiments, a single dosage unit of the antibody (optionally in a pharmaceutically acceptable carrier as part of a pharmaceutical composition) can be at least about 0.5, 1, 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 204, 206, 208, 210, 212, 214, 216, 218, 220, 222, 224, 226, 228, 230, 232, 234, 236, 238, 240, 242, 244, 246, 248, or 250 micrograms/m². In other embodiments, dose is up to 1 g per single dosage unit.

All of the above doses are exemplary and can be used in conjunction with the compositions and methods of the invention, however where an anti-CD22 antibody is used in conjunction with a toxin or radiotherapeutic agent the lower doses described above are preferred. In certain embodiments, where the patient has low levels of CD22 density, the lower doses described above are preferred.

In certain embodiments of the invention where chimeric anti-CD22 antibodies are used, the dose or amount of the chimeric antibody is greater than about 2, 3, 4, 5, 6, 7, 8, 9, 10, 11, 12, 13, 14, 15, or 16 mg/kg of patient body weight. In other embodiments of the invention where chimeric anti-CD22 antibodies are used, the dose or amount of the chimeric antibody is less than about 1, 0.9, 0.8, 0.7, 0.6, 0.5, 0.4, 0.3, 0.2, or 0.1 mg/kg of patient body weight.

In some embodiments of the methods of this invention, antibodies and/or compositions of this invention can be administered at a dose lower than about 375 mg/m²; at a dose lower than about 37.5 mg/m²; at a dose lower than about 0.375 mg/m²; and/or at a dose between about 0.075 mg/m² and about 125 mg/m². In preferred embodiments of the methods of the invention, dosage regimens comprise low doses, administered at repeated intervals. For example, in one embodiment, the compositions of the invention can be administered at a dose lower than about 375 mg/m$^2$ at intervals of approximately every 1, 2, 3, 4, 5, 6, 7, 8, 9, 10, 15, 20, 25, 30, 35, 40, 45, 50, 60, 70, 80, 90, 100, 125, 150, 175, or 200 days.

The specified dosage can result in B cell depletion in the human treated using the compositions and methods of the invention for a period of at least about 1, 2, 3, 5, 7, 10, 14, 20, 30, 45, 60, 75, 90, 120, 150 or 180 days or longer. In certain embodiments, pre-B cells (not expressing surface immunoglobulin) are depleted. In certain embodiments, mature B cells (expressing surface immunoglobulin) are depleted. In other embodiments, all non-malignant types of B cells can exhibit depletion. Any of these types of B cells can be used to measure B cell depletion. B cell depletion can be measured in bodily fluids such as blood serum, or in tissues such as bone marrow. In preferred embodiments of the methods of the invention, B cells are depleted by at least 30%, 40%, 50%, 60%, 70%, 80%, 90%, or 100% in comparison to B cell levels in the patient being treated before use of the compositions and methods of the invention. In preferred embodiments of the methods of the invention, B cells are depleted by at least 30%, 40%, 50%, 60%, 70%, 80%, 90%, or 100% in comparison to typical standard B cell levels for humans. In related embodiments, the typical standard B cell levels for humans are determined using patients comparable to the patient being treated with respect to age, sex, weight, and other factors.

In certain embodiments of the invention, a dosage of about 125 mg/m$^2$ or less of an antibody or antigen-binding fragment results in B cell depletion for a period of at least about 7, 14, 21, 30, 45, 60, 90, 120, 150, or 200 days. In another representative embodiment, a dosage of about 37.5 mg/m$^2$ or less depletes B cells for a period of at least about 7, 14, 21, 30, 45, 60, 90, 120, 150, or 200 days. In still other embodiments, a dosage of about 0.375 mg/m$^2$ or less results in depletion of B cells for at least about 7, 14, 21, 30, 45 or 60 days. In another embodiment, a dosage of about 0.075 mg/m$^2$ or less results in depletion of B cells for a period of at least about 7, 14, 21, 30, 45, 60, 90, 120, 150, or 200 days. In yet other embodiments, a dosage of about 0.01 mg/m$^2$, 0.005 mg/m$^2$ or even 0.001 mg/m$^2$ or less results in depletion of B cells for at least about 3, 5, 7, 10, 14, 21, 30, 45, 60, 90, 120, 150, or 200 days. According to these embodiments, the dosage can be administered by any suitable route, but is optionally administered by a subcutaneous route.

As another aspect, the invention provides the discovery that B cell depletion and/or treatment of B cell disorders can be achieved at lower dosages of antibody or antibody fragments than employed in currently available methods. Thus, in another embodiment, the invention provides a method of depleting B cells and/or treating a B cell disorder, comprising administering to a human, an effective amount of an antibody that specifically binds to CD22, wherein a dosage of about 500, 475, 450, 425, 400, 375, 350, 325, 300, 275, 250, 225, 200, 175, 150, 125, 100, 75, 60, 50, 37.5, 20, 10, 5, 2.5, 1, 0.5, 0.375, 0.25, 0.1, 0.075, 0.05, 0.001, 0.0005 mg/m$^2$ or less results in a depletion of B cells (circulating and/or tissue B cells) of 25%, 35%, 50%, 60%, 75%, 80%, 85%, 90%, 95%, 98% or more for a period at least about 3, 5, 7, 10, 14, 21, 30, 45, 60, 75, 90, 120, 150, 180, or 200 days or longer. In representative embodiments, a dosage of about 125 mg/m$^2$ or 75 mg/m$^2$ or less results in at least about 50%, 75%, 85% or 90% depletion of B cells for at least about 7, 14, 21, 30, 60, 75, 90, 120, 150 or 180 days. In other embodiments, a dosage of about 50, 37.5 or 10 mg/m$^2$ results in at least about a 50%, 75%, 85% or 90% depletion of B cells for at least about 7, 14, 21, 30, 60, 75, 90, 120 or 180 days. In still other embodiments, a dosage of about 0.375 or 0.1 mg/m$^2$ results in at least about a 50%, 75%, 85% or 90% depletion of B cells for at least about 7, 14, 21, 30, 60, 75 or 90 days. In further embodiments, a dosage of about 0.075, 0.01, 0.001, or 0.0005 mg/m$^2$ results in at least about a 50%, 75%, 85% or 90% depletion of B cells for at least about 7, 14, 21, 30 or 60 days.

In certain embodiments of the invention, the dose can be escalated or reduced to maintain a constant dose in the blood or in a tissue, such as, but not limited to, bone marrow. In related embodiments, the dose is escalated or reduced by about 2%, 5%, 8%, 10%, 15%, 20%, 30%, 40%, 50%, 60%, 70%, 80%, 90%, and 95% in order to maintain a desired level of the antibody of the compositions and methods of the invention.

In certain embodiments, the dosage can be adjusted and/or the infusion rate can be reduced based on patient's immunogenic response to the compositions and methods of the invention.

According to one aspect of the methods of the invention, a loading dose of the anti-CD22 antibody and/or composition of the invention can be administered first followed by a maintenance dose until the B cell malignancy being treated progresses or followed by a defined treatment course (e.g., CAMPATH™, MYLOTARG™, or RITUXAN™, the latter of which allow patients to be treated for a defined number of doses that has increased as additional data have been generated).

According to another aspect of the methods of the invention, a patient may be pretreated with the compositions and methods of the invention to detect, minimize immunogenic response, or minimize adverse effects of the compositions and methods of the invention.

5.20.4. Toxicity Testing

The tolerance, toxicity and/or efficacy of the compositions and/or treatment regimens of the present invention can be determined by standard pharmaceutical procedures in cell cultures or experimental animals, e.g., for determining the LD50 (the dose lethal to 50% of the population), the ED50 (the dose therapeutically effective in 50% of the population), and IC50 (the dose effective to achieve a 50% inhibition). In a preferred embodiment, the dose is a dose effective to achieve at least a 60%, 70%, 80%, 90%, 95%, or 99% depletion of circulating B cells or circulating immunoglobulin, or both. The dose ratio between toxic and therapeutic effects is the therapeutic index and it can be expressed as the ratio LD50/ED50. Therapies that exhibit large therapeutic indices are preferred. While therapies that exhibit toxic side effects may be used, care should be taken to design a delivery system that targets such agents to CD22-expressing cells in order to minimize potential damage to CD22 negative cells and, thereby, reduce side effects.

Data obtained from the cell culture assays and animal studies can be used in formulating a range of dosages of the compositions and/or treatment regimens for use in humans. The dosage of such agents lies preferably within a range of circulating concentrations that include the ED50 with little or no toxicity. The dosage may vary within this range depending upon the dosage form employed and the route of administration utilized. For any therapy used in the methods of the invention, the therapeutically effective dose can be estimated by appropriate animal models. Depending on the species of the animal model, the dose is scaled for human use according to art-accepted formulas, for example, as provided by Freireich et al., Quantitative comparison of toxicity of anticancer agents in mouse, rat, monkey, dog, and human, *Cancer Chemotherapy Reports*, NCI 1966 40:219-244. Data obtained from cell culture assays can be useful for predicting potential toxicity. Animal studies can be used to formulate a specific dose to achieve a circulating plasma concentration range that includes the IC50 (i.e., the concentration of the test compound that achieves a half-maximal inhibition of symptoms) as determined in cell culture. Such information can be used to more accurately determine useful doses in humans. Plasma drug levels may be measured, for example, by high performance liquid chromatography, ELISA, or by cell based assays.

5.21. Patient Diagnosis, Staging and Therapeutic Regimens Oncology

According to certain aspects of the invention, the treatment regimen and dose used with the compositions and methods of the invention is chosen based on a number of factors including, but not limited to, the stage of the B cell disease or disorder being treated. Appropriate treatment regimens can be determined by one of skill in the art for particular stages of a B cell disease or disorder in a patient or patient population. Dose response curves can be generated using standard protocols in the art in order to determine the effective amount of the compositions of the invention for treating patients having different stages of a B cell disease or disorder. In general, patients having more advanced stages of a B cell disease or disorder will require higher doses and/or more frequent doses which may be administered over longer periods of time in comparison to patients having an early stage B cell disease or disorder.

The anti-CD22 antibodies, compositions and methods of the invention can be practiced to treat B cell diseases, including B cell malignancies. The term "B cell malignancy" includes any malignancy that is derived from a cell of the B cell lineage. Exemplary B cell malignancies include, but are not limited to: B cell subtype non-Hodgkin's lymphoma (NHL) including low grade/follicular NHL, small lymphocytic (SL) NHL, intermediate grade/follicular NHL, intermediate grade diffuse NHL, high grade immunoblastic NHL, high grade lymphoblastic NHL, high grade small non-cleaved cell NHL; mantle-cell lymphoma, and bulky disease NHL; Burkitt's lymphoma; multiple myeloma; pre-B acute lymphoblastic leukemia and other malignancies that derive from early B cell precursors; common acute lymphocytic leukemia (ALL); chronic lymphocytic leukemia (CLL) including immunoglobulin-mutated CLL and immunoglobulin-unmutated CLL; hairy cell leukemia; Null-acute lymphoblastic leukemia; Waldenstrom's Macroglobulinemia; diffuse large B cell lymphoma (DLBCL) including germinal center B cell-like (GCB) DLBCL, activated B cell-like (ABC) DLBCL, and type 3 DLBCL; pro-lymphocytic leukemia; light chain disease; plasmacytoma; osteosclerotic myeloma; plasma cell leukemia; monoclonal gammopathy of undetermined significance (MGUS); smoldering multiple myeloma (SMM); indolent multiple myeloma (IMM); Hodgkin's lymphoma including classical and nodular lymphocyte pre-dominant type; lymphoplasmacytic lymphoma (LPL); and marginal-zone lymphoma including gastric mucosal-associated lymphoid tissue (MALT) lymphoma.

In one aspect of the invention, the antibodies and compositions of the invention can deplete mature B cells. Thus, as another aspect, the invention can be employed to treat mature B cell malignancies (i.e., express Ig on the cell surface) including but not limited to follicular lymphoma, mantle-cell lymphoma, Burkitt's lymphoma, multiple myeloma, diffuse large B-cell lymphoma (DLBCL) including germinal center B cell-like (GCB) DLBCL, activated B cell-like (ABC) DLBCL, and type 3 DLBCL, Hodgkin's lymphoma including classical and nodular lymphocyte pre-dominant type, lymphoplasmacytic lymphoma (LPL), marginal-zone lymphoma including gastric mucosal-associated lymphoid tissue (MALT) lymphoma, and chronic lymphocytic leukemia (CLL) including immunoglobulin-mutated CLL and immunoglobulin-unmutated CLL.

Further, CD22 is expressed earlier in B cell development than, for example, CD20, and is therefore particularly suited for treating pre-B cell and immature B cell malignancies (i.e., do not express Ig on the cell surface), for example, in the bone marrow. Illustrative pre-B cell and immature B cell malignancies include, but are not limited to, acute lymphoblastic leukemia.

In other particular embodiments, the invention can be practiced to treat extranodal tumors.

5.21.1. Diagnosis and Staging of B Cell Malignancies

The progression of cancer, such as a B cell disease or disorder capable of tumor formation (e.g., non-Hodgkin lymphoma, diffuse large B cell lymphoma, follicular lymphoma, and Burkitt's lymphoma) is typically characterized by the degree to which the cancer has spread through the body and is often broken into the following four stages which are prognostic of outcome. Stage I: The cancer is localized to a particular tissue and has not spread to the lymph nodes. Stage II: The cancer has spread to the nearby lymph nodes, i.e., metastasis. Stage III: The cancer is found in the lymph nodes in regions of the body away from the tissue of origin and may comprise a mass or multiple tumors as opposed to one. Stage IV: The cancer has spread to a distant part of the body. The stage of a cancer can be determined by clinical observations and testing methods that are well known to those of skill in the art. The stages of cancer described above are traditionally used in conjunction with clinical diagnosis of cancers characterized by tumor formation, and can be used in conjunction with the compositions and methods of the present invention to treat B cell diseases and disorders. Typically early stage disease means that the disease remains localized to a portion of a patient's body or has not metastasized.

With respect to non-tumor forming B cell diseases and disorders such as, but not limited to, multiple myeloma, the criteria for determining the stage of disease differs. The Durie-Salmon Staging System has been widely used. In this staging system, clinical stage of disease (stage I, II, or III) is based on several measurements, including levels of M protein, the number of lytic bone lesions, hemoglobin values, and serum calcium levels. Stages are further divided according to renal (kidney) function (classified as A or B). According to the Durie-Salmon Staging System Stage I (low cell mass) is characterized by all of the following: Hemoglobin value >10 g/dL; Serum calcium value normal or ≤12 mg/dL; Bone x-ray, normal bone structure (scale 0) or solitary bone plasmacytoma only; and Low M-component production rate: IgG value <5 g/dL, IgA value <3 g/d, Bence Jones protein <4 g/24 h. Stage I patients typically have no related organ or tissue impairment or symptoms. Stage II (intermediate cell mass) is characterized by fitting neither stage I nor stage III. Stage III (high cell mass) is characterized by one or more of the following: Hemoglobin value <8.5 g/dL; Serum calcium value >12 mg/dL; Advanced lytic bone lesions (scale 3); High M-component production rate: IgG value >7 g/dL, IgA value >5 g/dL, Bence Jones protein >12 g/24 h Subclassification (either A or B), where A is Relatively normal renal function (serum creatinine value <2.0 mg/dL) and B is Abnormal renal function (serum creatinine value ≥2.0 mg/dL).

Another staging system for myeloma is the International Staging System (ISS) for myeloma. This system can more effectively discriminate between staging groups and is based on easily measured serum levels of beta 2-microglobulin (β2-M) and albumin. According to the ISS for myeloma, Stage I is characterized by β2-M<3.5 and Albumin ≥3.5, Stage II is characterized by β2-M<3.5 and albumin <3.5 or β2-M 3.5-5.5, and Stage III is characterized by β2-M>5.5 (Multiple Myeloma Research Foundation, New Canaan, Conn.).

The stage of a B cell malignancy in a patient is a clinical determination. As indicated above, with respect to solid tumors, the spread, location, and number of tumors are the primary factors in the clinical determination of stage. Determination of stage in patients with non-tumor forming B cell malignancies can be more complex requiring serum level measurements as described above.

The descriptions of stages of B cell diseases and disorders above are not limiting. Other characteristics known in the art for the diagnosis of B cell diseases and disorders can be used as criteria for patients to determine stages of B cell diseases or disorders.

5.21.2. Clinical Criteria for Diagnosing B Cell Malignancies

Diagnostic criteria for different B cell malignancies are known in the art. Historically, diagnosis is typically based on a combination of microscopic appearance and immunophenotype. More recently, molecular techniques such as gene-expression profiling have been applied to develop molecular definitions of B cell malignancies (see, e.g., Shaffer et al., *Nature* 2:920-932 (2002)). Exemplary methods for clinical diagnosis of particular B cell malignancies are provided below. Other suitable methods will be apparent to those skilled in the art.

5.21.2.1. Follicular NHL

In general, most NHL (with the exception of mantle-cell lymphoma) have highly mutated immunoglobulin genes that appear to be the result of somatic hypermutation (SHM). The most common genetic abnormalities in NHL are translocations and mutations of the BCL6 gene.

Follicular NHL is often an indolent B cell lymphoma with a follicular growth pattern. It is the second most common lymphoma in the United States and Western Europe. The median age at which this disease presents is 60 years and there is a slight female predominance. Painless lymphadenopathy is the most common symptom. Tests often indicate involvement of the blood marrow and sometimes the peripheral blood. Follicular NHL is divided into cytologic grades based on the proportion of large cells in the follicle with the grades forming a continuum from follicular small cleaved-cell to large-cell predominance. (See, S. Freedman, et al., *Follicular Lymphoma*, pp. 367-388, *In Non-Hodgkin's Lymphomas*, P. Mauch et al., eds., Lippincott Williams & Wilkins, Philadelphia, Pa. (2004); T. Lister et al., *Follicular Lymphoma*, pp. 309-324, *In Malignant Lymphoma*, B. Hancock et al., eds., Oxford University Press, New York, N.Y. (2000)).

Most follicular NHL is characterized by a translocation between chromosomes 14 and 18 resulting in overexpression of BCL2. Follicular NHL is also characterized by both SHM and ongoing SHM and a gene expression profile similar to germinal center (GC) B cells (see, e.g., Shaffer et al., *Nature* 2:920-932 (2002)), which are the putative cells of origin for this malignancy. Heavy- and light chain rearrangements are typical. The tumor cells of this disease express monoclonal surface immunoglobulin with most expressing IgM. Nearly all follicular NHL tumor cells express the antigens CD22, CD20, CD79a, CD21, CD35 and CD10 but lack expression of CD5 and CD43. Paratrabecular infiltration with small cleaved cells is observed in the bone marrow. (See, S. Freedman et al., *Follicular Lymphoma*, pp. 367-388, In *Non-Hodgkin's Lymphomas*, P. Mauch et al., eds., Lippincott Williams & Wilkins, Philadelphia, Pa. (2004); T. Lister et al., *Follicular Lymphoma*, pp. 309-324, *In Malignant Lymphoma*, B. Hancock et al., eds., Oxford University Press, New York, N.Y. (2000)).

Diagnosis of follicular NHL generally relies on biopsy of an excised node in order to evaluate tissue architecture and cytological features. Fine-needle aspirations are usually not adequate since this procedure is less likely to provide tissue that can be evaluated and it fails to provide enough tissue for additional tests. Bilateral bone marrow biopsies are also indicated since involvement can be patchy. Additional diagnostic procedures include chest x-rays, chest, abdomen, neck and pelvis computed tomography (CT) scans, complete blood count, and chemistry profile. Flow cytometry and immunohistochemistry can be used to distinguish between follicular NHL and other mature B cell lymphomas. (See, S. Freedman et al., *Follicular Lymphoma*, pp. 367-388, *In Non-Hodgkin's Lymphomas*, P. Mauch et al., eds., Lippincott Williams & Wilkins, Philadelphia, Pa. (2004); T. Lister et al., *Follicular Lymphoma*, pp. 309-324, *In Malignant Lymphoma*, B. Hancock et al., eds., Oxford University Press, New York, N.Y. (2000)).

5.21.2.2. Mantle-Cell Lymphoma

Mantle-cell lymphoma localizes to the mantle region of secondary follicles and is characterized by a nodular and/or diffuse growth pattern. Mantle-cell lymphoma patients have median age of 60-65 years with the disease affecting predominantly males. For diagnostic purposes, the usual presenting feature is a generalized lymphadenopathy. Additionally, the spleen is often enlarged. This B cell lymphoma is associated with a t(11;14) between the IgH locus and cyclin D1 gene, which results in overexpression of cyclin D1. More than 50% of cases show additional chromosomal abnormalities. Mantle-cell lymphoma is typically not characterized by SHM. (See, W. Hiddemann et al., *Mantle Cell Lymphoma*, pp. 461-476, *In Non-Hodgkin's Lymphomas*, P. Mauch et al., eds., Lippincott Williams & Wilkins, Philadelphia, Pa. (2004); D. Weisenburger et al., *Mantle Cell Lymphoma*, pp. 28-41, *In Malignant Lymphoma*, B. Hancock et al., eds., Oxford University Press, New York, N.Y. (2000)).

Immunophenotyping (flow cytometry or frozen section) immunohistochemistry of mantle cell lymphoma cells shows them to nearly always be monoclonal, bearing surface IgM. Mantle cell lymphoma cells have also been noted to bear surface IgD. The cells express the antigens CD22, CD20, CD22 and CD24, but not CD23. They also express surface antigens CD5 but not for CD10, distinguishing them from true follicle center-cell lymphomas which are almost always CD5 negative. Frequently, extranodal involvement is found including bone marrow infiltration and tumors of the liver and gastrointestinal tract. Mild anemia and leukemic expression is not uncommon with mantle-cell lymphoma. (See, A. Lal et al., *Role of Fine Needle Aspiration in Lymphoma*, pp. 181-220, In W. Finn et al., eds., *Hematopathology in Oncology*, Kluwer Academic Publishers, Norwell, Mass. (2004); W. Hiddemann et al., *Mantle Cell Lymphoma*, pp. 461-476, *In Non-Hodgkin's Lymphomas*, P. Mauch et al., eds., Lippincott Williams & Wilkins, Philadelphia, Pa. (2004)).

Diagnosis of mantle-cell lymphoma involves examination of the peripheral blood as well as bone marrow and lymph node biopsies. In addition, cytogenetic studies and immunophenotyping are useful in differential diagnosis. (See, W. Hiddemann, et al., *Mantle Cell Lymphoma* pp. 461-476, In Non-Hodgkin's Lymphomas, P. Mauch, et al., eds., Lippincott Williams & Wilkins, Philadelphia, Pa. (2004); D. Weisenburger, et al., *Mantle Cell Lymphoma*, pp. 28-41, *In Malignant Lymphoma*, B. Hancock, et al., eds., Oxford University Press, New York, N.Y. (2000)).

5.21.2.3. Burkitt's Lymphoma

Burkitt's lymphoma is an aggressive B cell lymphoma typically observed in children and young adults and is usually associated with bulky disease of the jaw and/or abdomen. Approximately 20% of patients have bone marrow involvement. An endemic form of Burkitt's lymphoma involves Epstein-Barr virus (EBV) infection of malignant cells; the sporadic form is independent of EBV infection. A translocation of c-myc to immunoglobulin loci, which results in deregulation of the c-myc gene, is characteristic of this disease (t(8;14)(q24;q32)). Interestingly, deletions of the c-myc sequences appear to be involved in the sporadic form of the disease, while the endemic form usually involves point mutations or insertions. (See, V. Pappa, et al., *Molecular Biology*, pp. 133-157, *In Malignant Lymphoma*, B. Hancock, et al., eds., Oxford University Press, New York, N.Y. (2000)). Burkitt's lymphoma is also characterized by SHM, and the malignant cells have a gene expression profile similar to GC B cells, suggesting that this malignancy is derived from GC B cells.

Immunophenotype of Burkett's lymphoma shows the cells of this disease express CD22, CD20, CD22, and CD79a, but not CD5, CD23, cyclin D or terminal deoxynucleotidyl transferase. Frequently, these cells are positive for CD10 and BCL6 and usually negative for BCL2. (See, I. Magrath, et al., *Burkitt's Lymphoma*, pp. 477-501, *In Non-Hodgkin's Lymphomas*, P. Mauch, et al., eds., Lippincott Williams & Wilkins, Philadelphia, Pa. (2004)).

High grade B cell Burkitt's-like lymphoma is a lymphoma borderline between Burkitt's lymphoma and large B cell lymphoma. The cells of this lymphoma express CD22 and CD20 but expression of CD10, which is nearly always present in true Burkitt's lymphoma, is frequently absent. Because of this and other characteristics, some believe this lymphoma should be classified as a diffuse large B cell lymphoma. (See, K. Maclennan, *Diffuse Aggressive B cell Lymphoma*, pp. 49-54, *In Malignant Lymphoma*, B. Hancock, et al., eds., Oxford University Press, New York, N.Y. (2000)).

Diagnosis of Burkitt's lymphoma generally relies on detection of the translocation associated with this lymphoma; thus, conventional cytogenetic analysis is usually performed. Long distance polymerase chain reaction techniques and fluorescent in situ hybridization (FISH) have been used to detect Ig-myc junctions in the translocations and other genetic alterations associated with this disease. (See, R. Siebert, et al., *Blood* 91:984-990 (1998); T. Denyssevych, et al., *Leukemia*, 16:276-283 (2002)).

5.21.2.4. Diffuse Large B-Cell Lymphoma (DLBCL)

DLBCL is the most common non-Hodgkin's lymphoma and can arise from small B cell lymphoma, follicular lymphoma or marginal zone lymphoma. Typically, patients present with lymphadenopathy; however, a large percent of patients present in extranodal sites as well, with gastrointestinal involvement being the most common. Bone marrow involvement is observed in about 15% of patients. (See, Armitage, et al., *Diffuse Large B cell Lymphoma*, pp. 427-453, *In Non-Hodgkin's Lymphomas*, P. Mauch, et al., eds., Lippincott Williams & Wilkins, Philadelphia, Pa. (2004)). Heterogeneity in clinical, biological and morphological characteristics makes this group of lymphomas difficult to subclassify. However, two distinct subgroups have been identified with one expressing genes characteristic of germinal center B cells (GC-DLBCL) and the other overexpressing genes in peripheral blood B cells. Survival rates are significantly better for patients with GC-DLBCL than those with activated B cell type (ABC)-DLBCL. (See, W. Chan, *Archives of Pathology and Laboratory Medicine* 128(12): 1379-1384 (2004)).

DLBCLs express the cell surface antigens CD22, CD20, CD22, and CD79a. CD10 is expressed in the large majority of cases and CD5 expression is observed in about 10% of cases. (See, K. Maclennan, *Diffuse Aggressive B cell Lymphoma*, pp. 49-54, *In Malignant Lymphoma*, B. Hancock, et al., eds., Oxford University Press, New York, N.Y. (2000)). DLBCL is often marked by abnormalities of BCL6 and/or translocations of BCL2 to the IgH locus. GC B cell like (GC) DLBCL is characterized by SHM with highly mutated immunoglobulin genes and ongoing SHM in malignant clones with a GC B cell-like gene expression profile. Most GC DLBCL have undergone immunoglobulin class switching. ABC-DLBCL is characterized by high level expression of NF-κB target genes including BCL2, interferon regulatory factor 4, CD44, FLIP and cyclin D. SHM, but not ongoing SHM, is present, and ABC-DLBCL does not have a GC B cell gene expression profile. Almost all ABC-DLBCL express a high level of IgM.

5.21.2.5. Extranodal Marginal-Zone Lymphoma

Extranodal marginal-zone lymphoma is an extranodal lymphoma that occurs in organs normally lacking organized lymphoid tissue (e.g., stomach, salivary glands, lungs and thyroid glands). It is largely a disease that affects older adults with a median age of over 60 years. Often, chronic inflammation or autoimmune processes precede development of the lymphoma. Gastric mucosal-associated lymphoid tissue (MALT) lymphoma, the most common type of marginal-zone lymphoma, is associated with *Helicobacter pylori* infection. Studies have shown a resolution of symptoms with eradication of the *H. pylori* infection following an antibiotic regimen. The presenting symptoms for gastric MALT lymphoma include nonspecific dyspepsia, epigastric pain, nausea, gastrointestinal bleeding and anemia. Systemic symptoms are uncommon, as are elevated levels of lactate acid dehydrogenase. (See, J. Yahalom, et al., *Extranodal Marginal Zone B cell Lymphoma of Mucosa-Associated Lymphoid Tissue*, pp. 345-360, *In Non-Hodgkin's Lymphomas*, P. Mauch, et al., eds., Lippincott Williams & Wilkins, Philadelphia, Pa. (2004); J. Radford, *Other Low-Grade Non-Hodgkin's Lymphomas*, pp. 325-330, *In Malignant Lymphoma*, B. Hancock, et al., eds., Oxford University Press, New York, N.Y. (2000). Systemic B symptoms include fevers greater than 38° C. for longer than 2 weeks without sign of infection, night sweats, extreme fatigue or unintentional weight loss of greater than or equal to 10% of body weight over the previous 6 months).

The immunophenotye of MALT lymphoma is characterized by expression of CD20, CD79a, CD21 and CD35 and lack of expression of CD5, CD23, and CD10. About half of MALT lymphomas express CD43. The immunoglobulin typically expressed in the tumor cells of this disease is IgM while IgD is not expressed. These features are critical in distinguishing this lymphoma from other small B cell lymphomas such as mantle cell lymphoma, lymphocytic lymphoma and follicular lymphoma. Trisomy 3 has been reported in 60% of MALT lymphoma cases. In 25-40% of gastric and pulmonary MALT lymphomas a t(11;18) is observed. This translocation is observed much less frequently in other MALT lymphomas. T(11;18) is associated with nuclear expression of BCL10. (See, J. Yahalom, et al., *Extranodal Marginal Zone B cell Lymphoma of Mucosa-Associated Lymphoid Tissue*, pp. 345-360, *In Non-Hodgkin's Lymphomas*, P. Mauch, et al., eds., Lippincott Williams & Wilkins, Philadelphia, Pa. (2004)). Marginal-zone lymphomas are generally characterized by SHM and ongoing SHM.

Diagnostic procedures include immunophenotyping or flow cytometry to determine the identity of the cell surface markers. In addition, molecular genetic analysis should be done to determine the presence of t(11;18) as this is an indicator that the disease will not respond to antibiotics. Histology can be used to determine the presence of *H. pylori*. Additional tests should include a complete blood count, basic biochemical tests including that for lactate acid dehydrogenase; CT scans of the abdomen, chest and pelvis and a bone marrow biopsy. (See, J. Yahalom, et al., *Extranodal Marginal Zone B cell Lymphoma of Mucosa-Associated Lymphoid Tissue*, pp. 345-360, *In Non-Hodgkin's Lymphomas*, P. Mauch, et al., eds., Lippincott Williams & Wilkins, Philadelphia, Pa. (2004)).

5.21.2.6. Nodal Marginal Zone B Cell Lymphoma

Nodal Marginal Zone B cell Lymphoma is a relatively newly classified lymphoma thus little has been published on it. It is a primary nodal B cell lymphoma sharing genetic and morphological characteristics with extranodal and splenic marginal zone lymphomas, but does not localize to the spleen or extranodally. Hepatitis C virus has been reported to be associated with this lymphoma as has Sjögren's syndrome. (See, F. Berger, et al., *Nodal Marginal Zone B cell Lymphoma*, pp. 361-365, *In Non-Hodgkin's Lymphomas*, P. Mauch, et al., eds., Lippincott Williams & Wilkins, Philadelphia, Pa. (2004)).

Nodal marginal zone lymphoma has a heterogeneous cytology and morphology. Due to its relatively high proportion of large cells this lymphoma, unlike the other marginal lymphomas (splenic and extranodal), cannot be classified as true low grade B cell lymphoma. The genetic and immunological phenotype of nodal marginal zone lymphoma includes expression of CD22, CD20, BCL2, sIgM and cytoplasmic IgG (cIg). These cells do not express CD5, CD10, CD23, CD43 or cyclin D1. The translocation characteristic of MALT lymphoma, t(11;18), is not observed for nodal marginal zone lymphoma. These characteristics aid in the differential diagnosis of this lymphoma from other small B cell lymphomas. (See, F. Berger, et al., *Nodal Marginal Zone B cell Lymphoma*, pp. 361-365, *In Non-Hodgkin's Lymphomas*, P. Mauch, et al., eds., Lippincott Williams & Wilkins, Philadelphia, Pa. (2004)).

5.21.2.7. Splenic Marginal Zone Lymphoma

Splenic Marginal Zone Lymphoma is an indolent micronodular B cell lymphoma with a characteristic clinical presentation of prominent splenomegaly and infiltration of the peripheral blood and the bone marrow. In addition, a relatively high level of liver involvement has been reported. A role for hepatitis C virus has been postulated for this lymphoma. The immunophenotype of splenic marginal zone lymphoma is typically $CD20^+$, $IgD^+$, $BCL2^+$, $p27^+$, $CD3^-$, $CD5^-$, $CD10^-$, $CD23^-$, $CD38^-$, $CD43^-$, $BCL-6^-$, and cyclin $D1^-$. Genetic characteristics include a 7q deletion, p53 alterations and SHM. (See, M. Piris, et al., *Splenic Marginal Zone Lymphoma*, pp. 275-282, *In Non-Hodgkin's Lymphomas*, P. Mauch, et al., eds., Lippincott Williams & Wilkins, Philadelphia, Pa. (2004)).

Diagnosis generally relies on immunophenotyping to determine the identity of the cell surface markers. Genetic and biochemical analysis, in combination with data on cell surface markers, help to differentiate this lymphoma from other small B cell lymphomas. (See, M. Piris, et al., *Splenic Marginal Zone Lymphoma*, pp. 275-282, *In Non-Hodgkin's Lymphomas*, P. Mauch, et al., eds., Lippincott Williams & Wilkins, Philadelphia, Pa. (2004)).

5.21.2.8. Acute (B Cell) Lymphocytic Leukemia (ALL)

ALL is a marrow-based neoplasm largely affecting children with the highest incidence between 1-5 years. Most common symptoms at presentation include fatigue, lethargy, fever and bone and joint pain. Fatigue and lethargy correlates with the degree of anemia present. An elevated white blood cell count is common at presentment. Radiographs of the chest often show skeletal lesions. Extramedullary spread is common and involves the central nervous system, testes, lymph nodes, liver, spleen and kidney. Anterior mediastinal masses are observed in only about 5-10% of newly diagnosed cases. (See, J. Whitlock, et al., *Acute Lymphocytic Leukemia*, pp. 2241-2271, *In Wintrobe's Clinical Hematology*, Tenth Edition, G. Lee, et al., eds. Williams & Wilkins, Baltimore, Md. (1999)).

The immunophenotype of ALL is $CD10^+$, $CD22^+$, $CD20^+$, and $CD24^+$. Pre-B cell ALL cells express cytoplasmic but not surface immunoglobulin, while mature B cell ALL (which accounts for only 1-2% of ALL cases) is distinguished from other leukemias of B cell lineage by the expression of surface immunoglobulin. Cytogenetic characteristics of ALL includes t(8;14), t(2;8) and t(8;22). Although rarely detected at the cytogenetic level t(12;21) may be the most common cytogenetic abnormality associated with childhood ALL (observed in about 25% of cases). (See, M. Kinney, et al., *Classification and Differentiation of the Acute Leukemias*, pp. 2209-2240, *In Wintrobe's Clinical Hematology*, Tenth Edition, G. Lee, et al., eds. Williams & Wilkins, Baltimore, Md. (1999); J Whitlock, et al., *Acute Lymphocytic Leukemia*, pp. 2241-2271; *In Wintrobe's Clinical Hematology*, Tenth Edition, G. Lee, et al., eds. Williams & Wilkins, Baltimore, Md., (1999)).

Precise diagnosis of acute leukemia usually relies on a bone aspirate and biopsy. Aspirate smears are used for morphological, immunological and cytological assessments. The demonstration of lymphoblasts in the bone marrow is diagnostic of ALL. The presence of greater than 5% leukemic lymphoblast cells in the bone marrow confirms ALL diagnosis but most require greater than 25% for a definitive diagnosis. Lumbar punctures are used to diagnose central nervous system involvement. Serum uric acids levels and serum lactate dehydrogenase levels have been found to be elevated in ALL. (See, M. Kinney, et al., *Classification and Differentiation of the Acute Leukemias*, pp. 2209-2240, *In Wintrobe's Clinical Hematology*, Tenth Edition, G. Lee, et al., eds. Williams & Wilkins, Baltimore, Md. (1999); J. Whitlock, et al., *Acute Lymphocytic Leukemia*, pp. 2241-2271; *In Wintrobe's Clinical Hematology*, Tenth Edition, G. Lee, et al., eds. Williams & Wilkins, Baltimore, Md., (1999)).

5.21.2.9. Chronic Lymphocytic Leukemia (CLL)/Small B Cell Lymphocytic Lymphoma (SLL)

CLL/SLL is the most common type of leukemia. When the disease involves the peripheral blood and bone marrow it is referred to as CLL. However, when the lymph nodes and other tissues are infiltrated by cells that are immunologically and morphologically identical to those in CLL, but where leukemic characteristics of the disease are absent, then the disease is referred to as SLL. This disease largely afflicts the elderly with a greater incidence of the disease occurring in men than women. Painless lymphadenopathy is the most common finding at presentation. Hypogammaglobulinemia is common with most cases of CLL/SLL exhibiting reduced levels of all immunoglobulins rather than any particular subclass of immunoglobulins. Asymptomatic patients are frequently diagnosed during routine blood counts (lymphocyte count of over $5000 \times 10^9/L$). As many as 20% of CLL/SLL cases report B symptoms. An additional diagnostic feature is infiltration of the bone marrow by more than 30% by immature lymphocytes. Lymph node biopsies generally show infiltration of involved nodes with well-differentiated lymphocytes. Autoimmune phenomena are often associated with CLL/SLL including autoimmune hemolytic anemia and immune thrombocytopenia. (See, J. Gribben, et al., *Small B cell Lym-* phocytic Lymphoma/Chronic Lymphocytic Leukemia and Prolymphocytic Leukemia, pp. 243-261, In Non-Hodgkin's Lymphomas, P. Mauch, et al., eds., Lippincott Williams & Wilkins, Philadelphia, Pa. (2004); K. Maclennan, *Diffuse Indolent B cell Neoplasms*, pp. 43-47, *In Malignant Lymphoma*, B. Hancock, et al., eds., Oxford University Press, New York, N.Y. (2000); *Clinical Oncology*, A. Neal, et al., Neal, Hoskin and Oxford University Press, co-publ., New York, N.Y. (2003)).

In contrast with many of the low-grade B cell malignancies, nonrandom reciprocal translocations are rarely found in CLL/SLL. However, other cytogenetic abnormalities have been reported including deletions at 13q14, 11q22-23 and 17q13, with the latter two involving the p53 locus. Approximately 20% of cases exhibit trisomy 12. An elevated level of β-2 microglobulin, higher levels of CD38 expression and the production of tumor necrosis factor-alpha are all characteristic of CLL/SLL. The immunophenotype of CLL/SLL is very diagnostic and includes weak expression of surface immunoglobulin usually IgM, or IgM and IgG, as well as expression of the cell antigens CD22, CD20 and usually CD5 and CD23. (See, J. Gribben, et al., *Small B cell Lymphocytic Lymphoma/Chronic Lymphocytic Leukemia and Prolymphocytic Leukemia*, pp. 243-261, *In Non-Hodgkin's Lymphomas*, P. Mauch, et al., eds., Lippincott Williams & Wilkins, Philadelphia, Pa. (2004); K. Maclennan, *Diffuse Indolent B cell Neoplasms*, pp. 43-47, *In Malignant Lymphoma*, B. Hancock, et al., eds., Oxford University Press, New York, N.Y. (2000)).

5.21.2.10. B Cell Prolymphocytic Leukemia (PLL)

PLL, once considered a variant of CLL, is now understood to be a distinct disease. PLL is generally a disease of elderly men and is characterized by a very high white blood cell count (greater than $200 \times 10^9$/L) and splenomegaly. Additional symptoms include anemia and thrombocytopenia. Prolymphocytes in PLL comprise more than 55% of the cells in the blood and bone marrow. In contrast with CLL, autoimmune phenomena are rarely observed in PLL. (See, J. Gribben, et al., *Small B cell Lymphocytic Lymphoma/Chronic Lymphocytic Leukemia and Prolymphocytic Leukemia*, pp. 243-261, *In Non-Hodgkin's Lymphomas*, P. Mauch, et al., eds., Lippincott Williams & Wilkins, Philadelphia, Pa. (2004)).

The immunophenotype of PLL is characterized by expression of CD22, CD21, CD22, CD24 and FMC7. The cells of PLL do not express CD23 and most do not express CD5. PLL cells exhibit complex chromosomal abnormalities, with deletions at 13q14 and 11q23 being some of the most frequent. The pattern of p53 mutation in PLL cells is different from that observed for CLL. Differential diagnosis usually relies on complete blood count, histological, immunophenotypic, and genetic analyses. (See, J. Gribben, et al., *Small B cell Lymphocytic Lymphoma/Chronic Lymphocytic Leukemia and Prolymphocytic Leukemia*, pp. 243-261, *In Non-Hodgkin's Lymphomas*, P. Mauch, et al., eds., Lippincott Williams & Wilkins, Philadelphia, Pa. (2004)).

5.21.2.11. Hairy Cell Leukemia (HCL)

HCL is a rare, indolent chronic leukemia affecting more men than women and largely those of middle age. The typical symptoms include massive splenomegaly and pancytopenia. The peripheral blood and bone marrow contain the typical "hairy cells," which are B lymphocytes with cytoplasmic projections. Over 90% of HCL patients have bone marrow infiltration. (See, *Clinical Oncology*, A. Neal, et al., Neal, Hoskin and Oxford University Press, co-publ., New York, N.Y. (2003); J. Johnston, *Hairy Cell Leukemia*, pp. 2428-2446, *In Wintrobe's Clinical Hematology*, Tenth Edition, G. Lee et al., eds. Williams & Wilkins, Baltimore, Md. (1999)).

Cytogenetic analysis has shown that clonal abnormalities are present in 19% of cases and involve numerical and structural abnormalities of chromosomes 5, 7 and 14. The serum level of TNF-α is elevated in hairy cell leukemia and correlates with tumor burden. Hairy cell leukemia cells express surface immunoglobulins (IgG and IgM) and CD11c, CD22, CD20, CD22 and typically CD25. In addition, FMC7, HC-2 and CD103 are expressed. HCL cells do not express CD5 or CD10. Diagnosis generally involves the use of bone marrow aspirates, cytogenetics, blood smears and immunophenotyping. (See, *Clinical Oncology*, A. Neal, et al., Neal, Hoskin and Oxford University Press, co-publ., New York, N.Y. (2003); J. Johnston, *Hairy Cell Leukemia*, pp. 2428-2446, *In Wintrobe's Clinical Hematology*, Tenth Edition, G. Lee et al., eds. Williams & Wilkins, Baltimore, Md. (1999)).

5.21.2.12. Precursor B Cell Lymphoblastic Lymphoma/Pre-B Cell Acute Lymphoblastic Leukemia/Lymphoblastic Lymphoma Precursor B cell lymphoblastic lymphoma/pre-B cell acute lymphoblastic leukemia/Lymphoblastic lymphoma is a disease of precursor T or B cells. The T and B cell lymphoblastic lymphomas are morphologically identical, but clinical distinctions may be made based on degree of bone marrow infiltration or bone marrow involvement. 85-90% of lymphoblastic lymphomas are T-cell derived with the remainder being B cell derived. Lymphoblastic lymphoma has a median age of 20 years with a male predominance. Peripheral lymph node involvement is a common feature at presentation, occurring especially in the cervical, supraclavicular and axillary regions. This disease frequently presents with bone marrow involvement. Central nervous system is less common at presentment but often appears in cases of relapse. Other sites of involvement can include liver, spleen, bone, skin, pharynx and testes (See, J. Sweetenham, et al., *Precursor B-and T-Cell Lymphoblastic Lymphoma*, pp. 503-513, *In Non-Hodgkin's Lymphomas*, P. Mauch, et al., eds., Lippincott Williams & Wilkins, Philadelphia, Pa. (2004)).

Precursor B cell lymphoblastic lymphomas express immature markers B cell markers such as CD99, CD34 and terminal deoxynucleotidyl transferase. These cells also express CD79a, CD22, and sometimes CD20 and typically lack expression of CD45 and surface immunoglobulin. Translocations at 11q23, as well as t(9;22)(q34;q11.2) and t(12;21)(p13;q22), have been associated with poor prognosis. Good prognosis is associated with hyperdiploid karyotype, especially that associated with trisomy 4, 10, and 17 and t(12;21)(p13;q22). (See, J. Sweetenham, et al., *Precursor B-and T-Cell Lymphoblastic Lymphoma*, pp. 503-513, *In Non-Hodgkin's Lymphomas*, P. Mauch, et al., eds., Lippincott Williams & Wilkins, Philadelphia, Pa. (2004)).

Diagnostic tests include lymph node biopsies, blood tests, x-rays, CT scans, and lumbar punctures to examine the cerebralspinal fluid for malignant cells.

5.21.2.13. Primary Mediastinal Large B Cell Lymphoma

Primary mediastinal large B cell lymphoma is a diffuse large B cell lymphoma occurring predominantly in young women and characterized by a locally invasive anterior mediastinal mass originating in the thymus. Distant spread to peripheral nodes and bone marrow involvement is unusual. Systemic symptoms are common. While this disease resembles nodal large cell lymphomas, it has distinct genetic, immunological, and morphological characteristics.

The immunophenotype of tumor cells of primary mediastinal large B cell lymphoma are often surface immunoglobulin negative but do express such B cell associated antigens as CD22, CD20, CD19, and CD79a. CD10 and BCL6 are also commonly expressed. Expression of plasma cell associated markers CD15, CD30, epithelial membrane antigen (EMA) is rare. BCL6 and c-myc gene arrangements are also uncommon. The presence of clonal immunoglobulin rearrangements, immunoglobulin variable region and gene hypermutation along with BCL6 hypermutation suggest that this lymphoma derives from a mature germinal center or post-germinal center B cell. The chromosomal translocations that seem to be associated with tumors of this disease are similar to those observed in other forms of diffuse large cell lymphoma. (See, P. Zinzani, et al., *Primary Mediastinal Large B cell Lymphoma*, pp. 455-460, In *Non-Hodgkin's Lymphomas*, P. Mauch, et al., eds., Lippincott Williams & Wilkins, Philadelphia, Pa. (2004)).

The diagnostic evaluation for primary mediastinal large B cell lymphoma generally includes a complete physical examination, complete hematological and biochemical analysis, total-body computerized tomography and bone marrow biopsy. Gallium-67 scanning is a useful test for staging, response to treatment and for assessment of relapse. (See, P. Zinzani et al., *Primary Mediastinal Large B cell Lymphoma*, pp. 455-460, In *Non-Hodgkin's Lymphomas*, P. Mauch, et al., eds., Lippincott Williams & Wilkins, Philadelphia, Pa. (2004)).

5.21.2.14. Lymphoplasmacytic Lymphoma (LPL)/Lymphoplasmacytic Immunocytoma/Waldströms Macroglobulinemia LPL/Lymphoplasmacytic immunocytoma/Waldström's Macroglobulinemia is a nodal lymphoma that is usually indolent, and often involves bone marrow, lymph nodes and spleen. This is generally a disease of older adults with males slightly predominating. Most patients have monoclonal IgM paraprotein in their serum (>3 g/dL) resulting in hyperviscosity of the serum. Tumor cells have a plasmacytic morphology. A subset of LPL is characterized by recurrent translocations between chromosomes 9 and 14, which involves the PAX5 and immunoglobulin heavy-chain loci. LPL is characterized by SHM as well as ongoing SHM, and is believed to be derived from post-GC B cells. (See, A. Rohatiner, et al., *Lymphoplasmacytic Lymphoma and Waldström's Macroglobulinemia*, pp. 263-273, In *Non-Hodgkin's Lymphomas*, P. Mauch, et al., eds., Lippincott Williams & Wilkins, Philadelphia, Pa. (2004); K. Maclennan, *Diffuse Indolent B cell Neoplasms*, pp. 43-47, In *Malignant Lymphoma*, B. Hancock, et al., eds., Oxford University Press, New York, N.Y. (2000); A. Lal, et al., *Role of Fine Needle Aspiration in Lymphoma*, pp. 181-220, In W. Finn, et al., eds., *Hematopathology in Oncology*, Kluwer Academic Publishers, Norwell, Mass. (2004)).

The immunophenotype of this disease shows expression of the B cell associated antigens CD22, CD20, CD19, and CD79a and a lack of expression of CD5, CD10, and CD23. Presence of strong surface immunoglobulin and CD20, the lack of expression of CD5, and CD23 and the presence of cytoplasmic immunoglobulin are characteristics that aid in distinguishing this disease from chronic lymphocytic leukemia. Also diagnostic of this disease is t(9;14)(p13;q32). (See, A. Rohatiner, et al., *Lymphoplasmacytic Lymphoma and Waldström's Macroglobulinemia*, pp. 263-273, In *Non-Hodgkin's Lymphomas*, P. Mauch, et al., eds., Lippincott Williams & Wilkins, Philadelphia, Pa. (2004); K. Maclennan, *Diffuse Indolent B cell Neoplasms*, pp. 43-47, In *Malignant Lymphoma*, B. Hancock, et al., eds., Oxford University Press, New York, N.Y. (2000); R. Chaganti, et al., *Cytogenetics of Lymphoma*, pp. 809-824, In *Non-Hodgkin's Lymphomas*, P. Mauch, et al., eds., Lippincott Williams & Wilkins, Philadelphia, Pa. (2004)).

Diagnostic tests typically include a complete blood count, renal and liver function tests, CT scans, biopsy and aspiration of the bone marrow, protein electrophoresis to quantify and characterize the paraprotein and serum viscosity. Measurement of $\beta_2$-microglobulin is used as a prognostic test. (See, A. Rohatiner, et al., *Lymphoplasmacytic Lymphoma and Waldström's Macroglobulinemia*, pp. 263-273, In *Non-Hodgkin's Lymphomas*, P. Mauch, et al., eds., Lippincott Williams & Wilkins, Philadelphia, Pa. (2004)).

5.21.2.15. Null-Acute Lymphoblastic Leukemia

Null-acute lymphoblastic leukemia is a subset of ALL which lacks B- or T-cell characteristics. Phenotypic analysis of leukemic blasts shows a typical null ALL pattern, i.e., CD10 (common ALL antigen)-negative, strongly HLA-DR-positive, and CD22 (B4)-positive (see Katz et al. (1988) Blood 71(5):1438-47).

5.21.2.16. Hodgkin's Lymphoma

Hodgkin's lymphoma usually arises in the lymph nodes of young adults. It can be divided into classical subtype and a less common nodular lymphocytic predominant subtype. The classical type exhibits SHM, but not ongoing SHM, and does not have a GC B cell gene expression profile. The nodular lymphocyte predominant type, in contrast, is characterized by SHM and ongoing SHM and a GC B cell gene expression profile. While the two types differ clinically and biologically, they do share certain features such as a lack of neoplastic cells within a background of benign inflammatory cells. B. Schnitzer et al., *Hodgkin Lymphoma*, pp. 259-290, In W. Finn and L. Peterson, eds., *Hematopathology in Oncology*, Kluwer Academic Publishers, Norwell, Mass. (2004)).

The most common features at presentation are painless enlargement of lymph nodes, usually in the neck, but occasionally in the inguinal region. Waxing and waning of nodes is also characteristic of this disease. B symptoms are observed in about one-third of patients. Isolated extranodal involvement is rare and in cases where dissemination has occurred extranodal involvement is observed about 10-20% of the time. (See, P. Johnson et al., *Hodgkin's Disease: Clinical Features*, pp. 181-204, In *Malignant Lymphoma*, B. Hancock, et at, eds., Oxford University Press, New York, N.Y. (2000)).

Reed-Sternberg (RS) cells are the malignant cells of Hodgkin's lymphoma. RS cells and their variants express CD15, CD25, CD30 and transferrin receptor. In addition these cells express polyclonal cytoplasmic immunoglobulin. In most cases of Hodgkin's lymphoma the RS cells do not express CD45, a feature that aids in distinguishing this disease from non-Hodgkin's Lymphomas. Epstein Barr virus has been demonstrated to be present in Reed-Sternberg cells in about one-half of Hodgkin's lymphoma cases but its role is unclear.

Diagnosis is most frequently made by lymph node biopsy. Additional diagnostic tests include a full blood count (often hematological tests are normal; white blood cell counts of less than $1.0 \times 10^9$/L are seen in about 20% of cases), erythrocyte sedimentation rate (often elevated in advanced stages of the disease), biochemical tests including electrolytes, urea, creatinine, urate, calcium (hypercalcemia is rare but when present is associated with extensive bone involvement), liver blood tests, lactate dehydrogenase (elevated levels often associated with advanced disease), albumin and beta$_2$-microglobulin ($\beta$2-M). Lymphanigiograms and chest x-rays and CT scans of the chest, abdomen and pelvis are important in identifying abnormal lymph nodes and the extent of extranodal involvement. Bone marrow biopsies are typically considered optional as bone marrow involvement is unusual and the results of such biopsies appear not to affect clinical management or prognosis. Splenechtomies are not usually performed today as it rarely influences management and CT or MRI imaging provides information on splenic status. Significantly elevated levels of p55, TNF and sICAM-1 are correlated to the stage of the disease, presence of symptoms and complete response rate. (See, P. Johnson, et al., *Hodgkin's Disease: Clinical Features*, pp. 181-204, In *Malignant Lymphoma*, B. Hancock, et al., eds., Oxford University Press, New York, N.Y. (2000); *Clinical Oncology*, A. Neal, et al., Neal, Hoskin and Oxford University Press, co-publ., New York, N.Y. (2003); R. Stein, *Hodgkin's Disease*, pp. 2538-2571, In *Wintrobe's Clinical Hematology*, Tenth Edition, G. Lee et al., eds. Williams & Wilkins, Baltimore, Md. (1999)).

5.21.2.17. Multiple Myeloma

Multiple myeloma is a malignancy of plasma cells. Neoplastic cells are located in the bone marrow, and osteolytic bone lesions are characteristic. Reciprocal chromosomal translocations between one of the immunoglobulin loci and a variety of other genes, e.g., cyclin D1, cyclin D3, c-MAF, MMSET (multiple myeloma SET-domain protein) or fibroblast growth factor receptor 3 are believed to be the primary oncogenic events. Multiple myeloma is characterized by SHM, and the putative cell of origin is a post-GC B cell. Multiple myeloma is typically first identified by symptoms such as recurrent infection, fatigue, pain, and kidney problems and is confirmed with clinical testing (see, for example, Cancer: *Principles and Practice of Oncology*. 6th edition. DeVita, V. T., Hellman, S, and Rosenberg, S. A. editors. 2001 Lippincott Williams and Wilkins Philadelphia, Pa. 19106 pp. 2465-2499).

In certain embodiments, patients who are candidates for treatment by the compositions and methods of the invention can undergo further diagnostic tests on blood and/or urine to confirm the diagnosis or suspicion of multiple myeloma including, but not limited to, complete blood count (CBC) tests to determine if the types of cells reported in a CBC are within their normal ranges which are well known in the art, blood chemistry profile to determine whether levels of various blood components, such as albumin, blood urea nitrogen (BUN), calcium, creatinine, and lactate dehydrogenase (LDH), deviate from standard values. Serum levels of beta$_2$-microglobulin ($\beta_2$-M) can also be examined and surrogate markers for IL-6, a growth factor for myeloma cells. Urinalysis can be used to measure the levels of protein in the urine. Electrophoresis can be used to measure the levels of various proteins, including M protein in the blood (called serum protein electrophoresis, or SPEP) or urine (called urine electrophoresis, or UEP). An additional test, called immunofixation electrophoresis (IFE) or immunoelectrophoresis, may also be performed to provide more specific information about the type of abnormal antibody proteins present. Assessing changes and proportions of various proteins, particularly M protein, can be used to track the progression of myeloma disease and response to treatment regimens. Multiple myeloma is characterized by a large increase in M protein which is secreted by the myeloma tumor cells.

Diagnostic tests on bone can also be conducted to confirm the diagnosis or suspicion of multiple myeloma including, but not limited to, X-rays and other imaging tests—including a bone (skeletal) survey, magnetic resonance imaging (MRI), and computerized axial tomography (CAT), also known as computed tomography (CT)—can assess changes in the bone structure and determine the number and size of tumors in the bone. Bone marrow aspiration or bone marrow biopsy can be used to detect an increase in the number of plasma cells in the bone marrow. Aspiration requires a sample of liquid bone marrow, and biopsy requires a sample of solid bone tissue. In both tests, samples are preferably taken from the pelvis (hip bone). The sternum (breast bone) can also be used for aspiration of bone marrow.

Patients with multiple myeloma are typically categorized into the following three groups that help define effective treatment regimens. Monoclonal gammopathy of undetermined significance (MGUS) is typically characterized by a serum M protein level of less than 3 g/dL, bone marrow clonal plasma cells of less than 10%, no evidence of other B cell disorders, and no related organ or tissue impairment, such as hypercalcemia (increased serum calcium levels), impaired kidney function noted by increased serum creatinine, anemia, or bone lesions. Asymptomatic myelomas are typically stage I and includes smoldering multiple myeloma (SMM) and indolent multiple myeloma (IMM). SMM is characterized by serum M protein greater than or equal to 3 g/dL and IMM is characterized by bone marrow clonal plasma cells greater than or equal to 10% of the bone marrow cells. Symptomatic myeloma is characterized by M protein in serum and/or urine and includes Stage II multiple myeloma characterized by the presence of bone marrow clonal plasma cells or plasmacytoma and Stage III multiple myeloma characterized by related organ or tissue impairment.

Osteosclerotic myeloma is a component of the rare POEMS syndrome (polyneuropathy, organomegaly, endocrinopathy, monoclonal gammopathy and skin lesions). Peak incidence is at 40 to 50 years of age. Systemic features include skeletal lesions, marrow-plasma cells <5%, a normal CBC, increased platelets, and organomegaly. The CSF has a high protein with no cells present. The M-protein levels are low (<3 g/dl, median=1.1 g/dl); heavy chain class—usually $\alpha$ or $\gamma$; light chain class—usually $\lambda$; rare urine monoclonal and occasional cryoglobulinemia. Neuropathy occurs in 50% of the patients with weakness both proximal and distal, sensory loss is greater in larger than small fibers; and demyelination and long distal latency.

Smoldering multiple myeloma patients generally present with stable disease for months/years; no anemia, bone lesions, renal insufficiency or hypercalcemia; have >10% plasma cells in bone marrow and monoclonal serum protein. The criteria for smoldering multiple myeloma is compatible with the diagnosis of multiple myeloma; however, there is no evidence of progressive course. These are cases with a slow progression, the tumor cell mass is low at diagnosis and the percentage of bone marrow plasma cells in S phase is low (<0.5%). Characteristic clinical features include: serum M protein levels >3 g/dL and/or bone marrow plasma cells ≥10%; absence of anemia, renal failure, hypercalcemia, lytic bone lesions.

Indolent (or asymptomatic) multiple myeloma is a multiple myeloma diagnosed by chance in the absence of symptoms, usually after screening laboratory studies. Indolent multiple myeloma is similar to smoldering myeloma but with few bone lesions and mild anemia. Most cases of indolent multiple myeloma develop overt multiple myeloma within 3 years. Diagnostic criteria are the same as for multiple myeloma except: no bone lesions or one asymptomatic lytic lesion (X-ray survey); M component level <3 g/dL for IgG, 2 g/dL for IgA urine light chain <4 g/24 h; hemoglobin >10 g/dl, serum calcium normal, serum creatinine <2 mg/dL, and no infections.

5.21.2.18. Solitary Plasmacytoma

Solitary plasmacytoma is one of a spectrum of plasma cell neoplasms which range from benign monoclonal gammopathy to solitary plasmacytoma to multiple myeloma. Approximately seventy percent of all solitary plasmacytoma cases eventually result in multiple myeloma. These diseases are characterized by a proliferation of B cells which produce the characteristic paraprotein. Solitary plasmacytoma results in a proliferation of clonal plasma cells in a solitary site, usually a single bone or extramedullary tissue site. Diagnostic criteria of solitary plasmacytoma include a histologically confirmed single lesion, normal bone biopsy, negative skeletal survey, no anemia, normal calcium and renal function. Most cases exhibit minimally elevated serum M-protein (paraprotein). The median age at diagnosis is 50-55, about 5-10 years younger than the median age for multiple myeloma. (See, C. Wilson, *The Plasma Cell Dycrasias*, pp. 113-144, In W. Finn and L. Peterson, eds., *Hematopathology in Oncology*, Kluwer Academic Publishers, Norwell, Mass. (2004), S. Chaganti, et al., *Cytogenetics of Lymphoma*, pp. 809-824, *In Non-Hodgkin's Lymphomas*, P. Mauch, et al., eds., Lippincott Williams & Wilkins, Philadelphia, Pa., (2004)).

The immunophenotypic and genetic features of plasmacytoma appear to be similar to multiple myeloma.

5.21.2.19. Light Chain Disease/Light Chain Deposition Disease (LCDD)

LCDD is a plasma cell dycrasias disorder caused by the over-synthesis of immunoglobulin light chains (usually kappa light chains) that are deposited in tissues. Patients commonly present with organ dysfunction, weakness, fatigue and weight loss. In approximately 80% of cases of LCDD a monoclonal immunoglobulin is detected. Detection of monoclonal kappa light chains using immunofluorescent techniques is limited by the tendency of light chains to give excess background staining, therefore, ultrastructural immunogold labeling may be necessary. (See, C. Wilson, *The Plasma Cell Dycrasias*, pp. 113-144, In W. Finn and L. Peterson, eds., *Hematopathology in Oncology*, Kluwer Academic Publishers, Norwell, Mass. (2004)).

5.21.2.20. Plasma Cell Leukemia (PCL),

PCL, a plasma cell dycrasias, is a rare aggressive variant of multiple myeloma. The criteria for plasma cell leukemia is a peripheral blood absolute plasma cell count of greater than $2 \times 10^9$/L or plasma cells greater than 20% of white blood cells. Determination of the presence of a CD138$^+$ population with cytoplasmic light chain restriction by flow cytometry will distinguish PCL from lymphoid neoplasm with plasmacytic features. PCL cells are also characterized by the lack of surface light chain and CD22 expression, and either no or weak expression of CD45. About 50% of cases of PCL express CD20 and about 50% lack expression of CD56. The genetic abnormalities observed in PCL patients are the same as those observed for multiple myeloma patients but they are found at higher frequency in PCL. (See, C. Wilson, *The Plasma Cell Dycrasias*, pp. 113-144, In W. Finn and L. Peterson, eds., *Hematopathology in Oncology*, Kluwer Academic Publishers, Norwell, Mass., (2004)).

Plasma cell leukemia has two forms: if initial diagnosis is based on leukemic phase of myeloma then the primary form is present, otherwise it is secondary. Primary plasma cell leukemia is associated with a younger age, hepatosplenomegaly, lymphadenopathy, and fewer lytic bone lesions but poorer prognosis than the secondary form. The peripheral blood of plasma cell leukemic patients has greater than 20% plasma cells with absolute count of 2000/ml or more.

5.21.2.21. Monoclonal Gammopathy of Unknown Significance (MGUS)

MGUS is a relatively common condition characterized by the presence of electrophoretically homogeneous immunoglobulins or benign M-components. The occurrence of this condition appears to increase with age. Most individuals carrying the M-components never develop malignant plasma cell dycrasias, such as multiple myeloma. However, some individuals with this condition have associated malignant conditions. When symptomatic, patients can have enlarged liver or spleen and pleuroneuropathy. (See, J. Foerster, *Plasma Cell Dycrasias General Considerations*, pp. 2612-2630, In *Wintrobe's Clinical Hematology*, Tenth Edition, G. Lee et al., eds. Williams & Wilkins, Baltimore, Md. (1999)).

MGUS can be differentiated from multiple myeloma by the presence of increased number of monoclonal plasma cells circulating in the peripheral blood. The serological characteristics of M-components are identical to other plasma cell dycrasias conditions, however, the total concentration of M-component is usually less than 30 g/L. The paraprotein is usually IgG; however multiple paraproteins may be present including IgG, IgA, IgM. The relative amount of each of the individual immunoglobulin classes is typically proportional to that found in normal serum. Proteinemia or proteinuria is rare. Serial measurements of M-protein levels in the blood and urine, and continued monitoring of the clinical and laboratory features (including protein electrophoresis) is the most reliable method of differentiating MGUS from early stage plasma cell dycrasias. In *Wintrobe's Clinical Hematology*, Tenth Edition, G. Lee et al., eds. Williams & Wilkins, Baltimore, Md. (1999)).

5.21.2.22. Mature B Cell Malignancies:

In one aspect of the invention, the inventive anti-CD22 antibody compositions can deplete mature B cells. Thus, as another aspect, the invention can be practiced to treat mature B cell malignancies including but not limited to follicular lymphoma, mantle-cell lymphoma, Burkitt's lymphoma, multiple myeloma, diffuse large B-cell lymphoma (DLBCL) including germinal center B cell-like (GCB) DLBCL, activated B cell-like (ABC) DLBCL, and type 3 DLBCL, Hodgkin's lymphoma including classical and nodular lymphocyte pre-dominant type, lymphoplasmacytic lymphoma (LPL), marginal-zone lymphoma including gastric mucosal-associated lymphoid tissue (MALT) lymphoma, and chronic lymphocytic leukemia (CLL) including immunoglobulin-mutated CLL and immunoglobulin-unmutated CLL.

5.21.2.23. Pre-B Cell Malignancies:

Further, CD22 is expressed earlier in B cell development than, for example, CD20, and is therefore particularly suited for treating pre-B cell and immature B cell malignancies, e.g., in the bone marrow. Representative pre-B cell and immature B cell malignancies include but are not limited to mantle cell lymphoma, pre-B cell acute lymphoblastic leukemia, precursor B cell lymphoblastic lymphoma, and other malignancies characterized by CD22 expression.

5.22. Patient Diagnosis and Therapeutic Regimens Transplantation

According to certain aspects of the invention, the treatment regimen and dose used with the compositions and methods of the invention is chosen based on a number of factors including, for example, clinical manifestation that place a patient at risk for developing a humoral rejection, or clinical evidence that such a rejection is developing. The terms "humoral" and "antibody-mediated" are used interchangeably herein.

The criteria for assessing the risk that a patient will develop a humoral rejection are established according to the knowledge and skill in the art. In one embodiment, a positive complement dependent cytotoxicity or antiglobulin enhanced complement dependent cytotoxicity crossmatch indicates that a patient is at high risk for humoral rejection. In one embodiment, a positive crossmatch or a prior positive complement dependent cytotoxicity or anti-globulin enhanced complement dependent cytotoxicity crossmatch indicates that a patient is at an intermediate risk for humoral rejection. In one embodiment, a negative crossmatch indicates that a patient is at a low risk for humoral rejection.

In another embodiment, a transplant recipient in need of prophylaxis against graft rejection may be identified as a patient or patient population having detectable circulating anti-HLA alloantibodies prior to transplantation. In another example, the patient or patient population is identified as having panel reactive antibodies prior to transplantation. The presence of detectable circulating anti-HLA alloantibodies in a transplant recipient post-transplantation can also be used to identify the patient or patient population in need of treatment for humoral rejection according to the invention. The patient or patient population in need of treatment for humoral rejection can also be identified according to other clinical criteria that indicate that a transplant recipient is at risk for developing a humoral rejection or has already developed a humoral rejection. For example, a transplant recipient in need of treatment of humoral rejection may be identified as a patient or population in an early stage of humoral rejection, such as a latent humoral response characterized by circulating anti-donor alloantibodies. An early stage of humoral rejection may also be a silent reaction characterized by circulating anti-donor alloantibodies and C4d deposition, or a subclinical rejection characterized by circulating anti-donor alloantibodies, C4d deposition, and tissue pathology. In later stages, the recipient is identified as a patient or patient population presenting with clinical indications of humoral rejection characterized according to the knowledge and skill in the art, for example, by circulating anti-donor alloantibodies, C4d deposition, tissue pathology, and graft dysfunction.

The present invention provides compositions, therapeutic formulations, methods and regimens effective to reduce the incidence, severity, or duration of GVHD, a rejection episode, or post-transplant lymphoproliferative disorder. In certain embodiments, the compositions and methods of the invention are effective to attenuate the host response to ischemic reperfusion injury of a solid tissue or organ graft. In a preferred embodiment, that anti-CD22 antibody compositions and methods of the invention are effective to prolong survival of a graft in a transplant recipient.

The present invention encompasses grafts that are autologous, allogeneic, or xenogeneic to the recipient. The types of grafts encompassed by the invention include tissue and organ grafts, including but not limited to, bone marrow grafts, peripheral stem cell grafts, skin grafts, arterial and venous grafts, pancreatic islet cell grafts, and transplants of the kidney, liver, pancreas, thyroid, and heart. The terms "graft" and "transplant" are used interchangeably herein. In one embodiment, the autologous graft is a bone marrow graft, an arterial graft, a venous graft or a skin graft. In one embodiment, the allograft is a bone marrow graft, a corneal graft, a kidney transplant, a pancreatic islet cell transplant, or a combined transplant of a kidney and pancreas. In one embodiment, the graft is a xenograft, preferably wherein the donor, is a pig. The compositions and methods of the present invention may also be used to suppress a deleterious immune response to a non-biological graft or implant, including but not limited to an artificial joint, a stent, or a pacemaker device.

The anti-CD22 antibodies, compositions, and methods of the invention can be used to treat or prevent GVHD, humoral rejection, or post-transplant lymphoproliferative disorder without regard to the particular indications initially giving rise to the need fro the transplant or the particular type of tissue transplanted. However, the indications which gave rise to the need for a transplant and the type of tissue transplanted by provided basis for a comprehensive therapeutic regimen for the treatment or prevention of GVHD, graft rejection, and post-transplant lymphoproliferative disorder, which comprehensive regimen comprises the anti-CD22 antibody compositions and methods of the invention.

Therapeutic formulations and regimens of the present invention are described for treating human subjects diagnosed with autoimmune diseases or disorders, including but not limited to, rheumatoid arthritis, SLE, ITP, pemphigus-related disorders, diabetes, and scleroderma.

Appropriate treatment regimens can be determined by one of skill in the art for the particular patient or patient population. In particular embodiments, the treatment regimen is a pre-transplant conditioning regimen, a post-transplant maintenance regimen, or post-transplant treatment regimen for an acute or a chronic rejection. In certain embodiments, the particular regimen is varied for a patient who is assessed as being at a high or intermediate risk of developing a humoral response, compared with the regimen for a patient who is assessed as being at a low risk of developing a humoral response.

In certain embodiments, the particular regimen is varied according to the stage of humoral rejection, with more aggressive therapy being indicated for patients at later stages of rejection. The stages of humoral rejection may be classified according to the knowledge and skill in the art. For example, the stages of humoral rejection may be classified as one of stages I to IV according to the following criteria: Stage I Latent Response, characterized by circulating anti-donor alloantibodies, especially anti-HLA antibodies; Stage II Silent Reaction, characterized by circulating anti-donor alloantibodies, especially anti-HLA antibodies, and C4d deposition, but without histologic changes or graft dysfunction; Stage III Subclinical Rejection: characterized by circulating anti-donor alloantibodies, especially anti-HLA antibodies, C4d deposition, and tissue pathology, but without graft dysfunction; Stage IV Humoral Rejection: characterized by circulating anti-donor alloantibodies, especially anti-HLA antibodies, C4d deposition, tissue pathology, and graft dysfunction.

Dose response curves can be generated using standard protocols in the art in order to determine the effective amount of the compositions of the invention for use in a particular regimen, for example, in conditioning regimens prior to transplantation, and in post-transplantation regimens for prophylaxis and treatment of GVHD, humoral rejection, or post-transplantation lymphoproliferative disorders. In general, patients at high risk for developing a humoral rejection and those already exhibiting one or more clinical indicators of rejection will require higher doses and/or more frequent doses which may be administered over longer periods of time in comparison to patients who are not at high risk or who do not exhibit any indications of active rejection.

The anti-CD22 antibodies, compositions and methods of the invention can be practiced to treat or prevent GVHD, humoral rejection, or post-transplantation lymphoproliferative disorders, either alone or in combination with other therapeutic agents or treatment regimens. Other therapeutic regimens for the treatment or prevention of GVHD, humoral rejection, or post-transplantation lymphoproliferative disorders may comprise, for example, one or more of anti-lymphocyte therapy, steroid therapy, antibody depletion therapy, immunosuppression therapy, and plasmapheresis.

Anti-lymphocyte therapy may comprise the administration to the transplant recipient of anti-thymocyte globulins, also referred to as thymoglobulin. Anti-lymphocyte therapy may also comprise the administration of one or more monoclonal antibodies directed against T cell surface antigens. Examples of such antibodies include, without limitation, OKT3™ (muromonab-CD3), CAMPATH™-1H (alemtuzumab), CAMPATH™-1G, CAMPATH™-1M, SIMULECT™ (basiliximab), and ZENAPAX™ (daclizumab). In a specific embodiment, the anti-lymphocyte therapy comprises one or more additional antibodies directed against B cells, including, without limitation, RITUXAN™ (rituximab).

Steroid therapy may comprise administration to the transplant recipient of one or more steroids selected from the group consisting of cortisol, prednisone, methyl prednisolone, dexamethazone, and indomethacin. Preferably, one or more of the steroids are corticosteroids, including without limitation, cortisol, prednisone, and methylprednisolone.

Antibody depletion therapy may include, for example, administration to the transplant recipient of intravenous immunoglobulin. Antibody depletion therapy may also comprise immunoadsorption therapy applied to the graft ex vivo, prior to transplantation. Immunoadsorption may be accomplished using any suitable technique, for example, protein A affinity, or antibody based affinity techniques using antibodies directed against T cell or B cell surface markers such as anti-CD3 antibodies, anti-CD22 antibodies, anti-CD20 antibodies, and anti-CD22 antibodies.

Immunosuppression therapy may comprise the administration of one or more immunosuppressive agents such as inhibitors of cytokine transcription (e.g., cyclosporin A, tacrolimus), nucleotide synthesis (e.g., azathiopurine, mycophenolate mofetil), growth factor signal transduction (e.g., sirolimus, rapamycin), and the T cell interleukin 2 receptor (e.g., daclizumab, basiliximab). In a particular embodiment, an immunosuppressant agent used in combination with the compositions and methods of the invention includes one or more of the following: adriamycin, azathiopurine, busulfan, cyclophosphamide, cyclosporin A ("CyA"), cytoxin, fludarabine, 5-fluorouracil, methotrexate, mycophenolate mofetil (MOFETIL), nonsteroidal anti-inflammatories (NSAIDs), rapamycin, and tacrolimus (FK506). Immunosuppressive agents may also comprise inhibitors of complement, for example, soluble complement receptor-1, anti-05 antibody, or a small molecule inhibitor of C1s, for example as described in Buerke et al. (*J. Immunol.*, 167:5375-80 (2001).

In one embodiment, the compositions and methods of the invention are used in combination with one or more therapeutic regimens for suppressing humoral rejection, including, without limitation, tacrolimus and mycophenolate mofetil therapy, immunoadsorption, intravenous immunoglobulin therapy, and plasmapheresis.

5.22.1. Diagnosis and Clinical Criteria

The present invention provides antibodies, compositions and methods for treating and preventing GVHD, humoral rejection, and post-transplant lymphoproliferative disorder in human transplant recipients. The compositions and methods of the invention can be used regardless of the particular indications which gave rise to the need for a transplant. Similarly, the use of the compositions and methods of the invention for the treatment and prevention of GVHD, humoral rejection, and post-transplant lymphoproliferative disorders is not limited by the particular type of tissue which is intended for transplantation or which has been transplanted.

In one embodiment, the invention provides compositions and methods for the prevention of humoral rejection in a human transplant recipient wherein the transplant recipient is identified as a patient or patient population at increased risk for developing a humoral rejection. Such patients may also be referred to as "sensitized." The criteria for the identification of sensitized patients is known to the skilled practitioner. Such criteria may include, for example, patients having detectable levels of circulating antibodies against HLA antigens, e.g., anti-HLA alloantibodies. Such criteria may also include patients who have undergone previous transplantations, a pregnancy, or multiple blood transfusions. Patients who are at an increased risk for humoral rejection also include those having imperfect donor-recipient HLA matching, and those transplantations which are ABO-incompatible. Sensitized individuals are preferred candidates for pretreatment or conditioning prior to transplantation. Sensitized individuals are also preferred candidates for post-transplantation maintenance regimens for the prevention of humoral rejection.

In one embodiment, the antibodies, compositions, and methods of the invention comprise or are used in combination with a therapeutic regimen for the treatment of an acute or chronic rejection. In particular embodiments, the rejection is characterized as a Stage I, a Stage II, a Stage III, or a Stage IV humoral rejection.

In one embodiment, the antibodies, compositions, and methods of the invention comprise or are used in combination with a therapeutic regimen for the treatment of an early stage humoral rejection. In particular embodiments, the early stage humoral rejection is a Stage I, II, or III rejection. Clinical indications of an early stage humoral rejection are determined according to the knowledge and skill in the art and may include, for example, the development in the patient of circulating donor-specific anti-HLA antibodies, the presence of complement markers of antibody activity such as C4d and C3d deposits in graft biopsies, and the presence of anti-HLA antibodies in graft biopsies. Other indicators of an early stage humoral rejection are known to the skilled practitioner and may include, for example, the development of anti-endothelial antibodies, especially anti-vimentin antibodies, and the development of nonclassical MHC class I-related chain A (MICA) alloantibodies.

In one embodiment, the compositions and methods of the invention comprise or are used in combination with a therapeutic regimen for the treatment of humoral rejection characterized in part by graft dysfunction. In particular embodiments, the patient or patient population in need of treatment for humoral rejection is identified according to criteria known in the art for graft dysfunction. Examples of such criteria for particular types of grafts are provided in the sections that follow. In other embodiments, the patient or patient population in need of treatment for humoral rejection is identified according to other criteria that are particular to the type of tissue graft, such as histological criteria. Examples of such criteria are also provided in the sections that follow.

5.22.2. Bone Marrow Transplants

The compositions and methods of the invention are useful for treating or preventing GVHD, humoral rejection, and post-transplant lymphoproliferative disorder in a bone marrow transplant recipient. In one embodiment, the compositions and methods of the invention comprise or are used in combination with a pre-transplant conditioning regimen.

In one embodiment, the compositions and methods of the invention are used to deplete B cells from a bone marrow graft prior to transplantation. The graft may be from any suitable source, for example, cord blood stem cells, peripheral blood stem cells, or a bone marrow tap. Peripheral blood stem cells may be harvested from donor blood following a suitable conditioning regimen. Suitable regimens are known in the art and may include, for example, administration of one or more of the following to the donor prior to harvesting the donor blood: NEUPOGEN, cytokines such as GM-CSF, low dose chemotherapeutic regimens, and chemokine therapy. The graft may be either allogeneic or autologous to the transplant recipient. The graft may also be a xenograft.

The compositions and methods of the invention are useful in a number of contexts in which there is a hematopoietic indication for bone marrow transplantation. In one embodiment, an autologous bone marrow graft is indicated for a B cell leukemia or lymphoma, preferably acute lymphoblastic leukemia ("ALL") or non-Hodgkins lymphoma, and the compositions and methods of the invention are used for the depletion of residual malignant cells contaminating the graft. In one embodiment, an autologous bone marrow transplant is indicated for patients unable to clear a viral infection, for example a viral infection associated with Epstein Barr virus (EBV), human immunodeficiency virus (HIV), or cytomegalovirus (CMV), and the anti-CD22 antibody compositions and methods of the invention are used to deplete the graft of B cells which may harbor the virus. In another embodiment, the graft is an allogeneic graft and the anti-CD22 antibody compositions and methods of the invention are used for depleting donor B cells from the graft as prophylaxis against GVHD.

In one embodiment, the indication is a B cell associated autoimmune condition and the compositions and methods of the invention are used to deplete the deleterious B cells from the patient without the need for chemotherapy or radiation therapy conditioning regimens. In one embodiment, the compositions of the invention are administered in combination with a chemotherapy or radiation therapy regimen, which regimen comprises a lower dose of one or more chemotherapeutic agents, or a lower dose of radiation, than the dose that is administered in the absence of the compositions of the invention. In one embodiment, the patient receives an autologous bone marrow graft subsequent to chemotherapy or radiation therapy, wherein the graft is depleted of deleterious B cells prior to transplantation using the compositions and methods described herein.

A patient or patient population in need of, or likely to benefit from, a bone marrow transplant is identified according to the knowledge and skill in the art. Examples of patients that may be candidates for bone marrow transplantation include patients who have undergone chemotherapy or radiation therapy for the treatment of a cancer or an autoimmune disease or disorder, and patients who are unable to clear a viral infection residing in cells of the immune system.

5.22.3. Liver Transplants

The compositions and methods of the invention are useful for treating or preventing GVHD, humoral rejection, and post-transplant lymphoproliferative disorder in a liver transplant recipient. In particular embodiments, the rejection is an acute or a chronic rejection. In one embodiment, the compositions and methods of the invention are used for the prevention of GVHD, humoral rejection, and post-transplant lymphoproliferative disorder in a liver transplant recipient. In one embodiment, the compositions and methods of the invention comprise or are used in combination with a pre-transplant conditioning regimen. In one embodiment, the compositions of the invention are administered to the transplant recipient. In one embodiment, the compositions of the invention are contacted with the graft, ex vivo, prior to transplantation.

The liver transplant may be from any suitable source as determined according to the knowledge and skill in the art. In one embodiment, the liver is an HLA-matched allogeneic graft. In another embodiment, the Liver is a xenograft, preferably from a pig donor. In one embodiment, the liver is used ex vivo to filter the patient's blood, e.g., extracorporeal perfusion. Extracorporeal perfusion is a form of liver dialysis in which the patient is surgically connected to a liver maintained outside the body. This procedure is sometimes referred to as "bioartificial liver." In accordance with this embodiment, the compositions and methods of the invention are used to prevent the development of antibodies against liver antigens which may contaminate the patient's blood.

In one embodiment, the compositions and methods of the invention comprise an improved therapeutic regimen for the treatment and prevention of GVHD, humoral rejection, and post-transplant lymphoproliferative disorder. In a particular embodiment, the compositions and methods of the invention comprise an improved therapeutic regimen, wherein the improvement lies in a decreased incidence and/or severity of complications associated with traditional immunosuppressive agents. In one embodiment, the incidence and/or severity of nephrotoxicity, hepatotoxicity, and hirsutism is reduced compared with traditional regimens relying on cyclosporin A or other calcineurin inhibitors. In one embodiment, the incidence and/or severity of obesity, osteodystrophy, diabetes mellitus and susceptibility to bacterial and viral infections is reduced compared with traditional regimens relying on corticosteroids.

In a preferred embodiment, the compositions and methods of the invention are used in combination with lower doses of one or more traditional immunosuppressive agents than the doses that are used in the absence of anti-lymphocyte antibody therapy. Preferably, the lower doses result in a decreased incidence and/or severity of one or more complications associated with the one or more traditional immunosuppressive agents.

A patient or patient population in need of, or likely to benefit from, a liver transplant is identified according to the knowledge and skill in the art. Examples of patients that may be candidates for liver transplantation include persons having one or more of the following conditions, diseases, or disorders: acute liver failure, amyloidosis, bilirubin excretion disorders, biliary atresia, Budd-Chiari syndrome, chronic active autoimmune hepatitis, cirrhosis (either associated with viral hepatitis including hepatitis B and hepatitis C, alcoholic cirrhosis, or primary biliary cirrhosis), cholangitis, congenital factor VIII or IX disorder, copper metabolism disorders, cystic fibrosis, glycogenesis, hypercholesterolemia, lipidoses, mucopolysaccharidosis, primary sclerosing cholangitis, porphyrin metabolism disorders, purine and pyrimidine metabolism disorders, and primary benign and malignant neoplasms, especially of the liver and intrahepatic bile ducts, biliary system, biliary passages, or digestive system.

The clinical criteria for the identification of a patient or patient population in need of, or likely to benefit from, a liver transplant can be determined according to the knowledge and skill in the art. Such criteria may include, for example, one or more of the following symptoms: fatigue, weight loss, upper abdominal pain, purities, jaundice, liver enlargement, discolored urine, elevated alkaline phosphatase, and gamma glutamylpeptidase activity, elevated bilirubin levels, decreased serum albumin, elevated liver-specific enzymes, low bile production, increased blood urea nitrogen, increased creatinine and/or presence of anti-neutrophil cytoplasmic antibodies (ANCA) titers, recurrent variceal hemorrhage, intractable ascites, spontaneous bacterial peritonitis, refractory encephalopathy, severe jaundice, exacerbated synthetic dysfunction, sudden physiologic deterioration, and fulminant hepatic failure.

5.22.4. Kidney (Renal) Transplants

The compositions and methods of the invention are useful for treating or preventing GVHD, humoral rejection, and post-transplant lymphoproliferative disorder in a renal transplant recipient. As used herein, the term "renal transplant" encompasses the transplant of a kidney and the combined transplant of a kidney and a pancreas. In particular embodiments, the rejection is characterized as an acute rejection or a chronic rejection.

In one embodiment, the compositions and methods of the invention comprise or are used in combination with a pre-transplant conditioning regimen. In one embodiment, a single dose of one or more of the compositions of the present invention is effective to reduce panel reactive antibodies and deplete B cells in the patient or patient population. In another embodiment, multiple doses of one or more of the compositions of the invention are effective to reduce panel reactive antibodies and deplete B cells in the patient or patient population. In one embodiment, a single dose of one or more of the compositions of the present invention is administered in combination with one or more immunosuppressive agents and is effective to reduce panel reactive antibodies and deplete B cells in the patient or patient population.

In certain embodiments, the compositions and methods of the invention are for treating or preventing GVHD and graft rejection in a patient having received a renal transplant. In one embodiment, the patient has not yet exhibited clinical signs of rejection. In a related embodiment, the compositions and methods of the invention comprise or are used in combination with a maintenance regimen for the prevention of graft rejection in the transplant recipient. In one embodiment, the compositions and methods of the invention are for the treatment of a subclinical humoral rejection. In a related embodiment, the patient or patient population in need of treatment for a subclinical humoral rejection is indicated by the detection of Cd4 deposition in a biopsy from the graft or by the detection of circulating anti-HLA antibodies.

In one embodiment, the compositions and methods of the invention comprise or are used in combination with a therapeutic regimen for the treatment of an acute or chronic rejection episode in a transplant recipient. In one embodiment, the patient or patient population in need of treatment for an acute or chronic rejection episode is identified by the detection of one or more clinical indicators of rejection. In specific embodiments, the one or more clinical indicators of rejection are detected one to six weeks post-transplantation. In one embodiment, the one or more clinical indicators of rejection are detected 6, 12, 18, 24, 36, 48, or 60 months post-transplantation. In a preferred embodiment, the acute rejection is biopsy-confirmed acute humoral rejection.

In one embodiment, one or more of the compositions of the invention comprise a therapeutic regimen for the treatment of acute rejection. In a particular embodiment, the therapeutic regimen further comprises one or more of the following: plasmapheresis, tacrolimus/mycophenolate, intravenous immunoglobulin, immunoadsorption with protein A, and anti-CD20 antibody. In one embodiment, the patient has been on an immunosuppressive protocol prior to the development of the rejection. In a particular embodiment, the immunosuppressive protocol includes one or more of cyclosporine, azathioprine, and steroid therapy.

Clinical indicators of acute humoral rejection are known in the art and include, for example, a sudden severe deterioration of renal function, the development of oliguria, and compromised renal perfusion. Additional indicators include, for example, inflammatory cells in peritubular capillaries on biopsy and circulating donor-specific alloantibodies. In one embodiment, the patient presents with one or more of the following diagnostic criteria for a humoral rejection of a renal allograft: (1) morphological evidence of acute tissue injury; (2) evidence of antibody action, such as C4d deposits or immunoglobulin and complement in arterial fibrinoid necrosis; and (3) detectable circulating antibodies against donor HLA antigens or donor endothelial antigens. In one embodiment, the patient presents with all three of the above diagnostic criteria.

In one embodiment, the patient presents with one or more of the foregoing diagnostic criteria of acute humoral rejection and the compositions of the present invention are used in combination with one or more of the following immunosuppressive agents to treat the acute humoral rejection: intravenous immunoglobulin, anti-thymocyte globulins, anti-CD20 antibody, mycophenolate mofetil, or tacrolimus. In another embodiment, the compositions of the invention are used in combination with one or more immunosuppressive agents and a procedure for the removal of alloantibodies from the patient, such as plasmapheresis or immunoadsorption.

In one embodiment, the compositions and methods of the invention comprise or are used in combination with a therapeutic regimen for the treatment of a chronic renal allograft rejection. In one embodiment, one or more of the compositions of the invention are used alone or in combination with one or more immunosuppressive agents, including for example, anti-CD 154 (CD40L), tacrolimus, sirolimus, and mizoribin. In a preferred embodiment, one or more of the anti-CD22 antibodies of the invention are used in combination with tacrolimus and mycophenolate.

Clinical indicators of chronic rejection in the kidneys are known in the art and may include, for example, arterial intimal fibrosis with intimal mononuclear cells (chronic allograft vasculopathy), duplication of the glomerular basement membranes (chronic allograft glomerulopathy), lamination of the peritubular basement membrane, C4d in peritubular capillaries, and detectable circulating donor HLA-reactive antibodies. In a preferred embodiment, the compositions and methods of the invention comprise or are used in combination with a therapeutic regimen to treat chronic rejection before graft lesions develop.

In another embodiment, the patient or patient population in need of treatment is identified as having one or more clinical indicators of transplant glomerulopathy. In a related embodiment, the compositions of the invention comprise or are used in combination with a therapeutic regimen comprising one or more therapeutic agents. In a preferred embodiment, the therapeutic regimen is effective to stabilize renal function and inhibit graft rejection. In a particular embodiment, the one or more therapeutic agents include angiotensin converting enzyme (ACE) inhibitors and/or receptor antagonists, intravenous immunoglobulin, anti-thymocyte globulins, anti-CD20 antibody, mycophenolate mofetil, or tacrolimus. Preferably, the anti-CD22 antibodies of the invention are used in combination with mycophenolate mofetil and tacrolimus, with or without other therapeutic agents. Plasmapheresis may also be used as part of the therapeutic regimen.

A patient or patient population in need of, or likely to benefit from, a renal transplant is identified according to the knowledge and skill in the art. Examples of patients that may be candidates for renal transplantation include patients diagnosed with amyloidosis, diabetes (type I or type II), glomerular disease (e.g., glomerulonephritis), gout, hemolytic uremic syndrome, HIV, hereditary kidney disease (e.g., polycystic kidney disease, congenital obstructive uropathy, cystinosis, or prune bell syndrome), other kidney disease (e.g., acquired obstructive nephropathy, acute tubular necrosis, acute intersititial nephritis), rheumatoid arthritis, systemic lupus erythematosus, or sickle cell anemia. Other candidates for renal transplant include patients having insulin deficiency, high blood pressure, severe injury or burns, major surgery, heart disease or heart attack, liver disease or liver failure, vascular disease (e.g., progressive systemic sclerosis, renal artery thrombosis, scleroderma), vesicoureteral reflux, and certain cancers (e.g., incidental carcinoma, lymphoma, multiple myeloma, renal cell carcinoma, Wilms tumor). Other candidates for renal transplant may include, for example, heroin users, persons who have rejected a previous kidney or pancreas graft, and persons undergoing a therapeutic regimen comprising antibiotics, cyclosporin, or chemotherapy.

The clinical criteria for the identification of a patient or patient population in need of, or likely to benefit from, a kidney transplant can be determined according to the knowledge and skill in the art. Such criteria may include, for example, one or more of the following: urinary problems, bleeding, easy bruising, fatigue, confusion, nausea and vomiting, loss of appetite, pale skin (from anemia), pain in the muscles, joints, flanks, and chest, bone pain or fractures, and itching.

5.22.5. Cardiac Transplants

The compositions and methods of the invention are useful for treating or preventing GVHD, humoral rejection, and post-transplant lymphoproliferative disorder in a cardiac transplant recipient. In particular embodiments, the rejection is an acute or a chronic rejection. In one embodiment, the compositions and methods of the invention comprise or are used in combination with a pre-transplant conditioning regimen.

In certain embodiments, the compositions and methods of the invention comprise or are used in combination with a therapeutic regimen for the treatment of acute humoral rejection in a cardiac transplant recipient. In a particular embodiment, the therapeutic regimen further comprises one or more of the following: plasmapheresis, intravenous immunoglobulin, and anti-CD20 antibody therapy. The patient or patient population in need of treatment for an acute humoral rejection is identified by the detection of one or more of the clinical indications of acute humoral rejection. Examples of clinical indicators of acute humoral rejection may include one or more of the following: hemodynamic dysfunction, defined by shock, hypotension, decreased cardiac output, and a rise in capillary wedge or pulmonary artery pressure. In a particular embodiment, the acute humoral rejection is diagnosed within 6, 12, 18, 24, 36, 48, or 60 months post-transplantation.

In one embodiment, the compositions and methods of the invention comprise or are used in combination with a therapeutic regimen for the prevention of rejection in a cardiac transplant recipient. In one embodiment, the transplant recipient in need of prophylaxis against rejection is identified as a patient or patient population having one or more of the following risk factors: female sex, cytomegalovirus seropositivity, elevated response to panel reactive antibodies, positive pre- and/or post-transplant crossmatch, and presensitization with immunosuppressive agents.

In one embodiment, the compositions and methods of the invention are for the treatment or prevention of graft deterioration in a heart transplant recipient. In one embodiment, the transplant recipient in need of treatment for, or prophylaxis against, graft deterioration is identified as a patient or patient population having one or more of the following clinical indications of humoral rejection: deposition of immunoglobulin, C1q, C3, and/or C4d in capillaries, evidence of CD68-positive cells within capillaries, and evidence of infiltration of the graft by inflammatory cells upon biopsy. In one embodiment, the compositions of the present invention are used in combination with one or more of the following immunosuppressive agents to treat graft deterioration in a heart transplant recipient: intravenous immunoglobulin, anti-thymocyte globulins, anti-CD20 antibody, mycophenolate mofetil, or tacrolimus. In another embodiment, the anti-CD22 antibody compositions of the invention are used in combination with one or more immunosuppressive agents and a procedure for the removal of alloantibodies from the patient, such as plasmapheresis or immunoadsorption.

In one embodiment, the compositions and methods of the invention comprise or are used in combination with a therapeutic regimen for the treatment of chronic cardiac rejection, preferably chronic allograft vasculopathy, also referred to as transplant coronary artery disease. In another embodiment, the compositions and methods of the invention comprise or are used in combination with a therapeutic regimen for the prevention of transplant coronary artery disease in a patient or patient population at risk. The criteria for identifying a patient or patient population at risk of developing transplant coronary artery disease are known in the art and may include, for example, patients having poorly matched transplants, patients who develop circulating anti-HLA antibodies, and patients who develop one or more clinical indications of humoral rejection early after cardiac transplant.

A patient or patient population in need of, or likely to benefit from, a heart transplant is identified according to the knowledge and skill in the art. Examples of patients that may be candidates for heart transplantation include those who have been diagnosed with any of the following diseases and disorders: coronary artery disease, cardiomyopathy (noninflammatory disease of the heart), heart valve disease with congestive heart failure, life-threatening abnormal heart rhythms that do not respond to other therapy, idiopathic cardiomyopathy, ischemic cardiomyopathy, dilated cardiomyopathy, ischemic cardiomyopathy, and congenital heart disease for which no conventional therapy exists or for which conventional therapy has failed.

The clinical criteria for the identification of a patient or patient population in need of, or likely to benefit from, a heart transplant can be determined according to the knowledge and skill in the art. Such criteria may include, for example, one or more of the following: ejection fraction less than 25%, intractable angina or malignant cardiac arrhythmias unresponsive to conventional therapy, and pulmonary vascular resistance of less than 2 Wood units. In addition, the patient or patient population in need of a heart transplant may be identified by performing a series of tests according to the knowledge and skill in the art. Such tests include, for example, resting and stress echocardiograms, EKG, assay of blood creatinine levels, coronary arteriography, and cardiopulmonary evaluation including right- and left-heart catheterization.

5.22.6. Lung Transplant

The compositions and methods of the invention are useful for treating or preventing GVHD, humoral rejection, and post-transplant lymphoproliferative disorder in a lung transplant recipient. In particular embodiments, the rejection is characterized as an acute or a chronic rejection. In one embodiment, the compositions and methods of the invention comprise or are used in combination with a pre-transplant conditioning regimen.

A patient or patient population in need of, or likely to benefit from, a lung transplant is identified according to the knowledge and skill in the art. Examples of patients that may be candidates for lung transplantation include patients having one of the following diseases or conditions: bronchiectasis, chronic obstructive pulmonary disease, cystic fibrosis, Eisenmenger syndrome or congenital heart disease with Eisenmenger syndrome. emphysema, eosinophilic granuloma of the lung, or histiocytosis X, inhalation/burn trauma, lymphangioleiomyomatosis (LAM), primary pulmonary hypertension, pulmonary fibrosis (scarring of the lung), or sarcoidosis.

The clinical criteria for the identification of a patient or patient population in need of, or likely to benefit from, a lung transplant can be determined according to the knowledge and skill in the art. Such criteria may include, for example, one or more of the following: Chronic obstructive pulmonary disease (COPD) and alpha1-antitrypsin deficiency emphysema characterized by one or more of the following indicators: postbronchodilator FEV1 of less than 25% predicted, resting hypoxemia, i.e., $PaO_2$ of less than 55-60 mm Hg, hypercapnia. secondary pulmonary hypertension, a rapid rate of decline in FEV1, or life-threatening exacerbations; cystic fibrosis characterized by one or more of the following indicators: postbronchodilator FEV1 of less than 30% predicted, resting hypoxemia, hypercapnia, or increasing frequency and severity of exacerbations; idiopathic pulmonary fibrosis characterized by one or more of the following indicators: vital capacity (VC) and TLC of less than 60-65% predicted, and resting hypoxemia; secondary pulmonary hypertension characterized by clinical, radiographic, or physiologic progression while on medical therapy; primary pulmonary hypertension characterized by one or more of the following indicators: NYHA functional class III or IV, mean right atrial pressure of greater than 10 mm Hg, mean pulmonary arterial pressure of greater than 50 mm Hg, cardiac index of less than 2.5 L/min/$m^2$, and failure of therapy with long-term prostacyclin infusion.

5.22.7. Post-Transplant Lymphoproliferative Disorder

The immunosuppression necessary for successful transplantation can give rise to a post-transplant lymphoproliferative disorder of B cell origin. Generally, a post-transplant lymphoproliferative disorder is associated with Epstein-Barr virus infected cells. Post-transplant lymphoproliferative disorder (PTLD) can range in severity from a benign self-limiting mononucleosis-like syndrome to an aggressive non-Hodgkins lymphoma. The compositions and methods of the present invention may be used to treat PTLD arising from any transplant. Preferably, the transplant is a solid organ transplant, for example, a heart transplant, a liver transplant, a kidney transplant, or a combined kidney-pancreas transplant. In a preferred embodiment, the compositions and methods of the invention are used to treat PTLD as part of a therapeutic regimen that includes a temporary cessation or reduction of other immunosuppressive therapy.

In one embodiment, the anti-CD22 antibody compositions of the invention are administered as part of a therapeutic regimen including one or more of the following: high dose intravenous gamma globulin, a cytokine, an anti-viral agent, and an anti-CD20 monoclonal antibody. Preferably, the therapeutic regimen includes a temporary cessation or reduction of immunosuppression therapy. In a preferred embodiment, intravenous gamma globulin is administered at a daily dose of 0.4 g/kg for 1 to 5 days, preferably for 3 days, and the cytokine is interferon alpha administered for at least 7 days. In one embodiment, one or more cytokines is used in the regimen. In one embodiment, one or more anti-viral agents is used in the regimen. The anti-viral agent may be selected from any suitable anti-viral agent known to those of skill in the art. In one embodiment, the anti-viral agent is aciclovir or ganciclovir. Preferably the anti-viral agent is administered for at least one or two weeks. The anti-viral agent may also be administered for longer periods, for example, 1 month, 2 months, 3 months, 4 months, or 5 months.

5.23. Patient Diagnosis and Therapeutic Regimens: Autoimmune Disease

According to certain aspects of the invention, the treatment regimen and dose used with the compositions and methods of the invention is chosen based on a number of factors including, but not limited to, the stage of the autoimmune disease or disorder being treated. Appropriate treatment regimens can be determined by one of skill in the art for particular stages of a autoimmune disease or disorder in a patient or patient population. Dose response curves can be generated using standard protocols in the art in order to determine the effective amount of the compositions of the invention for treating patients having different stages of a autoimmune disease or disorder. In general, patients having more activity of a autoimmune disease or disorder will require higher doses and/or more frequent doses which may be administered over longer periods of time in comparison to patients having less activity of an autoimmune disease or disorder.

The anti-CD22 antibodies, compositions and methods of the invention can be practiced to treat an autoimmune disease or disorder. The term "autoimmune disease or disorder" refers to a condition in a subject characterized by cellular, tissue and/or organ injury caused by an immunologic reaction of the subject to its own cells, tissues and/or organs. The term "inflammatory disease" is used interchangeably with the term "inflammatory disorder" to refer to a condition in a subject characterized by inflammation, preferably chronic inflammation. Autoimmune disorders may or may not be associated with inflammation. Moreover, inflammation may or may not be caused by an autoimmune disorder. Thus, certain disorders may be characterized as both autoimmune and inflammatory disorders. Exemplary autoimmune diseases or disorders include, but are not limited to: alopecia greata, ankylosing spondylitis, antiphospholipid syndrome, autoimmune Addison's disease, autoimmune diseases of the adrenal gland, autoimmune hemolytic anemia, autoimmune hepatitis, autoimmune oophoritis and orchitis, autoimmune thrombocytopenia, Behcet's disease, bullous pemphigoid, cardiomyopathy, celiac sprue-dermatitis, chronic fatigue immune dysfunction syndrome (CFIDS), chronic inflammatory demyelinating polyneuropathy, Churg-Strauss syndrome, cicatrical pemphigoid, CREST syndrome, cold agglutinin disease, Crohn's disease, discoid lupus, essential mixed cryoglobulinemia, diabetes, eosinophilic fascites, fibromyalgia-fibromyositis, glomerulonephritis, Graves' disease, Guillain-Barre, Hashimoto's thyroiditis, Henoch-Schönlein purpura, idiopathic pulmonary fibrosis, idiopathic/autoimmune thrombocytopenia purpura (ITP), IgA neuropathy, juvenile arthritis, lichen planus, lupus erthematosus, Ménière's disease, mixed connective tissue disease, multiple sclerosis, type 1 or immune-mediated diabetes mellitus, myasthenia gravis, pemphigus-related disorders (e.g., pemphigus vulgaris), pernicious anemia, polyarteritis nodosa, polychrondritis, polyglandular syndromes, polymyalgia rheumatica, polymyositis and dermatomyositis, primary agammaglobulinemia, primary biliary cirrhosis, psoriasis, psoriatic arthritis, Raynauld's phenomenon, Reiter's syndrome, Rheumatoid arthritis, sarcoidosis, scleroderma, Sjögren's syndrome, stiff-man syndrome, systemic lupus erythematosis (SLE), Sweet's syndrome, Still's disease, lupus erythematosus, takayasu arteritis, temporal arteristis/giant cell arteritis, ulcerative colitis, uveitis, vasculitides such as dermatitis herpetiformis vasculitis, vitiligo, and Wegener's granulomatosis. Examples of inflammatory disorders include, but are not limited to, asthma, encephalitis, inflammatory bowel disease, chronic obstructive pulmonary disease (COPD), allergic disorders, septic shock, pulmonary fibrosis, undifferentitated spondyloarthropathy, undifferentiated arthropathy, arthritis, inflammatory osteolysis, graft versus host disease, urticaria, Vogt-Koyanagi-Hareda syndrome and chronic inflammation resulting from chronic viral or bacteria infections.

CD22 is expressed on immature B cells, e.g. CD22 concomitantly with Ig on the B cell surface. Therefore anti-CD22 mAb may be particularly suited for depleting pre-B cells and immature B cells, e.g., in the bone marrow.

5.23.1. Diagnosis of Autoimmune Diseases or Disorders

The diagnosis of an autoimmune disease or disorder is complicated in that each type of autoimmune disease or disorder manifests differently among patients. This heterogeneity of symptoms means that multiple factors are typically used to arrive at a clinical diagnosis. Generally, clinicians use factors, such as, but not limited to, the presence of autoantibodies, elevated cytokine levels, specific organ dysfunction, skin rashes, joint swelling, pain, bone remodeling, and/or loss of movement as primarily indicators of an autoimmune disease or disorder. For certain autoimmune diseases or disorders, such as RA and SLE, standards for diagnosis are known in the art. For certain autoimmune diseases or disorders, stages of disease have been characterized and are well known in the art. These art recognized methods for diagnosing autoimmune diseases and disorders as well as stages of disease and scales of activity and/or severity of disease that are well known in the art can be used to identify patients and patient populations in need of treatment for an autoimmune disease or disorder using the compositions and methods of the invention.

5.23.2. Clinical Criteria for Diagnosing Autoimmune Diseases or Disorders

Diagnostic criteria for different autoimmune diseases or disorders are known in the art. Historically, diagnosis is typically based on a combination of physical symptoms. More recently, molecular techniques such as gene-expression profiling have been applied to develop molecular definitions of autoimmune diseases or disorders. Exemplary methods for clinical diagnosis of particular autoimmune diseases or disorders are provided below. Other suitable methods will be apparent to those skilled in the art.

In certain embodiments of the invention, patients with low levels of autoimmune disease activity or patients with an early stage of an autoimmune disease (for diseases where stages are recognized) can be identified for treatment using the anti-CD22 antibody compositions and methods of the invention. The early diagnosis of autoimmune disease is difficult due to the general symptoms and overlap of symptoms among diseases. In such embodiments, a patient treated at an early stage or with low levels of an autoimmune disease activity has symptoms comprising at least one symptom of an autoimmune disease or disorder. In related embodiments, a patient treated at an early stage or with low levels of an autoimmune disease has symptoms comprising at least 1, 2, 3, 4, 5, 6, 7, 8, 9, 10, 11, 12, 13, 14, or 15 symptoms of an autoimmune disease or disorder. The symptoms may be of any autoimmune diseases and disorders or a combination thereof. Examples of autoimmune disease and disorder symptoms are described below.

5.23.3. Rheumatoid Arthritis

Rheumatoid arthritis is a chronic disease, mainly characterized by inflammation of the lining, or synovium, of the joints. It can lead to long-term joint damage, resulting in chronic pain, loss of function and disability. Identifying patients or patient populations in need of treatment for rheumatoid arthritis is a process. There is no definitive test that provides a positive or negative diagnosis of rheumatoid arthritis. Clinicians rely on a number of tools including, medical histories, physical exams, lab tests, and X-rays.

Physical symptoms vary widely among patients and commonly include, but are not limited to, joint swelling, joint tenderness, loss of motion in joints, joint malalignment, bone remodeling, fatigue, stiffness (particularly in the morning and when sitting for long periods of time), weakness, flu-like symptoms (including a low-grade fever), pain associated with prolonged sitting, the occurrence of flares of disease activity followed by remission or disease inactivity, rheumatoid nodules or lumps of tissue under the skin (typically found on the elbows, they can indicate more severe disease activity), muscle pain, loss of appetite, depression, weight loss, anemia, cold and/or sweaty hands and feet, and involvement of the glands around the eyes and mouth, causing decreased production of tears and saliva (Sjögren's syndrome). For Sjogren's specifically, the following references may be used, Fox et al. Arthritis Rheum. (1986) 29:577-586, and Vitali et al. Ann. Rheum. Dis. (2002). 61:554-558.

Apart form physical symptoms, clinicians commonly use tests, such as, but not limited to, complete blood count, erythrocyte sedimentation rate (ESR or sed rate), C-reactive protein, rheumatoid factor, anti-DNA antibodies, antinuclear antibodies (ANA), anti-cardiolipin antibodies, imaging studies, radiographs (X-rays), magnetic resonance imaging (MRI) of joints or organs, joint ultrasound, bone scans, and bone densitometry (DEXA). These tests are examples of tests that can be used in conjunction with the compositions and methods of the invention to check for abnormalities that might exist (i.e., identify patients or patient populations in need of treatment) or to monitor side effects of drugs and check progress.

Early symptoms of rheumatoid arthritis commonly are found in the smaller joints of the fingers, hands and wrists. Joint involvement is usually symmetrical, meaning that if a joint hurts on the left hand, the same joint will hurt on the right hand. In general, more joint erosion indicates more severe disease activity.

Symptoms of more advanced disease activity include damage to cartilage, tendons, ligaments and bone, which causes deformity and instability in the joints. The damage can lead to limited range of motion, resulting in daily tasks (grasping a fork, combing hair, buttoning a shirt) becoming more difficult. Skin ulcers, greater susceptibility to infection, and a general decline in health are also indicators of more advanced disease activity.

Progression of rheumatoid arthritis is commonly divided into three stages. The first stage is the swelling of the synovial lining, causing pain, warmth, stiffness, redness and swelling around the joint. Second is the rapid division and growth of cells, or pannus, which causes the synovium to thicken. In the third stage, the inflamed cells release enzymes that may digest bone and cartilage, often causing the involved joint to lose its shape and alignment, more pain, and loss of movement.

Molecular techniques can also be used to identify patients or patient populations in need of treatment. For example, rheumatoid arthritis has been shown to be associated with allelic polymorphisms of the human leukocyte antigen (HLA)-DR4 and HLA-DRB1 genes (Oilier and Winchester, 1999, Genes and Genetics of Autoimmunity. Basel, Switzerland; Stastny, 1978, N. Engl J Med 298:869-871; and Gregersen et al., 1987, Arthritis Rheum 30:1205-1213). Rheumatoid arthritis patients frequently express two disease-associated HLA-DRB1*04 alleles (Weyand et al., 1992 Ann Intern Med 117:801-806). Patients can be tested for allelic polymorphisms using methods standard in the art. MHC genes are not the only germline-encoded genes influencing susceptibility to RA that can be used to diagnose or identify patients or patient populations in need of treatment. Female sex clearly increases the risk, and female patients develop a different phenotype of the disease than do male patients. Any molecular indicators of rheumatoid arthritis can be used to identify patients or patient populations in need of treatment with the anti-CD22 antibody compositions and methods of the invention.

Methods for determining activity of rheumatoid arthritis in a patient in relation to a scale of activity are well known in the art and can be used in connection with the pharmaceutical compositions and methods of the invention. For example, the American College of Rheumatologists Score (ACR score) can be used to determine the activity of rheumatoid arthritis of a patient or a patient population. According to this method, patients are given a score that correlates to improvement. For example, patients with a 20% improvement in factors defined by the ACR would be given an ACR20 score.

Initially, a patient exhibiting the symptoms of rheumatoid arthritis may be treated with an analgesic. In other embodiments, a patient diagnosed with or exhibiting the symptoms of rheumatoid arthritis is initially treated with nonsteroidal anti-inflammatory (NSAID) compounds. As the disease progresses and/or the symptoms increase in severity, rheumatoid arthritis may be treated by the administration of steroids such as but not limited to dexamethasone and prednisone. In more severe cases, a chemotherapeutic agent, such as but not limited to methotrexate or cytoxin may be administered to relieve the symptoms of rheumatoid arthritis.

In certain instances, rheumatoid arthritis may be treated by administration of gold, while in other instances a biologic, such as an antibody or a receptor (or receptor analog) may be administered. Examples of such therapeutic antibodies are RITUXIN and REMICADE. An illustrative example of a soluble receptor that can be administered to treat rheumatoid arthritis is ENBREL.

In extremely severe cases of rheumatoid arthritis, surgery may be indicated. Surgical approaches may include, but not be limited to: synovectomy to reduce the amount of inflammatory tissue by removing the diseased synovium or lining of the joint; arthroscopic surgery to take tissue samples, remove loose cartilage, repair tears, smooth a rough surface or remove diseased synovial tissue; osteotomy, meaning "to cut bone," this procedure is used to increase stability by redistributing the weight on the joint; joint replacement surgery or arthroplasty for the surgical reconstruction or replacement of a joint; or arthrodesis or fusion to fuse two bones together.

In certain embodiments of the methods of invention, a patient can be treated with an anti-CD22 antibody prior, concurrent, or subsequent to any of the therapies disclosed above. Moreover, the anti-CD22 antibodies of the present invention may be administered in combination with any of the analgesic, NSAID, steroid, or chemotherapeutic agents noted above, as well as in combination with a biologic administered for the treatment of rheumatoid arthritis.

5.23.4. Systemic Lupus Erythematosis (SLE)

Systemic lupus erythematosis (SLE) is a chronic (long-lasting) rheumatic disease which affects joints, muscles and other parts of the body. Patients or patient populations in need of treatment for SLE can be identified by examining physical symptoms and/or laboratory test results. Physical symptoms vary widely among patients. For example, in SLE, typically 4 of the following 11 symptoms exist before a patient is diagnosed with SLE: 1) malar rash: rash over the cheeks; 2) discoid rash: red raised patches; 3) photosensitivity: reaction to sunlight, resulting in the development of or increase in skin rash; 4) oral ulcers: ulcers in the nose or mouth, usually painless; 5) arthritis: nonerosive arthritis involving two or more peripheral joints (arthritis in which the bones around the joints do not become destroyed); 6) serositis pleuritis or pericarditis: (inflammation of the lining of the lung or heart); 7) renal disorder: excessive protein in the urine (greater than 0.5 gm/day or 3+ on test sticks) and/or cellular casts (abnormal elements the urine, derived from red and/or white cells and/or kidney tubule cells); 8) neurologic disorder: seizures (convulsions) and/or psychosis in the absence of drugs or metabolic disturbances which are known to cause such effects; 9) hematologic disorder: hemolytic anemia or leukopenia (white blood count below 4,000 cells per cubic millimeter) or lymphopenia (less than 1,500 lymphocytes per cubic millimeter) or thrombocytopenia (less than 100,000 platelets per cubic millimeter) (The leukopenia and lymphopenia must be detected on two or more occasions. The thrombocytopenia must be detected in the absence of drugs known to induce it); 10) antinuclear antibody: positive test for antinuclear antibodies (ana) in the absence of drugs known to induce it; and/or 11) immunologic disorder: positive anti-double stranded anti-DNA test, positive anti-sm test, positive antiphospholipid antibody such as anticardiolipin, or false positive syphilis test (vdrl).

Other physical symptoms that may be indicative of SLE include, but are not limited to, anemia, fatigue, fever, skin rash, muscle aches, nausea, vomiting and diarrhea, swollen glands, lack of appetite, sensitivity to cold (Raynaud's phenomenon), and weight loss.

Laboratory tests can also be used to to identify patients or patient populations in need of treatment. For example, a blood test can be used to detect a autoantibodies found in the blood of almost all people with SLE. Such tests may include but are not limited to tests for antinuclear antibodies (ANA) in the absence of drugs known to induce it (Rahman, A. and Hiepe, F. *Lupus*. (2002). 11(12):770-773), anti-double stranded anti-DNA (Keren, D. F. *Clin. Lab. Med*. (2002) 22(2):447-474.), anti-Sm, antiphospholipid antibody such as anticardiolipin (Gezer, S. *Dis. Mon.* 2003. 49(12):696-741), or false positive syphilis tests (VDRL).

Other tests may include a complement test (C3, C4, CH50, CH100) can be used to measure the amount of complement proteins circulating in the blood (Manzi et al. *Lupus* 2004. 13(5):298-303), a sedimentation rate (ESR) or C-reactive protein (CRP) may be used to measure inflammation levels, a urine analysis can be used to detect kidney problems, chest X-rays may be taken to detect lung damage, and an EKG can be used to detect heart problems.

Chronic SLE is associated with accumulating collateral damage to involved organ, particularly the kidney. Accordingly, early therapeutic intervention is desirable, i.e. prior to, for example, kidney failure. Available treatments for SLE are similar to those available for rheumatoid arthritis. These include intial treatments, either with an analgesic or a nonsteroidal anti-inflammatory (NSAID) compound. As the disease progresses and/or the symptoms increase in severity, SLE may be treated by the administration of steroids such as but not limited to dexamethasone and prednisone.

In more severe cases, a chemotherapeutic agent, such as but not limited to methotrexate or cytoxin may be administered to relieve the symptoms of SLE. However, this approach is not preferred where the patient is a female of child-bearing age. In such instances, those therapeutic approaches that do not interfere with the reproductive capacity of the patient are strongly preferred.

In certain instances, SLE may be treated by administration of a biologic, such as an antibody or a receptor (or receptor analog). Examples of such therapeutic antibodies are RITUXIN and REMICADE. An illustrative example of a soluble receptor for an inflammatory cytokine that can be administered to treat SLE is ENBREL.

In certain embodiments of the methods of invention, a patient can be treated with an anti-CD22 antibody prior, concurrent, or subsequent to any of the therapies disclosed above that are used for the treatment of SLE. Moreover, the anti-CD22 antibodies of the present invention may be administered in combination with any of the analgesic, NSAID, steroid, or chemotherapeutic agents noted above, as well as in combination with a biologic administered for the treatment of SLE.

5.23.5. Idiopathic/Autoimmune Thrombocytopenia Purpura (ITP)

Idiopathic/autoimmune thrombocytopenia purpura (ITP) is a disorder of the blood characterized by immunoglobulin G (IgG) autoantibodies that interact with platelet cells and result in the destruction of those platelet cells. Typically, the antibodies are specific to platelet membrane glycoproteins. The disorder may be acute (temporary, lasting less than 2 months) or chronic (persisting for longer than 6 months). Patients or patient populations in need of treatment for ITP can be identified by examining a patient's medical history, physical symptoms, and/or laboratory test results. (Provan, D., and Newland, A., *Br. J. Haematol.* (2002) 118(4):933-944; George, J. N. *Curr. Hematol.* (2003) 2(5):381-387; Karptkin, S. *Autoimmunity*. (2004) 37(4):363-368; Cines, D. B., and Blanchette, V. S., *N. Engl. J. Med.* (2002) 346(13)995-1008).

Physical symptoms include purplish-looking areas of the skin and mucous membranes (such as the lining of the mouth) where bleeding has occurred as a result of a decrease in the number of platelet cells. The main symptom is bleeding, which can include bruising ("ecchymosis") and tiny red dots on the skin or mucous membranes ("petechiae"). In some instances bleeding from the nose, gums, digestive or urinary tracts may also occur. Rarely, bleeding within the brain occurs. Common signs, symptoms, and precipitating factors also include, but are not limited to, abrupt onset (childhood ITP), gradual onset (adult ITP), nonpalpable petechiae, purpura, menorrhagia, epistaxis, gingival bleeding, hemorrhagic bullae on mucous membranes, signs of GI bleeding, menometrorrhagia, evidence of intracranial hemorrhage, nonpalpable spleen, retinal hemorrhages, recent live virus immunization (childhood ITP), recent viral illness (childhood ITP), spontaneous bleeding when platelet count is less than 20,000/mm$^3$, and bruising tendency.

Laboratory test that can be used to diagnose ITP include, but are not limited to, a complete blood count test, or a bone marrow examination to verify that there are adequate platelet-forming cells (megakaryocyte) in the marrow and to rule out other diseases such as metastatic cancer and leukemia. Isolated thrombocytopenia is the key finding regarding laboratory evaluation. Giant platelets on peripheral smear are indicative of congenital thrombocytopenia. A CT scan of the head may be warranted if concern exists regarding intracranial hemorrhage.

The current treatments for ITP include, platelet transfusions and splenectomy. Other treatments include, the administration of glucocorticoids, administration of immunosuppressive agents, administration of agents that enhance platelet production, such as IL-11, and agents that activate megakaryocytes to produce platelets, such as thrombopoietin (TPO).

In more severe cases, a chemotherapeutic agent, such as but not limited to vincristine and vinblastine may be administered to relieve the symptoms of ITP. However, this approach is not preferred where the patient is a female of child-bearing age. In such instances, those therapeutic approaches that do not interfere with the reproductive capacity of the patient are strongly preferred.

In certain instances, ITP may be treated by administration of a biologic, such as an antibody or a receptor (or receptor analog). Examples of such therapeutic antibodies are anti-CD20 antibodies, such as, Rituximab.

In certain embodiments of the methods of invention, a patient can be treated with an anti-CD22 antibody prior, concurrent, or subsequent to any of the therapies disclosed above that are used for the treatment of ITP. Moreover, the anti-CD22 antibodies of the present invention may be administered in combination with any of the agents noted above, as well as in combination with a biologic administered for the treatment of ITP.

5.23.6. Pemphigus and Pemphigoid-Related Disorders

Both pemphigus- and pemphigoid-related disorders are a heterogeneous group of autoimmune diseases characterized by a blistering condition of the skin and/or mucosal surfaces. In both diseases, the blistering is caused by autoimmune antibodies that recognize various proteins expressed on the surface of epithelial cells in the dermis and/or epidermis.

In patients with pemphigus-related disease, the blistering occurs within the epidermis and is due to the binding of autoantibodies specific for desmoglein 1 (Dsg1) and/or desmoglein 3 (Dsg3). The classic subtypes of pemphigus can be distinguished according to anti-desmoglein antibody specificities. Patients with pemphigus foliaceus (PF) produce anti-Dsg1 antibodies only. Patients with pemphigus vulgaris (PV) and paraneoplastic pemphigus (PNP) produce anti-Dsg3 antibodies if their lesions are restricted to mucosal tissues. In contrast, PV and PNP patients with lesions of the skin and mucosa produce both anti-Dsg1 and -Dsg3 autoantibodies. (Nagasaka, T., et al. *J. Clin. Invest.* 2004. 114:1484-1492; Seishema, M., et al. *Arch Dermatol.* 2004. 140(12):1500-1503; Amagai, M., *J. Dermatol. Sci.* 1999. 20(2):92-102)

In patients with pemphigoid-related disease including but not limited to, bulous phemphigoid, urticarial bulous pemphigoid, cicatricial pemphigoid, epidermolysis bullosa acquisita, and Linear IgA bullous dermatosis, the blistering occurs at the interface of the dermis with the epidermis. The most common form of pemphigoid disease is bulous pemphigoid (BP) which is characterized by the presence of autoantibodies that bind the bullous pemphigoid antigen 180 (BP180), bullous pemphigoid antigen 230 (BP230), laminin 5, and/or beta 4 integrin. (Fontao, L., et al. *Mol. Biol. Cell.* 2003) 14(5):1978-1992; Challacombe, S. J., et al *Acta Odontol. Scand.* (2001). 59(4):226-234.)

Patients or patient populations in need of treatment for pemphigus- or pemphigoid-related disorders can be identified by examining a patient's medical history, physical symptoms, and/or laboratory test results (reviewed in: Mutasim, D. F. *Drugs Aging*. (2003).20(9):663-681; Yeh, S. W. et al. *Dermatol. Ther.* (2003). 16(3):214-223; Rosenkrantz, W. S. *Vet. Dermatol.* 15(2):90-98.).

Typically, diagnosis of these pemphigus- or pemphigoid-related disorders is made by skin biopsy. The biopsy skin sample is examined microscopically to determine the anatomical site of the blister (e.g. epidermis or between dermis and epidermis). These findings are correlated with direct or indirect immunohistochemical analyses to detect the presence of autoantibodies at the site of the lesion. Serum samples from patients may also be examined for the presence of circulating autoantibodies using an ELISA-based test for specific proteins. Several ELISA-based assays have been described for detection of desmoglein antibodies in human samples (Hashimoto, T. *Arch. Dermatol. Res.* (2003) 295 Suppl. 1:S2-11). The presence of these desmoglein autoantibodies in biopsy samples is diagnostic of pemphigus.

Clinically, pemphigus vulgaris can be diagnosed by the presence of blisters in the mouth. Inflammation or erosions may also be present in the lining of the eye and eyelids, and the membranes of the nose or genital tract. Half of the patients also develop blisters or erosions of the skin, often in the groin, underarm, face, scalp and chest areas. Pemphigus foliaceus is a superficial, relatively mild form of pemphigus. It usually manifests on the face and scalp, but also involves the back and chest. Lesions do not occur in the mouth. The blisters are more confined to the outermost surface and often itch. Paraneoplastic pemphigus is very rare and generally occurs in people who have cancer. The lesions are painful and affect the mouth, lips and esophagus (swallowing tube) as well as the skin. Due to involvement of the airways, signs of respiratory disease may occur and can be life-threatening.

The current treatments for pemphigus or pemphigoid-related disease includes the topical administration of creams and ointments to alleviate the discomfort associated with the skin condition, the administration of anti-inflammatory agents or the administration of immunosuppressive agents.

In certain embodiments of the methods of invention, a patient can be treated with an anti-CD22 antibody prior, concurrent, or subsequent to any of the therapies disclosed above that are used for the treatment of pemphigoid or pemphigoid related disease. Moreover, the anti-CD22 antibodies of the present invention may be administered in combination with any of the agents noted above.

5.23.7. Autoimmune Diabetes

According to certain aspects of the invention, a patient in need of treatment for autoimmune diabetes, also known as type 1A diabetes, can be treated with the anti-CD22 antibody compositions and methods of the invention. Type 1A diabetes is an autoimmune disease caused by the synergistic effects of genetic, environmental, and immunologic factors that ultimately destroy the pancreatic beta cells. The consequences of pancreatic beta cell destruction is a decrease in beta cell mass, insulin production/secretion declines and blood glucose levels gradually rise.

Patients or patient populations in need of treatment for type 1A diabetes can be identified by examining a patient's medical history, physical symptoms, and/or laboratory test results. Symptoms often come on suddenly and include, but are not limited to, low or non-existent blood insulin levels, increased thirst, increased urination, constant hunger, weight loss, blurred vision, and/or fatigue. Overt diabetes does not usually become evident until a majority of beta cells are destroyed (>80%). Typically, diabetes is clinically diagnosed if a patient has a random (without regard to time since last meal) blood glucose concentration ≥11.1 mmol/L (200 mg/dL) and/or a fasting (no caloric intake for at least 8 hours) plasma glucose ≥7.0 mmol/L (126 mg/dL) and/or a two-hour plasma glucose ≥11.1 mmol/L (200 mg/dL). Ideally, these tests should be repeated on different days with comparable results before diagnosis is confirmed. (Harrison's Principles of Internal Medicine, 16$^{th}$ ed./editors, Dennis L. Kasper, et al. The McGraw-Hill Companies, Inc. 2005 New York, N.Y.).

Although the precise etiology of type 1A diabetes is unknown, there exists clear genetic linkage to specific HLA serotypes. In particular, autoimmune diabetes is associated with HLA DR3 and DR4 serotypes. The presence of both DR3 and DR4 confers the highest known genetic risk. Susceptibility to autoimmune diabetes is also linked to HLA class II (HLA-DQB1*0302. In contrast, HLA haplotypes with DRB1-1501 and DQA1-0102-DQB1-0602 are associated with protection from type 1A diabetes (Redondo, M. J., et al. *J. Clin. Endocrinol. Metabolism* (2000) 10:3793-3797.)

The destruction of the insulin producing beta islet cells can be accompanied by islet cell autoantibodies, activated lymphocytic infiltrates in the pancreas and draining lymph nodes, T lymphocytes responsive to islet cell proteins, and release of inflammatory cytokines within the islets (Harrison's Principles of Internal Medicine, 16$^{th}$ ed./editors, Dennis L. Kasper, et al. The McGraw-Hill Companies, Inc. 2005 New York, N.Y.).

Autoantibodies associated with type 1A diabetes include but are not limited to antibodies that bind insulin, glutamic acid decarboxylase (GAD), ICA-512/IA-2, phogrin, islet ganglioside and carboxypeptidase H (Gianani, R. and Eisenbarth, G. S. *Immunol. Rev.* (2005) 204:232-249; Kelemen, K. et al, *J. Immunol.* (2004) 172(6):3955-3962); Falorni, A. and Borozzetti, A. *Best Pract. Res. Clin. Endocrinol. Metab.* 2005. 19(1):119-133.)

The current treatments for autoimmune diabetes include the administration of vitamin D, corticosteroids, agents which control blood pressure and agents that control glycemia (blood sugar levels).

In certain embodiments of the methods of invention, a patient can be treated with an anti-CD22 antibody prior, concurrent, or subsequent to any of the therapies disclosed above that are used for the treatment of autoimmune diabetes. Moreover, the anti-CD22 antibodies of the present invention may be administered in combination with any of the agents noted above.

5.23.8. Systemic Sclerosis (Scleroderma) and Related Disorders

Systemic sclerosis also known as Scleroderma encompasses a heterogeneous group of diseases including but not limited to, Limited cutaneous disease, Diffuse cutaneous disease, Sine scleroderma, Undifferentiated connective tissue disease, Overlap syndromes, Localized scleroderma, Morphea, Linear scleroderma, En coup de saber, Scleredema adultorum of Buschke, Scleromyxedema, Chronic graft-vs.-host disease, Eosinophilic fasciitis, Digital sclerosis in diabetes, and Primary anylooidosisand anyloidosis associated with multiple myeloma. (Reviewed in: Harrison's Principles of Internal Medicine, 16$^{th}$ ed./editors, Dennis L. Kasper, et al. The McGraw-Hill Companies, Inc. 2005 New York, N.Y.).

Clinical features associated with scleroderma can include Raynaud's phenomenon, skin thickening, subcutaneious calcinosis, telangiectasia, arthralgias/arthritis, myopathy, esophageal dysmotility. pulmonary fibrosis, isolated pulmonary arterial hypertension, congestive heart failure and renal crisis. The extent to which an patient displays one or more of these disease manifestations can influence the diagnosis and potential treatment plan.

Autoantibodies include: Anti-topoisomerase 1, anticentromere, anti-RNA polymerase I, II, and/or III, anti-Th RNP, anti-U, RNP (anti-fibrillarin), anti-PM/Sci, anti-nuclear antibodies (ANA).

Identification of patients and patient populations in need of treatment of scleroderma can be based on clinical history and physical findings. Patients or patient populations in need of treatment for scleroderma can be identified by examining a patient's medical history, physical symptoms, and/or laboratory test results. Diagnosis may be delayed in patients without significant skin thickening. Laboratory, X-ray, pulmonary function tests, and skin or renal (kidney) biopsies can be used to determine the extent and severity of internal organ involvement.

In the early months or years of disease onset, scleroderma may resemble many other connective tissue diseases, such as, but not limited to, Systemic Lupus Erythematosus, Polymyositis, and Rheumatoid Arthritis.

The most classic symptom of systemic sclerosis (scleroderma) is sclerodactyl). Initial symptoms include swollen hands, which sometimes progress to this tapering and claw-like deformity. Not everyone with scleroderma develops this degree of skin hardening. Other symptoms can include morphea, linear sclerodactyl (hardened fingers), Raynaud's syndrome, calcinosis, and telangiectasia.

Blood tests such as anti-nuclear antibody (ANA) tests can be used in the diagnosis of both localized and systemic scleroderma. For example, anti-centromere antibodies (ACA) and anti-Scl-70 antibodies are indicative of patients in need of treatment for systemic sclerosis (Ho et al., 2003, Arthritis Res Ther. 5:80-93); anti-topo II alpha antibody are indicative of patients in need of treatment for local scleroderma; and anti-topo I alpha antibody are indicative of patients in need of treatment for systemic scleroderma. Several types of scleroderma and methods for diagnosing these types are recognized and well known in the art, including, but not limited to, juvenile scleroderma (Foeldvari, Curr Opin Rheumatol 14:699-703 (2002); Cefle et al., Int J Clin Pract. 58:635-638 (2004)); localized scleroderma; Nodular Scleroderma (Cannick, J Rheumatol. 30:2500-2502 (2003)); and Systemic scleroderma, including, but not limited to, Calcinosis, Raynaud's, Esophagus, Sclerodactyl), and Telangiectasia (CREST), limited systemic scleroderma, and diffuse systemic scleroderma. Systemic scleroderma is also known as systemic sclerosis (SSc). It may also be referred to as Progressive Systemic Sclerosis (PSSc), or Familial Progressive Systemic Sclerosis (FPSSc) (Nadashkevich et al., Med Sci Monit. 10:CR615-621 (2004); Frances et al., Rev Prat. 52:1884-90 (2002)). Systemic sclerosis is a multisystem disorder characterized by the presence of connective tissue sclerosis, vascular abnormalities concerning small-sized arteries and the microcirculation, and autoimmune changes.

The type of systemic scleroderma known as CREST is not characterized by any skin tightening. CREST is characterized by Calcinosis (calcium deposits), usually in the fingers; Raynaud's; loss of muscle control of the Esophagus, which can cause difficulty swallowing; Sclerodactyl), a tapering deformity of the bones of the fingers; and Telangiectasia, small red spots on the skin of the fingers, face, or inside of the mouth. Typically two of these symptoms is sufficient for diagnosis of CREST. CREST may occur alone, or in combination with any other form of Scleroderma or with other autoimmune diseases.

Limited Scleroderma is characterized by tight skin limited to the fingers, along with either pitting digital ulcers (secondary to Raynaud's) and/or lung fibrosis. The skin of the face and neck may also be involved in limited scleroderma.

Diffuse Scleroderma is diagnosed whenever there is proximal tight skin.

Proximal means located closest to the reference point. Proximal tight skin can be skin tightness above the wrists or above the elbows. Typically, a patient with skin tightness only between their elbows and their wrists will receive a diagnosis of either diffuse or limited systemic Scleroderma, depending on which meaning of proximal the diagnosing clinician uses.

The current therapies for scleroderma include extracorporeal photophoresis following 6-methoxypsoralen, and autologous stem cell transplant, The current treatments for scleroderma include the administration of the following agents, penicillamine, cholchicine, interferon alpha, interpheron gamma, chlorambucil, cyclosporine, 5-fluorouracil, cyclophosphamide, minocycline, thalidomide, etanercept, or methotrexate.

5.24. Determining CD22 Density in a Sample or Subject

While not required, assays for CD22 density can be employed to further characterize the patient's diagnosis. Methods of determining the density of antibody binding to cells are known to those skilled in the art (See, e.g., Sato et al., J. Immunology 165:6635-6643 (2000); which discloses a method of assessing cell surface density of specific CD antigens). Other standard methods include Scatchard analysis. For example, the antibody or fragment can be isolated, radiolabeled, and the specific activity of the radiolabeled antibody determined. The antibody is then contacted with a target cell expressing CD22. The radioactivity associated with the cell can be measured and, based on the specific activity, the amount of antibody or antibody fragment bound to the cell determined.

Alternatively, fluorescence activated cell sorting (FACS) analysis can be employed. Generally, the antibody or antibody fragment is bound to a target cell expressing CD22. A second reagent that binds to the antibody is then added, for example, a fluorochrome labeled anti-immunoglobulin antibody. Fluorochrome staining can then be measured and used to determine the density of antibody or antibody fragment binding to the cell.

As another suitable method, the antibody or antibody fragment can be directly labeled with a detectable label, such as a fluorophore, and bound to a target cell. The ratio of label to protein is determined and compared with standard beads with known amounts of label bound thereto. Comparison of the amount of label bound to the cell with the known standards can be used to calculate the amount of antibody bound to the cell.

In yet another aspect, the present invention provides a method for detecting in vitro or in vivo the presence and/or density of CD22 in a sample or individual. This can also be useful for monitoring disease and effect of treatment and for determining and adjusting the dose of the antibody to be administered. The in vivo method can be performed using imaging techniques such as PET (positron emission tomography) or SPECT (single photon emission computed tomography). Alternatively, one could label the anti-CD22 antibody with Indium using a covalently attached chelator. The resulting antibody can be imaged using standard gamma cameras the same way as ZEVALIN™ (Indium labeled anti-CD20 mAb) (Biogen Idec, Cambridge Mass.) is used to image CD20 antigen.

In one embodiment, the in vivo method can be performed by contacting a sample to be tested, optionally along with a control sample, with a human anti-CD22 antibody of the invention under conditions that allow for formation of a complex between an antibody of the invention and the human CD22 antigen. Complex formation is then detected (e.g., using an FACS analysis or Western blotting). When using a control sample along with the test sample, a complex is detected in both samples and any statistically significant difference in the formation of complexes between the samples is indicative of the presence of human CD22 in the test sample.

In other embodiments, mean fluorescence intensity can be used as a measure of CD22 density. In such embodiments, B cells are removed from a patient and stained with CD22 antibodies that have been labeled with a fluorescent label and the fluorescence intensity is measured using flow cytometry. Fluorescence intensities can be measured and expressed as an average of intensity per B cell. Using such methods, mean florescence intensities that are representative of CD22 density can be compared for a patient before and after treatment using the methods and compositions of the invention, or between patients and normal levels of hCD22 on B cells.

In patients where the density of CD22 expression on B cells has been determined, the density of CD22 may influence the determination and/or adjustment of the dosage and/or treatment regimen used with the anti-CD22 antibody of the compositions and methods of the invention. For example, where density of CD22 is high, it may be possible to use anti-CD22 antibodies that less efficiently mediate ADCC in humans. In certain embodiments, where the patient treated using the compositions and methods of the invention has a low CD22 density, a higher dosage of the anti-CD22 antibody of the compositions and methods of the invention may be used. In other embodiments, where the patient treated using the compositions and methods of the invention has a low CD22 density, a low dosage of the anti-CD22 antibody of the compositions and methods of the invention may be used. In certain embodiments, where the patient treated using the compositions and methods of the invention has a high CD22 density, a lower dosage of the anti-CD22 antibody of the compositions and methods of the invention may be used. In certain embodiments, CD22 density can be compared to CD20 density in a patient, CD22 density can be compared to an average CD22 density for humans or for a particular patient population, or CD22 density can be compared to CD22 levels in the patient prior to therapy or prior to onset of a B cell disease or disorder. In certain embodiments, the patient treated using the compositions and methods of the invention has a B cell malignancy where CD22 is present on the surface of B cells.

5.25. Immunotherapeutic Protocols

The anti-CD22 antibody compositions used in the therapeutic regimen/protocols, referred to herein as "anti-CD22 immunotherapy" can be naked antibodies, immunoconjugates and/or fusion proteins. The compositions of the invention can be used as a single agent therapy or in combination with other therapeutic agents or regimens. The anti-CD22 antibodies or immunoconjugates can be administered prior to, concurrently with, or following the administration of one or more therapeutic agents. Therapeutic agents that can be used in combination therapeutic regimens with the compositions of the invention include any substance that inhibits or prevents the function of cells and/or causes destruction of cells. Examples, include, but are not limited to, radioactive isotopes, chemotherapeutic agents, and toxins such as enzymatically active toxins of bacterial, fungal, plant or animal origin, or fragments thereof.

The therapeutic regimens described herein, or any desired treatment regimen can be tested for efficacy using the transgenic animal model, such as the mouse model described below, which expresses human CD22 antigen in place of native CD22 antigen. Thus, an anti-CD22 antibody treatment regimen can be tested in an animal model to determine efficacy before administration to a human.

The anti-CD22 antibodies, compositions and methods of the invention can be practiced to treat B cell diseases, including B cell malignancies. The term "B cell malignancy" includes any malignancy that is derived from a cell of the B cell lineage. Exemplary B cell malignancies include, but are not limited to: B cell subtype non-Hodgkin's lymphoma (NHL) including low grade/follicular, NHL, small lymphocytic (SL) NHL, intermediate grade/follicular NHL, intermediate grade diffuse NHL, high grade immunoblastic NHL, high grade lymphoblastic NHL, high grade small non-cleaved cell NHL; mantle-cell lymphoma, and bulky disease NHL; Burkitt's lymphoma; multiple myeloma; pre-B acute lymphoblastic leukemia and other malignancies that derive from early B cell precursors; common acute lymphocytic leukemia (ALL); chronic lymphocytic leukemia (CLL) including immunoglobulin-mutated CLL and immunoglobulin-unmutated CLL; hairy cell leukemia; Null-acute lymphoblastic leukemia; Waldenström's Macroglobulinemia; diffuse large B cell lymphoma (DLBCL) including germinal center B cell-like (GCB) DLBCL, activated B cell-like (ABC) DLBCL, and type 3 DLBCL; pro-lymphocytic leukemia; light chain disease; plasmacytoma; osteosclerotic myeloma; plasma cell leukemia; monoclonal gammopathy of undetermined significance (MGUS); smoldering multiple myeloma (SMM); indolent multiple myeloma (IMM); Hodgkin's lymphoma including classical and nodular lymphocyte pre-dominant type; lymphoplasmacytic lymphoma (LPL); and marginal-zone lymphoma including gastric mucosal-associated lymphoid tissue (MALT) lymphoma.

In one aspect of the invention, the inventive antibodies and compositions disclosed herein can deplete mature B cells. Thus, as another aspect, the invention can be employed to treat mature B cell malignancies (i.e., express Ig on the cell surface) including but not limited to follicular lymphoma, mantle-cell lymphoma, Burkitt's lymphoma, multiple myeloma, diffuse large B-cell lymphoma (DLBCL) including germinal center B cell-like (GCB) DLBCL, activated B cell-like (ABC) DLBCL, and type 3 DLBCL, Hodgkin's lymphoma including classical and nodular lymphocyte predominant type, lymphoplasmacytic lymphoma (LPL), marginal-zone lymphoma including gastric mucosal-associated lymphoid tissue (MALT) lymphoma, and chronic lymphocytic leukemia (CLL) including immunoglobulin-mutated CLL and immunoglobulin-unmutated CLL.

Further, CD22 is expressed earlier in B cell development than, for example, CD20, and is therefore particularly suited for treating pre-B cell and immature B cell malignancies (i.e., do not express Ig on the cell surface), for example, in the bone marrow. Illustrative pre-B cell and immature B cell malignancies include but are not limited to acute lymphoblastic leukemia In other particular embodiments, the invention can be practiced to treat extranodal tumors.

5.26. Anti-CD22 Immunotherapy

In accordance with the present invention "anti-CD22 immunotherapy" encompasses the administration of any of the anti-CD22 antibodies of the invention in accordance with any of the therapeutic regimens described herein or known in the art. The anti-CD22 antibodies can be administered as a naked antibodies, or immunoconjugates or fusion proteins.

Anti-CD22 immunotherapy encompasses the administration of the anti-CD22 antibody as a single agent therapeutic for the treatment of a B cell malignancy. Anti-CD22 immunotherapy encompasses methods of treating an early stage disease resulting from a B cell malignancy. Anti-CD22 immunotherapy encompasses methods of treating a B cell malignancy wherein the anti-CD22 antibody mediates ADCC and/or apoptosis. Anti-CD22 immunotherapy encompasses methods of treating a B cell malignancy wherein the anti-CD22 antibody is administered before the patient has received any treatment for the malignancy, whether that therapy is chemotherapy, radio chemical based therapy or surgical therapy.

In a preferred embodiment, a human subject having a B cell malignancy can be treated by administering a human or humanized antibody that preferably mediates human ADCC and/or apoptosis. In cases of early stage disease, or single agent therapies, any anti-CD22 antibody that preferably mediates ADCC and/or apoptosis can be used in the human subjects (including murine and chimeric antibodies); however, human and humanized antibodies are preferred.

Antibodies of IgG1 or IgG3 human isotypes are preferred for therapy. However, the IgG2 or IgG4 human isotypes can be used, provided they mediate human ADCC and/or apoptosis. Such effector function can be assessed by measuring the ability of the antibody in question to mediate target cell lysis by effector cells or to induce or modulate apoptosis in target cells in vitro or in vivo.

The dose of antibody used should be sufficient to deplete circulating B cells. Progress of the therapy can be monitored in the patient by analyzing blood samples. Other signs of clinical improvement can be used to monitor therapy.

Methods for measuring depletion of B cells that can be used in connection with the compositions and methods of the invention are will known in the art and include, but are not limited to the following embodiments. In one embodiment, circulating B cells depletion can be measured with flow cytometry using a reagent other than an anti-CD22 antibody that binds to B cells to define the amount of B cells. In other embodiments, B cell levels in the blood can be monitored using standard serum analysis. In such embodiments, B cell depletion is indirectly measured by defining the amount to an antibody known to be produced by B cells. The level of that antibody is then monitored to determine the depletion and/or functional depletion of B cells. In another embodiment, B cell depletion can be measured by immunochemical staining to identify B cells. In such embodiments, B cells or tissues or serum comprising B cells extracted from a patient can be placed on microscope slides, labeled and examined for presence or absence. In related embodiments, a comparison is made between B cells extracted prior to therapy and after to determine differences in the presence of B cells.

Tumor burden can be measured and used in connection with the compositions and methods of the invention. Methods for measuring tumor burden are will known in the art and include, but are not limited to the following embodiments. In certain embodiments, PET scans can be used to measure metabolic activity and identify areas of higher activity which are indicative of tumors. CT scans and MRI can also be used to examine soft tissue for the presence and size of tumors. In other embodiments, bone scan can be sued to measure tumor volume and location. In yet other embodiments, tumor burden can be measured by examining the blood flow into and out of a tumor using doppler technology (e.g., ultrasound). In such embodiments, changes in blood flow over time or deviations from normal blood flow in the appropriate tissue of a patient can be used to calculate an estimate to tumor burden. Such methods for measuring tumor burden can be used prior to and following the methods of treatment of the invention.

In preferred embodiments of the methods of the invention B cells are depleted and/or tumor burden is decreased while ADCC function is maintained.

In embodiments of the invention where the anti-CD22 antibody is administered as a single agent therapy, the invention contemplates use of different treatment regimens.

According to certain aspects of the invention, the anti-CD22 antibody used in the compositions and methods of the invention, is a naked antibody. In related embodiments, the dose of naked anti-CD22 antibody used is at least about 0.1, 0.2, 0.3, 0.4, 0.5, 0.6, 0.7, 0.8, 0.9, 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20, 20.5, 25, 30, 35, 40, 45, or 50 mg/kg of body weight of a patient. In certain embodiments, the dose of naked anti-CD22 antibody used is at least about 1 to 10, 5 to 15, 10 to 20, or 15 to 25 mg/kg of body weight of a patient. In certain embodiments, the dose of naked anti-CD22 antibody used is at least about 1 to 20, 3 to 15, or 5 to 10 mg/kg of body weight of a patient. In preferred embodiments, the dose of naked anti-CD22 antibody used is at least about 5, 6, 7, 8, 9, or 10 mg/kg of body weight of a patient.

In certain embodiments, the dose of naked anti-CD22 antibody used is at least about 25, 50, 75, 100, 125, 150, 175, 200, 225, 250, 275, 300, 325, 350, 375, 400, 425, 450, 475, or 500 mg/m². In other embodiments, the dose of naked anti-CD22 antibody used is at least about 1, 5, 10, 15, 20, 25, 50, 75, 100, 125, 150, 175, 200, 225, 250, 275, 300, 325, 350, 375, 400, 425, 450, 475, or 500 mg per administration.

In certain embodiments, the dose comprises about 375 mg/m² of anti-CD22 antibody administered weekly for 4 to 8 consecutive weeks. In certain embodiments, the dose is at least about 1, 2, 3, 4, 5, 6, 7, 8, 9, 10, 11, 12, 13, 14, or 15 mg/kg of body weight of the patient administered weekly for 4 to 8 consecutive weeks.

The exemplary doses of anti-CD22 antibody described above can be administered as described in Section 5.20.3. In one embodiment, the above doses are single dose injections. In other embodiments, the doses are administered over a period of time. In other embodiments, the doses are administered multiple times over a period of time. The period of time may be measured in days, weeks, or months. Multiple doses of the anti-CD22 antibody can be administered at intervals suitable to achieve a therapeutic benefit while balancing toxic side effects. For example, where multiple doses are used, it is preferred to time the intervals to allow for recovery of the patient's monocyte count prior to the repeat treatment with antibody. This dosing regimen will optimize the efficiency of treatment, since the monocyte population reflects ADCC function in the patient.

In certain embodiments, the compositions of the invention are administered to a human patient as long as the patient in responsive to therapy. In other embodiments, the compositions of the invention are administered to a human patient as long as the patient's disease does not progress. In related embodiments, the compositions of the invention are administered to a human patient until a patient's disease does not progress or has not progressed for a period of time, then the patient is not administered the compositions of the invention unless the disease reoccurs or begins to progress again. For example, a patient can be treated with any of the above doses for about 4 to 8 weeks, during which time the patient is monitored for disease progression. If disease progression stops or reverses, then he patient will not be administered the compositions of the invention until that patient relapses, i.e., the disease being treated reoccurs or progresses. Upon this reoccurrence or progression, the patient can be treated again with the same dosing regimen initially used or using other doses described above.

In certain embodiments, the compositions of the invention can be administered as a loading dose followed by multiple lower doses (maintenance doses) over a period of time. In such embodiments, the doses may be timed and the amount adjusted to maintain effective B cell depletion. In preferred embodiments, the loading dose is about 10, 11, 12, 13, 14, 15, 16, 17, or 18 mg/kg of patient body weight and the maintenance dose is at least about 5 to 10 mg/kg of patient body weight. In preferred embodiments, the maintenance dose is administered at intervals of every 7, 10, 14 or 21 days. The maintenance doses can be continued indefinitely, until toxicity is present, until platelet count decreases, until there is no disease progression, until the patient exhibits immunogenicity, or until disease progresses to a terminal state. In yet other embodiments, the compositions of the invention are administered to a human patient until the disease progresses to a terminal stage.

In embodiments of the invention where circulating monocyte levels of a patient are monitored as part of a treatment regimen, doses of anti-CD22 antibody administered may be spaced to allow for recovery of monocyte count. For example, a composition of the invention may be administered at intervals of every 8, 9, 10, 11, 12, 13, 14, 15, 16, 17, 18, 19, 20, 21, 22, 23, 24, 25, 26, 27, 28, 29, or 30 days.

In embodiments of the invention where an anti-CD22 antibody is conjugated to or administered in conjunction with a toxin, one skilled in the art will appreciate that the dose of anti-CD22 antibody can be adjusted based on the toxin dose and that the toxin dose will depend on the specific type of toxin being used. Typically, where a toxin is used, the dose of anti-CD22 antibody will be less than the dose used with a naked anti-CD22 antibody. The appropriate dose can be determined for a particular toxin using techniques well known in the art. For example, a dose ranging study can be conducted to determine the maximum tolerated dose of anti-CD22 antibody when administered with or conjugated to a toxin.

In embodiments of the invention where an anti-CD22 antibody is conjugated to or administered in conjunction with a radiotherapeutic agent, the dose of the anti-CD22 antibody will vary depending on the radiotherapeutic used. In certain preferred embodiments, a two step process is used. First, the human patient is administered a composition comprising a naked anti-CD22 antibody and about 6, 7, 8, 9, or 10 days later a small amount of the radiotherapeutic is administered. Second, once the tolerance, distribution, and clearance of the low dose therapy has been determined, the patient is administered a dose of the naked anti-CD22 antibody followed by a therapeutic amount of the radiotherapeutic is administered. Such treatment regimens are similar to those approved for treatment of Non-Hodgkin's lymphoma using ZEVALIN™ (Indium labeled anti-CD20 mAb) (Biogen Idec) or BEXXAR™ (GSK, Coulter Pharmaceutical).

5.27. Combination with Chemotherapeutic Agents

Anti-CD22 immunotherapy (using naked antibody, immunoconjugates, or fusion proteins) can be used in conjunction with other therapies including but not limited to, chemotherapy, radioimmunotherapy (RIT), chemotherapy and external beam radiation (combined modality therapy, CMT), or combined modality radioimmunotherapy (CMRIT) alone or in combination, etc. In certain preferred embodiments, the anti-CD22 antibody therapy of the present invention can be administered in conjunction with CHOP (Cyclophosphamide-Hydroxydoxorubicin-Oncovin (vincristine)-Prednisolone), the most common chemotherapy regimen for treating non-Hodgkin's lymphoma. As used herein, the term "administered in conjunction with" means that the anti-CD22 immunotherapy can be administered before, during, or subsequent to the other therapy employed.

In certain embodiments, the anti-CD22 immunotherapy is in conjunction with a cytotoxic radionuclide or radiotherapeutic isotope. For example, an alpha-emitting isotope such as $^{225}$Ac, $^{224}$Ac, $^{211}$At, $^{212}$Bi, $^{213}$Bi, $^{212}$Pb, $^{224}$Ra, or $^{223}$Ra. Alternatively, the cytotoxic radionuclide may a beta-emitting isotope such as $^{186}$Re, $^{188}$Re, $^{90}$Y, $^{131}$I, $^{67}$Cu, $^{177}$Lu, $^{153}$Sm, $^{166}$Ho, or $^{64}$Cu. Further, the cytotoxic radionuclide may emit Auger and low energy electrons and include the isotopes $^{125}$I, $^{123}$I or $^{77}$Br. In other embodiments the isotope may be $^{198}$Au, $^{32}$P, and the like. In certain embodiments, the amount of the radionuclide administered to the subject is between about 0.001 mCi/kg and about 10 mCi/kg.

In some preferred embodiments, the amount of the radionuclide administered to the subject is between about 0.1 mCi/kg and about 1.0 mCi/kg. In other preferred embodiments, the amount of the radionuclide administered to the subject is between about 0.005 mCi/kg and 0.1 mCi/kg.

In certain embodiments, the anti-CD22 immunotherapy is in conjunction with a chemical toxin or chemotherapeutic agent. Preferably the chemical toxin or chemotherapeutic agent is selected from the group consisting of an enediyne such as calicheamicin and esperamicin; duocarmycin, methotrexate, doxorubicin, melphalan, chlorambucil, ARA-C, vindesine, mitomycin C, cis-platinum, etoposide, bleomycin and 5-fluorouracil.

Suitable chemical toxins or chemotherapeutic agents that can be used in combination therapies with the anti-CD22 immunotherapy include members of the enediyne family of molecules, such as calicheamicin and esperamicin. Chemical toxins can also be taken from the group consisting of duocarmycin (see, e.g., U.S. Pat. No. 5,703,080 and U.S. Pat. No. 4,923,990), methotrexate, doxorubicin, melphalan, chlorambucil, ARA-C, vindesine, mitomycin C, cis-platinum, etoposide, bleomycin and 5-fluorouracil. Examples of chemotherapeutic agents also include adriamycin, doxorubicin, 5-fluorouracil, cytosine arabinoside ("Ara-C"), cyclophosphamide, thiotepa, taxotere (docetaxel), busulfan, cytoxin, taxol, methotrexate, cisplatin, melphalan, vinblastine, bleomycin, etoposide, ifosfamide, mitomycin C, mitoxantrone, vincreistine, vinorelbine, carboplatin, teniposide, daunomycin, caminomycin, aminopterin, dactinomycin, mitomycins, esperamicins (see, U.S. Pat. No. 4,675,187), melphalan and other related nitrogen mustards.

In other embodiments, for example, "CVB" (1.5 g/m$^2$ cyclophosphamide, 200-400 mg/m$^2$ etoposide, and 150-200 mg/m$^2$ carmustine) can be used in the combination therapies of the invention. CVB is a regimen used to treat non-Hodgkin's lymphoma. Patti et al., *Eur. J. Haematol.* 51:18 (1993). Other suitable combination chemotherapeutic regimens are well-known to those of skill in the art. See, for example, Freedman et al., "*Non-Hodgkin's Lymphomas*," in CANCER MEDICINE, VOLUME 2, 3rd Edition, Holland et al. (eds.), pp. 2028-2068 (Lea & Febiger 1993). As an illustration, first generation chemotherapeutic regimens for treatment of intermediate-grade non-Hodgkin's lymphoma include C-MOPP (cyclophosphamide, vincristine, procarbazine and prednisone) and CHOP (cyclophosphamide, doxorubicin, vincristine, and prednisone). A useful second generation chemotherapeutic regimen is m-BACOD (methotrexate, bleomycin, doxorubicin, cyclophosphamide, vincristine, dexamethasone and leucovorin), while a suitable third generation regimen is MACOP-B (methotrexate, doxorubicin, cyclophosphamide, vincristine, prednisone, bleomycin and leucovorin). Additional useful drugs include phenyl butyrate and brostatin-1. In a preferred multimodal therapy, both chemotherapeutic drugs and cytokines are co-administered with an antibody, immunoconjugate or fusion protein according to the present invention. The cytokines, chemotherapeutic drugs and antibody, immunoconjugate or fusion protein can be administered in any order, or together.

Other toxins that are preferred for use in the compositions and methods of the invention include poisonous lectins, plant toxins such as ricin, abrin, modeccin, botulina and diphtheria toxins. Of course, combinations of the various toxins could also be coupled to one antibody molecule thereby accommodating variable cytotoxicity. Illustrative of toxins which are suitably employed in the combination therapies of the invention are ricin, abrin, ribonuclease, DNase I, *Staphylococcal* enterotoxin-A, pokeweed antiviral protein, gelonin, diphtherin toxin, *Pseudomonas* exotoxin, and *Pseudomonas* endotoxin. See, for example, Pastan et al., *Cell* 47:641 (1986), and Goldenberg et al., *Cancer Journal for Clinicians* 44:43 (1994). Enzymatically active toxins and fragments thereof which can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *momordica charantia* inhibitor, curcin, crotin, *sapaonaria officinalis* inhibitor, gelonin, mitogellin, restrictocin, phenomycin, enomycin and the tricothecenes. See, for example, WO 93/21232 published Oct. 28, 1993.

Suitable toxins and chemotherapeutic agents are described in REMINGTON'S PHARMACEUTICAL SCIENCES, 19th Ed. (Mack Publishing Co. 1995), and in GOODMAN AND GILMAN'S THE PHARMACOLOGICAL BASIS OF THERAPEUTICS, 7th Ed. (MacMillan Publishing Co. 1985). Other suitable toxins and/or chemotherapeutic agents are known to those of skill in the art.

The anti-CD22 immunotherapy of the present invention may also be in conjunction with a prodrug-activating enzyme which converts a prodrug (e.g., a peptidyl chemotherapeutic agent, see, WO 81/01145) to an active anti-cancer drug. See, for example, WO 88/07378 and U.S. Pat. No. 4,975,278. The enzyme component of such combinations includes any enzyme capable of acting on a prodrug in such a way so as to covert it into its more active, cytotoxic form. The term "prodrug" as used in this application refers to a precursor or derivative form of a pharmaceutically active substance that is less cytotoxic to tumor cells compared to the parent drug and is capable of being enzymatically activated or converted into the more active parent form. See, e.g., Wilman, *"Prodrugs in Cancer Chemotherapy" Biochemical Society Transactions*, 14, pp. 375-382, 615th Meeting Belfast (1986) and Stella et al., *"Prodrugs: A Chemical Approach to Targeted Drug Delivery," Directed Drug Delivery*, Borchardt et al. (ed.), pp. 247-267, Humana Press (1985). Prodrugs that can be used in combination with the anti-CD22 antibodies of the invention include, but are not limited to, phosphate-containing prodrugs, thiophosphate-containing prodrugs, sulfate-containing prodrugs, peptide-containing prodrugs, D-amino acid-modified prodrugs, glycosylated prodrugs, α-lactam-containing prodrugs, optionally substituted phenoxyacetamide-containing prodrugs or optionally substituted phenylacetamide-containing prodrugs, 5-fluorocytosine and other 5-fluorouridine prodrugs which can be converted into the more active cytotoxic free drug. Examples of cytotoxic drugs that can be derivatized into a prodrug form for use in this invention include, but are not limited to, those chemotherapeutic agents described above.

In certain embodiments, administration of the compositions and methods of the invention may enable the postponement of toxic therapy and may help avoid unnecessary side effects and the risks of complications associated with chemotherapy and delay development of resistance to chemotherapy. In certain embodiments, toxic therapies and/or resistance to toxic therapies is delayed in patients administered the compositions and methods of the invention delay for up to about 6 months, 1, 2, 3, 4, 5, 6, 7, 8, 9, or 10 years.

5.28. Combination with Therapeutic Antibodies

The anti-CD22 immunotherapy described herein may be administered in combination with other antibodies, including, but not limited to, anti-CD20 mAb, anti-CD52 mAb, anti-CD19 antibody (as described, for example, in U.S. Pat. No. 5,484,892, U.S. patent publication number 2004/0001828 of U.S. application Ser. No. 10/371,797, U.S. patent publication number 2003/0202975 of U.S. application Ser. No. 10/372,481 and U.S. provisional application Ser. No. 60/420,472, the entire contents of each of which are incorporated by reference herein for their teachings of CD22 antigens and anti-CD22 antibodies), and anti-CD20 antibodies, such as RITUXAN™ (C2B8; RITUXIMAB™; IDEC Pharmaceuticals). Other examples of therapeutic antibodies that can be used in combination with the antibodies of the invention or used in the compositions of the invention include, but are not limited to, HERCEPTIN™ (Trastuzumab; Genentech), MYLOTARG™ (Gemtuzumab ozogamicin; Wyeth Pharmaceuticals), CAMPATH™ (Alemtuzumab; Berlex), ZEVALIN™ (Ipritumomab tiuxetan; Biogen Idec), BEXXAR™ (Tositumomab; GlaxoSmithKline Corixa), ERBITUX™ (Cetuximab; Imclone), and AVASTIN™ (Bevacizumab; Genentech).

In certain embodiments, the anti-CD22 and anti-CD20 and/or anti-CD52 mAb and/or anti-CD 19 mAb can be administered, optionally in the same pharmaceutical composition, in any suitable ratio. To illustrate, the ratio of the anti-CD22 and anti-CD20 antibody can be a ratio of about 1000:1, 500:1, 250:1, 100:1, 90:1, 80:1, 70:1, 60:1, 50:1, 40:1, 30:1, 20:1, 19:1, 18:1, 17:1, 16:1, 15:1, 14:1, 13:1, 12:1, 11:1, 10:1, 9:1, 8:1, 7:1, 6:1, 5:1, 4:1, 3:1, 2:1, 1:1, 1:2, 1:3, 1:4, 1:5, 1:6, 1:7, 1:8, 1:9, 1:10, 1:11, 1:12, 1:13, 1:14, 1:15, 1:16, 1:17, 1:18, 1:19, 1:20, 1:30, 1:40, 1:50, 1:60, 1:70, 1:80, 1:90, 1:100, 1:250, 1:500 or 1:1000 or more. Likewise, the ratio of the anti-CD22 and anti-CD52 antibody can be a ratio of about 1000:1, 500:1, 250:1, 100:1, 90:1, 80:1, 70:1, 60:1, 50:1, 40:1, 30:1, 20:1, 19:1, 18:1, 17:1, 16:1, 15:1, 14:1, 13:1, 12:1, 11:1, 10:1, 9:1, 8:1, 7:1, 6:1, 5:1, 4:1, 3:1, 2:1, 1:1, 1:2, 1:3, 1:4, 1:5, 1:6, 1:7, 1:8, 1:9, 1:10, 1:11, 1:12, 1:13, 1:14, 1:15, 1:16, 1:17, 1:18, 1:19, 1:20, 1:30, 1:40, 1:50, 1:60, 1:70, 1:80, 1:90, 1:100, 1:250, 1:500 or 1:1000 or more. Similarly, the ratio of the anti-CD22 and anti-CD 19 antibody can be a ratio of about 1000:1, 500:1, 250:1, 100:1, 90:1, 80:1, 70:1, 60:1, 50:1, 40:1, 30:1, 20:1, 19:1, 18:1, 17:1, 16:1, 15:1, 14:1, 13:1, 12:1, 11:1, 10:1, 9:1, 8:1, 7:1, 6:1, 5:1, 4:1, 3:1, 2:1, 1:1, 1:2, 1:3, 1:4, 1:5, 1:6, 1:7, 1:8, 1:9, 1:10, 1:11, 1:12, 1:13, 1:14, 1:15, 1:16, 1:17, 1:18, 1:19, 1:20, 1:30, 1:40, 1:50, 1:60, 1:70, 1:80, 1:90, 1:100, 1:250, 1:500 or 1:1000 or more.

5.29. Combination Compounds that Enhance Monocyte or Macrophage Function

In certain embodiments of the methods of the invention, a compound that enhances monocyte or macrophage function (e.g., at least about 10%, 15%, 20%, 25%, 30%, 35%, 40%, 45%, 50%, 55%, 60%, 65%, 70%, 75%, 80%, 85%, 90%, 95% or more) can be used in conjunction with the anti-CD22 antibody immunotherapy. Such compounds are known in the art and include, without limitation, cytokines such as interleukins (e.g., IL-12), and interferons (e.g., alpha or gamma interferon).

The compound that enhances monocyte or macrophage function or enhancement can be formulated in the same pharmaceutical composition as the antibody, immunoconjugate or antigen-binding fragment. When administered separately, the antibody/fragment and the compound can be administered concurrently (within a period of hours of each other), can be administered during the same course of therapy, or can be administered sequentially (i.e., the patient first receives a course of the antibody/fragment treatment and then a course of the compound that enhances macrophage/monocyte function or vice versa). In such embodiments, the compound that enhances monocyte or macrophage function is administered to the human subject prior to, concurrently with, or following treatment with other therapeutic regimens and/or the compositions of the invention. In one embodiment, the human subject has a blood leukocyte, monocyte, neutrophil, lymphocyte, and/or basophil count that is within the normal range for humans. Normal ranges for human blood leukocytes (total) is about 3.5-about 10.5 ($10^9$/L). Normal ranges for human blood neutrophils is about 1.7-about 7.0 ($10^9$/L), monocytes is about 0.3-about 0.9 ($10^9$/L), lymphocytes is about 0.9-about 2.9 ($10^9$/L), basophils is about 0-about 0.3 ($10^9$/L), and eosinophils is about 0.05-about 0.5 ($10^9$/L). In other embodiments, the human subject has a blood leukocyte count that is less than the normal range for humans, for example at least about 0.01, 0.05, 0.1, 0.2, 0.3, 0.4, 0.5, 0.6, 0.7, or 0.8 ($10^9$/L) leukocytes.

This embodiment of the invention can be practiced with the antibodies, immunoconjugates or antibody fragments of the invention or with other antibodies known in the art and is particularly suitable for subjects that are resistant to anti-CD 19, anti-CD52 and/or anti-CD20 antibody therapy (for example, therapy with existing antibodies such as C2B8), subjects that are currently being or have previously been treated with chemotherapy, subjects that have had a relapse in a B cell disorder, subjects that are immunocompromised, or subjects that otherwise have an impairment in macrophage or monocyte function. The prevalence of patients that are resistant to therapy or have a relapse in a B cell disorder may be attributable, at least in part, to an impairment in macrophage or monocyte function. Thus, the invention provides methods of enhancing ADCC and/or macrophage and/or monocyte function to be used in conjunction with the methods of administering anti-CD22 antibodies and antigen-binding fragments.

5.30. Combination with Immunoregulatory Agents

The anti-CD22 immunotherapy of the invention of the present invention may also be in conjunction with an immunoregulatory agent. In this approach, the use of chimerized antibodies is preferred; the use of human or humanized anti-CD22 antibody is most preferred. The term "immunoregulatory agent" as used herein for combination therapy refers to substances that act to suppress, mask, or enhance the immune system of the host. This would include substances that suppress cytokine production, downregulate or suppress self-antigen expression, or mask the MHC antigens. Examples of such agents include 2-amino-6-aryl-5-substituted pyrimidines (see, U.S. Pat. No. 4,665,077), azathioprine (or cyclophosphamide, if there is an adverse reaction to azathioprine); bromocryptine; glutaraldehyde (which masks the MHC antigens, as described in U.S. Pat. No. 4,120,649); anti-idiotypic antibodies for MHC antigens and MHC fragments; cyclosporin A; steroids such as glucocorticosteroids, e.g., prednisone, methylprednisolone, and dexamethasone; cytokine or cytokine receptor antagonists including anti-interferon-γ, -β, or -α antibodies; anti-tumor necrosis factor-α antibodies; anti-tumor necrosis factor-β antibodies; anti-interleukin-2 antibodies and anti-IL-2 receptor antibodies; anti-L3T4 antibodies; heterologous anti-lymphocyte globulin; pan-T antibodies, preferably anti-CD3 or anti-CD4/CD4a antibodies; soluble peptide containing a LFA-3 binding domain (WO 90/08187 published Jul. 26, 1990); streptokinase; TGF-β; streptodornase; RNA or DNA from the host; FK506; RS-61443; deoxyspergualin; rapamycin; T-cell receptor (U.S. Pat. No. 5,114,721); T-cell receptor fragments (Offner et al., Science 251:430-432 (1991); WO 90/11294; and WO 91/01133); and T-cell receptor antibodies (EP 340, 109) such as T10B9. Examples of cytokines include, but are not limited to lymphokines, monokines, and traditional polypeptide hormones. Included among the cytokines are growth hormone such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor; fibroblast growth factor; prolactin; placental lactogen; tumor necrosis factor-α; mullerian-inhibiting substance; mouse gonadotropin-associated peptide; inhibin; activin; vascular endothelial growth factor; integrin; thrombopoietin (TPO); nerve growth factors such as NGF-α; platelet-growth factor; transforming growth factors (TGFs) such as TGF-α and TGF-α; insulin-like growth factor-I and -II; erythropoietin (EPO); osteoinductive factors; interferons; colony stimulating factors (CSFs) such as macrophage-CSF (M-CSF); granulocyte-macrophage-CgP (GM-CSP); and granulocyte-CSF (G-CSF); interleuking (ILs) such as IL-1, IL-1a, IL-2, IL-3, IL-4, IL-5, IL-6, IL-7, IL-8, IL-9, IL-1 I, IL-12, IL-15; a tumor necrosis factor such as TNF-α or TNF-β; and other polypeptide factors including LIF and kit ligand (KL). As used herein, the term cytokine includes proteins from natural sources or from recombinant cell culture and biologically active equivalents of the native sequence cytokines. In certain embodiments, the methods further include administering to the subject one or more immunomodulatory agents, preferably a cytokine. Preferred cytokines are selected from the group consisting of interleukin-1 (IL-1), IL-2, IL-3, IL-12, IL-15, IL-18, G-CSF, GM-CSF, thrombopoietin, and γ interferon.

These immunoregulatory agents are administered at the same time or at separate times from the anti-CD22 antibodies of the invention, and are used at the same or lesser dosages than as set forth in the art. The preferred immunoregulatory agent will depend on many factors, including the type of disorder being treated, as well as the patient's history, but a general overall preference is that the agent be selected from cyclosporin A, a glucocorticosteroid (most preferably prednisone or methylprednisolone), OKT-3 monoclonal antibody, azathioprine, bromocryptine, heterologous anti-lymphocyte globulin, or a mixture thereof.

5.31. Combination with Other Therapeutic Agents

Agents that act on the tumor neovasculature can also be used in conjunction with anti-CD22 immunotherapy and include tubulin-binding agents such as combrestatin A4 (Griggs et al., Lancet Oncol. 2:82, (2001)) and angiostatin and endostatin (reviewed in Rosen, Oncologist 5:20 (2000), incorporated by reference herein). Immunomodulators suitable for use in combination with anti-CD22 antibodies include, but are not limited to, of α-interferon, γ-interferon, and tumor necrosis factor alpha (TNF-α). In certain embodiments, the therapeutic agents used in combination therapies using the compositions and methods of the invention are peptides.

In certain embodiments, the anti-CD22 immunotherapy is in conjunction with one or more calicheamicin molecules. The calicheamicin family of antibiotics are capable of producing double-stranded DNA breaks at sub-picomolar concentrations. Structural analogues of calicheamicin which may be used include, but are not limited to, $\gamma 1^1$, $\gamma 2^1$, $\gamma 3^1$, N-acetyl-$\gamma 1^1$, PSAG and 011 Hinman et al., Cancer Research 53:3336-3342 (1993) and Lode et al., Cancer Research 58: 2925-2928 (1998)).

Alternatively, a fusion protein comprising an anti-CD22 antibody of the invention and a cytotoxic agent may be made, e.g., by recombinant techniques or peptide synthesis.

In yet another embodiment, an anti-CD22 antibody of the invention may be conjugated to a "receptor" (such as streptavidin) for utilization in tumor pretargeting wherein the antagonist-receptor conjugate is administered to the patient, followed by removal of unbound conjugate from the circulation using a clearing agent and then administration of a "ligand" (e.g., avidin) which is conjugated to a therapeutic agent (e.g., a radionucleotide).

In certain embodiments, a treatment regimen includes compounds that mitigate the cytotoxic effects of the anti-CD22 antibody compositions of the invention. Such compounds include analgesics (e.g., acetaminophen), bisphosphonates, antihistamines (e.g., chlorpheniramine maleate), and steroids (e.g., dexamethasone, retinoids, deltoids, betamethasone, cortisol, cortisone, prednisone, dehydrotestosterone, glucocorticoids, mineralocorticoids, estrogen, testosterone, progestins).

In certain embodiments, the therapeutic agent used in combination with the anti-CD22 immunotherapy of the invention is a small molecule (i.e., inorganic or organic compounds having a molecular weight of less than about 2500 daltons). For example, libraries of small molecules may be commercially obtained from Specs and BioSpecs B.V. (Rijswijk, The Netherlands), Chembridge Corporation (San Diego, Calif.), Comgenex USA Inc. (Princeton, N.J.), and Maybridge Chemicals Ltd. (Cornwall PL34 OHW, United Kingdom).

In certain embodiments the anti-CD22 immunotherapy can be administered in combination with an anti-bacterial agent. Non-limiting examples of anti-bacterial agents include proteins, polypeptides, peptides, fusion proteins, antibodies, nucleic acid molecules, organic molecules, inorganic molecules, and small molecules that inhibit and/or reduce a bacterial infection, inhibit and/or reduce the replication of bacteria, or inhibit and/or reduce the spread of bacteria to other cells or subjects. Specific examples of anti-bacterial agents include, but are not limited to, antibiotics such as penicillin, cephalosporin, imipenem, axtreonam, vancomycin, cycloserine, bacitracin, chloramphenicol, erythromycin, clindamycin, tetracycline, streptomycin, tobramycin, gentamicin, amikacin, kanamycin, neomycin, spectinomycin, trimethoprim, norfloxacin, rifampin, polymyxin, amphotericin B, nystatin, ketocanazole, isoniazid, metronidazole, and pentamidine.

In certain embodiments the anti-CD22 immunotherapy of the invention can be administered in combination with an anti-fungal agent. Specific examples of anti-fungal agents include, but are not limited to, azole drugs (e.g., miconazole, ketoconazole (NIZORAL®), caspofungin acetate (CANCIDAS®), imidazole, triazoles (e.g., fluconazole (DIFLUCAN®)), and itraconazole (SPORANOX®)), polyene (e.g., nystatin, amphotericin B (FUNGIZONE®), amphotericin B lipid complex ("ABLC") (ABELCET®), amphotericin B colloidal dispersion ("ABCD") (AMPHOTEC®), liposomal amphotericin B (AMBISONE®)), potassium iodide (KI), pyrimidine (e.g., flucytosine (ANCOBON®), and voriconazole (VFEND®)). Administration of anti bacterial and anti-fungal agents can mitigate the effects or escalation of infectious disease that may occur in the methods of the invention where a patient's B cells are significantly depleted.

In certain embodiments of the invention, the anti-CD22 immunotherapy of the invention can be administered in combination with one or more of the agents described above to mitigate the toxic side effects that may accompany administration of the compositions of the invention. In other embodiments, the anti-CD22 immunotherapy of the invention can be administered in combination with one or more agents that are well known in the art for use in mitigating the side effects of antibody administration, chemotherapy, toxins, or drugs.

In certain embodiments of the invention where the anti-CD22 immunotherapy of the invention is administered to treat multiple myeloma, the compositions of the invention may be administered in combination with or in treatment regimens with high-dose chemotherapy (melphalan, melphalan/prednisone (MP), vincristine/doxorubicin/dexamethasone (VAD), liposomal doxorubicin/vincristine, dexamethasone (DVd), cyclophosphamide, etoposide/dexamethasone/cytarabine, cisplatin (EDAP)), stem cell transplants (e.g., autologous stem cell transplantation or allogeneic stem cell transplantation, and/or mini-allogeneic (non-myeloablative) stem cell transplantation), radiation therapy, steroids (e.g., corticosteroids, dexamethasone, thalidomide/dexamethasone, prednisone, melphalan/prednisone), supportive therapy (e.g., bisphosphonates, growth factors, antibiotics, intravenous immunoglobulin, low-dose radiotherapy, and/or orthopedic interventions), THALOMID™ (thalidomide, Celgene), and/or VELCADE™ (bortezomib, Millennium).

In embodiments of the invention where the anti-CD22 immunotherapy of the invention are administered in combination with another antibody or antibodies and/or agent, the additional antibody or antibodies and/or agents can be administered in any sequence relative to the administration of the antibody of this invention. For example, the additional antibody or antibodies can be administered before, concurrently with, and/or subsequent to administration of the anti-CD22 antibody or immunoconjugate of the invention to the human subject. The additional antibody or antibodies can be present in the same pharmaceutical composition as the antibody of the invention, and/or present in a different pharmaceutical composition. The dose and mode of administration of the antibody of this invention and the dose of the additional antibody or antibodies can be the same or different, in accordance with any of the teachings of dosage amounts and modes of administration as provided in this application and as are well known in the art.

5.32. Use of Anti-CD22 Antibodies in Diagnosing B Cell Malignancies

The present invention also encompasses anti-CD22 antibodies, and compositions thereof, that immunospecifically bind to the human CD22 antigen, which anti-CD22 antibodies are conjugated to a diagnostic or detectable agent. In preferred embodiments, the antibodies are human or humanized anti-CD22 antibodies. Such anti-CD22 antibodies can be useful for monitoring or prognosing the development or progression of a B cell malignancy as part of a clinical testing procedure, such as determining the efficacy of a particular therapy. Such diagnosis and detection can be accomplished by coupling an anti-CD22 antibody that immunospecifically binds to the human CD22 antigen to a detectable substance including, but not limited to, various enzymes, such as but not limited to, horseradish peroxidase, alkaline phosphatase, beta-galactosidase, or acetylcholinesterase; prosthetic groups, such as but not limited to, streptavidin/biotin and avidin/biotin; fluorescent materials, such as but not limited to, umbelliferone, fluorescein, fluorescein isothiocynate, rhodamine, dichlorotriazinylamine fluorescein, dansyl chloride or phycoerythrin; luminescent materials, such as but not limited to, luminol; bioluminescent materials, such as but not limited to, luciferase, luciferin, and aequorin; radioactive materials, such as but not limited to iodine ($^{131}$I, $^{125}$I, $^{123}$I, $^{121}$I), carbon ($^{14}$C), sulfur ($^{35}$S), tritium ($^{3}$H), indium ($^{115}$In, $^{113}$In, $^{112}$In, $^{111}$In), and technetium ($^{99}$Tc), thallium ($^{201}$Ti), gallium ($^{68}$Ga, $^{67}$Ga), palladium ($^{103}$Pd), molybdenum ($^{99}$Mo), xenon ($^{133}$Xe), fluorine ($^{18}$F), $^{153}$Sm, $^{177}$Lu, $^{159}$Gd, $^{149}$Pm, $^{140}$La, $^{175}$Yb, $^{166}$Ho, $^{90}$Y, $^{47}$Sc, $^{186}$Re, $^{188}$Re, $^{142}$Pr, $^{105}$Rh, $^{97}$Ru, $^{68}$Ge, $^{57}$Co, $^{65}$Zn, $^{85}$Sr, $^{32}$P, $^{153}$Gd, $^{169}$Yb, $^{51}$Cr, $^{54}$Mn, $^{75}$Se, $^{113}$Sn, and $^{117}$Tin; positron emitting metals using various positron emission tomographies, noradioactive paramagnetic metal ions, and molecules that are radiolabelled or conjugated to specific radioisotopes. Any detectable label that can be readily measured can be conjugated to an anti-CD22 antibody and used in diagnosing B cell malignancies. The detectable substance may be coupled or conjugated either directly to an antibody or indirectly, through an intermediate (such as, for example, a linker known in the art) using techniques known in the art. See, e.g., U.S. Pat. No. 4,741,900 for metal ions which can be conjugated to antibodies for use as a diagnostics according to the present invention. In certain embodiments, the invention provides for diagnostic kits comprising an anti-CD22 antibody conjugated to a diagnostic or detectable agent.

5.33. Use of Anti-CD22 Antibodies in Monitoring Immune Reconstitution

The present invention also encompasses anti-CD22 antibodies, and compositions thereof, that immunospecifically bind to the human CD22 antigen, which anti-CD22 antibodies are conjugated to a diagnostic or detectable agent. In preferred embodiments, the antibodies are human or humanized anti-CD22 antibodies. Such anti-CD22 antibodies can be useful for monitoring immune system reconstitution following immunosuppressive therapy or bone marrow transplantation. Such monitoring can be accomplished by coupling an anti-CD22 antibody that immunospecifically binds to the human CD22 antigen to a detectable substance including, but not limited to, various enzymes, such as, but not limited to, horseradish peroxidase, alkaline phosphatase, beta-galactosidase, or acetylcholinesterase; prosthetic groups, such as, but not limited to, streptavidin/biotin and avidin/biotin; fluorescent materials, such as, but not limited to, umbelliferone, fluorescein, fluorescein isothiocynate, rhodamine, dichlorotriazinylamine fluorescein, dansyl chloride or phycoerythrin; luminescent materials, such as, but not limited to, luminol; bioluminescent materials, such as, but not limited to, luciferase, luciferin, and aequorin; radioactive materials, such as, but not limited to, iodine ($^{131}$I, $^{125}$I, $^{123}$I, $^{121}$I), carbon ($^{14}$C), sulfur ($^{35}$S), tritium ($^{3}$H), indium ($^{115}$In, $^{113}$In, $^{112}$In, $^{111}$In), and technetium ($^{99}$Tc), thallium ($^{201}$Ti), gallium ($^{68}$Ga, $^{67}$Ga), palladium ($^{103}$Pd), molybdenum ($^{99}$Mo), xenon ($^{133}$Xe), fluorine ($^{18}$F), $^{153}$Sm, $^{177}$Lu, $^{159}$Gd, $^{149}$Pm, $^{140}$La, $^{175}$Yb, $^{166}$Ho, $^{90}$Y, $^{47}$Sc, $^{186}$Re, $^{188}$Re, $^{142}$Pr, $^{105}$Rh, $^{97}$Ru, $^{68}$Ge, $^{57}$Co, $^{65}$Zn, $^{85}$Sr, $^{32}$P, $^{153}$Gd, $^{169}$Yb, $^{51}$Cr, $^{54}$Mn, $^{75}$Se, $^{113}$Sn, and $^{117}$Tin; positron-emitting metals using various positron-emission tomographies, noradioactive paramagnetic metal ions, and molecules that are radiolabelled or conjugated to specific radioisotopes. Any detectable label that can be readily measured can be conjugated to an anti-CD22 antibody and used in diagnosing an autoimmune disease or disorder. The detectable substance may be coupled or conjugated either directly to an antibody or indirectly, through an intermediate (such as, for example, a linker known in the art) using techniques known in the art. See, e.g., U.S. Pat. No. 4,741,900 for metal ions which can be conjugated to antibodies for use as a diagnostics according to the present invention. In certain embodiments, the invention provides for diagnostic kits comprising an anti-CD22 antibody conjugated to a diagnostic or detectable agent.

5.34. Use of Anti-CD22 Antibodies in Diagnosing Autoimmune Diseases or Disorders The present invention also encompasses anti-CD22 antibodies, and compositions thereof, that immunospecifically bind to the human CD22 antigen, which anti-CD22 antibodies are conjugated to a diagnostic or detectable agent. In preferred embodiments, the antibodies are human or humanized anti-CD22 antibodies. Such anti-CD22 antibodies can be useful for monitoring or prognosing the development or progression of an autoimmune disease or disorder as part of a clinical testing procedure, such as determining the efficacy of a particular therapy. Such diagnosis and detection can be accomplished by coupling an anti-CD22 antibody that immunospecifically binds to the human CD22 antigen to a detectable substance including, but not limited to, various enzymes, such as but not limited to, horseradish peroxidase, alkaline phosphatase, beta-galactosidase, or acetylcholinesterase; prosthetic groups, such as but not limited to, streptavidin/biotin and avidin/biotin; fluorescent materials, such as but not limited to, umbelliferone, fluorescein, fluorescein isothiocynate, rhodamine, dichlorotriazinylamine fluorescein, dansyl chloride or phycoerythrin; luminescent materials, such as but not limited to, luminol; bioluminescent materials, such as but not limited to, luciferase, luciferin, and aequorin; radioactive materials, such as but not limited to iodine ($^{131}$I, $^{125}$I, $^{123}$I, $^{121}$I), carbon ($^{14}$C), sulfur ($^{35}$S), tritium ($^{3}$H), indium ($^{115}$In, $^{113}$In, $^{112}$In, $^{111}$In) and technetium ($^{99}$Tc), thallium ($^{201}$Ti), gallium ($^{68}$Ga, $^{67}$Ga), palladium ($^{103}$Pd), molybdenum ($^{99}$Mo), xenon ($^{133}$Xe), fluorine ($^{18}$F), $^{153}$Sm, $^{177}$Lu, $^{159}$Gd, $^{149}$Pm, $^{140}$La, $^{175}$Yb, $^{166}$Ho, $^{90}$Y, $^{47}$Sc, $^{186}$Re, $^{188}$Re, $^{142}$Pr, $^{105}$Rh, $^{97}$Ru, $^{68}$Ge, $^{57}$Co, $^{65}$Zn, $^{85}$Sr, $^{32}$P, $^{153}$Gd, $^{169}$Yb, $^{51}$Cr, $^{54}$Mn, $^{75}$Se, $^{113}$Sn, and $^{117}$Tin; positron emitting metals using various positron emission tomographies, noradioactive paramagnetic metal ions, and molecules that are radiolabelled or conjugated to specific radioisotopes. Any detectable label that can be readily measured can be conjugated to an anti-CD22 antibody and used in diagnosing an autoimmune disease or disorder. The detectable substance may be coupled or conjugated either directly to an antibody or indirectly, through an intermediate (such as, for example, a linker known in the art) using techniques known in the art. See, e.g., U.S. Pat. No. 4,741,900 for metal ions which can be conjugated to antibodies for use as a diagnostics according to the present invention. In certain embodiments, the invention provides for diagnostic kits comprising an anti-CD22 antibody conjugated to a diagnostic or detectable agent.

5.35. Kits

The invention provides a pharmaceutical pack or kit comprising one or more containers filled with a composition of the invention for the prevention, treatment, management or amelioration of a B cell malignancy, or one or more symptoms thereof, potentiated by or potentiating a B cell malignancy.

The present invention provides kits that can be used in the above-described methods. In one embodiment, a kit comprises a composition of the invention, in one or more containers. In another embodiment, a kit comprises a composition of the invention, in one or more containers, and one or more other prophylactic or therapeutic agents useful for the prevention, management or treatment of a B cell malignancy, or one or more symptoms thereof, potentiated by or potentiating a B cell malignancy in one or more other containers. Preferably, the kit further comprises instructions for preventing, treating, managing or ameliorating a B cell malignancy, as well as side effects and dosage information for method of administration. Optionally associated with such container(s) can be a notice in the form prescribed by a governmental agency regulating the manufacture, use or sale of pharmaceuticals or biological products, which notice reflects approval by the agency of manufacture, use or sale for human administration.

6. EXAMPLES

The following sections describe the design and construction of a chimeric variant of HB22.7 (chHB227) in which the mouse heavy chain and light chain constant regions have been replaced with human IgGγ1 and IgGκ regions respectively. These sections also describe two strategies for generation of humanized variants of HB22.7 heavy and light chain variable regions which comprise the antibodies of the invention.

The CD22-binding activity of the antibodies produced from various combinations of heavy and light chain variable regions is also described. Humanized forms of HB22.7 which exhibit a CD22 binding profile comparable to that of chHB22.7 are described.

The sections below also describe several mutations in the human framework regions that, when introduced into certain anti-CD22 antibodies of the invention, achieve the CD22 binding of the reference antibody produced by the parental mouse hybridoma, HB22.7. In the VH these residues are, for example, the Vernier residues N73 and G49, the canonical residue V24 and a CDR flanking residue S30. In the VK these are, for example, the VH interaction residue F87 and the CDR-flanking residues D60 and Y67.

6.1. Gene Assembly

Constructs were generated by a PCR-based gene assembly method first described by Stemmer (Stemmer, W. P. et al. 1995 *Gene,* 164:49-53). This method consists of four steps: oligonucleotide synthesis; gene assembly; gene amplification and cloning. Twenty-two 39-mer oligonucleotide primers were synthesized for each variable region. These primers were designed to overlap by 20 nucleotides and were ligated into a complete variable region during thermal cycling. The resulting PCR-products of the correct size were cloned into the pCR® 2.1 vector, provided with the TOPO-TA Cloning® kit, and used to transform DH5a competent cells according to the manufacturer's protocols. Colonies containing the plasmid, with a correctly sized insert, were identified by PCR-screening using oligonucleotide primers provided with the kit. Plasmid clones, identified with correct sized insert, were sequenced using the ABI Prism 310 genetic analyzer. The BigDye® Terminator v3.0 Cycle Sequencing Ready Reaction Kit was used for DNA sequencing according to the manufacturer's protocols. Plasmid DNA was prepared from selected clones using the QIAGEN Plasmid Maxi Kit according to the manufacturer's protocols.

Pairs of DNA plasmid expression vector preparations encoding (humanized or chimeric) heavy and light chains were used to transfect COS-7 cells, by electroporation as described by Kettleborough et al. 1991 *Protein Eng.,* 4:773-783. These transfected COS cells were cultured for 3 days to yield antibody-containing conditioned medium suitable for determining total IgG concentrations and CD22 binding activity.

Total Ig concentrations in the COS cell supernatant were quantified using a capture ELISA assay. IgG molecules were captured on a Nunc-Immuno MaxiSorp plate via an immobilized goat anti-human Igγ chain-specific antibody, and detected with anti-human kappa light chain HRP-conjugated antibody. The ELISA was calibrated using a reference IgG1 mAb of irrelevant specificity. CD22 binding activity was assessed using a cell-based CD22 ELISA as described in Section 6.2 and was normalized using equivalent concentrations of each humanized or chimeric antibody, thereby facilitating direct comparisons between alternative humanized versions of the HB22.7 antibodies and chHB227

6.2. The BHK-CD22 Binding Assay

The ability of chHB227 and its humanized variants to bind hCD22 was assessed in a cell based CD22 binding assay utilizing BHK cells expressing cell-surface human CD22 as a capture agent. Untransfected BHK cells not expressing hCD22 served as a control for non-specific binding. The BHK and BHK-CD22 lines were grown in DMEM supplemented with 10% Fetal Clone I and antibiotics. G418/Geneticin (0.75 mg/ml) was also added to the growth medium for BHK-CD22 only. The standard NCI protocol was used for the binding assay.

6.3. Expression Vectors

Plasmid DNA preparations of the expression vectors pKN10 and pG1D20 (AERES Biomedical, London) were produced using Qiagen Maxi kits following the manufacturers protocol to process 500 ml cultures of DH5α bacteria transfected with either vector. This produced 494 micrograms of pKN10 and 827 micrograms of pG1D20, each in 0.5 ml.

Expression vectors containing HB22.7 heavy and light chain genes were grown using the same protocol 6.4. Construction, Expression and Binding Characteristics of chHB227

The chHB227 expression vectors were constructed by (1) adding a suitable leader sequence to the VH and VK sequences, preceded by a HindIII restriction site and a Kozak sequence; and (2) introducing a 5' fragment of the human γ1 constant region, up to a natural ApaI restriction site, contiguous with the 3' end of the JH region of HB22.7 for the VH sequences and, for the VK sequence, adding a splice donor site and BamHI site.

The Kozak consensus sequence is used to obtain efficient translation of a variable region sequence. It defines the correct AUG codon from which a ribosome can commence translation. The mouse VH leader sequence (MUSIGHXL (SEQ ID NO:68) from the PCG1-1 VH gene, (Stenzel-Poore, M. P., et al 1987. *J. Immunol.* 139 (5), 1698-1703) and the mouse VK leader sequence (SK/CamRK) (SEQ ID NO:71) were selected based on their natural association with VH and VK genes that share high sequence homology with the mouse VH and VK expressed in HB22.7. Forward primers were designed to incorporate these leader sequences into the appropriate constructs. The splice donor sequence is important for the correct in-frame attachment of the variable region to its appropriate constant region, thus splicing out the V:C intron. The intron and CH are encoded in the expression vector downstream of the HB22.7 VH sequence.

The HB22.7 VH and VK genes were first carefully analyzed to identify any unwanted splice donor sites, splice acceptor sites, Kozak sequences and for the presence of any extra sub-cloning restriction sites which would later interfere with the subcloning and/or expression of functional whole antibody. In this case none were found.

6.4.1. The Light Chain Chimerization Primers

The region of the HB22.7 kappa chain leader sequence outside the primer site was used to search a database of mouse immunoglobulin leader sequences. A match was found with both SK/CamRK and BALB/c VkSer leader sequences. Primers were designed to generate a PCR product containing the complete SK/CamRK leader, and the HB22.7 VL region, with terminal restriction sites Hind III and Bam HI for cloning into the pKN10 expression vector. The forward primers introduced a Hind III restriction site; a Kozak translation initiation site and the SK/CamRK immunoglobulin leader sequence. The back primers introduced a splice donor site and a Bam HI restriction site.

6.4.2. The Heavy Chain Chimerization Primers

The region of the HB22.7 heavy chain leader sequence outside the primer site was used to search a database of mouse immunoglobulin leader sequences. A single match was found with MUSIGHXL also known as PCG1-1 VH (GenBank M17774) Primers were designed to generate a PCR product containing this complete leader, and the HB22.7 variable region, with terminal restriction sites and Hind III and Apa I for cloning into the pG1D20 expression vector. The forward primers introduced a Hind III restriction site, a Kozak translation initiation site, and the PCG1-1 immunoglobulin leader sequence. The back primers introduced the 5' end of the γ1 C region and a natural Apa I restriction site.

6.4.3. Generation of the chHB22.7Hc Heavy Chain Expression Construct

The HB22.7 VH clone S51/1 was amplified with VH Forward and VH Back primers in a polymerase chain reaction using ADVANTAGE®-HF 2 DNA polymerase. The 400 bp PCR product was cut with HindIII and Apa I and ligated into the vector pG1D20 (FIGS. 1A and 1B). Chemically competent DH5α bacteria were transformed with the ligation product. Clones were isolated and selected for the appearance of a 400 bp insert released by HindIII+Apa I digestion of individual plasmid preps. Selected plasmids were sequenced in both directions. The clone S76/12 was chosen after the sequence was confirmed in both directions as corresponding to the predicted sequence of the modified HB22.7 heavy chain. This clone was grown in 500 ml culture to produce 0.7 mg of plasmid DNA using the Qiagen Maxi Kit using the manufacturer's protocol.

6.4.4. Generation of the chHB22.7Kc Light Chain Expression Construct

Figure 2A:
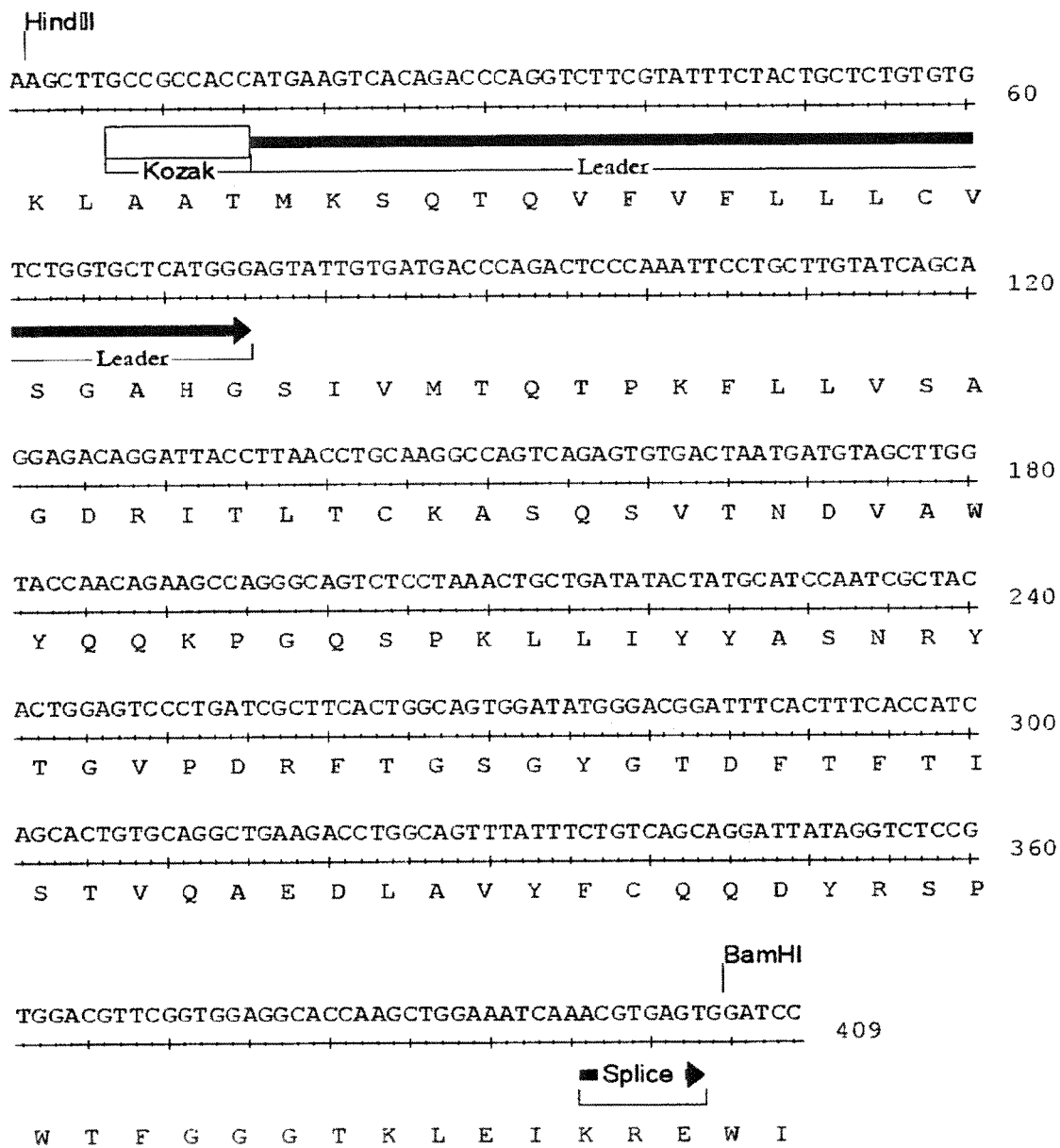

The HB22.7 VK clone S36/5 was amplified with VK Forward and VK Back primers in a polymerase chain reaction using ADVANTAGE®-HF 2 DNA polymerase. The 400 bp PCR product was cut with Bam HI and Hind III and ligated into the vector pKN10 (FIGS. 2A and 2B). Chemically competent DH5α bacteria were transformed with the ligation product. Clones were isolated and selected for the appearance of a 400 bp insert released by Bam HI+Hind III digestion of individual plasmid preps. Selected plasmids were sequenced in both directions. The clone S67/7 was chosen after the sequence was confirmed in both directions as corresponding to the predicted sequence of the modified HB22.7 light chain. This clone was grown in 500 ml culture to produce 0.54 mg of plasmid DNA using the Qiagen Maxi Kit using the manufacturers protocol.

6.4.5. Production and Binding Properties of chHB22.7 Antibody

COS 7 cells were cultured in DMEM supplemented with 10% Fetal Clone I and antibiotics. One week later, cells (0.7 ml at $10^7$/ml) were electroporated with the chimeric heavy and light chain expression plasmids (10 μg DNA each) or no DNA. The cells were plated in 8 ml of growth medium and cultured for 3 days.

6.4.6. Chimeric Antibody Production

A sandwich ELISA was used to measure antibody concentrations in the COS 7 supernatants. The transiently transformed COS 7 cells secreted a significant level of IgG1-kappa antibody, e.g., 916.4±83.2 and 1554.4±146 ng/ml.

6.4.7. Chimeric Antibody Activity

The BHK-CD22 binding assay was used to test the binding activity of the chHB227 antibody in the transiently transformed COS 7 culture supernatants. A goat anti-human Ig-HRP conjugate (Sigma Chemicals) was used to detect binding of chHB22.7 mAb while a goat anti-mouse Ig-HRP conjugate (Southern Biotechnology) was used to detect binding of the parental mouse HB22.7 mAb. The bound HRP conjugates were exposed to the substrate o-phenyldiamine (OPD) and the resulting products detected at 450 nm. As shown in FIG. 3, the binding of the parental mouse antibody produced by HB22.7 and the novel chHB227 antibody were found to be comparable. For concentrations of antibody above 100 ng/ml, there was a significant specific binding of both mouse and chimeric antibody to CD22, indicating that the chHB22.7 has retained CD22 binding activity.

6.5. Identification of Human Acceptor Framework Regions

The protein sequences of human and mouse immunoglobulins from The International Immunogenetics Database (2003) and the last available downloadable Kabat Database of Sequences of Proteins of Immunological Interest (1997) were used to compile a database of immunoglobulin protein sequences in Kabat alignment. This database contains 45,948 files. The sequence analysis program, SR v7.6, was used together with the Perl script program, Autohum, to query the human VH and human VK databases with the mouse antibody HB227 VH and VK protein sequences, SEQ ID NO:7 (VH) and SEQ ID NO:27 (VK) respectively.

The antibody structures from Protein Data Bank (PDB), release 103 (2003), (Berman H. M. et al., (2000) The Protein Data Bank. *Nucleic Acids Res.* 28, 235-242) were compiled into a sequence database containing 378 heavy and 378 light chain structures, which was queried with the mouse antibody HB227 VH and VK protein sequences, SEQ ID NO:7 (VH) and SEQ ID NO:27 (VK). The pair of heavy and light chains having the best overall sequence homology to HB22.7 was found in the 43C9 antibody (Thayer, M. M. et al. (1999) *J Mol. Biol.* 291, 329-345).

The program AbM was used to generate the molecular model of HB22.7 mouse antibody based on the antibody 43C9 heavy and light chain structures. The canonical structure of HB22.7 was used to select VH and VL CDR structures within the molecular modeling program, and to assist in the selection of human acceptor sequences with similar canonical structures. HB227 VH framework region residues predicted to have a packing interaction with the CDR, by virtue of being within 200% van der Waal's radius of a CDR atom, are indicated with asterisks as shown in FIG. 4. These framework positions in the humanized VH can be changed back to the corresponding residue in the VH of the mouse antibody HB22.7 (a process referred to herein as "backmutation"), according to methods known in the art.

6.5.1. Selection of a Human Variable Heavy Chain Framework for CDR Grafting

The nearest mouse germline gene to HB227 VH is V00767. The mutations from that germline sequence which are present in HB22.7 VH may relate to the binding specificity and/or affinity of HB22.7 antibody for human CD22. The HB227 VH framework region was compared with the human VH database. Among the 20 human VH sequences with high Vernier and framework homology to the mouse HB227 VH, seven were selected for further analyses (V46898, V46897, AY190826, AB066856, P2, OU, and CLL-11). These VH regions were determined not to be of mouse origin, humanized, or from a scFv library. VH 46897, had 63/87 identities in the framework region; CLL-11, had 62/87 identities in the framework region; and 46898, had 61/87 identities in the framework region. Each of these three antibodies had two Vernier mismatches, i.e., 14/16 Vernier residues are shared with the HB22.7 heavy chain. VH 46897 has an additional disadvantage of a mismatched Vernier residue at position 71, which is a glutamine instead of lysine. This mismatch is not present in the next four high-scoring candidate VH sequences, CLL-11, 46898, AY190826, and AB066856. Each of these four candidates also has a conservative substitution of alanine for the glycine at Vernier position 49, i.e., they each have the point mutation G49A compared to the HB227 VH sequence. VH 46898 also has a conservative substitution of arginine for the lysine at position 81 in FW 3, i.e., it contains the point mutation K81R compared to the HB227 VH sequence. The candidate VH sequences CLL-11, AY190826, and AB066856 have a nonconservative substitution of threonine for the lysine at this position, while candidate sequence 46897 has a serine at this position. The candidate VH sequences 46898, AY190826, and AB066856 also contain non-HB22.7 residues at positions 24 and 49.

Sequence VH 46898 (SEQ ID NO:6) was chosen as an acceptor framework region for the humanization of the HB227 VH. This antibody is a human anti-RSV antibody designated RF-2 and is derived from SCID mice implanted with human spleen cells (Heard C. et al. (1999) Two neutralizing human anti-RSV antibodies: cloning, expression, and characterization. *Mol. Med.* 5, 35-45).

6.5.2. Generation of HB22.7RHB

Figure 5A:
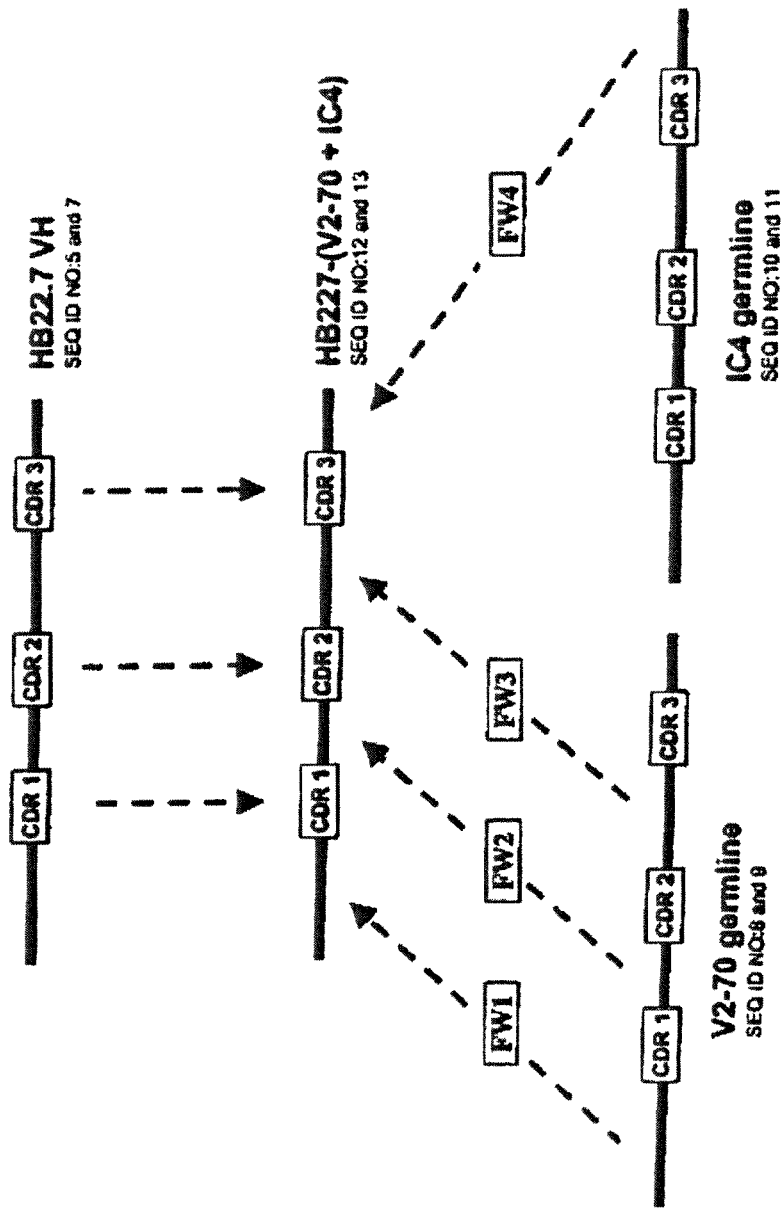
Figure 5C:
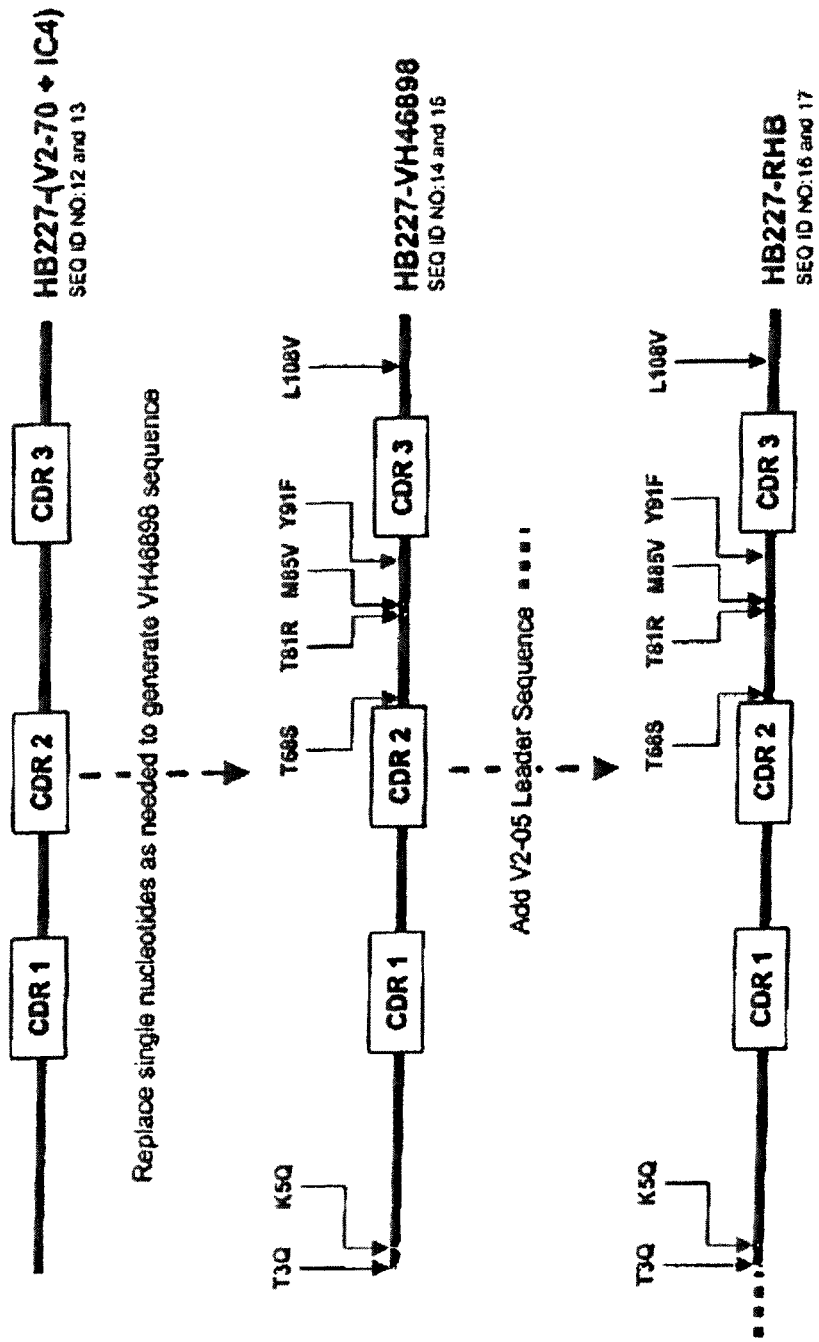

At the protein level, the humanization of HB227 VH required grafting the CDRs from the HB22.7 VH into the published VH 46898 framework amino acid sequence to generate the humanized HB227RHB construct depicted in FIGS. 5A and 5B. However, because the VH 46898 was not available as a nucleic acid sequence, the nearest germline VH genes, V2-70 and IC4 were used to derive the desired VH 46898 framework acceptor sequence. The acceptor nucleotide sequence was generated by mutation of the DNA sequence of VH2-70, combined with the framework 4 region of antibody IC4 (FIGS. 5A and 5B). The CDR DNA sequences of HB227 VH were combined with the framework DNA sequences of the newly created 46898 to generate the mature framework and CDR coding sequence (FIGS. 5A and 5B). As shown in FIGS. 5C and 5D, the resulting construct was further modified by replacing VH2-70 and IC4 codons and individual nucleotides with common codons needed to generate a VH 46898 nucleic acid sequence. To allow efficient expression of this sequence, a leader sequence from the nearest germline gene VH2-05 (FIGS. 5C and 5D) was positioned upstream of the VH construct. The VH2-50 leader was used because there is no published leader for VH2-70. The resulting humanized sequence with the VH2-50 leader sequence was named HB227RHB (SEQ ID NO:16 and 17) (FIGS. 5C and 5D).

Figure 5E:
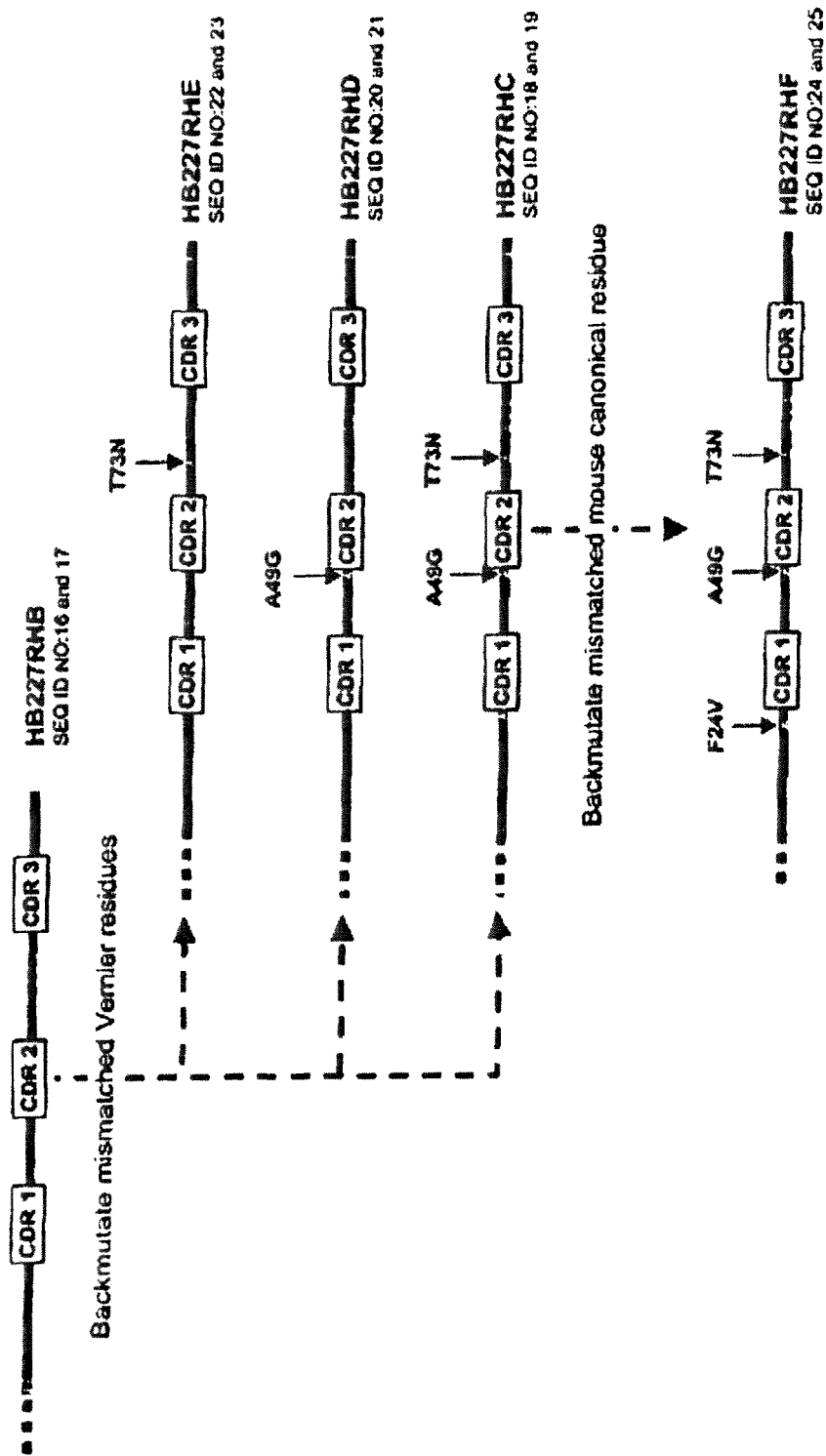

Several variants of HB227RHB were generated by back-mutating specific mismatched Vernier residues at positions 49 and 73 (FIGS. 5E and 5F). The resulting sequences, HB227RHC (SEQ ID NO:18 and 19), HB227RHD (SEQ ID NO:20 and 21) and HB227RHE (SEQ ID NO:22 and 23) are depicted in FIGS. 5E and 5F.

Inspection of the Vernier and canonical residues in the humanized VH, HB227RHC, indicated that only one of these residues, canonical residue F24, is not identical with the corresponding mouse residue (see FIGS. 5E and 5G). Accordingly, the next version of the humanized VH, HB227RHF, was designed to change the canonical residue F24 to V24. HB227RHF was generated from HB227RHC by mutating F24V using a mutagenesis kit (FIGS. 5E and 5G).

6.5.3. Selection of a Human Variable Light Chain Framework for CDR Grafting

The HB22.7 VK FW region was compared with the human VK database. The most closely related mouse germline gene is AJ235968. Somatic mutations present in the HB227 VK sequence may suggest critical residues for the specificity or affinity of the HB22.7 antibody for human CD22. FIG. 6 identifies the Vernier, Canonical, Interface residues and those residues predicted to be within the 200% van der Waal's radii (200% VdW) from a CDR atom in the AbM model of HB22.7 antibody. Twenty human VK sequences with the highest Vernier and FW homology to the HB22.7 VK sequence were selected from the available human VK sequences. Of the high FW homology scoring human light chains, all matched the mouse Vernier positions (FIG. 6) and two were neither mouse nor recombinant. These were AJ388641 and VL clone 47. These sequences have similar FW regions except for two important differences. First, the AJ388641 sequence contains two non-conservative substitutions compared with the HB22.7 VK sequence. The first is a substitution of Glutamine for Valine at position 3 and the second is a substitution of Glutamine for Glycine at position 100. Accordingly, the VL clone 47 sequence was chosen as the candidate human acceptor sequence for humanizing HB227 VK. The nearest human germline gene for the human acceptor sequence, VL clone 47 is DPK018. The nearest germline JK gene is JK2.

6.5.3.1. Generation of HB22.7RKA

Figure 7A:
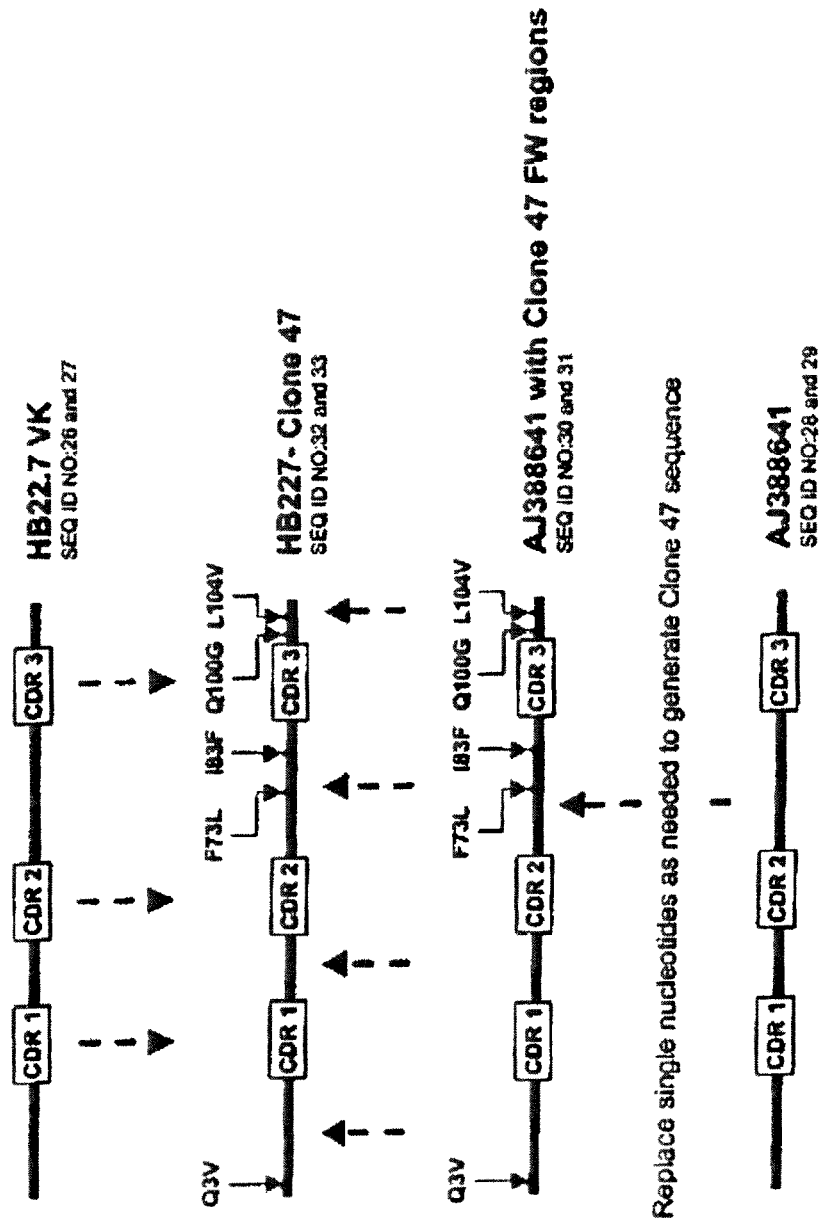

The generation of the humanized variant of HB22.7 VK, HB227RKA is shown in FIG. 7A-B. Because the desired kappa acceptor sequence, VL clone 47 was available only as a protein sequence (Welschof M. et al. (1995) *J Immunol Methods* 179, 203-214), a closely related available VL sequence, AJ388641, was mutated to generate the VL clone 47 sequence as shown in FIGS. 7A and 7B. The leader sequence from the germline human VK gene, DPK018 (FIGS. 7C and 7D), was attached to the mature HB227RKA to yield the complete HB22.7RKA sequence shown in FIGS. 7C and 7D.

Figure 7C:
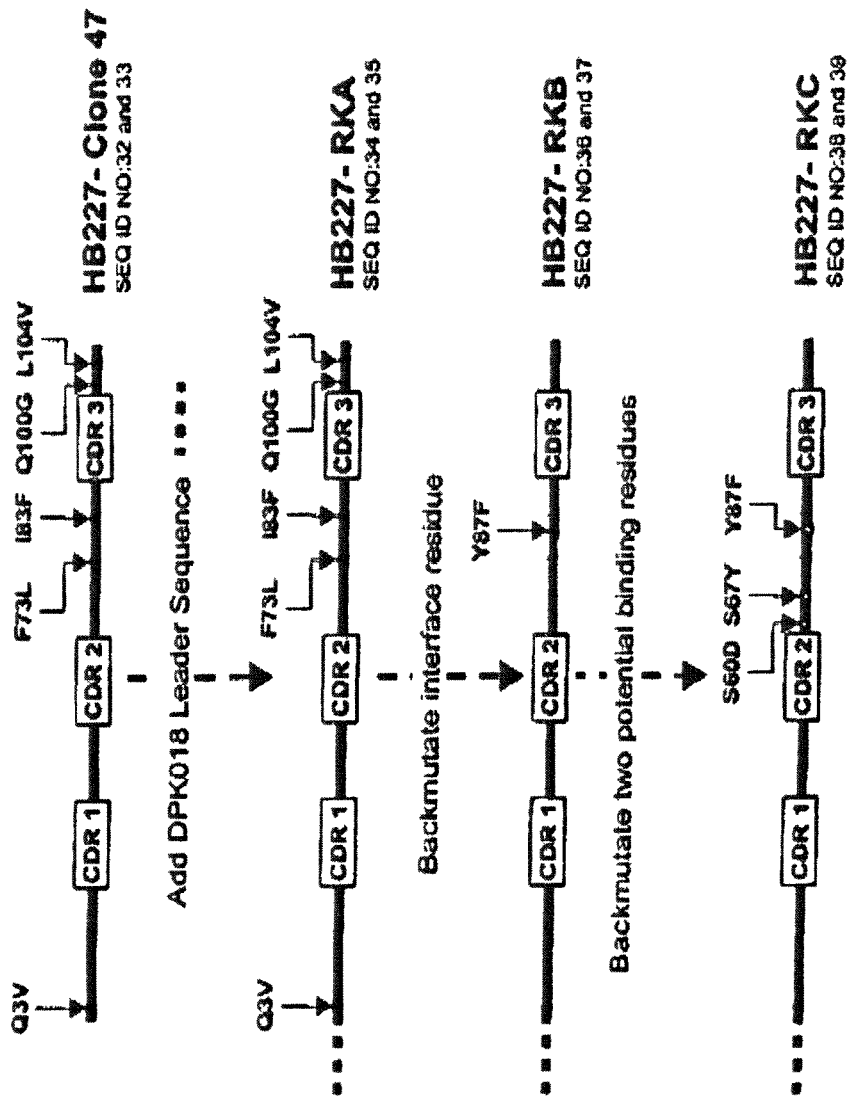

Inspection of the Vernier, canonical and VH interaction residues ("VCI" residues) in the humanized VK, HB227RKA (SEQ ID NO:34 and 35), indicated that only one residue was different from the mouse sequence, the VH-interface residue Y87 (FIGS. 7C and 7D). Accordingly, a new version of HB227RKA having the point mutation Y87F was constructed and designated HB227RKB (SEQ ID NO:36 and 37). However, the CD22 binding affinity of antibodies comprising HB227RKB was markedly less than that observed with the chHB22.7 mAb (FIG. 8). Accordingly, the model of the mouse HB22.7 Fv was examined in an effort to identify additional light chain residues that may influence binding. The model suggested the backmutations S60D and S67Y because these residues may participate in the antigen-antibody interface. Accordingly, these backmutations were introduced into HB22.7RKB to create HB227RKC (SEQ ID NO:38 and 39). The aspartic residue at 60 and the tyrosine at position 67 introduced into HB227RKC are found in the HB227 VK sequence (SEQ ID NO:26 and 27).

6.6. hCD22 Binding Characteristics of Antibodies Derived from Transiently Expressed Humanized HB22.7 VH and VK Sequences.

The VK versions HB227RKA, HB227RKB, and HB227RKC were expressed in combination with chimeric or humanized variable heavy chain sequences. The binding of the resulting antibodies to hCD22 is shown in FIG. 8. Antibodies comprising either HB227RHB or HB227RHC paired with HB227RKA did not effectively bind to hCD22 expressed on BHK cells. However, each VH and VK chain separately combined with its cognate chimeric light or heavy chain showed significant binding. The combination of the chimeric light chain with HB227RHC bound CD22 about two-fold better than with the same chimeric light chain associated with HB227RHB.

The CD22 binding of the HB227RHF+chL combination was comparable to that of the chHB227 antibody indicating that back mutation of canonical residue 24 is a beneficial step in the humanization of HB227 VH (FIG. 9) Successive increases in binding effectiveness from HB227RKA to HB227RKB to HB227RKC were observed when each light chain variant was combined with HB227RHF (FIG. 9), indicating that these VK mutations are providing important structural features and that the CDR-flanking non-VCI residues, D60 and Y67, are important for antigen binding. The RHF+RKC binding curve overlies the CH+CK fully chimeric binding curve, indicating that this humanized antibody (HB227RHF+HB227RKC) has CD22 binding activity similar to that of the chimeric antibody.

To confirm the binding effectiveness of the RHF+RKC humanized antibody, a competitive ELISA was performed with increasing amounts of the mouse HB22.7 antibody mixed with 250 ng/ml of chimeric or humanized antibody: FIG. 10 shows that the $IC_{50}$ for both the chimeric and the humanized antibody was about 4 μg/ml, indicating that the CD22 binding affinity of the humanized antibody is comparable to that of the chimeric antibody.

The CD22 binding assay was further used to demonstrate that HB227RKC in combination with HB227RHF resulted in an antibody with enhanced binding activity over the HB227RKC with either HB227 RHB or HB227RHC (FIG. 10). The improved binding of RHF results from the canonical F24V mutation and not the VL-interface mismatches at WI residues 37 and 91 that had little effect on binding (FIG. 11). Therefore back mutation of these residues is not necessary for binding to CD22.

6.7. Selection of an Alternative VH Framework for CDR Grafting Based on Conserved Vernier, Canonical, and Interface Residues Between HB227VH and a Human Acceptor VH.

Figure 13A:
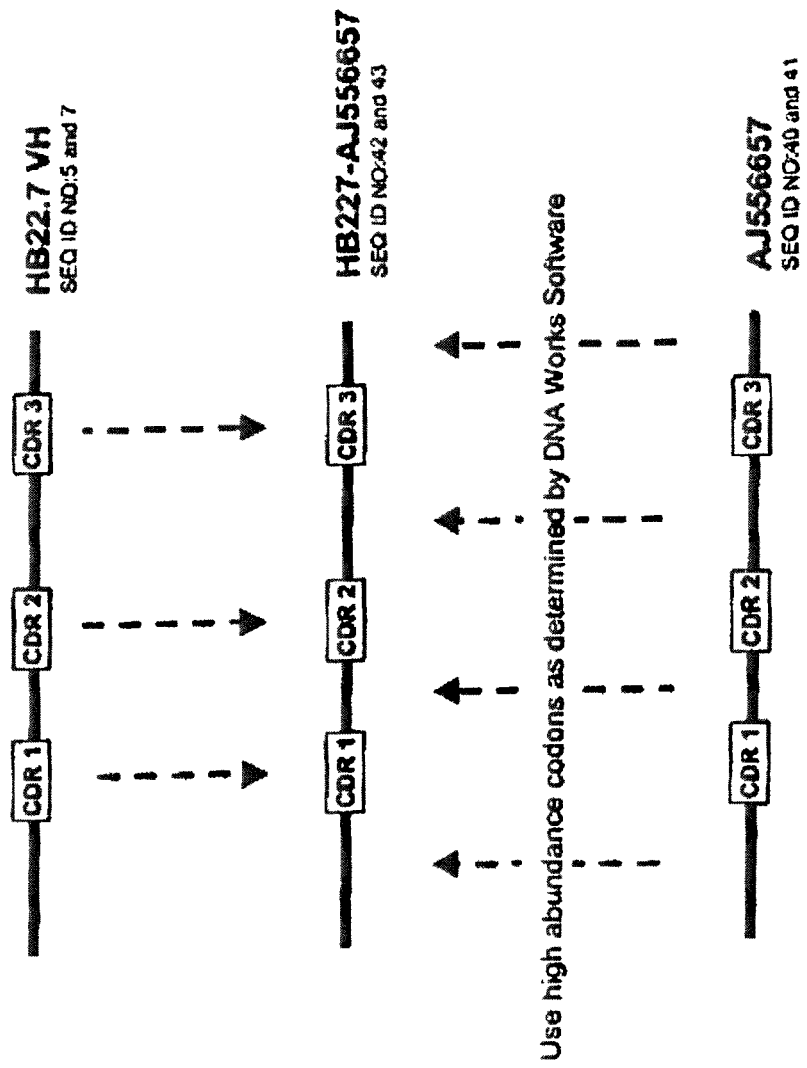
Figure 13C:
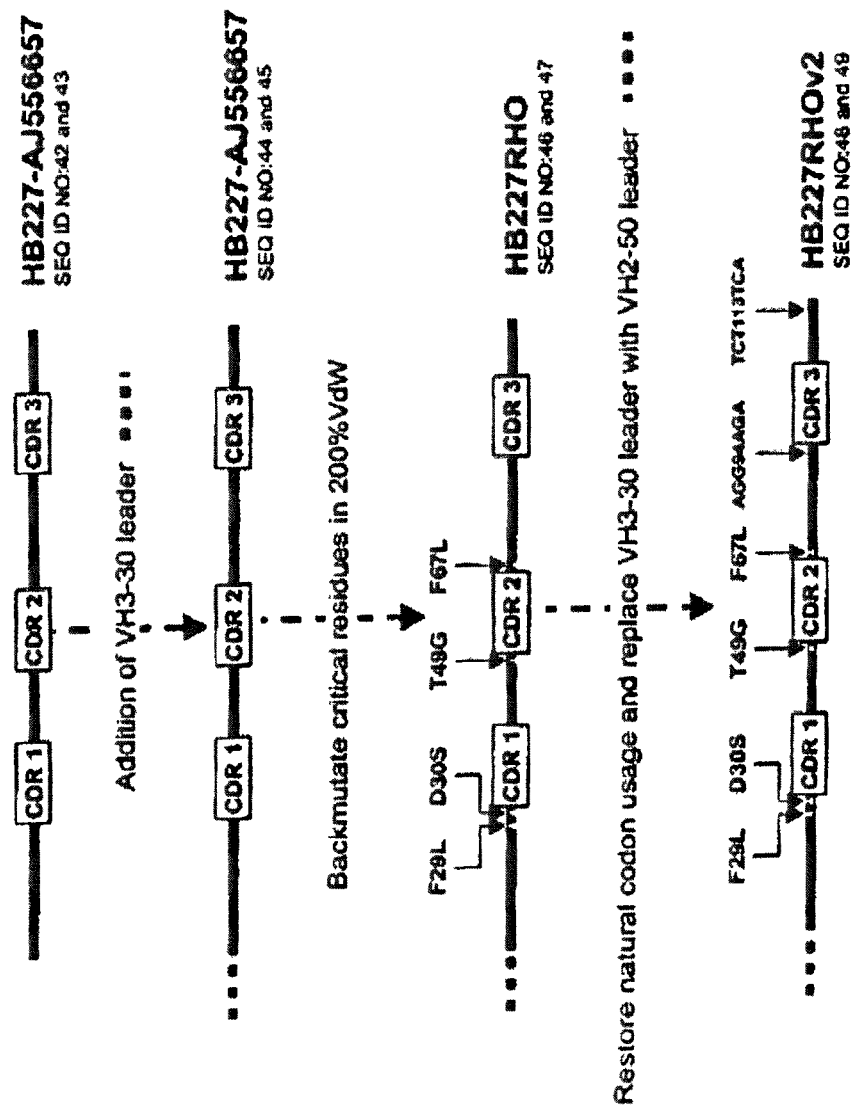
Figure 13E:
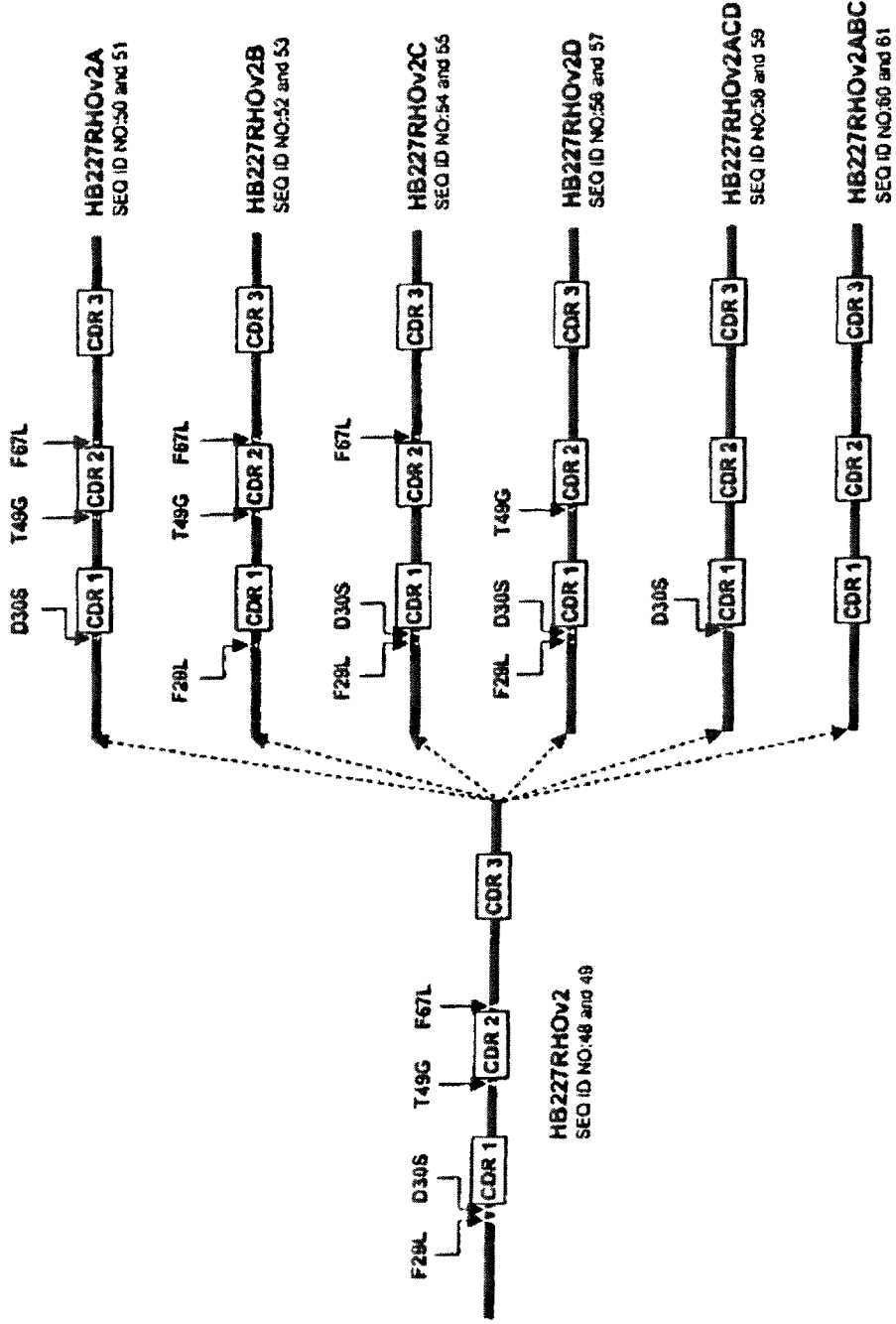
Figure 14A:
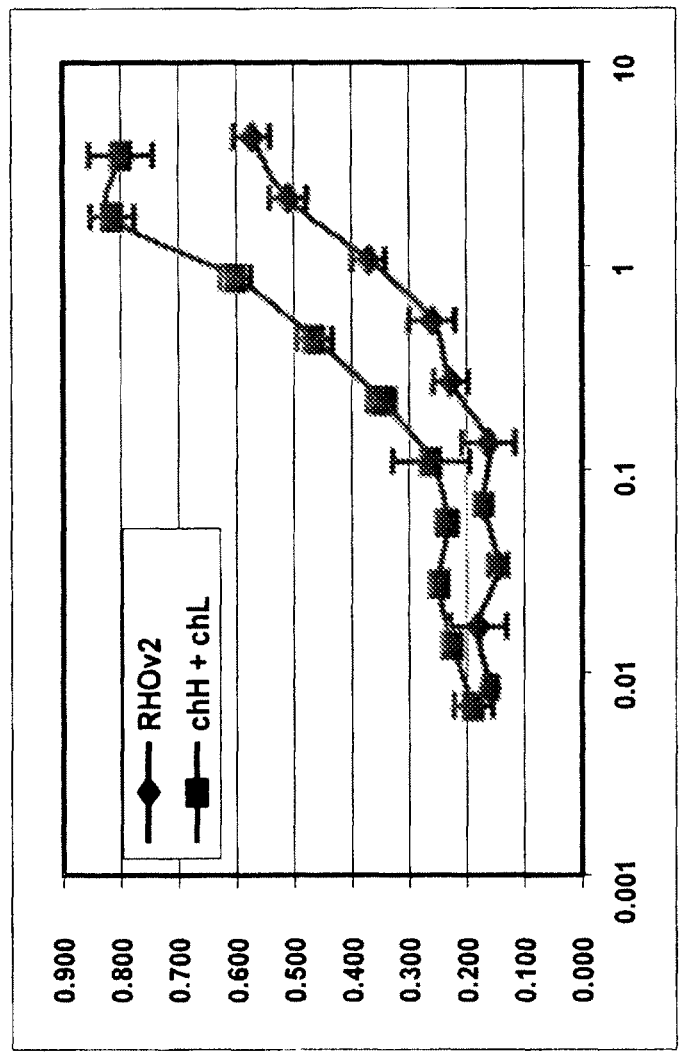
Figure 14B:
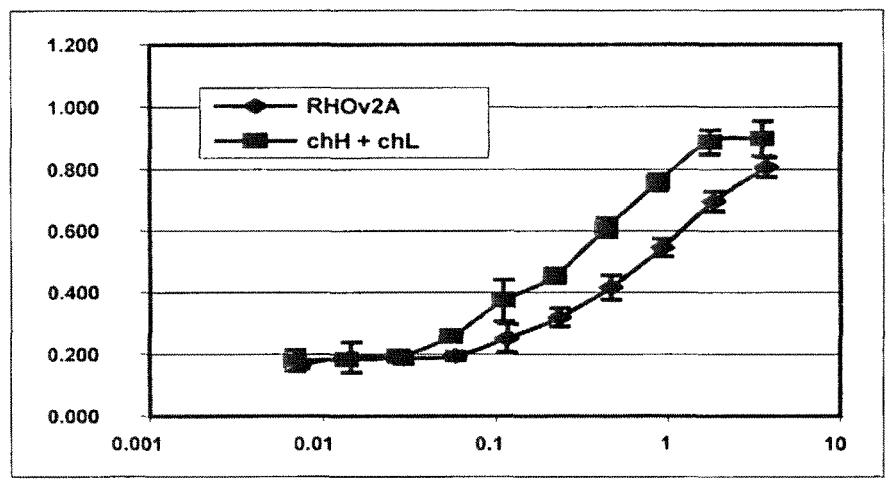
Figure 14C:
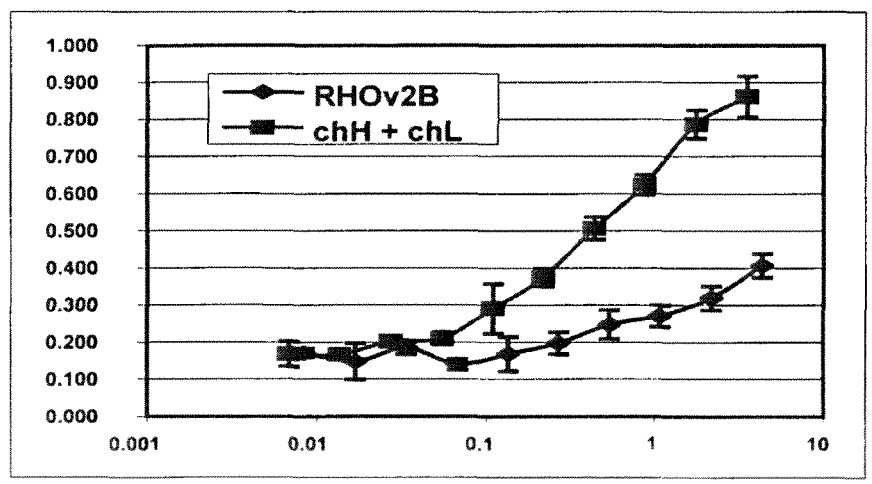
Figure 14D:
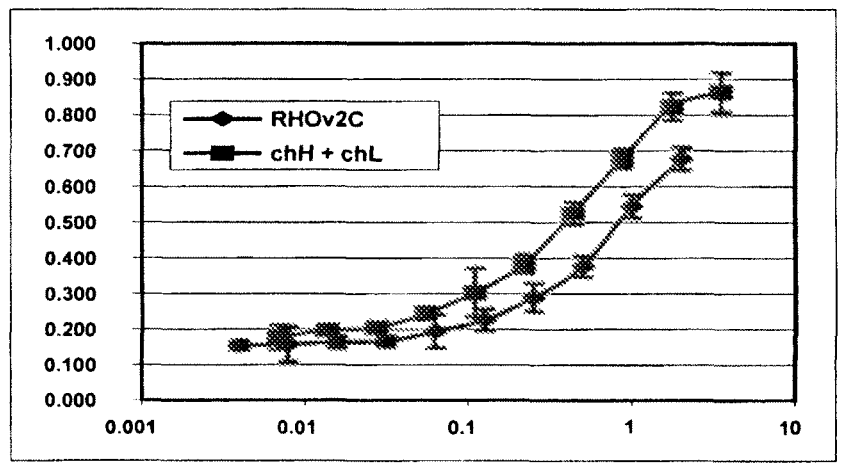
Figure 14E:
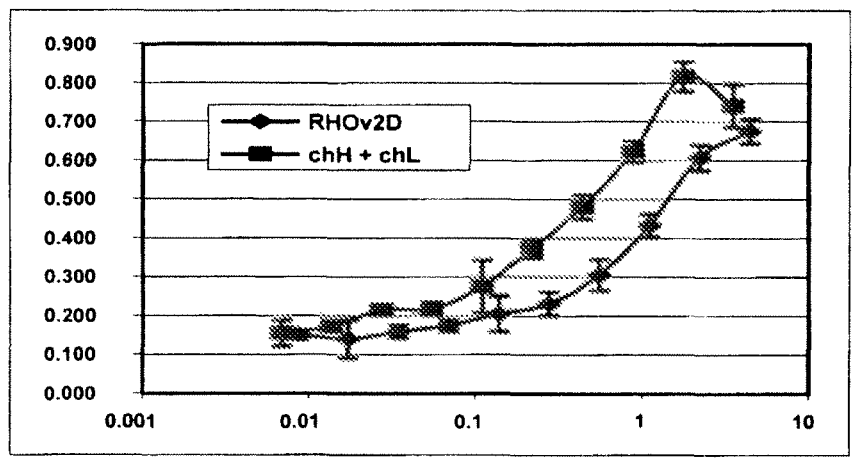
Figure 15A:
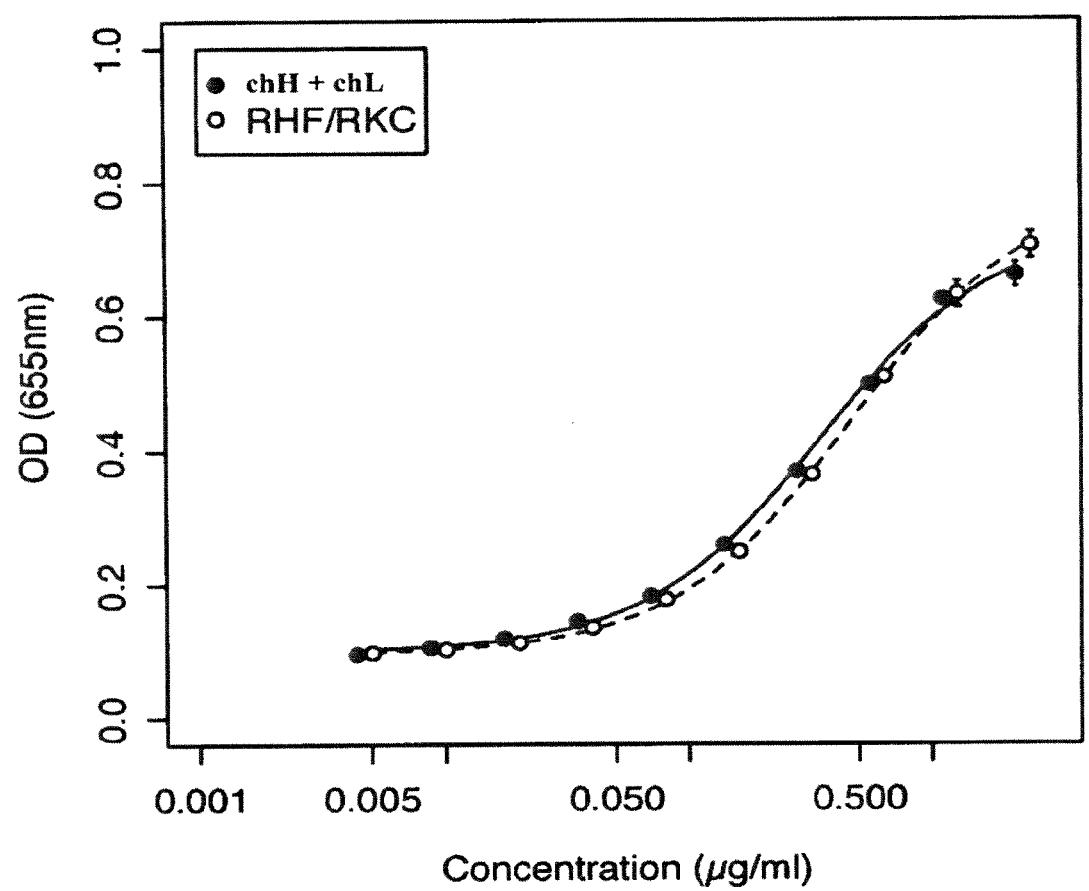
Figure 15B:
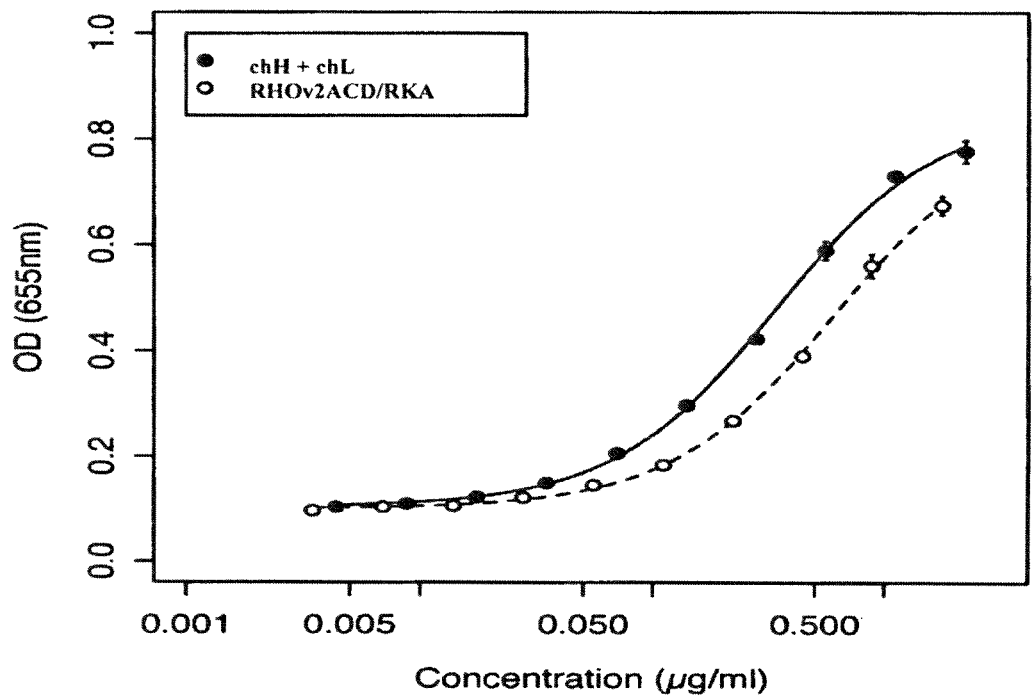
Figure 15C:
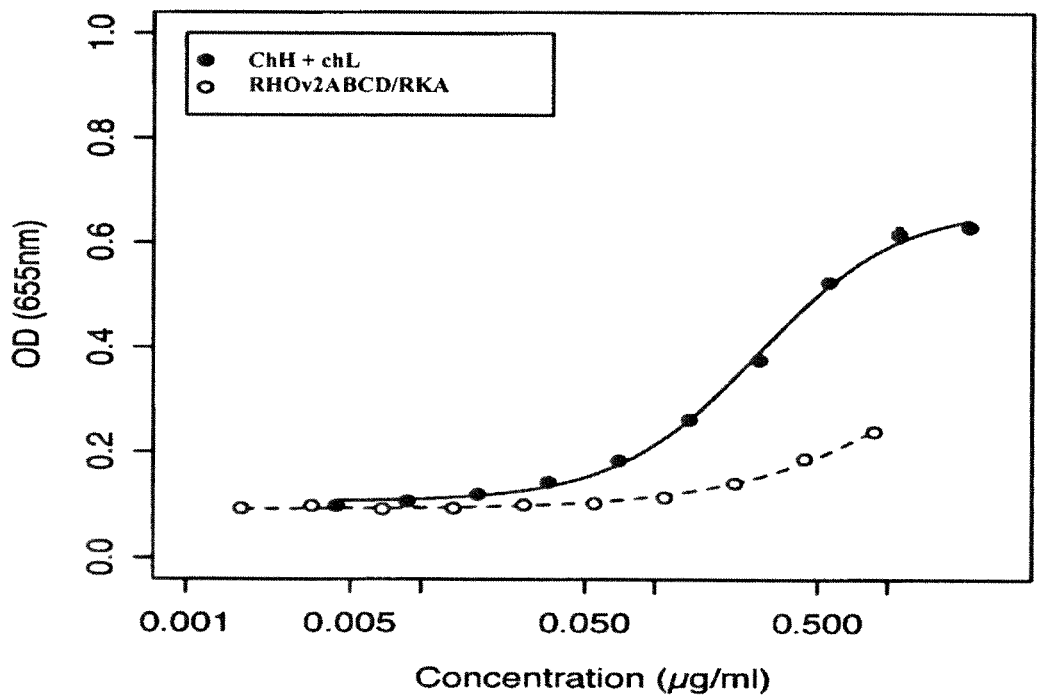
Figure 15D:
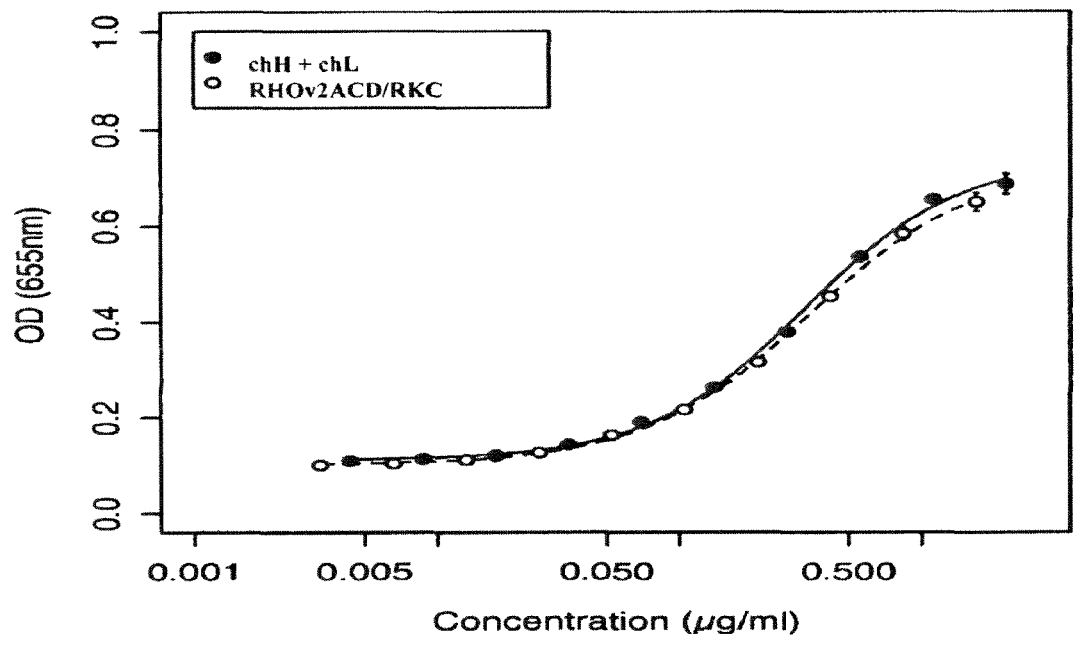
Figure 15E:
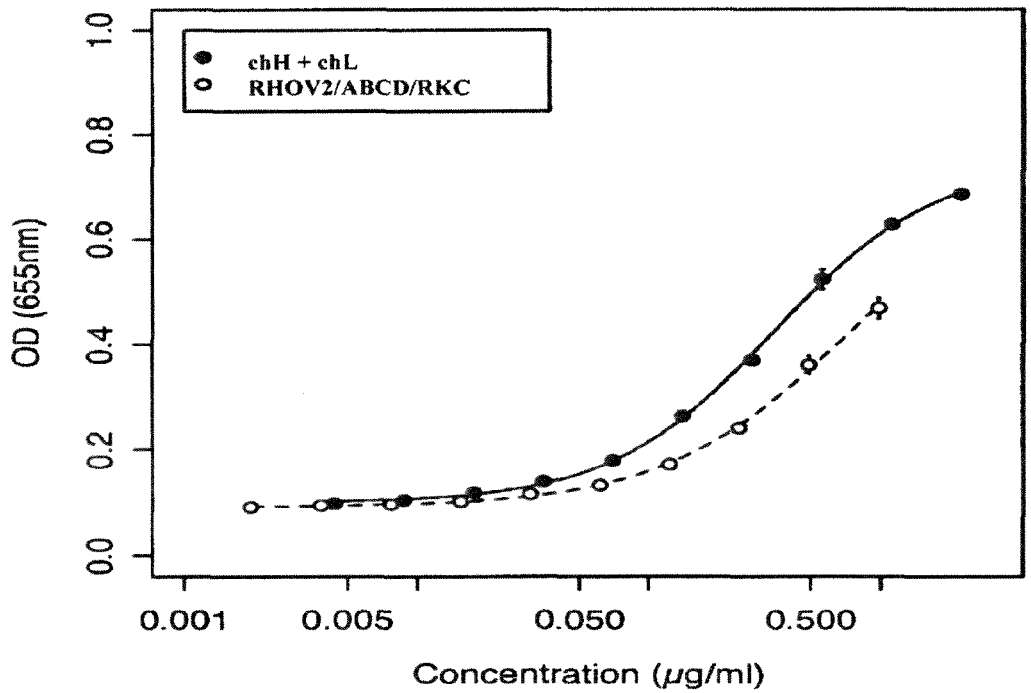

A molecular model of HB22.7 mouse antibody was used to determine those framework residues which are in a 200% van der Waal's ("VdW") envelope around the CDRs. These are framework amino acid residues containing an atom whose center is within 200% of its van der Waal's radius from the outer electron shell of an atom contained in a CDR residue, as described by Winter in U.S. Pat. No. 6,548,640. FIG. 12 shows these residues along with the Vernier, canonical, and interface residues. The VdW radii used were from Li, A. J. and R. Nussinov (1998) *Proteins* 32:111-127. Eight residues are not back-mutable because they lie outside the area defined by the 200% VdW envelope. Those VCI residues which are not in this envelope are the following: three canonicals, V24, G26, F27; one Vernier, N73; and the VL interaction residues V37, Q39, L45, and Y91. All other Vernier and canonical residues are positioned within the 200% VdW envelope.

The eight important VCI residues (V24, G26, F27, N73, V37, Q39, L45, and Y91) outside the VdW envelope were subsequently used to search the human VH sequence databases for VH regions encoding these residues at the specified positions. Among the approximately 2500 VH sequences analyzed, VCI positions 27, 37 and 91 were frequently conserved (FIG. 16). However, there were only 19 Vh sequences that matched at 4 of the 5 residues: 24; 26; 39; 45 and 73, and had fewer than 55 matching framework residues after back mutation of 4 framework residues (F29L, D30S, T49G, and F67L). Of these 19 sequences, 14 matching at framework position 73 were selected for further study. Eight of these 14 sequences have Pro or Cys residues at unusual positions, rendering them less acceptable as an acceptor sequence. A final shortlist of five human VH sequences was identified (FIG. 17). The AJ556657, AB067248, AJ556642, AJ556644, and AF376954 VH sequences shared 63.2%, 67.8%, 64.4%, 64.4% and 65.6% identity, respectively, with the FW of the parental mouse HB22.7 VH after backmutation of the four FW residues (F29L, D30S, T49G, and F67L) that fall within the 200% VdW envelope (FIGS. 12, 13A and 13B). From this data and close inspection of each framework position in each candidate framework acceptor, the AJ556657 VH (SEQ ID NO:40 and 41) (see Colombo, M. M. et al. (2003) *Eur. J. Immunol.* 33:3433-3438) was chosen as the alternative human VH acceptor.

6.8. Generation of Alternative Humanized Variant of HB227 VH

The strategy used for grafting the HB227 VH CDRs onto the human AJ556657 framework regions (SEQ ID NO:40 and 41) is shown if FIG. 13A-D. The HB227-AJ556657 (SEQ ID NO:42 and 43) protein sequence was further modified by introducing back mutations (F29L, D30S, T49G, and F67L) that fall within the 200% VdW envelope. The resulting protein sequence, HB227RHO, (SEQ ID NO:46 and 47) is shown in FIGS. 13C and 13D.

The signal sequence from the most homologous germline gene to AJ556657, VH 3-30, was assessed for the correct scission site when used with FW1 from AJ556657. Using a the signal protease algorithm (see Nielsen, H. J. et al. (1997) *Protein Eng.* 10:1-6), the VH3-30 leader sequence was found to predict the correct scission site, confirming that the VH 3-30 leader is an appropriate choice for RHO. The DNA and protein sequence of RHO with the VH 3-30 leader sequence are shown in FIGS. 13C and D. For this gene assembly only, we used an offline program for generating the DNA sequence directly from the protein sequence known as DNAWorks (see Hoover, D. M. and J. Lubkowski (2002) *Nucleic Acids Res.* 30:e43) which is designed to use high abundance human codons.

6.9. FACS Analyses of the Binding of HB227RHO+HB227RKC Antibody to hCD22 Expressed on BHK Cells.

The HB227RHO heavy chain was expressed along with the HB227RKC light chain and tested for CD22 binding. As shown in FIG. 11, the binding of HB227RHO is better than HB227RHC and similar to that observed with HB227RHF. Thus, the RHO heavy chain represents a functional low sequence identity alternative to the RHF heavy chain. It should be pointed out that RHO-mediated binding is achieved despite the presence of 6 mismatched vernier, 1 mismatched canonical, and 1 mismatched VL interaction residues i.e. 8 VCI residues are mismatched in RHO, but each of these mismatches is conservative in the AJ556657 acceptor framework. The mismatch at canonical residue 24, which was shown to be important in HB227RHF, was a non-conservative mismatch, whereas in 1-113227RHO, there was a conservative mismatch, which has less impact on binding.

6.10. Generation and Expression of RHOv2 by Backmutation of Residues within the 200% VdW Envelope Around the HB227 VH CDRs.

Critical framework residues within the 200% VdW envelope around the CDRs according to the molecular model which can be backmutated are F29; D30; T49; and F67. These four positions were backmutated to generate the RHO sequence and codon optimization was used to generate RHOv2 as shown in FIGS. 13C and 13D. The leader sequence of the VH2-05 gene was appended to the RHOv2 sequence. The codon usage of RHOv2 differs from that of RHO in that it is from the natural sequences, while for RHO, the codons were generated by the computer program DNA Works.

As shown in FIG. 14A, HB227RHOv2 VH in combination with HB227RKC VK resulted in an antibody that bound hCD22. To determine which of the backmutated residues were important for binding activity, the F29L; D30S; T49G; and F67L mutations were individually reversed to generate HB227v2A (SEQ ID NO:50 and 51), HB227v2B (SEQ ID NO:52 and 53), HB227v2C (SEQ ID NO:54 and 55), and HB227v2D (SEQ ID NO:56 and 57) (FIG. 13E-G).

COS cell transfections with each HB227RHOv2 variant in combination with the HB227RKC VK yielded antibodies that bound BHK-hCD22 expressing cells with differing intensities (FIGS. 14A-14E). Human CD22 binding was adversely affected by reversing the D30S backmutation (i.e. introducing an aspartic residue at position 30) as was done in HB227RHOv2B. Therefore, the mouse Serine 30 residue is important for strong binding but the Leu29, Gly 49 and Leu67 can be replaced by the corresponding amino acids in human AJ556657 sequence without significantly compromising binding.

In an effort to reduce the number of backmutations, the HB227RHOv2A VH was further mutated so as to re-insert the corresponding human residues at positions 49 and 67 (tyrosine and phenylalanine respectively). The resulting construct, RHOv2ACD (SEQ ID NO:58 and 59) is shown in FIGS. 13E and 13G along with a construct, HB227RHOv2ABCD (SEQ ID NO:60 and 61) in which all four backmutations were reversed (FIGS. 13E and 13G). As shown in FIGS. 15A, 15B and 15D, the HB227RHOv2ACD VH in combination with either HB227RKA or HB227RKC VK yields an antibody that binds hCD22 similarly to that of the HB227RHF VH in combination with HB227RKC. The HB227RHOv2ABCD VH yielded a hCD22 binding antibody when associated with the HB227RKC VK (FIG. 15E) but binding was significantly compromised when the same VH was associated with the HB227RKA light chain. (FIG. 15C).

Taken together, these data indicate that a number of humanized versions of the HB22.7 VH and VK chains were created that retain the binding properties of the parental mouse antibody derived from the HB22.7 hybridoma.

6.10.1. Antibodies and Immunofluorescence Analysis

The anti-CD22 antibodies described above, which bind to the human CD22 antigen, can be used in the approaches disclosed below. Other antibodies, which could be employed in the experiments described below include monoclonal mouse anti-CD19 antibodies that bind to mouse CD19, e.g. MB19-1 (IgA) (Sato et al., *J. Immunol.*, 157:4371-4378 (1996)); monoclonal mouse CD20-specific antibodies (Uchida et al., *Intl. Immunol.*, 16:119-129 (2004)); B220 antibody RA3-6B2 (DNAX Corp., Palo Alto, Calif.); and CD5, CD43 and CD25 antibodies (BD PHARMINGEN™, Franklin Lakes, N.J.). Isotype-specific and anti-mouse Ig or IgM antibodies can be obtained from Southern Biotechnology Associates, Inc. (Birmingham, Ala.).

Either mouse pre-B cell lines, transfected with hCD22 cDNA, which can be developed using methods and materials known in the art (see e.g. Alt et al., *Cell*, 27:381-388 (1981) and Tedder and Isaacs, *J. Immunol.*, 143:712-717 (1989)), or single-cell leukocyte suspension, are stained on ice using predetermined, optimal concentrations of each fluorescently-labeled antibody for 20-30 minutes according to established methods (Zhou et al., *Mol. Cell. Biol.*, 14:3884-3894 (1994)). Cells with the forward and side light scatter properties of lymphocytes can then be analyzed on FACSCAN® or FACSCALIBUR® flow cytometers (Becton Dickinson, San Jose, Calif.). Background staining would be determined using unreactive control antibodies (CALTAG™ Laboratories, Burlingame, Calif.) with gates positioned to exclude nonviable cells. For each sample examined, ten thousand cells with the forward and side light scatter properties of mononuclear cells are analyzed whenever possible, with fluorescence intensities shown on a four-decade log scale.

Mice.

Transgenic mice expressing hCD22 and their wild-type (WT) littermates can be produced as described in the art (Zhou et al., *Mol. Cell. Biol.*, 14:3884-3894 (1994)). For example, hCD22tg mice can be generated from original hCD22 founders (e.g. C57BL/6×B6/SJL), and then crossed onto a C57BL/6 background for at least 7 generations. hCD22tg mice would be generated from original hCD22 founders (e.g. C57BL16×B6/SJL). After multiple generations of backcrossing, mice would be obtained in which their B cells would express cell surface density of human CD22 at about the same density found on human B cells.

Mice bred with FcR (Fc receptor) common γ chain (FcRγ)-deficient mice (FcRγ$^{-/-}$, B6.129P2-Fcerg1$^{tm1}$) are available from Taconic Farms (Germantown, N.Y.) and could be used to generate hCD22$^{+/-}$ FcRγ$^{-/-}$ and WT littermates. Mice hemizygous for a c-Myc transgene (Eμ-cMycTG, C57Bl/6J-TgN (IghMyc); The Jackson Laboratory, Bar Harbor, Me.) are described in the art (Harris et al., *J. Exp. Med.*, 167:353 (1988) and Adams et al., *Nature*, 318:533 (1985)). c-MycTG mice (B6/129 background) could be crossed with hCD22tg mice to generate hemizygous hCD22tg cMycTG$^{+/-}$ offspring that could be identified by PCR screening. Rag1$^{-/-}$ (B6.129S7-Rag1$^{tm1Mom}$/J) mice are available from The Jackson Laboratory. Macrophage-deficient mice can be generated by tail vein injections of clodronate-encapsulated liposomes (0.1 mL/10 gram body weight; Sigma Chemical Co., St. Louis, Mo.) into C57BL/6 mice on day −2, 1 and 4 in accordance with standard methods (Van Rooijen and Sanders, *J. Immunol. Methods*, 174:83-93 (1994)). All mice should be housed in a specific pathogen-free barrier facility and first used at 6-9 weeks of age.

ELISAs.

Serum Ig concentrations are determined by ELISA using affinity-purified mouse IgM, IgG1, IgG2a, IgG2b, IgG3, and IgA (Southern Biotechnology Associates, Inc., Birmingham, Ala.) to generate standard curves as described (Engel et al., *Immunity*, 3:39 (1995)). Serum IgM and IgG autoantibody levels against dsDNA, ssDNA and histone are determined by ELISA using calf thymus double-stranded (ds) DNA (Sigma-Aldrich, St. Louis, Mo.), boiled calf thymus DNA (which contains single-stranded (ss) DNA) or histone (Sigma-Aldrich) coated microtiter plates as described (Sato et al., *J. Immunol.*, 157:4371 (1996)).

Immunotherapy.

Sterile anti-CD22 and unreactive, isotype control antibodies (0.5-250 μg) in 200 μL phosphate-buffered saline (PBS) are injected through lateral tail veins. For example, experiments would use a fixed amount (e.g. 250 μg) of antibody. Blood leukocyte numbers are quantified by hemocytometer following red cell lysis, B220$^+$ B cell frequencies are determined by immunofluorescence staining with flow cytometry analysis. Antibody doses in humans and mice would be compared using the Oncology Tool Dose Calculator (www.fda.gov/cder/cancer/animalframe.htm).

Immunizations.

Two-month old WT mice are immunized i.p. with 50 μg of 2,4,6-trinitrophenyl (TNP)-conjugated lipopolysaccharide (LPS) (Sigma, St. Louis, Mo.) or 25 2,4-dinitrophenol-conjugated (DNP)-FICOLL® (Biosearch Technologies, San Rafael, Calif.) in saline. Mice are also immunized i.p. with 100 μg of DNP-conjugated keyhole limpet hemocyanin (DNP-KLH, CALBIOCHEM®-NOVABIOCHEM® Corp., La Jolla, Calif.) in complete Freund's adjuvant and are boosted 21 days later with DNP-KLH in incomplete Freund's adjuvant. Mice are bled before and after immunizations as indicated. DNP- or TNP-specific antibody titers in individual serum samples are measured in duplicate using ELISA plates coated with DNP-BSA (CALBIOCHEM®-NOVABIOCHEM® Corp., La Jolla, Calif.) or TNP-BSA (Biosearch Technologies, San Rafael, Calif.) according to standard methods (Engel et al., *Immunity*, 3:39-50 (1995)). Sera from TNP-LPS immunized mice are diluted 1:400, with sera from DNP-FICOLL® and DNP-BSA immunized mice diluted 1:1000 for ELISA analysis.

Statistical Analysis.

All data would be shown as means±SEM with Student's t-test used to determine the significance of differences between sample means 6.10.2.1 Human CD22 Expression in Transgenic Mice Transgenic hCD22tg mice, which can be developed as described herein, or other transgenic animals expressing human CD22 can be used to assess different therapeutic regimens comprising the anti-CD22 antibodies of the invention, such as variations in dosing concentration, amount, and timing. The efficacy in human patients of different therapeutic regimens can be predicted using the two indicators described below, i.e., B cell depletion in certain bodily fluids and/or tissues and the ability of a monoclonal human or humanized anti-CD22 antibody to bind B cells. In particular embodiments, treatment regimens that are effective in human CD22 transgenic mice could be used with the compositions and methods of the invention to treat autoimmune diseases or disorders in humans.

In order to determine whether human CD22 is expressed on B cells from transgenic mice (hCD22tg) expressing the human CD22 transgene, B cells would be extracted from the bone marrow, blood, spleen and peritoneal lavage of these mice. Human CD22 and mouse CD22 expression would be assessed in these cells by contacting the cells with anti-CD22 antibodies that bind CD22. Binding of the antibody to the B lineage cells would be detected using two-color immunofluorescence staining with flow cytometry analysis. The relative expression levels of mCD22 and hCD22, would be assessed by measuring mean fluorescence intensity (anti-hCD22 for hCD22 and anti-mCD22 for mCD22) respectively.

6.10.3. Anti-CD22 Antibody Depletion of B Cells In Vivo

The anti-CD22 antibodies of the invention, which bind to human CD22, can be assessed for their ability to deplete hCD22tg blood, spleen, and lymph node B cells in vivo. For example, each antibody would be given to mice at either 250 or 50 µg/mouse, a single dose about 10 to 50-fold lower than the 375 mg/m$^2$ dose primarily given four times for anti-CD20 therapy in humans (Maloney et al., *J. Clin. Oncol.*, 15:3266-74 (1997) and McLaughlin et al., *Clinical status and optimal use of rituximab for B cell lymphomas, Oncology* (Williston Park), 12:1763-9 (1998)). B cell depletion from blood, spleen and lymph nodes of hCD22tg mice would be determined by immunofluorescence staining with flow cytometry analysis. The results using anti-CD22 antibodies identified as capable of depleting B cells can be correlated to use in humans and antibodies with properties of the identified antibodies can be used in the compositions and methods of the invention for the treatment of autoimmune diseases and disorders in humans.

6.10.4. CD22 Density Influences the Effectiveness of CD22 Antibody-Induced B Cell Depletion To determine whether an anti-CD22 antibody's ability to deplete B cells is dependent on CD22 density, anti-CD22 antibodies of the invention can be administered to mice having varying levels of hCD22 expression. The results obtained will demonstrate that human CD22 density on B cells and antibody isotype can influence the depletion of B cells in the presence of an anti-CD22 antibody. The same assay can be used to determine whether other anti-CD22 antibodies can effectively deplete B cells and the results can be correlated to treatment of human patients with varying levels of CD22 expression. Thus, the methods for examining CD22 presence and density, described herein, can be used in human subjects to identify patients or patient populations for which certain anti-CD22 antibodies can deplete B cells and/or to determine suitable dosages.

To determine whether CD22 density influences the effectiveness of anti-CD22 antibody-induced B cell depletion representative blood and spleen B cell depletion can be examined in hCD22tg mice after treatment with the anti-CD22 antibodies of the invention (7 days, 250 µg/mouse). The results are expected to demonstrate that CD22 density influences the efficiency of B cell depletion by anti-CD22 antibodies in vivo. For example, low-level CD22 expression in hCD22tg mice would be expected to have a marked influence on circulating or tissue B cell depletion by the administered antibody. B cell clearance can be assessed 24 hours after anti-CD22 or control mAb treatment of individual mice.

6.10.5. Tissue B Cell Depletion is not Expected to be FcγR-Dependent

Should administration of an anti-CD22 mAb of the invention result in tissue B cell depletion, the following assays can be used to demonstrate dependence upon FcγR expression. Through a process of interbreeding hCD22tg mice with mice lacking expression of certain FcγR, mice can be generated that express hCD22 and lack expression of certain FcγR. Such mice can be used in assays to assess the ability of anti-CD22 antibodies to deplete B cells through pathways that involve FcγR expression, e.g., ADCC. Thus, anti-CD22 antibodies identified in these assays can be used to engineer chimeric, human or humanized anti-CD22 antibodies using the techniques described above. Such antibodies can in turn be used in the compositions and methods of the invention for the treatment of autoimmune diseases and disorders in humans.

The innate immune system mediates B cell depletion following anti-CD20 antibody treatment through FcγR-dependent processes. Mouse effector cells express four different FcγR classes for IgG, the high-affinity FcγRI (CD64), and the low-affinity FcγRII (CD32), FcγRIII (CD16), and FcγRIV molecules. FcγRI, FcγRIII and FcγRIV are hetero-oligomeric complexes in which the respective ligand-binding α chains associate with a common γ chain (FcRγ). FcRγ chain expression is required for FcγR assembly and for FcγR triggering of effector functions, including phagocytosis by macrophages. Since FcRγ$^{-/-}$ mice lack high-affinity FcγRI (CD64) and low-affinity FcγRIII (CD16) and FcγRIV molecules, FcRγ$^{-/-}$ mice expressing hCD22 can be used to assess the role of FcγR in tissue B cell depletion following anti-CD22 antibody treatment.

6.10.6. Durability of Anti-CD22 Antibody-Induced B Cell Depletion

To assess the efficacy and duration of B cell depletion, hCD22tg mice can be administered a single low dose (e.g. 250 µg) injection of anti-CD22 antibody and the duration and dose response of B cell depletion followed as a function of time. The results are expected to demonstrate that circulating B cells are depleted for a substantial amount of time (e.g. one week to six months), followed by a gradual recovery of blood-borne B cells.

6.10.7. Persistence of CD22 on the Surface of B Cells after Administration of Anti-CD22 Antibody Whether CD22 internalization will influence B cell depletion in vivo can be assessed by comparing cell-surface CD22 expression following administration of the anti-CD22 antibodies of the present invention (250 µg). For example, cell surface CD22 expression and B cell clearance in hCD22tg mice treated with an anti-CD22 antibody of the present invention or isotype-matched control antibody (250 µg) in vivo can be studied as a function of time. Thus, spleen B cells can be harvested and assayed for CD22 at time zero (prior to anti-CD22 administration), and at 1, 4, and 24 hours post-antibody administration. Isolated B cells may also be treated in vitro with saturating concentrations of each anti-CD22 antibody plus isotype-specific secondary antibody in vitro with flow cytometry analysis to visualize total cell surface CD22 expression. Where CD22 on the surface of B cells is maintained, it will indicate continued susceptibility to ADCC, CDC, and/or apoptosis. If CD22 persists on the cell surface following binding of an anti-CD22 antibody, the B cell will remain accessible to the ADCC, CDC, and/or apoptotic activity. Such results would demonstrate, in part, why the anti-CD22 antibodies and treatment regimens of the invention will be efficacious in providing therapy for transplantation and treating autoimmune diseases and disorders.

6.10.8. Anti-CD22 Antibody Treatment Will Abrogate Humoral Immunity and Autoimmunity In the event CD22 therapy decreases B cell representation, then the assays described in this example can be used to demonstrate that the anti-CD22 antibodies of the invention are capable of eliminating or attenuating immune responses. These assays can also be used to identify other anti-CD22 antibodies that can be used to engineer chimeric, human or humanized anti-CD22 antibodies using the techniques described above. Such antibodies can in turn be used in the compositions and methods of the invention for the treatment of autoimmune disease and disorders in humans, as well as for transplantation therapy.

The effect of anti-CD22 antibody-induced B cell depletion on serum antibody levels can be assessed by giving hCD22tg mice a single injection of anti-CD22 antibody and then assessing the reduction in immunoglobulin levels in those mice. For example, two-month-old littermates can be treated with a single injection of an anti-CD22 antibody of the present invention or a control antibody (e.g. 250 µg) on day 0. Antibody levels are then determined by ELISA. It is expected that the results will show that after 1 to 2 weeks, serum IgM, IgG2b, IgG3, and IgA antibody levels are significantly reduced, and remain reduced for at least 10 weeks.

Since hCD22tg mice are expected to produce detectable autoantibodies after 2 months of age (Sato et al., *J. Immunol.*, 157:4371 (1996)), serum autoantibody binding to ssDNA, dsDNA and histones may also be assessed. It is expected that anti-CD22 antibody treatment will reduce autoantibody anti-dsDNA, anti-ssDNA and anti-histone autoantibody levels after anti-CD22 antibody treatment; it is expected that anti-CD22 antibody treatment will significantly reduce serum IgM autoantibody levels after 2 weeks and prevent the generation of isotype-switched IgG autoantibodies for up to 10 weeks. Accordingly, B cell depletion will substantially reduce acute and long-term antibody responses and attenuate class-switching of normal and pathogenic immune responses.

The influence of B cell depletion on T cell-independent type 1 (TI-1) and type 2 (TI-2) antibody responses may also be assessed by immunizing hCD22tg mice with TNP-LPS or DNP-Ficoll (at day zero), 7 days after anti-CD22 antibody or control antibody treatment. Significant hapten-specific IgM, IgG, and IgA antibody responses are expected not to be observed in anti-CD22 antibody-treated mice immunized with either antigen. Antibody responses to the T cell-dependent (TD) Ag, DNP-KLH, may also be assessed using mice treated with anti-CD22 antibody 7 days before immunization, where it is expected that DNP-KLH immunized mice treated with anti-CD22 antibody will show reduced humoral immunity.

6.10.9. Anti-CD22 Antibody Treatment in Conjunction with Anti-CD20 Antibody Treatment The assay described herein can be used to determine whether other combination therapies, e.g., anti-CD22 antibodies in combination with chemotherapy, toxin therapy or radiotherapy, have beneficial effects, such as an additive or more that additive depletion in B cells. The results of combination therapies tested in animal models can be correlated to humans by means well-known in the art.

Anti-CD20 antibodies are effective in depleting human and mouse B cells in vivo. Therefore, the benefit of simultaneous treatment with an anti-CD22 antibody of the present invention and anti-CD20 (MB20-11) antibodies can be assessed to determine whether this will enhance B cell depletion. Mice can be treated with suboptimal doses (e.g. 2 µg, 5 µg, 10 µg, 20 µg, or 50 µg) of each antibody either individually, or as a combination of both antibodies. It is expected that the results will demonstrate that simultaneous anti-CD22 and anti-CD20 antibody treatments are beneficial. In a similar manner, the efficacy may be determine for treatment with a combination of an anti-CD22 antibody of the present invention with an anti-CD19 antibody, or a combination of an anti-CD22 antibody of the present invention, an anti-CD19 antibody, and an anti-CD20 antibody.

6.10.10. Therapeutic Efficacy of Subcutaneous (S.C.) Administration of an Anti-CD22 Antibody of the Invention The assay described herein can be used to determine whether a subcutaneous route of administration of an anti-CD22 antibody of the invention can effectively deplete B cells. The results of the efficacy of different delivery routes tested in animal models can be correlated to humans by means well-known in the art.

For example, hCD22tg mice can be treated with an anti-CD22 antibody of the invention at 250 µg either by subcutaneous (s.c.), intraperitoneal (i.p.) or intravenous (i.v.) administration. Values are determined for the mean (±SEM) blood (per mL), bone marrow, spleen, lymph node, and peritoneal cavity B220$^+$ B cell numbers on day seven as assessed using flow cytometry. Results are expected to demonstrate that subcutaneous (s.c.), intraperitoneal (i.p.) and intravenous (i.v.) administration of an anti-CD22 antibody of the invention will effectively deplete circulating and tissue B cells in vivo.

6.10.11. Binding Affinity of Murine Antibody HB22.7 and Humanized Antibody RHOv2ACD/RKA Binding affinity of HB22.7 and RHOv2ACD/RKA were determined on a BIAcore 3000 instrument (BIAcore, Inc., Uppsala, Sweden). The ligand, hCD22, was prepared at 50 nM in 10 mM NaOAc, pH4 buffer. It was injected onto an EDC/NHS-activated CM5 sensor chip (BIAcore, Inc. Uppsala, Sweden) using a standard immobilization protocol. Following this, any unreacted active ester moieties were quenched using 1M Et-NH2 (ethanolamine; coupling reagents purchased from BIAcore, Inc.). A total of 535 and 689 RUs hCD22 remained bound to two sensor chip surfaces used in these experiments. Separately, a blank surface was prepared on each sensor chip using the identical protocol (minus protein). The blank surfaces were used as a reference cell in the experiments, and served to correct for both non-specific binding and some housekeeping artifacts.

For the kinetic experiments, HB22.7 and RHOv2ACD/RKA were prepared as two dilution series, starting at 22 nM and 100 nM, then diluted three- and two-fold, respectively, down to final concentrations of 0.03 nM and 0.39 nM in HBS-EP buffer (BIAcore, Inc., consisting of the following: 10 mM HEPES buffer, pH7.4, 150 mM NaCl, 3 mM EDTA, and 0.005% P20). Each concentration of IgG was then injected over both the CD22 and reference cell surfaces, which are connected in series. Between injections, surfaces were regenerated with a 1-minute injection of 3M MgCl2.

Raw binding data was corrected in the manner described by Myszka (D. G. Myszka, Improving biosensor analysis. *J. Mol. Recognit.* 12 (1999), pp. 279-284). Fully corrected binding data was then globally fit using a 1:1 binding model (BIAevaluation 4.1 software, BIAcore, Inc, Uppsala, Sweden) to obtain the rate and apparent binding constants. The affinity determinations for the HB22.7 and RHOv2ACD/RKA antibodies are as follows:

|  | $k_{on}$ (M-1s-i) | $k_{off}$ (s-1) | $K_D$ (nM) |
|---|---|---|---|
| HB22.7 | $1.2 \times 10^4$ | $1.7 \times 10^{-4}$ | 14 |
| RHOv2ACD/RKA | $3.2 \times 10^4$ | $6.9 \times 10^{-4}$ | 22 |

6.10.12. Murine Antibody HB22.7 and Humanized Antibody RHOv2ACD/RKA Bind to COS Cells Transfected to Express hCD22

CHO cells expressing hCD22 were prepared by transfection with a plasmid encoding human CD22 using the Lipofectamine procedure. Two days post-transfection, both transfected and non-transfected cells were harvested, resuspended in PBS at a concentration of $1 \times 10^6$/ml and stained with antibodies over a range of 0.0625 µg antibody/$10^6$ cells to 10 µg antibody/$10^6$ cells. Cells were incubated on ice for 20 minutes then washed and resuspended in PBS followed by addition of secondary antibody, either a goat anti-human (GAH) or GAM-F(ab)'2 anti human-RPE at a 1:1000 dilution. Cells were incubated on ice for an additional 10 minutes and binding activity was evaluated via FACS analysis on a Guava flow cytometer. FIG. 18 shows the median fluorescence intensity (MFI) caused by binding of HB22.7 and RHOv2ACD/RKA to hCD22 expressing CHO cells.

6.10.13. Murine Antibody HB22.7 and Humanized Antibody RHOv2ACD/RKA Bind to Daudi Cells Humanized RHOvACD/RKA and murine HB22.7 anti-hCD22 mAbs were labeled with Alexa-fluor 488. The Alexa-fluor (AF) labeled antibodies were separately incubated with Daudi cells that had been prepared at a concentration of $1 \times 10^6$ cells/ml. Briefly, Daudi cells were incubated on ice for 20 minutes with either of the HB22.7 or RHOv2ACD/RKA antibodies at a microgram amount ranging from 0 to 5 per $1 \times 10^6$ cells. After 20 minute incubations on ice, cells were washed, resuspended in PBS and analyzed by FACS on a Guava flow cytometer. FIG. 19 provides the FACS analysis of binding of each of the HB22.7 and RHOv2ACD antibodies to Daudi cells.

6.10.14. Anti-hCD22 Antibodies HB22.7 and RHOv2ACD/RKA Promote Internalization of CD22

Figure 20B:
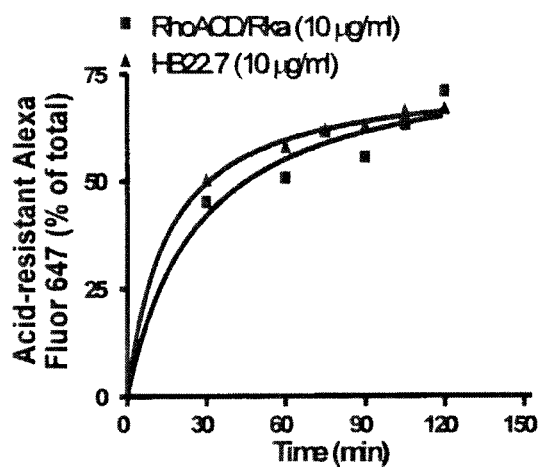
Figure 21B:
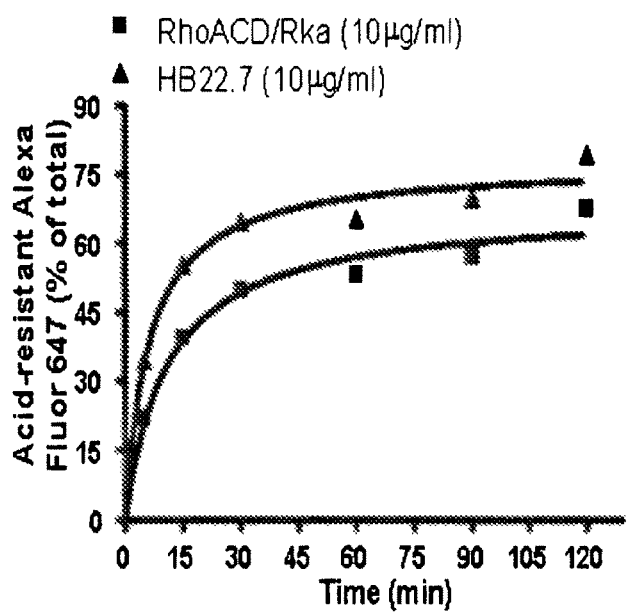

Anti-hCD22 antibodies HB22.7 and RHOv2ACD/RKA were labeled with the pH insensitive fluorophore Alexa Fluor-647. B cells (Daudi, human tonsillar, or human peripheral blood) were stained with 10 µg/ml of the Alexa Fluor-647 labeled anti-hCD22 mAbs or left in medium alone for 20 minutes on ice. Cells were then incubated with antibody or medium alone for up to 2 hours. The cells were harvested and washed in ice-cold staining buffer and either fixed or stripped with an acidic solution (PBS containing 30 mM sucrose, pH 2.5) for 45 seconds on ice, washed in complete media and resuspended in staining-fixative buffer. CD22 expression (total and internalized) was assessed by flow cytometry. The data provided in each of FIGS. 20-22 are depicted both as the total antibody binding activity (a) and as percentage of internalized (acid-resistant fluoro-labeled) mAb (b). FIG. 20 provides this data for total antibody binding and percentage internalization on Daudi cells. FIG. 21 provides this data for total antibody binding and percentage internalization on human magnetic cell sorted (MACS)-enriched tonsillar B cells. FIG. 22 provides this data for total antibody binding and percentage internalization on human MACS-enriched peripheral blood B cells.

6.10.15. Comparison of CD22 Internalization with Blocking, HB22.7 and RHOv2ACD/RKA, Versus Non-Blocking, HB22.15, Anti-hCD22 Antibodies Anti-hCD22 antibodies HB22.7, RHOv2ACD/RKA, and HB22.15 were each labeled with Alexa Fluor-647. Daudi cells were stained with 10 mg/ml of each of the Alexa Fluor-647 labeled anti-hCD22 mAbs or left in medium alone for 20 minutes on ice. Cells were then incubated with antibody or medium alone for up to 2 hours. The cells were harvested and washed in ice-cold staining buffer and either fixed or stripped with an acidic solution (PBS containing 30 mM sucrose, pH 2.5) for 45 seconds on ice, washed in complete media and resuspended in staining-fixative buffer. CD22 expression was assessed by flow cytometry. FIG. 23 shows that each of the anti-hCD22 antibodies, HB22.7, RHOv2ACD/RKA, and HB22.15, was internalized by the Daudi cells. Non-ligand blocking anti-hCD22 antibody, HB22.15 mediated faster antigen internalization relative to ligand blocking anti-hCD22 antibodies HB22.7 and RHOv2ACD/RKA on Daudi cells.

6.10.16. ADCC Effector Function of Anti-hCD22 RHOv2ACD/RKA Antibody

Antibodies Rituxan and RHOv2ACD/RKA were each diluted from 0.1 ng/ml to 10 µg/ml in media and transferred to a 96 well plate. Target cells, Raji cells, at a concentration of $0.4 \times 10^6$/ml were added to each well followed by effector cells, KC 1333 at a concentration of $1 \times 10^6$/ml (for a ratio of 1:2.5 target (Raji):effector (KC 1333) cells). Proper controls such as target cells only, effector cells only, and target cells only with and without lysis buffer were also included. After a 3 hour incubation at 37 C, lysis buffer was added to appropriate control wells and the 96 well plate was returned to the incubator for an additional hour. After the 4 hour total incubation period, the plate was centrifuged, a sample of the supernatant was removed from each well, and the sample transferred to a new 96 well dish. The LDH assay was performed using the Promega non-radioactive cytotoxicity assay as outlined in the kit protocol. FIG. 24 provides the ADCC effector function mediated by each of the Rituxan and RHOv2ACD/RKA antibodies.

6.10.17. CDC Effector Function of Anti-hCD22 RHOv2ACD/RKA Antibody

Figure 25B:
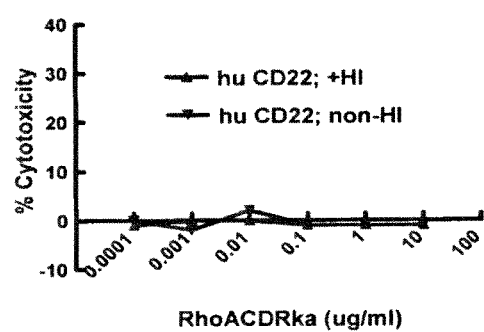
Figure 26A:
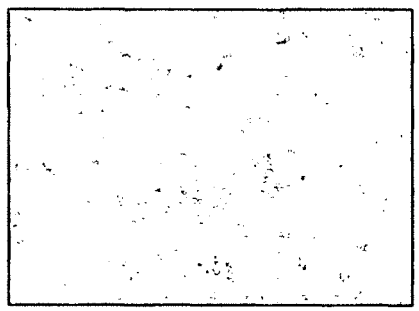
Figure 26B:
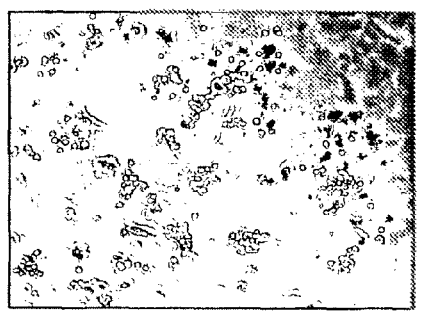
Figure 26C:
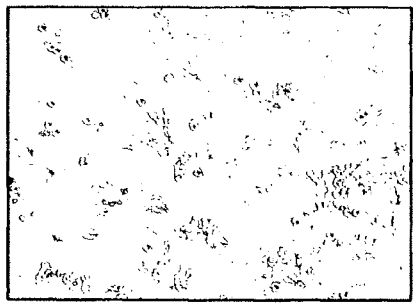
Figure 26D:
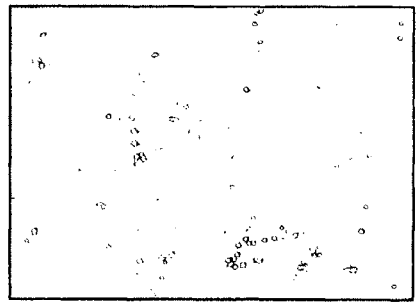

Antibodies Rituxan and RHOv2ACD/RKA were each diluted from 0.1 ng/ml to 10 µg/ml in either RPMI Phenol Free media containing 10% heat inactivated or untreated human serum and transferred to a 96 well plate. Target cells, Raji cells, at a concentration of $0.4 \times 10^6$/ml and effector cells, KC1333 at a concentration of $1 \times 10^6$/ml were also prepared in RPMI Phenol Free medium containing either 10% heat inactivated or untreated human serum. Appropriate target cells were added to each well containing antibody, followed by appropriate effector cells. Proper controls such as target cells only, effector cells only, and target cells only with and without lysis buffer were also included. After a 3 hour incubation at 37 C, lysis buffer was added to appropriate control wells and the 96 well plate was returned to the incubator for an additional hour. After the 4 hour total incubation period, the plate was centrifuged, a sample of the supernatant was removed from each well, and the sample transferred to a new 96 well dish. The LDH assay performed using the Promega non-radioactive cytotoxicity assay as outlined in the kit protocol. FIG. 25 provides the CDC effector function mediated by each of the Rituxan and RHOv2ACD/RKA antibodies. Fresh donor serum was the source of complement for this Example, HI indicates use of heat inactivated serum.

6.10.18. HB22.7 and RHOv2ACD/RKA Antibodies Interfere with Daudi Cell Adhesion to hCD22-Expressing COS Cells COS cells were transfected with a hCD22 encoding plasmid using the Lipofectamine procedure. Two days post-transfection, both transfected and non-transfected COS cells were harvested. Transfection efficiency was evaluated by incubating transfected cells with murine and human CD22 antibodies.

Once binding to the transfected COS cells was established, the transfected COS cells were incubated with either no antibody or murine HB22.7 or humanized RHOv2ACD-RKA CD22 antibodies at 10 µg/ml for 30 minutes on ice. The cells were washed with media. Daudi cells were then added to all wells and the wells were incubated for an additional 30 minutes on ice. Again, the cells were washed with media, formalin fixed and the images photographed. FIG. 26 shows that while Daudi cells did not adhere to the non-transfected COS cells (A), Daudi cells clustered with the COS cells transfected with the hCD22-encoding plasmid (B). Incubation of the COS cells transfected with the hCD22-encoding plasmid with either HB22.7 (C) or RHOv2ACD/RKA (D) interfered with adhesion of Daudi cells.

6.10.19. Effect of RHOv2ACD/RKA Antibody on Anti-CD22 Signaling Activity

Figure 27B:
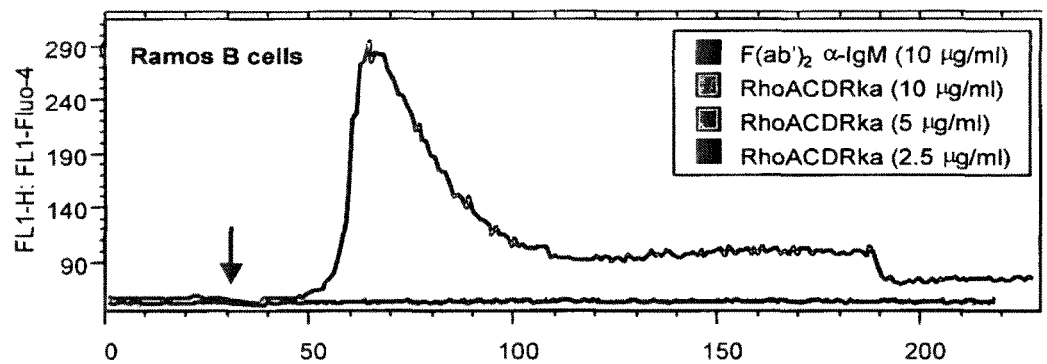

Ramos B cell lymphoma were suspended in DPBS containing 3% FBS (staining buffer) at $10 \times 10^7$ cells/ml. The cells were loaded for 40 minutes at 37° C. with 1 µM of Fluor-4 ester, washed and resuspended in staining buffer at $2 \times 10^6$ cells/ml. Prior to FACS analysis, the cells were incubated for 10 minutes at 37° C., followed by addition of increasing concentrations of either anti-IgM (FIG. 27A) or the indicated concentrations of anti h-CD22 RHOv2ACD/RKA mAb (FIG. 27B). Baseline emission fluorescence was collected for 30 seconds before the addition of F(ab')$_2$ anti-IgM (0.5 µg/ml to 10 µg/ml) or RHOv2ACD/RKA (2.5 µg/ml to 10 µg/ml). Increases of calcium mobilization are represented as increase of fluorescence intensity after anti-IgM relative to the fluorescence intensity of untreated cells. Similar results to those observed for RHOv2ACD/RKA were obtained for HB22.7.

Figure 28B:
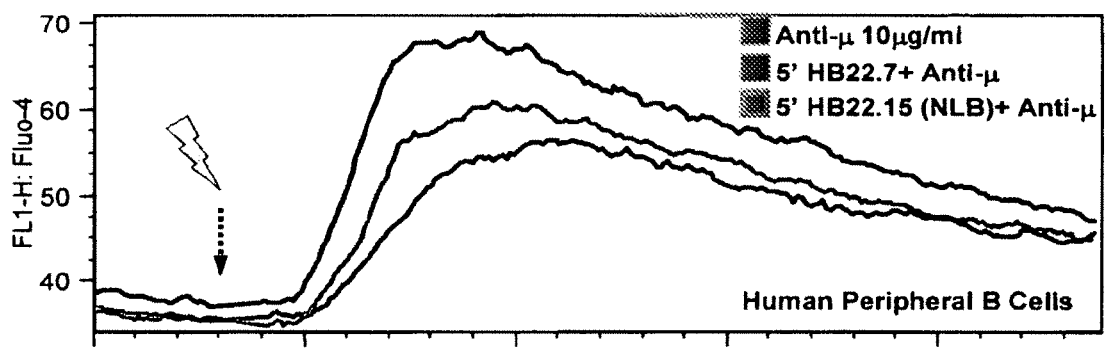
Figures 29A, 29B, 29C, 29D, 29E, 29F, 29G, 29H:
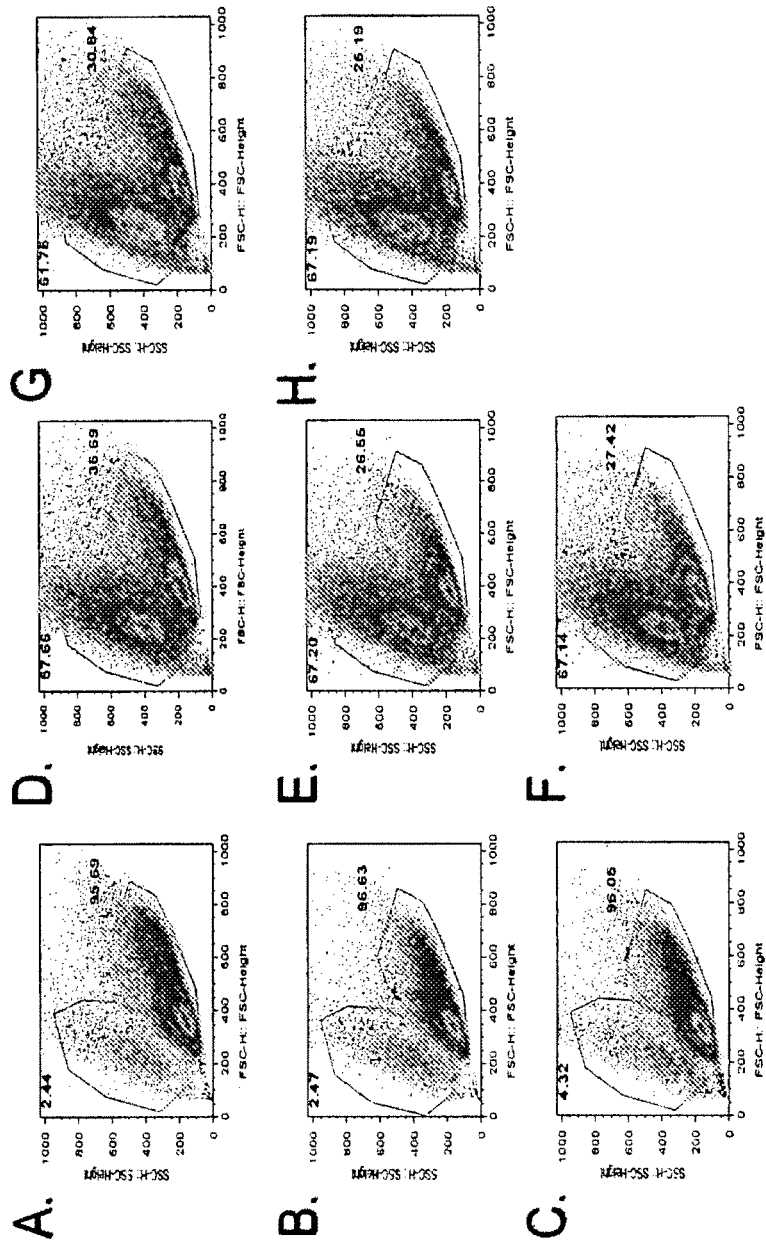

6.10.20. Anti-IgM-Induced Ca-Flux is Enhanced by Ligand Blocking hCD22 Antibodies, HB22.7 and RHOv2ACD/RKA MACS-enriched human peripheral blood B cells were suspended in DPBS containing 3% FBS (staining buffer) at $10 \times 10^7$ cells/ml. The cells were loaded for 40 minutes at 37° C. with 1 µM of Fluor-4 ester, washed and resuspended in staining buffer at $2 \times 10^6$ cells/ml. Prior to FACS analysis, the cells were incubated for 15 minutes at 37° C., followed by addition of the indicated anti hCD22 mAbs (HB22.7, RHOv2ACD/RHO, and HB22.15) for 5 minutes. Baseline emission fluorescence was collected for 30 seconds before the addition of F(ab')$_2$ anti-IgM (10 µg/ml). Increases of calcium mobilization are represented as increased fluorescence intensity after either anti hCD22 alone or anti hCD22 followed by anti-IgM relative to the fluorescence intensity of untreated cells. It can be seen in both FIGS. 28A and 28B that Ca-flux in cells treated with both a hCD22 ligand blocking antibody (either RHOACD/RKA (28A) or HB22.7 (28B)) and anti-IgM is greater than with anti-IgM alone. Neither an isotype control (IC) antibody R347 (FIG. 28A) nor a non-ligand blocking (NLB) antibody HB22.15 (FIG. 28B) enhanced anti-IgM Ca-flux in the human peripheral B cells.

6.10.21. Effect of HB22.7 and RHOv2ACD/RKA on Ramos Cell Survival

Ramos B cell lymphoma ($4 \times 10^5$/ml) were incubated at 37° C. with 10 µg/ml of anti h-CD22 mAbs (RHOv2ACD/RKA and HB22.7) or isotype control (R347) (not shown) for 15 minutes followed by addition of F(ab')$_2$ anti-IgM (3.3 µg/ml and 10 µg/ml) or complete media as indicated. Cells were cultured for 48 hours, washed twice with cold DPBS, and analyzed by flow cytometry on a FACSCalibur. The gated live cells (FSC right gates) was confirmed by staining the cells with Annexin V-APC and propidium iodide (PI) according to the manufacturer's protocol (BD) (live cells appeared as Annexin V and PI double negative population, not shown). Treatment of Ramos B cells was as follows: (A) no antibody; (B) 10 µg/ml HB22.7; (C) 10 µg/ml RHOv2ACD/RKA; (D) 3.3 µg/ml anti-IgM; (E) 3.3 µg/ml anti-IgM+10 µg/ml HB22.7; (F) 3.3 µg/ml anti-IgM+10 µg/ml RHOv2ACD/RKA; (G) 10 µg/ml anti-IgM; (H) 10 µg/ml anti-IgM+10 µg/ml HB22.7.

6.10.22. Dissociation of HB22.7 and RHOv2ACD Antibodies from Daudi Cells

Daudi lymphoma B cells were stained for 20 minutes on ice with fluorescence-labeled anti h-CD22 mAbs (10 µg/ml). The cells were then washed and resuspended in complete medium at $5 \times 10^6$ cells/ml. Cells were incubated at indicated times at 37° C. or left on ice, washed and resuspended in staining buffer-containing fixative followed by flow cytometry analysis. FIG. 30 provides the dissociation of the antibodies from Daudi cells over 2 hr. The RHOv2ACD/RKA antibody may have a higher dissociate rate than HB22.7 from Daudi cells, which correlates to its lower affinity to CD22 on these cells.

The present invention is not to be limited in scope by the specific embodiments described herein. Indeed, various modifications of the invention in addition to those described will become apparent to those skilled in the art from the foregoing description and accompanying figures. Such modifications are intended to fall within the scope of the appended claims.

Various publications are cited herein, the disclosures of which are incorporated by reference in their entireties.

---

What is claimed is:

1. A monoclonal humanized anti-CD22 antibody comprising a heavy chain variable region and a light chain variable region, (A) wherein the heavy chain variable region comprises three complementarity determining regions, CDR1, CDR2, and CDR3, and four framework regions, FW1, FW2, FW3, and FW4, in the order FW1-CDR1-FW2-CDR2-FW3-CDR3-FW4;

wherein CDR1 comprises the amino acid sequence DYGVN (SEQ ID NO:62), CDR2 comprises the amino acid sequence IIWGDGRTDYNSALKS (SEQ ID NO:63), and CDR3 comprises the amino acid sequence APGNRAMEY (SEQ ID NO:64); and wherein FW1 comprises the amino acid sequence QVQLQESGPALVKPTQTLTLTCTVSGFSLS (SEQ ID NO:74), FW2 comprises the amino acid sequence WIRQPPGKALEWLG (SEQ ID NO:76), FW3 comprises the amino acid sequence RLSISKDNSKNQVVLRMTNVDPVDTATYFCAR (SEQ ID NO:78), and FW4 comprises the amino acid sequence WGQGTVTVSS (SEQ ID NO:79); and (B) wherein the light chain variable region ("VK") comprises three complementarity determining regions (CDRs), VK CDR1, VK CDR2, and VK CDR3, and four framework regions, VK FW1, VK FW2, VK FW3, and VK FW4, in the order VK FW1-VK CDR1-VK FW2-VK CDR2-VK FW3-VK CDR3-VK FW4;

wherein VK CDR1 comprises the amino acid sequence KASQSVTNDVA (SEQ ID NO:65), VK CDR2 comprises the amino acid sequence YASNRYT (SEQ ID NO:66), and VK CDR3 comprises the amino acid sequence QQDYRSPWT (SEQ ID NO:67); and wherein VK FW1 comprises the amino acid sequence DIVMTQSPSSLSASVGDRVTITC (SEQ ID NO:117), VK FW2 comprises the amino acid sequence WYQQKPGKAPKLLIY (SEQ ID NO:118), VK FW3 comprises the amino acid sequence GVPDRFSGSGYGTDFTLTISSLQPEDFATYFC (SEQ ID NO:126), and VK FW4 comprises the amino acid sequence FGGGTKVEIKRT (SEQ ID NO:127).

2. A pharmaceutical composition comprising a humanized anti-CD22 monoclonal antibody of claim 1, in a pharmaceutically-acceptable carrier.

3. The pharmaceutical composition of claim 2, wherein the humanized anti-CD22 monoclonal antibody is of the IgG1, IgG2, IgG3, or IgG4 human isotype.

4. The monoclonal humanized anti-CD22 antibody of claim 1, wherein the antibody is conjugated to a therapeutic agent or a toxin.

5. A bispecific antibody comprising the monoclonal humanized anti-CD22 antibody of claim 1.

6. The monoclonal humanized anti-CD22 antibody of claim 1 which is isolated.

7. A method of treating a B cell malignancy in a human, comprising administering to a human in need thereof a therapeutically-effective amount of the humanized anti-CD22 monoclonal antibody of claim 1.

8. A method of treating an autoimmune disease or disorder in a human, or in treating or preventing humoral rejection in a human transplant patient, comprising administering to a human in need thereof a therapeutically-effective amount of the humanized anti-CD22 monoclonal antibody of claim 1.

9. The method of claim 7, wherein the B cell malignancy is B cell subtype non-Hodgkin's lymphoma, Burkitt's lymphoma, multiple myeloma, pre-B acute lymphoblastic leukemia, common acute lymphocytic leukemia, chronic lymphocytic leukemia, hairy cell leukemia, Null-acute lymphoblastic leukemia, Waldenstrom's Macroglobulinemia, diffuse large B cell lymphoma, pro-lymphocytic leukemia, light chain disease, plasmacytoma, osteosclerotic myeloma, plasma cell leukemia, monoclonal gammopathy of undetermined significance, smoldering multiple myeloma, indolent multiple myeloma, Hodgkin's lymphoma, lymphoplasmacytic lymphoma, marginal-zone lymphoma, follicular lymphoma, mantle-cell lymphoma, or acute lymphoblastic leukemia.

\* \* \* \* \*